(12) United States Patent
Arista et al.

(10) Patent No.: US 8,263,782 B2
(45) Date of Patent: *Sep. 11, 2012

(54) AZABICYCLO (3.1.0) HEXANE DERIVATIVES USEFUL AS MODULATORS OF DOPAMINE $D_3$ RECEPTORS

(75) Inventors: Luca Arista, Verona (IT); Giorgio Bonanomi, Verona (IT); Gabriella Gentile, Verona (IT); Dieter Hamprecht, Verona (IT); Fabrizio Micheli, Verona (IT); Anna Maria Capelli, Verona (IT); Federica Damiani, Verona (IT); Romano Di Fabio, Verona (IT); Luca Tarsi, Verona (IT); Giovanna Tedesco, Verona (IT); Silvia Terreni, Verona (IT)

(73) Assignee: Glaxo Group Limited, Greenford, Middlesex (GB)

( * ) Notice: Subject to any disclaimer, the term of this patent is extended or adjusted under 35 U.S.C. 154(b) by 245 days.

This patent is subject to a terminal disclaimer.

(21) Appl. No.: 12/639,129

(22) Filed: Dec. 16, 2009

(65) Prior Publication Data

US 2010/0152195 A1 Jun. 17, 2010

Related U.S. Application Data

(62) Division of application No. 10/598,200, filed on Aug. 21, 2006, now Pat. No. 7,855,298.

(30) Foreign Application Priority Data

Feb. 23, 2004 (GB) ................................ 0403990.5
Feb. 24, 2004 (GB) ................................ 0404083.8
Jul. 30, 2004 (GB) ................................ 0417120.3

(51) Int. Cl.
   *C07D 215/38* (2006.01)
(52) U.S. Cl. ............... 548/262.2; 548/262.4; 548/263.4; 548/264.2
(58) Field of Classification Search ............... 548/262.2, 548/262.4, 263.3, 264.2, 264.24
   See application file for complete search history.

(56) References Cited

U.S. PATENT DOCUMENTS

| | | | |
|---|---|---|---|
| 7,799,815 B2 * | 9/2010 | Bonanomi et al. ............ 514/383 |
| 7,803,820 B2 * | 9/2010 | Andreotti et al. ............ 514/341 |
| 7,855,298 B2 * | 12/2010 | Arista et al. ............... 548/264.2 |
| 7,863,299 B2 * | 1/2011 | Capelli et al. ................ 514/341 |
| 7,875,643 B2 * | 1/2011 | Hamprecht et al. .......... 514/383 |
| 7,947,683 B2 * | 5/2011 | Bonanomi et al. ....... 514/252.06 |
| 2007/0249642 A1 | 10/2007 | Bertani et al. ............... 514/269 |
| 2008/0058398 A1 | 3/2008 | Anderton et al. ............. 514/374 |
| 2008/0167357 A1 | 7/2008 | Hamprecht et al. .......... 514/384 |
| 2008/0176917 A1 | 7/2008 | Andreotti et al. ............. 514/384 |
| 2008/0227837 A1 | 9/2008 | Arista et al. ................. 514/384 |
| 2008/0242715 A1 | 10/2008 | Capelli et al. ................ 514/384 |
| 2009/0030062 A1 | 1/2009 | Gentile et al. ................ 514/412 |
| 2009/0036461 A1 | 2/2009 | Hamprecht et al. ..... 514/252.06 |
| 2009/0124629 A1 | 5/2009 | Bonanomi et al. ....... 514/252.06 |
| 2009/0221593 A1 | 9/2009 | Bonanomi et al. ........ 514/249 |
| 2009/0221618 A1 | 9/2009 | Arista et al. ................. 514/274 |
| 2010/0160336 A1 * | 6/2010 | Arista et al. ............. 514/252.06 |

FOREIGN PATENT DOCUMENTS

| | | | |
|---|---|---|---|
| WO | WO00/42037 A | 7/2000 |
| WO | WO01/98267 A | 12/2001 |
| WO | WO02/40471 A | 5/2002 |
| WO | WO03/035622 A | 5/2003 |

OTHER PUBLICATIONS

U.S. Appl. No. 11/917,352, filed Jun. 13, 2006, Arista, et al.
U.S. Appl. No. 12/295,024, filed Mar. 30, 2007, Bertani, et al.
U.S. Appl. No. 12/295,304, filed Mar. 30, 2007, Bertani, et al.

* cited by examiner

Primary Examiner — D M Seaman
(74) Attorney, Agent, or Firm — Bonnie L. Deppenbrock

(57) ABSTRACT

The present invention relates to novel compounds of formula (I) or a pharmaceutically acceptable salt thereof:

1.

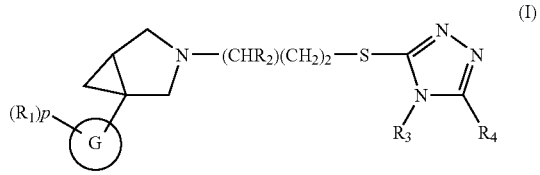

(I)

wherein
G is selected from a group consisting of: phenyl, pyridyl, benzothiazolyl, indazolyl;
p is an integer ranging from 0 to 5;
$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl; or corresponds to a group $R_5$;
$R_2$ is hydrogen or $C_{1-4}$alkyl;
$R_3$ is $C_{1-4}$alkyl;
$R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl;
$R_5$ is a moiety selected from the group consisting of: isoxazolyl, —$CH_2$—N-pyrrolyl, 1,1-dioxido-2-isothiazolidinyl, thienyl, thiazolyl, pyridyl, 2-pyrrolidinonyl, and such a group is optionally substituted by one or two substituents selected from: halogen, cyano, $C_{1-4}$alkyl, halo$C_{1-4}$alkyl, $C_{1-4}$alkoxy, $C_{1-4}$alkanoyl;
and when $R_1$ is chlorine and p is 1, such $R_1$ is not present in the ortho position with respect to the linking bond to the rest of the molecule; and when $R_1$ corresponds to $R_5$, p is 1;
processes for their preparation, intermediates used in these processes, pharmaceutical compositions containing them and their use in therapy, as modulators of dopamine $D_3$ receptors, e.g. to treat drug dependency or as antipsychotic agents.

22 Claims, No Drawings

AZABICYCLO (3.1.0) HEXANE DERIVATIVES USEFUL AS MODULATORS OF DOPAMINE D₃ RECEPTORS

This application is a divisional of application Ser. No. 10/598,200 filed 21 Aug. 2006, which claims priority to GB 0417120.3 filed 30 Jul. 2004, GB 0404083.8 filed 24 Feb. 2004 and GB 0403990.5 filed 23 Feb. 2004, the disclosures of which are incorporated herein in their entirety.

The present invention relates to novel compounds, processes for their preparation, intermediates used in these processes, pharmaceutical compositions containing them and their use in therapy, as modulators of dopamine $D_3$ receptors.

WO 2002/40471 (SmithKline Beecham) discloses certain benzazepine compounds having activity at the dopamine $D_3$ receptor.

A new class of compounds which have affinity for dopamine receptors, in particular the dopamine $D_3$ receptor has been found. These compounds have potential in the treatment of conditions wherein modulation, especially antagonism/inhibition, of the $D_3$ receptor is beneficial, e.g. to treat drug dependency or as antipsychotic agents.

The present invention provides a compound of formula (I) or a salt thereof:

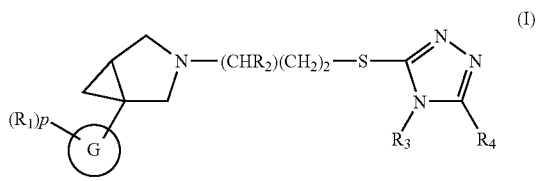

(I)

wherein
G is selected from a group consisting of: phenyl, pyridyl, benzothiazolyl, indazolyl;
p is an integer ranging from 0 to 5;
$R_1$ is independently selected from a group consisting of: halogen, hydroxy, cyano, $C_{1-4}$alkyl, halo$C_{1-4}$alkyl, $C_{1-4}$alkoxy, halo$C_{1-4}$alkoxy, $C_{1-4}$alkanoyl; or corresponds to a group $R_5$;
$R_2$ is hydrogen or $C_{1-4}$alkyl;
$R_3$ is $C_{1-4}$alkyl;
$R_4$ is hydrogen, or a phenyl group, a heterocyclyl group, a 5- or 6-membered heteroaromatic group, or a 8- to 11-membered bicyclic group, any of which groups is optionally substituted by 1, 2, 3 or 4 substituents selected from the group consisting of: halogen, cyano, $C_{1-4}$alkyl, halo$C_{1-4}$alkyl, $C_{1-4}$alkoxy, $C_{1-4}$alkanoyl;
$R_5$ is a moiety selected from the group consisting of: isoxazolyl, —CH₂—N-pyrrolyl, 1,1-dioxido-2-isothiazolidinyl, thienyl, thiazolyl, pyridyl, 2-pyrrolidinonyl, and such a group is optionally substituted by one or two substituents selected from: halogen, cyano, $C_{1-4}$alkyl, halo$C_{1-4}$alkyl, $C_{1-4}$alkoxy, $C_{1-4}$alkanoyl;
and when $R_1$ is chlorine and p is 1, such $R_1$ is not present in the ortho position with respect to the linking bond to the rest of the molecule; and when $R_1$ corresponds to $R_5$, p is 1.

Because of the presence of the fused cyclopropane compounds of formula (I) are believed to have a "cis" disposition of the substituents (both groups linked to the bicyclic ring system are on the same face of this bicyclic ring system).

In another embodiment of the present invention compounds of formula (I)' are provided which correspond to the compounds of formula (I) having "cis" disposition, represented by the bold highlight of the bonds

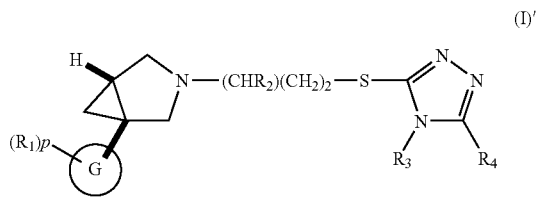

(I)' wherein G, p, $R_1$, $R_2$, $R_3$, $R_4$, and $R_5$ are defined as above for compounds of formula (I).

It will be appreciated that compounds of formula (I)' possess at least two chiral centres, namely at position 1 and 5 in the 3-azabicyclo[3.1.0]hexane portion of the molecule. Because of the fixed cis disposition, the compounds may exist in two stereoisomers which are enantiomers with respect to the chiral centres in the cyclopropane. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In compounds of formula (I)' there are at least two chiral centres, which are located in the cyclopropane portion, as depicted below (the bold highlight of the bonds means the "cis" configuration):

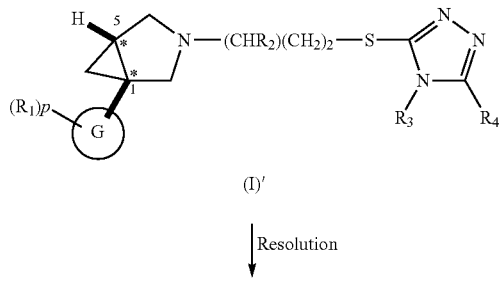

(I)'

↓ Resolution

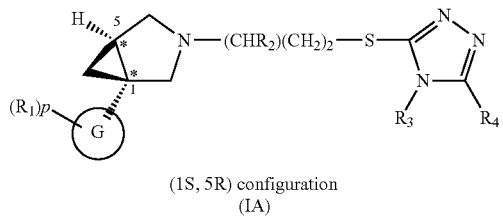

(1S, 5R) configuration
(IA)

when G is a 2-pyridyl derivative the configuration becomes (1R,5R) due to different Cahn-Ingold-Prelog nomenclature priorities In a further embodiment of the present invention compounds of formula (IA) are provided that correspond to stereochemical isomers of compounds of formula (I)', enriched in configuration (1S,5R) or (1R,5R)

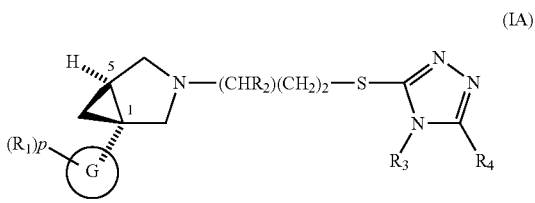

(IA)

wherein G, p, $R_1$, $R_2$, $R_3$, $R_4$, and $R_5$ are defined as above for compounds of formula (I)' or a pharmaceutically acceptable salt thereof.

It is intended in the context of the present invention that stereochemical isomers enriched in configuration (1S,5R) or (1R,5R) of formula (IA) correspond in one embodiment to at least 90% e.e. In another embodiment the isomers correspond to at least 95% e.e. In another embodiment the isomers correspond to at least 99% e.e.

In another embodiment of the present invention the stereochemical isomers enriched in configuration (1R,5S) are provided:

5-[5-({3-[(1R,5S)-1-(4-Methoxyphenyl)-3-azabicyclo [3.1.0]hex-3-yl]propyl}thio)-4-methyl-4H-1,2,4-triazol-3-yl]-2-methylquinoline, Enantiomer 2;

5-[5-({3-[(1R,5S)-1-(4-Bromophenyl)-3-azabicyclo[3.1.0] hex-3-yl]propyl}thio)-4-methyl-4H-1,2,4-triazol-3-yl]-2-methylquinoline, Enantiomer 1;

5-[5-({3-[(1R,5S)-1-(4-tert-Butylphenyl)-3-azabicyclo [3.1.0]hex-3-yl]propyl}thio)-4-methyl-4H-1,2,4-triazol-3-yl]-2-methylquinoline, Enantiomer 1;

(1R,5S)-3-(3-{[4-Methyl-5-(4-methyl-1,3-oxazol-5-yl)-4H-1,2,4-triazol-3-yl]thio}propyl)-1-[3-(trifluoromethyl) phenyl]-3-azabicyclo[3.1.0]hexane, Enantiomer 2;

(1R,5S)-1-(3-Chlorophenyl)-5-methyl-3-(3-{[4-methyl-5-(4-methyl-1,3-oxazol-5-yl)-4H-1,2,4-triazol-3-yl] thio}propyl)-3-azabicyclo[3.1.0]hexane, Enantiomer 2;

1-[5-[(1R,5S)-3-{3-[4-Methyl-5-(4-methyl-1,3-oxazol-5-yl)-4H-1,2,4-triazol-3-yl]thio}-propyl)-3-azabicyclo[3.1.0] hex-1-yl]-2-(methyloxy)phenyl]-1-propanone, Enantiomer 2;

2-Methyl-5-[(1R,5S)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole, Enantiomer 2; or a pharmaceutically acceptable salt thereof.

The term "5- or 6-membered heteroaromatic group" refers to a monocyclic 5- or 6-membered heterocyclic group containing 1, 2, 3 or 4 heteroatoms, for example from 1 to 3 heteroatoms, selected from O, N and S. When the group contains 2-4 heteroatoms, one may be selected from O, N and S and the remaining heteroatoms may be N. Examples of 5 and 6-membered heteroaromatic groups include pyrrolyl, imidazolyl, pyrazolyl, oxazolyl, isoxazolyl, oxadiazolyl, isothiazolyl, thiazolyl, furyl, thienyl, thiadiazolyl, pyridyl, triazolyl, triazinyl, pyridazinyl, pyrimidinyl and pyrazinyl.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl. The term "n-$C_{1-4}$alkyl" refers to the unbranched alkyls as defined above.

The term "$C_{1-4}$alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

The term "8- to 11-membered bicyclic group" refers to a bicyclic ring system containing a total of 8, 9, 10 or 11 carbon atoms, wherein 1, 2, 3 or 4 or 5 of the carbon atoms are optionally replaced by a heteroatom independently selected from O, S and N. The term includes bicyclic systems wherein both rings are aromatic, as well as bicyclic ring systems wherein one of the rings is partially or fully saturated. Examples of 8- to 11-membered bicyclic groups wherein both rings are aromatic include indenyl, naphthyl and azulenyl.

Examples of 8- to 11-membered bicyclic groups having 1, 2, 3, 4 or 5 heteroatoms, in which both rings are aromatic, include: 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl e.g. benzimidazol-2-yl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl and isoquinolyl. Examples of 8- to 11-membered bicyclic groups having 1, 2, 3, 4 or 5 heteroatoms, in which one of the rings is partially or fully saturated includes dihydrobenzofuranyl, indanyl, tetrahydronaphthyl, indolinyl, isoindolinyl, tetrahydroisoquinolinyl, tetrahydroquinolyl, benzoxazinyl and benzoazepinyl.

The term "heterocyclyl" refers to a 5 or 6-membered monocyclic or 8 to 11-membered bicyclic group wherein 1, 2, 3, 4 or 5 of the carbon atoms are replaced by a heteroatom independently selected from O, S and N and which is partially or fully saturated. Examples of "heterocyclyl" which are fully saturated 5 or 6-membered monocyclic rings include pyrrolidinyl, imidazolidinyl, pyrazolidinyl, isothiazolyl, thiazolyl, tetrahydrofuranyl, dioxolanyl, piperidinyl, piperazinyl, morpholinyl, thiomorpholinyl, tetrahydrothienyl, dioxanyl, tetrahydro-2H-pyranyl and dithianyl. Examples of "heterocyclyl" groups which are partially saturated 5 or 6-membered monocyclic rings include oxazolinyl, isoaxazolinyl, imidazolinyl, pyrazolinyl, 1,2,3,6-tetrahydropyridyl and 3,6-dihydro-2H-pyranyl. Examples of "heterocyclyl" groups which are fully saturated 8 to 11-membered bicyclic rings include decahydroquinolinyl, octahydro-2H-1,4-benzoxazinyl and octahydro-1H-cyclopenta-[b]pyridinyl. Examples of "heterocyclyl" groups which are partially saturated 8 to 11-membered bicyclic rings include 2,3-dihydro-1H-indolyl, 1,2,3,4-tetrahydroquinolinyl, 1,2,3,4-tetrahydroisoquinolinyl and 2,3,4,5-tetrahydro-1H-3-benzazepinyl.

Any of these groups may be attached to the rest of the molecule at any suitable position.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

In one embodiment, $R_1$ is halogen, cyano, acetyl, trifluoromethyl, trifluoromethoxy.

In one embodiment, $R_2$ is hydrogen. In another embodiment $R_2$ is $C_{1-4}$ alkyl (e.g. methyl).

In one embodiment, $R_5$ is a group selected from: isoxazolyl, 2-pyrrolidinonyl, 1,1-dioxido-2-isothiazolidinyl which is optionally substituted by one or two substituents selected from: halogen, cyano, $C_{1-2}$alkyl (e.g. methyl), halo$C_{1-2}$alkyl (e.g. trifluoromethyl), $C_{1-2}$alkoxy (e.g. methoxy), $C_{1-3}$alkanoyl (e.g. acetyl).

Suitably, $R_1$ is bromo, fluoro, trifluoromethoxy, cyano, hydroxy, chloro, methoxy, tert-butyl, trifluoromethyl.

Suitably, $R_5$ is isoxazolyl, 2-pyrrolidinonyl, —$CH_2$—N-pyrrolyl, 1,1-dioxido-2-isothiazolidinyl, 2-thienyl, 2-pyridyl, 2-thiazolyl.

In one embodiment, p is 1 or 2.

In another embodiment p is 0.

In one embodiment, $R_4$ may be optionally substituted phenyl (e.g. phenyl, 4-trifluoromethyl-phenyl, 3,4-difluorophenyl), an optionally substituted bicyclic group such as quinolinyl (e.g. 2-methylquinoline, 8-fluoro-2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl (e.g. 5-chloro-1-methyl-1H-pyrazol-4-yl, 1-methyl-3-trifluoromethyl-1H-pyrazol-4-yl 1,5-dimethyl-1H-pyrazoly-4-yl), an optionally substituted pyrimidyl (e.g. 5-pyrimidinyl), an optionally substituted pyridazinyl (e.g. 4-pyridazinyl), an optionally substituted pyrazinyl (e.g. 5-methyl-2-pyrazinyl), an optionally substituted furanyl (e.g. 3-methyl-2-furanyl, 2,5-dimethyl-3-furanyl), an optionally substituted thienyl (e.g. 5-chloro-2-thienyl), an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

In one embodiment, $R_3$ is methyl.

In one embodiment, a compound of formula (IB) or a salt thereof is provided, wherein $R_1$, P, $R_3$ and $R_4$ are as defined for formula (I):

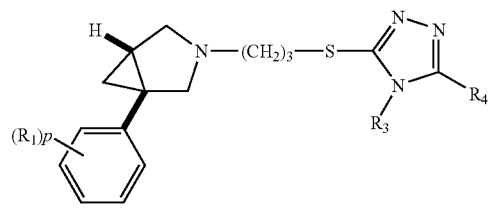

(IB)

In Formula (IB), in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl; and when $R_1$ is chlorine and p is 1, such $R_1$ is not present in the ortho position with respect to the linking bond to the rest of the molecule.

Examples of $R_4$ include an optionally substituted phenyl (e.g. phenyl, 4-trifluoromethyl-phenyl, 3,4-difluorophenyl), an optionally substituted bicyclic group such as quinolinyl (e.g. 2-methylquinoline, 8-fluoro-2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl (e.g. 5-chloro-1-methyl-1H-pyrazol-4-yl, 1-methyl-3-trifluoromethyl-1H-pyrazol-4-yl 1,5-dimethyl-1H-pyrazoly-4-yl), an optionally substituted pyrimidyl (e.g. 5-pyrimidinyl), an optionally substituted pyridazinyl (e.g. 4-pyridazinyl), an optionally substituted pyrazinyl (e.g. 5-methyl-2-pyrazinyl), an optionally substituted furanyl (e.g. 3-methyl-2-furanyl, 2,5-dimethyl-3-furanyl), an optionally substituted thienyl (e.g. 5-chloro-2-thienyl), an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

In another embodiment, a compound of formula (IC) or a salt thereof is provided, wherein $R_1$, p, $R_3$ and $R_4$ are as defined for formula (I):

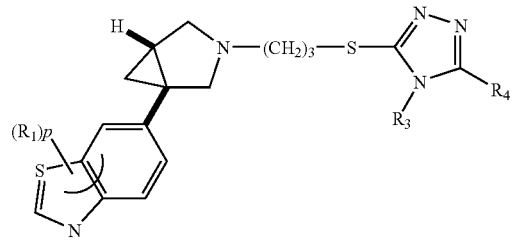

(IC)

In Formula (IC), in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl; and when $R_1$ is chlorine and p is 1, such $R_1$ is not present in the ortho position with respect to the linking bond to the rest of the molecule. Examples of $R_4$ include those defined previously for compounds (IB).

In another embodiment, a compound of formula (ID) or a salt thereof is provided, wherein $R_1$, p, $R_3$ and $R_4$ are as defined for formula (I):

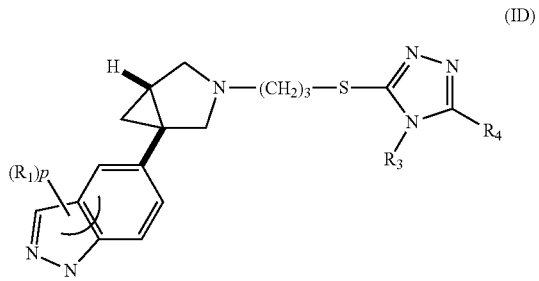

(ID)

In Formula (ID), in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl; and when $R_1$ is chlorine and p is 1, such $R_1$ is not present in the ortho position with respect to the linking bond to the rest of the molecule.

Examples of $R_4$ include those defined previously for compounds (IB).

In another embodiment, a compound of formula (IE) or a salt thereof is provided, wherein G is 2-pyridyl or 3-pyridyl and $R_1$, p, $R_3$ and $R_4$ are as defined for formula (I):

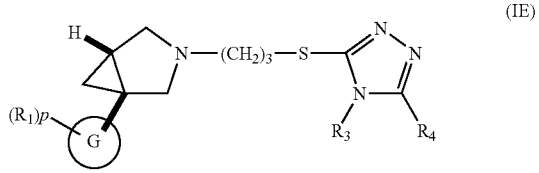

(IE)

In Formula (IE), in one embodiment, G corresponds to 2-pyridyl (Compounds (IE$_1$)) and in another embodiment to 3-pyridyl (Compounds (IE$_2$)), as illustrated below:

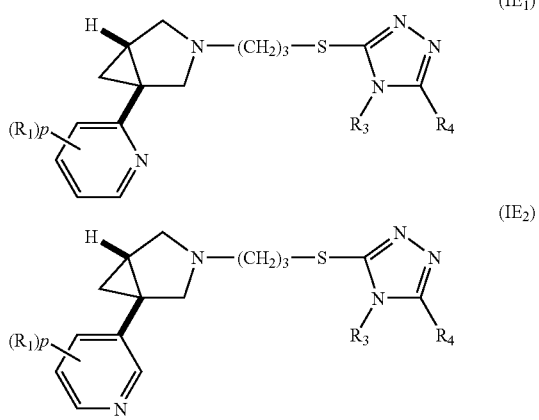

(IE$_1$)

(IE$_2$)

In Formulae (IE), (IE$_1$) and (IE$_2$), in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl; and when $R_1$ is chlorine and p is 1, such $R_1$ is not present in the ortho position with respect to the linking bond to the rest of the molecule.

Examples of $R_4$ include those defined previously for compounds (IB).

In another embodiment, a compound of formula (IF) or a salt thereof is provided, wherein $R_1$, p, $R_3$ and $R_4$ are as defined for formula (I):

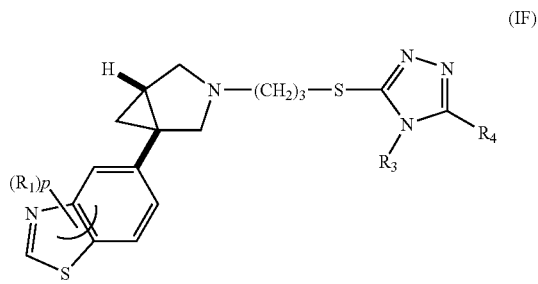

(IF)

In Formula (IF), in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl; and when $R_1$ is chlorine and p is 1, such $R_1$ is not present in the ortho position with respect to the linking bond to the rest of the molecule.

Examples of $R_4$ include those defined previously for compounds (IB).

The strategy for determining the absolute configuration of the compounds of the present invention comprised as a first step the preparation of the chiral intermediate, (1S,5R)-1-[4-(trifluoromethyl)phenyl]-3-azabicyclo[3.1.0]hexane,

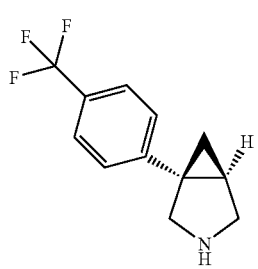

(preparation 18), by using (S)-(+) acetyl mandelic acid as resolving agent.

In the literature the absolute configuration of a series of compounds similar to this chiral intermediate is known, see J. Med Chem 1981, 24(5), 481-90. For some compounds disclosed in the reference the absolute configuration was proved by single crystal X-ray analysis.

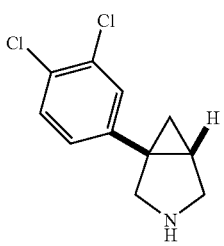

Among them, 1-(3,4-dichlorophenyl)-3-azabicyclo[3.1.0]hexane was disclosed.

The absolute configuration of the optical isomers of the compounds of the present invention was assigned using comparative VCD (vibrational circular dichroism) and OR (optical rotation) analyses.

The configuration of (1S,5R)-1-(3,4-dichlorophenyl)-3-azabicyclo[3.1.0]hexane was assigned by comparing its experimental VCD spectrum and observed specific rotation to ab initio derived calculated data for (1S,5R)-1-(3,4-dichlorophenyl)-3-azabicyclo[3.1.0]hexane (see Preparation 48) as the reference sample.

The assignment of the absolute configuration of the title compound was confirmed by a single crystal X-ray structure obtained from a crystal of (1S,5R)-1-[4-(trifluoromethyl)phenyl]-3-azabicyclo[3.1.0]hexane, (S)-(+)-mandelic acid salt. Both the analysis based on the known configuration of the (S)-(+)-mandelic acid and on the basis of anomalous dispersion effects confirmed the assignment of the title compound as being (1S,5R)-1-[4-(trifluoromethyl)phenyl]-3-azabicyclo[3.1.0]hexane.

For those compounds which were subjected to detailed analysis (VCD; OR included in the experimental details) a common trend was recognised between absolute configuration of the 3-azabicyclo[3.1.0]hexane moiety and measured binding activity at the dopamine D3 receptor for each pair of enantiomers. For the remainder of the compounds of the present invention, where stereoisomers were evaluated separately, absolute configuration was assigned based on a reasonable assumption by a skilled person in the art, i.e. absolute configuration was then assigned based on measured binding activity at the dopamine D3 receptor for both enantiomers and comparison with the data of those compounds which were subjected to detailed analysis.

Chiral molecules exhibit vibrational circular dichroism (VCD). Vibrational circular dichroism (VCD) is the differential interaction of a chiral molecule with left and right circularly polarized infrared radiation during vibrational excitation.

The VCD spectrum of a chiral molecule is dependent on its three-dimensional structure.

Most importantly, the VCD spectrum of a chiral molecule is a sensitive function of its absolute configuration and, in the case of flexible molecules, of its conformation. In principle, therefore, VCD permits the determination of the structure of a chiral molecule. VCD spectra were first measured in the 1970s. Subsequently, VCD instrumentation has developed enormously in spectral range and in sensitivity. Currently, VCD spectra of liquids and solutions can be measured over the majority of the fundamental infrared (IR) spectral range ($v \geqq 650$ cm-1) with high sensitivity at acceptable resolution (1-5 cm-1) using both dispersive and Fourier Transform (FT) VCD instrumentation. Very recently, commercial FT VCD instrumentation has become available, greatly enhancing the accessibility of VCD spectra.

The use of VCD as a reliable method for the determination of absolute configuration of chiral molecules is now well established (see for example Shah R D. et al., Curr Opin Drug Disc Dev 2001; 4:764-774; Freedman T B, et al., Helv Chim Acta 2002; 85:1160-1165; Dyatkin A B, et al. Chirality 2002; 14:215-219; Solladié-Cavallo A, Balaz M et al., Tetrahedron Assym 2001; 12:2605-2611; Nafie L A, et al. Circular dichroism, principles and applications, 2nd ed. New York: John Wiley & Sons; 2000. p 97-131; Nafie L A, et al. in: Yan B, Gremlish H-U, editors. Infrared and Raman spectroscopy of biological materials. New York: Marcel Dekker; 2001. p 15-54; Polavarapu P L, et al., J Anal Chem 2000; 366:727-734; Stephens P J, et al., Chirality 2000; 12:172-179; Solladié-Cavallo A, et al., Eur J Org Chem 2002: 1788-1796).

The method entails comparison of observed IR and VCD spectra with calculations of the spectra for a specific configuration and provides information both on the absolute configuration and on the solution conformation.

Given an experimental spectrum of a chiral molecule whose absolute configuration and/or conformation are unknown and to be determined, the general procedure is as follows: 1) all possible structures are defined; 2) the spectra of these structures are predicted; and 3) predicted spectra are compared to the experimental spectrum. The correct structure will give a spectrum in agreement with experiment; incorrect structures will give spectra in disagreement with experiment.

VCD spectra are always measured simultaneously with vibrational unpolarized absorption spectra ("infrared (IR) spectra") and the two vibrational spectra together provide more information than does the VCD spectrum alone. In addition, vibrational unpolarized absorption spectra are automatically predicted simultaneously with VCD spectra.

For ab initio assignments, VCD and unpolarized IR spectra were calculated using the Gaussian 98 software package.

When chiral organic molecules are synthesized (or, if natural products, isolated) their optical rotations are routinely measured at one frequency or at a small number of discrete frequencies in the visible—near ultraviolet spectral region. Most commonly, the specific rotation at one frequency, that of the sodium D line, $[\alpha]_D$, is measured. The frequencies used lie below the threshold for electronic absorption, i.e., they are in the "transparent" spectral region. Optical rotation is a reflection of the enantiomeric excess (ee) of the sample and of the absolute configuration (AC) of the predominant enantiomer.

When the optical rotation at a given frequency for 100% ee is available, the measured optical rotation at the same frequency enables the sample ee to be determined.

The determination of ee is the predominant application of discrete frequency, transparent spectral region optical rotations. In principle, the AC of the predominant enantiomer, if unknown, can also be determined. However, the determination of AC from optical rotation requires an algorithm which reliably predicts the optical rotations of molecules of known AC and a number of methodologies have been proposed for predicting discrete frequency, transparent spectral region optical rotations (Eliel E L, Wilen S H. Stereochemistry of organic compounds. New York: John Wiley & Sons; 1994. Chapter 13).

Very recently, developments in ab initio Density Functional Theory (DFT) have radically improved the accuracy of optical rotation calculation. As a result, for the first time it has become possible to routinely obtain ACs from optical rotations.

For ab initio OR assignments, the Dalton Quantum Chemistry Program was used.

Further embodiments of the present invention are compounds of formula (IB)', (IC)', (ID)', and (IF)' which, respectively, correspond to the stereochemical isomers of compounds of formula (IB), (IC), (ID) and (IF) as defined above enriched in configuration (1S,5R).

Compounds of formula (IE)' correspond to the stereochemical isomers of compounds of formula (IE) as above defined, enriched in configuration (1R,5R) or (1R,5S) depending on the presence of a 2-pyridine ring.

In one embodiment, a stereochemical isomer enriched in the (1S,5R) configuration of formula (IB)' or a salt thereof is provided, wherein $R_1$, p, $R_3$ and $R_4$ are as defined for formula (I):

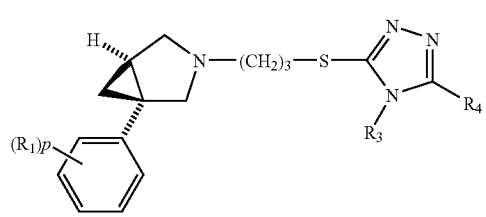
(IB)'

In Formula (IB)', in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl; and when $R_1$ is chlorine and p is 1, such $R_1$ is not present in the ortho position with respect to the linking bond to the rest of the molecule.

Examples of $R_4$ include optionally substituted phenyl (e.g. phenyl, 4-trifluoromethyl-phenyl, 3,4-difluorophenyl), an optionally substituted bicyclic group such as quinolinyl (e.g. 2-methylquinoline, 8-fluoro-2-methylquinoline), an optionally substituted pyranyl (e.g. 4-tetrahydro-2H-pyranyl), an optionally substituted pyridinyl (e.g. 3-methyl-2-pyridinyl, 2-methyl-3-pyridinyl, 3-pyridinyl, 2-methyl-6-trifluoromethyl-3-pyridinyl), an optionally substituted pyrazolyl (e.g. 5-chloro-1-methyl-1H-pyrazol-4-yl, 1-methyl-3-trifluoromethyl-1H-pyrazol-4-yl 1,5-dimethyl-1H-pyrazoly-4-yl), an optionally substituted pyrimidyl (e.g. 5-pyrimidinyl), an optionally substituted pyridazinyl (e.g. 4-pyridazinyl), an optionally substituted pyrazinyl (e.g. 5-methyl-2-pyrazinyl), an optionally substituted furanyl (e.g. 3-methyl-2-furanyl, 2,5-dimethyl-3-furanyl), an optionally substituted thienyl (e.g. 5-chloro-2-thienyl), an optionally substituted oxazolyl (e.g. 4-methyl-1,3-oxazol-5-yl, 2-methyl-5-trifluoromethyl-1,3-oxazol-4-yl), an optionally substituted isoxazolyl (e.g. 3-methyl-5-isoxazolyl), an optionally substituted thiazolyl (e.g. 2,4-dimethyl-1,3-thiazol-5-yl), an optionally substituted triazolyl (e.g. 1-methyl-1H-1,2,3-triazol-4-yl).

In another embodiment, a stereochemical isomer enriched in the (1S,5R) configuration of formula (IC)' or a salt thereof is provided, wherein $R_1$, p, $R_3$ and $R_4$ are as defined for formula (I):

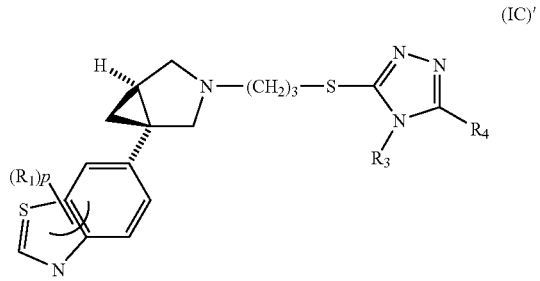
(IC)'

In Formula (IC), in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl; and when $R_1$ is chlorine and p is 1, such $R_1$ is not present in the ortho position with respect to the linking bond to the rest of the molecule. Examples of $R_4$ include those defined previously for compounds (IB)'.

In another embodiment, a stereochemical isomer enriched in the (1S,5R) configuration of formula (ID)' or a salt thereof is provided, wherein $R_1$, p, $R_3$ and $R_4$ are as defined for formula (I):

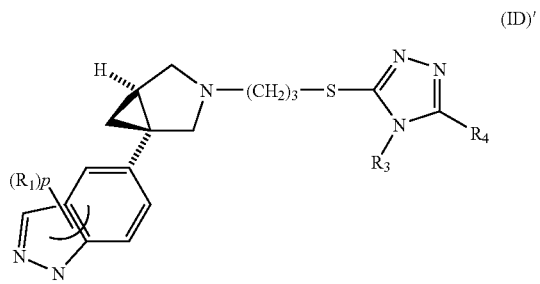
(ID)'

In Formula (ID)', in one embodiment, $R_3$ is methyl. $R_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, $C_{1-4}$alkyl, fluoro$C_{1-4}$alkyl, $C_{1-4}$alkoxy, fluoro$C_{1-4}$alkoxy, $C_{1-4}$alkanoyl; and when $R_1$ is chlorine and p is 1, such $R_1$ is not present in the ortho position with respect to the linking bond to the rest of the molecule. Examples of $R_4$ include those defined previously for compounds (IB)'.

In another embodiment, a stereochemical isomer enriched in the (1S,5R) configuration or (1R,5R) configuration of formula (IE)' or a salt thereof is provided, wherein G is 2-pyridyl or 3-pyridyl and $R_1$, p, $R_3$ and $R_4$ are as defined for formula (I):

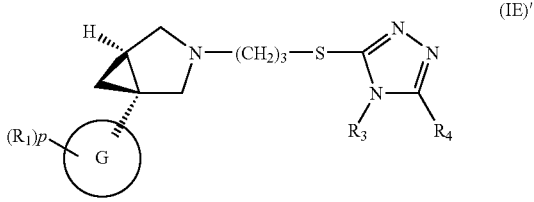

In Formula (IE)', in one embodiment, G corresponds to 2-pyridyl (Compounds (IE$_1$)') and in another embodiment to 3-pyridyl (Compounds (IE$_2$)'), as illustrated below:

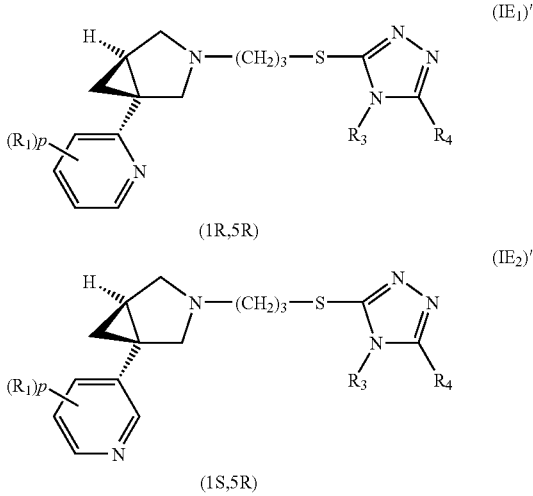

The configuration will then change depending on the type of pyridine ring, as mentioned above.

In Formulae (IE)', (IE$_1$)' and (IE$_2$)', in one embodiment, R$_3$ is methyl. R$_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, C$_{1-4}$alkyl, fluoroC$_{1-4}$alkyl, C$_{1-4}$alkoxy, fluoroC$_{1-4}$alkoxy, C$_{1-4}$alkanoyl; and when R$_1$ is chlorine and p is 1, such R$_1$ is not present in the ortho position with respect to the linking bond to the rest of the molecule.

Examples of R$_4$ include those defined previously for compounds (IB)'.

In another embodiment, a stereochemical isomer enriched in the (1S,5R) configuration of formula (IF)' or a salt thereof is provided, wherein R$_1$, p, R$_3$ and R$_4$ are as defined for formula (I):

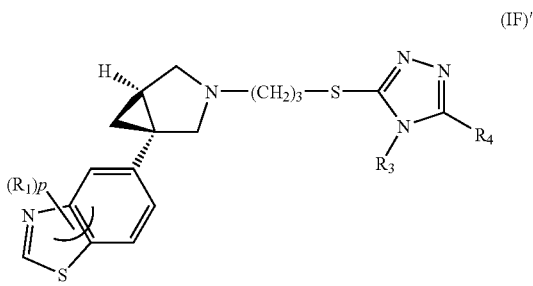

In Formula (IF)', in one embodiment, R$_3$ is methyl. R$_4$ may be phenyl, heterocyclyl, 5- or 6-membered heteroaromatic group or a 9- to 11-membered bicyclic group, any of which is optionally substituted by 1, 2, 3 or 4 substituents selected from the group consisting of: halogen, hydroxy, oxo, cyano, nitro, C$_{1-4}$alkyl, fluoroC$_{1-4}$alkyl, C$_{1-4}$alkoxy, fluoroC$_{1-4}$alkoxy, C$_{1-4}$alkanoyl; and when R$_1$ is chlorine and p is 1, such R$_1$ is not present in the ortho position with respect to the linking bond to the rest of the molecule. Examples of R$_4$ include those defined previously for compounds (IB)'.

Certain of the compounds of the invention may form acid addition salts with one or more equivalents of the acid. The present invention includes within its scope all possible stoichiometric and non-stoichiometric forms.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

In one embodiment of the present invention compounds are provided e a molecular weight of 800 or less. In another embodiment compounds are provided having a molecular weight of 600 or less. Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

Example compounds of the present invention include:

5-[5-({3-[(1R,5S/1S,5R)-1-(4-Methoxyphenyl)-3-azabicyclo[3.1.0]hex-3-yl]propyl}-thio)-4-methyl-4H-1,2,4-triazol-3-yl]-2-methylquinoline;

5-[5-({3-[(1S,5R)-1-(4-Methoxyphenyl)-3-azabicyclo[3.1.0]hex-3-yl]propyl}thio)-4-methyl-4H-1,2,4-triazol-3-yl]-2-methylquinoline, Enantiomer 1;

5-[5-({3-[(1R,5S/1S,5R)-1-(4-Bromophenyl)-3-azabicyclo[3.1.0]hex-3-yl]propyl}thio)-4-methyl-4H-1,2,4-triazol-3-yl]-2-methylquinoline;

5-[5-({3-[(1S,5R)-1-(4-Bromophenyl)-3-azabicyclo[3.1.0]hex-3-yl]propyl}thio)-4-methyl-4H-1,2,4-triazol-3-yl]-2-methylquinoline, Enantiomer 2;

2-Methyl-5-[4-methyl-5-({3-[(1R,5S/1S,5R)-1-phenyl-3-azabicyclo[3.1.0]hex-3-yl]propyl}thio)-4H-1,2,4-triazol-3-yl]quinoline;

2-Methyl-5-[4-methyl-5-({3-[(1S,5R)-1-phenyl-3-azabicyclo[3.1.0]hex-3-yl]propyl}thio)-4H-1,2,4-triazol-3-yl]quinoline, Enantiomer 2;

5-[5-({3-[(1R,5S/1S,5R)-1-(3,4-Dichlorophenyl)-3-azabicyclo[3.1.0]hex-3-yl]propyl}thio)-4-methyl-4H-1,2,4-triazol-3-yl]-2-methylquinoline;

5-[5-({3-[(1S,5R)-1-(3,4-Dichlorophenyl)-3-azabicyclo[3.1.0]hex-3-yl]propyl}thio)-4-methyl-4H-1,2,4-triazol-3-yl]-2-methylquinoline, Enantiomer 1;

5-[5-({3-[(1R,5S/1S,5R)-1-(4-tert-Butylphenyl)-3-azabicyclo[3.1.0]hex-3-yl]propyl}thio)-4-methyl-4H-1,2,4-triazol-3-yl]-2-methylquinoline;

5-[5-({3-[(1S,5R)-1-(4-tert-Butylphenyl)-3-azabicyclo[3.1.0]hex-3-yl]propyl}thio)-4-methyl-4H-1,2,4-triazol-3-yl]-2-methylquinoline, Enantiomer 2;

4-[(1R,5S/1S,5R)-3-(3-{[4-Methyl-5-(2-methylquinolin-5-yl)-4H-1,2,4-triazol-3-yl]thio}propyl)-3-azabicyclo[3.1.0]hex-1-yl]benzonitrile;

4-[(1R,5S/1S,5R)-3-(3-{[4-Methyl-5-(2-methylquinolin-5-yl)-4H-1,2,4-triazol-3-yl]thio}propyl)-3-azabicyclo[3.1.0]hex-1-yl]phenol;

(1R,5S/1S,5R)-3-(3-{[4-methyl-5-(4-methyl-1,3-oxazol-5-yl)-4H-1,2,4-triazol-3-yl]thio}propyl)-1-phenyl-3-azabicyclo[3.1.0]hexane;

(1R,5S/1S,5R)-1-(4-Bromophenyl)-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-1-(4-Bromophenyl)-3-(3-{[4-methyl-5-(4-methyl-1,3-oxazol-5-yl)-4H-1,2,4-triazol-3-yl]thio}propyl)-3-azabicyclo[3.1.0]hexane, Enantiomer 1;

(1R,5S/1S,5R)-1-(4-tert-Butylphenyl)-3-(3-{[4-methyl-5-(4-methyl-1,3-oxazol-5-yl)-4H-1,2,4-triazol-3-yl]thio}propyl)-3-azabicyclo[3.1.0]hexane;

(1R,5S/1S,5R)-1-(3,4-Dichlorophenyl)-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-1-(3,4-Dichlorophenyl)-3-(3-{[4-methyl-5-(4-methyl-1,3-oxazol-5-yl)-4H-1,2,4-triazol-3-yl]thio}propyl)-3-azabicyclo[3.1.0]hexane, Enantiomer 2;

(1R,5S/1S,5R)-1-(4-methoxyphenyl)-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-1-(4-methoxyphenyl)-3-(3-{[4-methyl-5-(4-methyl-1,3-oxazol-5-yl)-4H-1,2,4-triazol-3-yl]thio}propyl)-3-azabicyclo[3.1.0]hexane, Enantiomer 2;

(1R,5S/1S,5R)-1-[4-(5-methyl-3-isoxazolyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[4-Methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane; (1S,5R)-3-(3-{[4-Methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane;

(1R,5S/1S,5R)-1-[2-Fluoro-4-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1R,5S/1S,5R)-3-(3-{[4-Methyl-5-(4-methyl-1,3-oxazol-5-yl)-4H-1,2,4-triazol-3-yl]thio}propyl)-1-[3-(trifluoromethyl)phenyl]-3-azabicyclo[3.1.0]hexane;

(1R,5S/1S,5R)-1-[4-Fluoro-3-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

1-[5-[(1S,5R/1R,5S)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]ethanone;

1-[5-[(1S,5R)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]ethanone, Enantiomer 1;

(1S,5R/1R,5S)-1-(4-Chlorophenyl)-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-1-(4-Chlorophenyl)-3-(3-{[4-methyl-5-(4-methyl-1,3-oxazol-5-yl)-4H-1,2,4-triazol-3-yl]thio}propyl)-3-azabicyclo[3.1.0]hexane, Enantiomer 1;

(1S,5R/1R,5S)-1-(4-Fluorophenyl)-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-1-(4-Fluorophenyl)-3-(3-{[4-methyl-5-(4-methyl-1,3-oxazol-5-yl)-4H-1,2,4-triazol-3-yl]thio}propyl)-3-azabicyclo[3.1.0]hexane, Enantiomer 1;

(1S,5R/1R,5S)-1-(3-Chlorophenyl)-5-methyl-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-1-(3-Chlorophenyl)-5-methyl-3-(3-{[4-methyl-5-(4-methyl-1,3-oxazol-5-yl)-4H-1,2,4-triazol-3-yl]thio}propyl)-3-azabicyclo[3.1.0]hexane, Enantiomer 1;

(1S,5R/1R,5S)-1-(3-Fluorophenyl)-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-1-(3-Fluorophenyl)-3-(3-{[4-methyl-5-(4-methyl-1,3-oxazol-5-yl)-4H-1,2,4-triazol-3-yl]thio}propyl)-3-azabicyclo[3.1.0]hexane, Enantiomer 1;

(1S,5R/1R,5S)-3-(3-{[4-methyl-5-(4-methyl-1,3-oxazol-5-yl)-4H-1,2,4-triazol-3-yl]thio}propyl)-1-[3-(methyloxy)phenyl]-3-azabicyclo[3.1.0]hexane;

(1S,5R)-3-(3-{[4-methyl-5-(4-methyl-1,3-oxazol-5-yl)-4H-1,2,4-triazol-3-yl]thio}propyl)-1-[3-(methyloxy)phenyl]-3-azabicyclo[3.1.0]hexane, Enantiomer 1;

(1S,5R)-1-(4-Bromophenyl)-3-(3-{[4-methyl-5-(tetrahydro-2H-pyran-4-yl)-4H-1,2,4-triazol-3-yl]thio}propyl)-3-azabicyclo[3.1.0]hexane;

(1S,5R)-1-(4-Bromophenyl)-3-[3-({4-methyl-5-[4-(trifluoromethyl)phenyl]-4H-1,2,4-triazol-3-yl}thio)propyl]-3-azabicyclo[3.1.0]hexane;

(1S,5R)-1-(4-Bromophenyl)-3-(3-{[4-methyl-5-(3-pyridinyl)-4H-1,2,4-triazol-3-yl]thio}-propyl)-3-azabicyclo[3.1.0]hexane, (1S,5R)-1-(4-Bromophenyl)-3-(3-{[5-(3,4-difluorophenyl)-4-methyl-4H-1,2,4-triazol-3-yl]thio}propyl)-3-azabicyclo[3.1.0]hexane;

5-[5-({3-[(1S,5R/1R,5S)-1-(4-Chlorophenyl)-3-azabicyclo[3.1.0]hex-3-yl]propyl}thio)-4-methyl-4H-1,2,4-triazol-3-yl]-2-methylquinoline;

5-[5-({3-[(1S,5R/1R,5S)-1-(4-Chlorophenyl)-3-azabicyclo[3.1.0]hex-3-yl]propyl}thio)-4-methyl-4H-1,2,4-triazol-3-yl]-2-methylquinoline, Enantiomer 1;

(1S,5R/1R,5S)-3-(3-{[4-Methyl-5-(4-methyl-1,3-oxazol-5-yl)-4H-1,2,4-triazol-3-yl]thio}propyl)-1-{4-[(trifluoromethyl)oxy]phenyl}-3-azabicyclo[3.1.0]hexane;

(1S,5R)-3-(3-{[4-Methyl-5-(4-methyl-1,3-oxazol-5-yl)-4H-1,2,4-triazol-3-yl]thio}-propyl)-1-{4-[(trifluoromethyl)oxy]phenyl}-3-azabicyclo[3.1.0]hexane, Enantiomer 1

(1S,5R/1R,5S)-3-(3-{[4-Methyl-5-(4-methyl-1,3-oxazol-5-yl)-4H-1,2,4-triazol-3-yl]-thio}propyl)-1-[2-methyl-4-(trifluoromethyl)phenyl]-3-azabicyclo[3.1.0]hexane;

(1S,5R/1R,5S)-3-(3-{[4-Methyl-5-(tetrahydro-2H-pyran-4-yl)-4H-1,2,4-triazol-3-yl]thio}propyl)-1-{4-[(trifluoromethyl)oxy]phenyl}-3-azabicyclo[3.1.0]hexane;

(1S,5R)-3-(3-{[4-Methyl-5-(tetrahydro-2H-pyran-4-yl)-4H-1,2,4-triazol-3-yl]thio}propyl)-1-{4-[(trifluoromethyl)oxy]phenyl}-3-azabicyclo[3.1.0]hexane, Enantiomer 2;

(1R,5S/1S,5R)-1-(3-Bromophenyl)-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(1-Methyl-3-{[4-methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane;

(1S,5R)-3-(1-Methyl-3-{[4-methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane, Diastereoisomer 1;

(1S,5R)-3-(1-Methyl-3-{[4-methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane, Diastereoisomer 2;

(1R,5S/1S,5R)-1-[2-Fluoro-5-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-1-[2-Fluoro-5-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane, Enantiomer 2;

1-[4-[(1R,5S/1S,5R)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]ethanone;

1-[4-[(1R,5S/1S,5R)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]-1-propanone;

(1R,5S/1S,5R)-3-(3-{[4-Methyl-5-(4-methyl-1,3-oxazol-5-yl)-4H-1,2,4-triazol-3-yl]thio}propyl)-1-[2-(trifluoromethyl)phenyl]-3-azabicyclo[3.1.0]hexane;

(1S,5R)-1-[2-Fluoro-4-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[4-Methyl-5-(2-methyl-3-pyridinyl)-4H-1,2,4-triazol-3-yl]thio}propyl)-1-[4-(trifluoromethyl)phenyl]-3-azabicyclo[3.1.0]hexane;

(1S,5R)-3-(3-{[4-Methyl-5-(4-pyridazinyl)-4H-1,2,4-triazol-3-yl]thio}propyl)-1-[4-(trifluoromethyl)phenyl]-3-azabicyclo[3.1.0]hexane;

(1S,5R)-3-(3-{[5-(1,5-Dimethyl-1H-pyrazol-4-yl)-4-methyl-4H-1,2,4-triazol-3-yl]thio}propyl)-1-[4-(trifluoromethyl)phenyl]-3-azabicyclo[3.1.0]hexane;

(1S,5R)-3-(3-{[4-Methyl-5-(5-pyrimidinyl)-4H-1,2,4-triazol-3-yl]thio}propyl)-1-[4-(trifluoromethyl)phenyl]-3-azabicyclo[3.1.0]hexane;

(1S,5R)-3-(3-{[4-Methyl-5-(3-methyl-2-furanyl)-4H-1,2,4-triazol-3-yl]thio}propyl)-1-[4-(trifluoromethyl)phenyl]-3-azabicyclo[3.1.0]hexane;

(1S,5R)-3-(3-{[4-Methyl-5-(6-methyl-3-pyridinyl)-4H-1,2,4-triazol-3-yl]thio}propyl)-1-[4-(trifluoromethyl)phenyl]-3-azabicyclo[3.1.0]hexane;

(1S,5R)-3-(3-{[5-(2,4-Dimethyl-1,3-thiazol-5-yl)-4-methyl-4H-1,2,4-triazol-3-yl]thio}propyl)-1-[4-(trifluoromethyl)phenyl]-3-azabicyclo[3.1.0]hexane;

(1S,5R)-3-(3-{[4-Methyl-5-(5-methyl-2-pyrazinyl)-4H-1,2,4-triazol-3-yl]thio}propyl)-1-[4-(trifluoromethyl)phenyl]-3-azabicyclo[3.1.0]hexane;

(1S,5R)-3-(3-{[4-Methyl-5-(tetrahydro-2H-pyran-4-yl)-4H-1,2,4-triazol-3-yl]thio}propyl)-1-[4-(trifluoromethyl)phenyl]-3-azabicyclo[3.1.0]hexane;

2-Methyl-6-{4-methyl-5-[(3-{(1S,5R)-1-[4-(trifluoromethyl)phenyl]-3-azabicyclo[3.1.0]hex-3-yl}propyl)thio]-4H-1,2,4-triazol-3-yl}quinoline;

8-Fluoro-2-methyl-5-{4-methyl-5-[(3-{(1S,5R)-1-[4-(trifluoromethyl)phenyl]-3-azabicyclo[3.1.0]hex-3-yl}propyl)thio]-4H-1,2,4-triazol-3-yl}quinoline;

2-Methyl-5-{4-methyl-5-[(3-{(1S,5R)-1-[4-(trifluoromethyl)phenyl]-3-azabicyclo[3.1.0]hex-3-yl}propyl)thio]-4H-1,2,4-triazol-3-yl}quinoline;

(1S,5R)-1-[2-Fluoro-4-(trifluoromethyl)phenyl]-3-(3-{[4-methyl-5-(2-methyl-3-pyridinyl)-4H-1,2,4-triazol-3-yl]thio}propyl)-3-azabicyclo[3.1.0]hexane;

(1S,5R)-1-[2-Fluoro-4-(trifluoromethyl)phenyl]-3-(3-{[4-methyl-5-(4-pyridazinyl)-4H-1,2,4-triazol-3-yl]thio}propyl)-3-azabicyclo[3.1.0]hexane;

(1S,5R)-1-[2-Fluoro-4-(trifluoromethyl)phenyl]-3-(3-{[4-methyl-5-(5-pyrimidinyl)-4H-1,2,4-triazol-3-yl]thio}propyl)-3-azabicyclo[3.1.0]hexane;

(1S,5R)-3-(3-{[5-(2,4-Dimethyl-1,3-thiazol-5-yl)-4-methyl-4H-1,2,4-triazol-3-yl]thio}propyl)-1-[2-fluoro-4-(trifluoromethyl)phenyl]-3-azabicyclo[3.1.0]hexane; (1S,5R)-1-[2-Fluoro-4-(trifluoromethyl)phenyl]-3-(3-{[4-methyl-5-(5-methyl-2-pyrazinyl)-4H-1,2,4-triazol-3-yl]thio}propyl)-3-azabicyclo[3.1.0]hexane;

(1S,5R)-1-[2-Fluoro-4-(trifluoromethyl)phenyl]-3-[3-({4-methyl-5-[4-(trifluoro-methyl)phenyl]-4H-1,2,4-triazol-3-yl}thio)propyl]-3-azabicyclo[3.1.0]hexane;

1-{4-[(1R,5S/1S,5R)-3-(3-{[4-Methyl-5-(2-methyl-5-quinolinyl)-4H-1,2,4-triazol-3-yl]thio}propyl)-3-azabicyclo[3.1.0]hex-1-yl]phenyl}-2-pyrrolidinone;

5-{5-[(3-{(1R,5S/1S,5R)-1-[4-(1,1-Dioxido-2-isothiazolidinyl)phenyl]-3-azabicycle-[3.1.0]hex-3-yl}propyl)thio]-4-methyl-4H-1,2,4-triazol-3-yl}-2-methylquinoline;

(1R,5S/1S,5R)-1-[3-Fluoro-4-(trifluoromethyl)phenyl]-5-methyl-3-(3-{[4-methyl-5-(4-methyl-1,3-oxazol-5-yl)-4H-1,2,4-triazol-3-yl]thio}propyl)-3-azabicyclo[3.1.0]hexane;

1-(2-(Methyloxy)-5-{(1R,5S/1S,5R)-3-[3-({4-methyl-5-[4-(trifluoromethyl)phenyl]-4H-1,2,4-triazol-3-yl}thio)propyl]-3-azabicyclo[3.1.0]hex-1-yl}phenyl)ethanone;

1-[5-[(1R,5S/1S,5R)-3-(3-{[5-(3,4-Difluorophenyl)-4-methyl-4H-1,2,4-triazol-3-yl]thio}propyl)-3-azabicyclo[3.1.0]hex-1-yl]-2-(methyloxy)phenyl]ethanone;

1-{2-(Methyloxy)-5-[(1R,5S/1S,5R)-3-(3-{[4-methyl-5-(3-pyridinyl)-4H-1,2,4-triazol-3-yl]thio}propyl)-3-azabicyclo[3.1.0]hex-1-yl]phenyl}ethanone;

1-[5-[(1R,5S/1S,5R)-3-(3-{[4-Methyl-5-(2-methyl-5-quinolinyl)-4H-1,2,4-triazol-3-yl]thio}propyl)-3-azabicyclo[3.1.0]hex-1-yl]-2-(methyloxy)phenyl]ethanone;

1-{2(Methyloxy)-5-[(1R,5S/1S,5R)-3-(3-{[4-methyl-5-(tetrahydro-2H-pyran-4-yl)-4H-1,2,4-triazol-3-yl]thio}propyl)-3-azabicyclo[3.1.0]hex-1-yl]phenyl}ethanone;

1-(2-Hydroxy-5-{(1R,5S/1S,5R)-3-[3-({4-methyl-5-[4-(trifluoromethyl)phenyl]-4H-1,2,4-triazol-3-yl}thio)propyl]-3-azabicyclo[3.1.0]hex-1-yl}phenyl)ethanone;

1-{5-[(1R,5S/1S,5R)-3-(3-{[5-(3,4-Difluorophenyl)-4-methyl-4H-1,2,4-triazol-3-yl]thio}propyl)-3-azabicyclo[3.1.0]hex-1-yl]-2-hydroxyphenyl}ethanone;

1-{2-Hydroxy-5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]phenyl}ethanone;

1-{2-Hydroxy-5-[(1R,5S/1S,5R)-3-(3-{[4-methyl-5-(2-methyl-5-quinolinyl)-4H-1,2,4-triazol-3-yl]thio}propyl)-3-azabicyclo[3.1.0]hex-1-yl]phenyl}ethanone;

1-[5-[(1R,5S/1S,5R)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]-1-propanone;

1-[5-[(1S,5R)-3-(3-{[4-Methyl-5-(4-methyl-1,3-oxazol-5-yl)-4H-1,2,4-triazol-3-yl]thio}-propyl)-3-azabicyclo[3.1.0]hex-1-yl]-2-(methyloxy)phenyl]-1-propanone Enantiomer 1;

2-Methyl-5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole;

2-Methyl-5-[(1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole, Enantiomer 1;

2-Methyl-6-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole;

1-Methyl-5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1H-indazole;

1-Methyl-5-[(1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1H-indazole, Enantiomer 1;

(1R,5S/1S,5R)-3-(3-{[4-Methyl-5-(4-methyl-1,3-oxazol-5-yl)-4H-1,2,4-triazol-3-yl]thio}propyl)-1-[6-(trifluoromethyl)-3-pyridinyl]-3-azabicyclo[3.1.0]hexane;

(1R,5S/1S,5R)-1-(4-Bromophenyl)-3-(3-{[4-methyl-5-(2-methyl-3-pyridinyl)-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(4-pyridazinyl)-4H-1,2,4-triazol-3-yl]thio}propyl)-3-azabicyclo[3.1.0]hexane;

(1R,5S/1S,5R)-1-(4-Bromophenyl)-3-(3-{[5-(5-chloro-1-methyl-1H-pyrazol-4-yl)-4-methyl-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(1-methyl-1H-1,2,3-triazol-4-yl)-4H-1,2,4-triazol-3-yl]thio}propyl)-3-azabicyclo[3.1.0]hexane;

(1R,5S/1S,5R)-1-(4-Bromophenyl)-3-(3-{[5-(1,5-dimethyl-1H-pyrazol-4-yl)-4-methyl-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(5-pyrimidinyl)-4H-1,2,4-triazol-3-yl]thio}propyl)-3-azabicyclo[3.1.0]hexane;

(1R,5S/1S,5R)-1-(4-Bromophenyl)-3-[3-({4-methyl-5-[1-methyl-3-(trifluoromethyl)-1H-pyrazol-4-yl]-4H-1,2,4-triazol-3-yl}thio)propyl]-3-azabicyclo[3.1.0]hexane;

(1R,5S/1S,5R)-1-(4-Bromophenyl)-3-(3-{[4-methyl-5-(3-methyl-2-furanyl)-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(3-methyl-5-isoxazolyl)-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(6-methyl-3-pyridinyl)-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(1-methyl-1H-pyrazol-5-yl)-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(5-methyl-3-pyridinyl)-4H-1,2,4-triazol-3-yl]thio}propyl)-3-azabicyclo[3.1.0]hexane;

(1R,5S/1S,5R)-1-(4-Bromophenyl)-3-[3-({4-methyl-5-[2-methyl-5-(trifluoromethyl)-1,3-oxazol-4-yl]-4H-1,2,4-triazol-3-yl}thio)propyl]-3-azabicyclo[3.1.0]hexane;

(1R,5S/1S,5R)-1-(4-Bromophenyl)-3-(3-{[4-methyl-5-(3-methyl-2-pyridinyl)-4H-1,2,4-triazol-3-yl]thio}propyl)-3-azabicyclo[3.1.0]hexane;

(1R,5S/1S,5R)-1-(4-Bromophenyl)-3-(3-{[5-(2,4-dimethyl-1,3-thiazol-5-yl)-4-methyl-4H-1,2,4-triazol-3-yl]thio}propyl)-3-azabicyclo[3.1.0]hexane;

(1R,5S/1S,5R)-1-(4-Bromophenyl)-3-(3-{[5-(2,5-dimethyl-3-furanyl)-4-methyl-4H-1,2,4-triazol-3-yl]thio}propyl)-3-azabicyclo[3.1.0]hexane;

(1R,5S/1S,5R)-1-(4-Bromophenyl)-3-(3-{-[5-(5-chloro-2-thienyl)-4-methyl-4H-1,2,4-triazol-3-yl]thio}propyl)-3-azabicyclo[3.1.0]hexane;

(1R,5S/1S,5R)-1-(4-Bromophenyl)-3-(3-{[4-ethyl-5-(3-pyridinyl)-4H-1,2,4-triazol-3-yl]thio}propyl)-3-azabicyclo[3.1.0]hexane;

(1R,5S/1S,5R)-1-(4-Bromophenyl)-3-[3-({4-methyl-5-[2-methyl-6-(trifluoromethyl)-3-pyridinyl]-4H-1,2,4-triazol-3-yl}thio)propyl]-3-azabicyclo[3.1.0]hexane.

5-[5-({3-[(1R,5S/1S,5R)-1-(4-Bromophenyl)-3-azabicyclo[3.1.0]hex-3-yl]propyl}thio)-4-methyl-4H-1,2,4-triazol-3-yl]-1-methyl-3-(trifluoromethyl)-1H-thieno[2,3-c]pyrazole;

3-(3-{[4-Methyl-5-(4-methyl-1,3-oxazol-5-yl)-4H-1,2,4-triazol-3-yl]thio}propyl)-(1R,5R/1S,5S)-1-[5-(trifluoromethyl)-2-pyridinyl]-3-azabicyclo[3.1.0]hexane;

3-(3-{[4-Methyl-5-(4-methyl-1,3-oxazol-5-yl)-4H-1,2,4-triazol-3-yl]thio}propyl)-(1R,5R)-1-[5-(trifluoromethyl)-2-pyridinyl]-3-azabicyclo[3.1.0]hexane, Enantiomer 2;

3-(3-{[4-methyl-5-(4-methyl-1,3-oxazol-5-yl)-4H-1,2,4-triazol-3-yl]thio}propyl)-(1R,5R/1S,5S)-1-[6-(trifluoromethyl)-2-pyridinyl]-3-azabicyclo[3.1.0]hexane;

(1R,5S/1S,5R)-1-[3-Fluoro-4-(1H-pyrrol-1-ylmethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R/1R,5S)-3-(3-{[4-Methyl-5-(5-methyl-2-pyrazinyl)-4H-1,2,4-triazol-3-yl]thio}propyl)-1-[6-(trifluoromethyl)-3-pyridinyl]-3-azabicyclo[3.1.0]hexane;

(1S,5R/1R,5S)-3-(3-{[4-Methyl-5-(6-methyl-3-pyridinyl)-4H-1,2,4-triazol-3-yl]thio}propyl)-1-[6-(trifluoromethyl)-3-pyridinyl]-3-azabicyclo[3.1.0]hexane;

(1S,5R/1R,5S)-3-(3-{[4-Methyl-5-(2-methyl-3-pyridinyl)-4H-1,2,4-triazol-3-yl]thio}propyl)-1-[6-(trifluoromethyl)-3-pyridinyl]-3-azabicyclo[3.1.0]hexane;

(1S,5R/1R,5S)-3-{3-[(4-Methyl-5-phenyl-4H-1,2,4-triazol-3-yl)thio]propyl}-1-[6-(trifluoromethyl)-3-pyridinyl]-3-azabicyclo[3.1.0]hexane;

(1S,5R/1R,5S)-3-(3-{[5-(2,4-Dimethyl-1,3-thiazol-5-yl)-4-methyl-4H-1,2,4-triazol-3-yl]thio}propyl)-1-[6-(trifluoromethyl)-3-pyridinyl]-3-azabicyclo[3.1.0]hexane;

(1S,5R/1R,5S)-3-[3-({4-Methyl-5-[4-(trifluoromethyl)phenyl]-4H-1,2,4-triazol-3-yl}thio)propyl]-1-[6-(trifluoromethyl)-3-pyridinyl]-3-azabicyclo[3.1.0]hexane;

(1S,5R/1R,5S)-2-Methyl-5-[3-(3-{[4-methyl-5-(5-methyl-2-pyrazinyl)-4H-1,2,4-triazol-3-yl]thio}propyl)-3-azabicyclo[3.1.0]hex-1-yl]-1,3-benzothiazole;

(1S,5R/1R,5S)-2-Methyl-5-[3-(3-{[4-methyl-5-(6-methyl-3-pyridinyl)-4H-1,2,4-triazol-3-yl]thio}propyl)-3-azabicyclo[3.1.0]hex-1-yl]-1,3-benzothiazole;

(1S,5R/1R,5S)-2-Methyl-5-(3-{3-[(4-methyl-5-phenyl-4H-1,2,4-triazol-3-yl)thio]propyl}-3-azabicyclo[3.1.0]hex-1-yl)-1,3-benzothiazole;

(1S,5R/1R,5S)-5-[3-(3-{[5-(2,4-Dimethyl-1,3-thiazol-5-yl)-4-methyl-4H-1,2,4-triazol-3-yl]thio}propyl)-3-azabicyclo[3.1.0]hex-1-yl]-2-methyl-1,3-benzothiazole;

(1S,5R/1R,5S)-2-Methyl-5-{3-[3-({4-methyl-5-[4-(trifluoromethyl)phenyl]-4H-1,2,4-triazol-3-yl}thio)propyl]-3-azabicyclo[3.1.0]hex-1-yl}-1,3-benzothiazole;

(1R,5S/1S,5R)-1-[3-Fluoro-5-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane;

(1S,5R)-1-[3-Fluoro-5-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane, Enantiomer 1;

(1R,5S/1S,5R)-1-[2-Fluoro-3-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane;

(1S,5R)-1-[2-Fluoro-3-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane, Enantiomer 2;

(1R,5S/1S,5R)-1-[4-(Methyloxy)-5-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane;

(1R,5S/1S,5R)-1-[4-(4-Chloro-2-fluorophenyl]-3-(3-{[4-methyl-5-(4-methyl-1,3-oxazol-5-yl)-4H-1,2,4-triazol-3-yl]thio}propyl)-azabicyclo[3.1.0]hexane;

(1R,5S/1S,5R)-1-[3-(2-{[4-Methyl-5-(4-methyl-1,3-oxazol-5-yl)-4H-1,2,4-triazol-3-yl]thio}propyl)-1-{3-[(trifluoromethyl)oxy]phenyl}-3-azabicyclo[3.1.0]hexane;

(1R,5S/1S,5R)-1-(2-Chloro-4-methylphenyl)-3-(2-{[4-methyl-5-(4-methyl-1,3-oxazol-5-yl)-4H-1,2,4-triazol-3-yl]thio}propyl)-3-azabicyclo[3.1.0]hexane;

(1R,5S/1S,5R)-1-[3-Chloro-4-(methyloxy)phenyl]-3-(2-{[4-methyl-5-(4-methyl-1,3-oxazol-5-yl)-4H-1,2,4-triazol-3-yl]thio}propyl)-3-azabicyclo[3.1.0]hexane;

(1R,5S/1S,5R)-1-[4-(2,4-Dimethyl-1,3-thiazol-5-yl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1R,5S/1S,5R)-3-(3-{[4-methyl-5-(4-methyl-1,3-oxazol-5-yl)-4H-1,2,4-triazol-3-yl]thio}propyl)-1-{4-[6-(trifluoromethyl)-2-pyridinyl]phenyl}-3-azabicyclo[3.1.0]hexane;

(1R,5S/1S,5R)-1-[3-(2,4-dimethyl-1,3-thiazol-5-yl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1R,5S/1S,5R)-3-(3-{[4-methyl-5-(4-methyl-1,3-oxazol-5-yl)-4H-1,2,4-triazol-3-yl]thio}propyl)-1-[3-(5-methyl-2-thienyl)phenyl]-3-azabicyclo[3.1.0]hexane;

(1R,5S/1S,5R)-1-[4-(3,5-dimethyl-4-isoxazolyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[5-(2,4-Dimethyl-1,3-oxazol-5-yl)-4-methyl-4H-1,2,4-triazol-3-yl]thio}propyl)-1-[2-fluoro-4-(trifluoromethyl)phenyl]-3-azabicyclo[3.1.0]hexane and pharmaceutically acceptable salts thereof.

Example compounds of the present invention include the following, which are obtainable by the processes of the present invention:

4-[(1S,5R)-3-(3-{[4-Methyl-5-(2-methylquinolin-5-yl)-4H-1,2,4-triazol-3-yl]thio}propyl)-3-azabicyclo[3.1.0]hex-1-yl]benzonitrile;

4-[(1S,5R)-3-(3-{[4-Methyl-5-(2-methylquinolin-5-yl)-4H-1,2,4-triazol-3-yl]thio}propyl)-3-azabicyclo[3.1.0]hex-1-yl]phenol;

(1S,5R)-3-(3-{[4-methyl-5-(4-methyl-1,3-oxazol-5-yl)-4H-1,2,4-triazol-3-yl]thio}propyl)-1-phenyl-3-azabicyclo[3.1.0]hexane;

(1S,5R)-1-(4-tert-Butylphenyl)-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-1-[4-(5-methyl-3-isoxazolyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[4-Methyl-5-(4-methyl-1,3-oxazol-5-yl)-4H-1,2,4-triazol-3-yl]thio}propyl)-1-[3-(trifluoromethyl)phenyl]-3-azabicyclo[3.1.0]hexane;

(1S,5R)-1-[4-Fluoro-3-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[4-Methyl-5-(4-methyl-1,3-oxazol-5-yl)-4H-1,2,4-triazol-3-yl]-thio}propyl)-1-[2-methyl-4-(trifluoromethyl)phenyl]-3-azabicyclo[3.1.0]hexane;

(1S,5R)-1-(3-Bromophenyl)-3-(3-{[4-methyl-5-(4-methyl-1,3-oxazol-5-yl)-4H-1,2,4-triazol-3-yl]thio}propyl)-3-azabicyclo[3.1.0]hexane;

1-[4-[(1S,5R)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]ethanone;

1-[4-[(1S,5R)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]-1-propanone;

(1S,5R)-3-(3-{[4-Methyl-5-(4-methyl-1,3-oxazol-5-yl)-4H-1,2,4-triazol-3-yl]thio}propyl)-1-[2-(trifluoromethyl)phenyl]-3-azabicyclo[3.1.0]hexane;

1-{4-[(1S,5R)-3-(3-{[4-Methyl-5-(2-methyl-5-quinolinyl)-4H-1,2,4-triazol-3-yl]thio}propyl)-3-azabicyclo[3.1.0]hex-1-yl]phenyl}-2-pyrrolidinone;

5-{5-[(3-{(1S,5R)-1-[4-(1,1-Dioxido-2-isothiazolidinyl)phenyl]-3-azabicycle[3.1.0]hex-3-yl}propyl)thio]-4-methyl-4H-1,2,4-triazol-3-yl}-2-methylquinoline;

1-(2-(Methyloxy)-5-{(1S,5R)-3-3-({4-methyl-5-[4-(trifluoromethyl)phenyl]-4H-1,2,4-triazol-3-yl}thio)propyl]-3-azabicyclo[3.1.0]hex-1-yl}phenyl)ethanone;

1-{5-[(1S,5R)-3-(3-{[5-(3,4-Difluorophenyl)-4-methyl-4H-1,2,4-triazol-3-yl]thio}propyl)-3-azabicyclo[3.1.0]hex-1-yl]-2-(methyloxy)phenyl}ethanone;

1-{2-(Methyloxy)-5-[(1S,5R)-3-(3-{[4-methyl-5-(3-pyridinyl)-4H-1,2,4-triazol-3-yl]thio}propyl)-3-azabicyclo[3.1.0]hex-1-yl]phenyl}ethanone;

1-{5-[(1S,5R)-3-(3-{[4-Methyl-5-(2-methyl-5-quinolinyl)-4H-1,2,4-triazol-3-yl]thio}propyl)-3-azabicyclo[3.1.0]hex-1-yl]-2-(methyloxy)phenyl}ethanone;

1-{2-(Methyloxy)-5-[(1S,5R)-3-(3-{[4-methyl-5-(tetrahydro-2H-pyran-4-yl)-4H-1,2,4-triazol-3-yl]thio}propyl)-3-azabicyclo[3.1.0]hex-1-yl]phenyl}ethanone;

1-(2-Hydroxy-5-{(1S,5R)-3-[3-({4-methyl-5-[4-(trifluoromethyl)phenyl]-4H-1,2,4-triazol-3-yl}thio)propyl]-3-azabicyclo[3.1.0]hex-1-yl}phenyl)ethanone;

1-{5-[(1S,5R)-3-(3-{[5-(3,4-Difluorophenyl)-4-methyl-4H-1,2,4-triazol-3-yl]thio}propyl)-3-azabicyclo[3.1.0]hex-1-yl]-2-hydroxyphenyl}ethanone;

1-{2-Hydroxy-5-[(1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]phenyl}ethanone;

1-{2-Hydroxy-5-[(1S,5R)-3-(3-{[4-methyl-5-(2-methyl-5-quinolinyl)-4H-1,2,4-triazol-3-yl]thio}propyl)-3-azabicyclo[3.1.0]hex-1-yl]phenyl}ethanone;

2-Methyl-6-[(1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole;

(1S,5R)-3-(3-{[4-Methyl-5-(4-methyl-1,3-oxazol-5-yl)-4H-1,2,4-triazol-3-yl]thio}propyl)-1-[6-(trifluoromethyl)-3-pyridinyl]-3-azabicyclo[3.1.0]hexane;

(1S,5R)-1-(4-Bromophenyl)-3-(3-{[4-methyl-5-(2-methyl-3-pyridinyl)-4H-1,2,4-triazol-3-yl]thio}propyl)-3-azabicyclo[3.1.0]hexane;

(1S,5R)-1-(4-Bromophenyl)-3-(3-{[4-methyl-5-(4-pyridazinyl)-4H-1,2,4-triazol-3-yl]thio}propyl)-3-azabicyclo[3.1.0]hexane;

(1S,5R)-1-(4-Bromophenyl)-3-(3-{[5-(5-chloro-1-methyl-1H-pyrazol-4-yl)-4-methyl-4H-1,2,4-triazol-3-yl]thio}propyl)-3-azabicyclo[3.1.0]hexane;

(1S,5R)-1-(4-Bromophenyl)-3-(3-{[4-methyl-5-(1-methyl-1H-1,2,3-triazol-4-yl)-4H-1,2,4-triazol-3-yl]thio}propyl)-3-azabicyclo[3.1.0]hexane;

(1S,5R)-1-(4-Bromophenyl)-3-(3-{[5-(1,5-dimethyl-1H-pyrazol-4-yl)-4-methyl-4H-1,2,4-triazol-3-yl]thio}propyl)-3-azabicyclo[3.1.0]hexane;

(1S,5R)-1-(4-Bromophenyl)-3-(3-{[4-methyl-5-(5-pyrimidinyl)-4H-1,2,4-triazol-3-yl]thio}propyl)-3-azabicyclo[3.1.0]hexane;

(1S,5R)-1-(4-Bromophenyl)-3-[3-({4-methyl-5-[1-methyl-3-(trifluoromethyl)-1H-pyrazol-4-yl]-4H-1,2,4-triazol-3-yl}thio)propyl]-3-azabicyclo[3.1.0]hexane;

(1S,5R)-1-(4-Bromophenyl)-3-(3-{[4-methyl-5-(3-methyl-2-furanyl)-4H-1,2,4-triazol-3-yl]thio}propyl)-3-azabicyclo[3.1.0]hexane;

(1S,5R)-1-(4-Bromophenyl)-3-(3-{[4-methyl-5-(3-methyl-5-isoxazolyl)-4H-1,2,4-triazol-3-yl]thio}propyl)-3-azabicyclo[3.1.0]hexane;

(1S,5R)-1-(4-Bromophenyl)-3-(3-{[4-methyl-5-(6-methyl-3-pyridinyl)-4H-1,2,4-triazol-3-yl]thio}propyl)-3-azabicyclo[3.1.0]hexane;

(1S,5R)-1-(4-Bromophenyl)-3-(3-{[4-methyl-5-(1-methyl-1H-pyrazol-5-yl)-4H-1,2,4-triazol-3-yl]thio}propyl)-3-azabicyclo[3.1.0]hexane;

(1S,5R)-1-(4-Bromophenyl)-3-(3-{[4-methyl-5-(5-methyl-3-pyridinyl)-4H-1,2,4-triazol-3-yl]thio}propyl)-3-azabicyclo[3.1.0]hexane;

(1S,5R)-1-(4-Bromophenyl)-3-[3-({4-methyl-5-[2-methyl-5-(trifluoromethyl)-1,3-oxazol-4-yl]-4H-1,2,4-triazol-3-yl}thio)propyl]-3-azabicyclo[3.1.0]hexane;

(1S,5R)-1-(4-Bromophenyl)-3-(3-{[4-methyl-5-(3-methyl-2-pyridinyl)-4H-1,2,4-triazol-3-yl]thio}propyl)-3-azabicyclo[3.1.0]hexane;

(1S,5R)-1-(4-Bromophenyl)-3-(3-{[5-(2,4-dimethyl-1,3-thiazol-5-yl)-4-methyl-4H-1,2,4-triazol-3-yl]thio}propyl)-3-azabicyclo[3.1.0]hexane;

(1S,5R)-1-(4-Bromophenyl)-3-(3-{[5-(2,5-dimethyl-3-furanyl)-4-methyl-4H-1,2,4-triazol-3-yl]thio}propyl)-3-azabicyclo[3.1.0]hexane;

(1S,5R)-1-(4-Bromophenyl)-3-(3-{-[5-(5-chloro-2-thienyl)-4-methyl-4H-1,2,4-triazol-3-yl]thio}propyl)-3-azabicyclo[3.1.0]hexane;

(1S,5R)-1-(4-Bromophenyl)-3-(3-{[4-ethyl-5-(3-pyridinyl)-4H-1,2,4-triazol-3-yl]thio}propyl)-3-azabicyclo[3.1.0]hexane;

(1S,5R)-1-(4-Bromophenyl)-3-[3-({4-methyl-5-[2-methyl-6-(trifluoromethyl)-3-pyridinyl]-4H-1,2,4-triazol-3-yl}thio)propyl]-3-azabicyclo[3.1.0]hexane.

5-[5-({3-[(1S,5R)-1-(4-Bromophenyl)-3-azabicyclo[3.1.0]hex-3-yl]propyl}thio)-4-methyl-4H-1,2,4-triazol-3-yl]-1-methyl-3-(trifluoromethyl)-1H-thieno[2,3-c]pyrazole;

3-(3-{[4-methyl-5-(4-methyl-1,3-oxazol-5-yl)-4H-1,2,4-triazol-3-yl]thio}propyl)-(1R,5R)-1-[6-(trifluoromethyl)-2-pyridinyl]-3-azabicyclo[3.1.0]hexane;

(1S,5R)-1-[3-Fluoro-4-(1H-pyrrol-1-ylmethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[4-Methyl-5-(5-methyl-2-pyrazinyl)-4H-1,2,4-triazol-3-yl]thio}propyl)-1-[6-(trifluoromethyl)-3-pyridinyl]-3-azabicyclo[3.1.0]hexane;

(1S,5R)-3-(3-{[4-Methyl-5-(6-methyl-3-pyridinyl)-4H-1,2,4-triazol-3-yl]thio}propyl)-1-[6-(trifluoromethyl)-3-pyridinyl]-3-azabicyclo[3.1.0]hexane;

(1S,5R)-3-(3-{[4-Methyl-5-(2-methyl-3-pyridinyl)-4H-1,2,4-triazol-3-yl]thio}propyl)-1-[6-(trifluoromethyl)-3-pyridinyl]-3-azabicyclo[3.1.0]hexane;

(1S,5R)-3-{3-[(4-Methyl-5-phenyl-4H-1,2,4-triazol-3-yl)thio]propyl}-1-[6-(trifluoromethyl)-3-pyridinyl]-3-azabicyclo[3.1.0]hexane;

(1S,5R)-3-(3-{[5-(2,4-Dimethyl-1,3-thiazol-5-yl)-4-methyl-4H-1,2,4-triazol-3-yl]thio}propyl)-1-[6-(trifluoromethyl)-3-pyridinyl]-3-azabicyclo[3.1.0]hexane;

(1S,5R)-3-[3-({4-Methyl-5-[4-(trifluoromethyl)phenyl]-4H-1,2,4-triazol-3-yl}thio)propyl]-1-[6-(trifluoromethyl)-3-pyridinyl]-3-azabicyclo[3.1.0]hexane;

(1S,5R)-2-Methyl-5-[3-(3-{[4-methyl-5-(5-methyl-2-pyrazinyl)-4H-1,2,4-triazol-3-yl]thio}propyl)-3-azabicyclo[3.1.0]hex-1-yl]-1,3-benzothiazole;

(1S,5R)-2-Methyl-5-[3-(3-{[4-methyl-5-(6-methyl-3-pyridinyl)-4H-1,2,4-triazol-3-yl]thio}propyl)-3-azabicyclo[3.1.0]hex-1-yl]-1,3-benzothiazole;

(1S,5R)-2-Methyl-5-(3-{3-[(4-methyl-5-phenyl-4H-1,2,4-triazol-3-yl)thio]propyl}-3-azabicyclo[3.1.0]hex-1-yl)-1,3-benzothiazole;

(1S,5R)-5-[3-(3-{[5-(2,4-Dimethyl-1,3-thiazol-5-yl)-4-methyl-4H-1,2,4-triazol-3-yl]thio}propyl)-3-azabicyclo[3.1.0]hex-1-yl]-2-methyl-1,3-benzothiazole;

(1S,5R/1R,5S)-2-Methyl-5-{3-[3-({4-methyl-5-[4-(trifluoromethyl)phenyl]-4H-1,2,4-triazol-3-yl}thio)propyl]-3-azabicyclo[3.1.0]hex-1-yl}-1,3-benzothiazole;

(1S,5R)-1-[4-(4-Chloro-2-fluorophenyl)-3-(3-{[4-methyl-5-(4-methyl-1,3-oxazol-5-yl)-4H-1,2,4-triazol-3-yl]thio}propyl)-azabicyclo[3.1.0]hexane;

(1S,5R)-1-[3-(2-{[4-Methyl-5-(4-methyl-1,3-oxazol-5-yl)-4H-1,2,4-triazol-3-yl]thio}propyl)-1-{3-[(trifluoromethyl)oxy]phenyl}-3-azabicyclo[3.1.0]hexane;

(1S,5R)-1-(2-Chloro-4-methylphenyl)-3-(2-{[4-methyl-5-(4-methyl-1,3-oxazol-5-yl)-4H-1,2,4-triazol-3-yl]thio}propyl)-3-azabicyclo[3.1.0]hexane;

(1S,5R)-1-[3-Chloro-4-(methyloxy)phenyl]-3-(2-{[4-methyl-5-(4-methyl-1,3-oxazol-5-yl)-4H-1,2,4-triazol-3-yl]thio}propyl)-3-azabicyclo[3.1.0]hexane;

(1S,5R)-1-[4-(2,4-Dimethyl-1,3-thiazol-5-yl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[4-methyl-5-(4-methyl-1,3-oxazol-5-yl)-4H-1,2,4-triazol-3-yl]thio}propyl)-1-{4-[6-(trifluoromethyl)-2-pyridinyl]phenyl}-3-azabicyclo[3.1.0]hexane;

(1S,5R)-1-[3-(2,4-dimethyl-1,3-thiazol-5-yl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[4-methyl-5-(4-methyl-1,3-oxazol-5-yl)-4H-1,2,4-triazol-3-yl]thio}propyl)-1-[3-(5-methyl-2-thienyl)phenyl]-3-azabicyclo[3.1.0]hexane;

(1S,5R)-1-[4-(3,5-dimethyl-4-isoxazolyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[5-(2,4-Dimethyl-1,3-oxazol-5-yl)-4-methyl-4H-1,2,4-triazol-3-yl]thio}propyl)-1-[2-fluoro-4-(trifluoromethyl)phenyl]-3-azabicyclo[3.1.0]hexane and pharmaceutically acceptable salts thereof.

The present invention also provides a process for preparing a compound of formula (I) or a salt thereof as defined above.

The process of the present invention for preparing compounds of formula (I) in which G is a phenyl derivative, comprises the steps of:

(a) reacting a compound of formula (II):

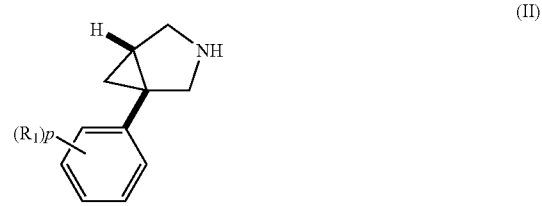

wherein $R_1$ and p are as defined for formula (I), with a compound of formula (III):

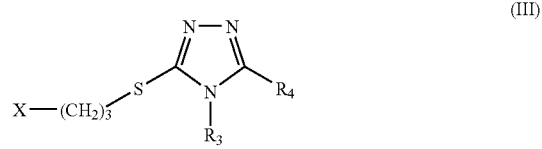

wherein $R_2$, $R_3$ and $R_4$ are as defined for formula (I) and X is a leaving group, or (b) for a compound of formula (I) wherein p is 1 or 2, reacting a compound of formula (IV):

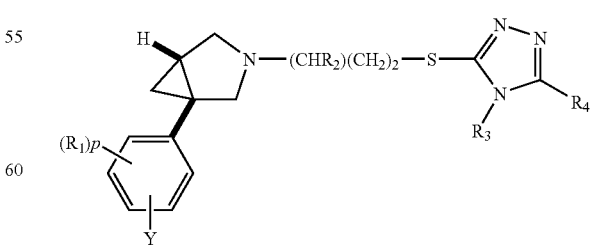

wherein $R_1$, $R_2$, $R_3$, and $R_4$ are as defined for formula (I), p is 0 or 1 and Y is halogen, a perfluoroalkylsulfonyloxy group (e.g. trifluoromethylsulfonyloxy), or Y is a group M selected from a boron derivative (e.g. a boronic acid function $B(OH)_2$) or a metal function such as trialkylstannyl (e.g. $SnBu_3$), zinc halide or magnesium halide; with a compound R1-Y1, wherein Y1 is halogen when Y is a group M; or when Y is halogen or a perfluoroalkylsulfonyloxy group Y1 is a group M as defined above or hydrogen that can be activated by a suitable base (e.g. $Cs_2CO_3$) in the presence of a suitable transition metal (e.g. Pd); "leaving group" is as understood by a skilled chemist, i.e. a group which can be displaced by a nucleophile in e.g. a $S_N2$, $S_N1$ or $S_NAr$ type reaction; and thereafter optionally for process (a) or process (b):
(i) removing any protecting group(s); and/or
(ii) forming a salt; and/or
(iii) converting a compound of formula (I) or a salt thereof to another compound of formula (I) or a salt thereof.

Process (a) may be performed using conventional methods for the formation of a tertiary amine. The leaving group X can be halogen such as chlorine. Alternatively X can be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When X is a halogen the reaction may be carried out using a base such as potassium carbonate in the presence of a source of iodide such as sodium iodide in a solvent such as N,N-dimethylformamide at a suitable temperature, e.g. 60° C.

Compounds of formula (II) may be prepared by methods well known in the art (e.g. *J. Med. Chem.* 1981, 24, 481-490). For typical conditions see Preparations 1-6 and 15-18 hereinafter. Interconversion of groups $R_1$ may be affected by methodology well known in the art (e.g. demethylation of a methoxy group resulting in a hydroxy group using a suitable Lewis acidic reagent such as boron tribromide in an inert solvent such as dichloromethane). Preparations 7-11 hereinafter give additional examples of such interconversions in the presence of a suitable protecting group for the secondary amine, such as N-trifluoroacetyl.

Reaction of a compound of formula (IV) with R1-Y1 according to process (b) may be effected in the presence of a transition metal e.g., palladium catalyst such as bis-triphenylphosphinepalladium dichloride, tetrakis-triphenylphosphinepalladium (0) or the complex formed in situ from tris(dibenzylideneacetone) dipalladium(0) and 4,5-bis(diphenylphosphino)-9,9-dimethylxanthene. When M is a boronic acid function such as $B(OH)_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. When M is hydrogen that can be activated by a suitable base (e.g. $Cs_2CO_3$) in the presence of a suitable transition metal (e.g. Pd) the reaction may be carried out in an inert solvent such as dioxane in the presence of a suitable base such as $Cs_2CO_3$. The substituent Y may be halogen such as bromine, or a sulfonyloxy group such as trifluoromethylsulfonyloxy; and Y1 is may be a group M, such as hydrogen that can be activated by a suitable base (e.g. $Cs_2CO_3$) in the presence of a suitable transition metal (e.g. Pd).

In one aspect of the present invention there is provided a synthetic process for the preparation of compounds of formula (II). The process may be conveniently performed also for preparing compounds of formula (IIa), in which the phenyl moiety is replaced by pyridine, useful for preparing compounds of formula (IE). This process comprises the following steps:

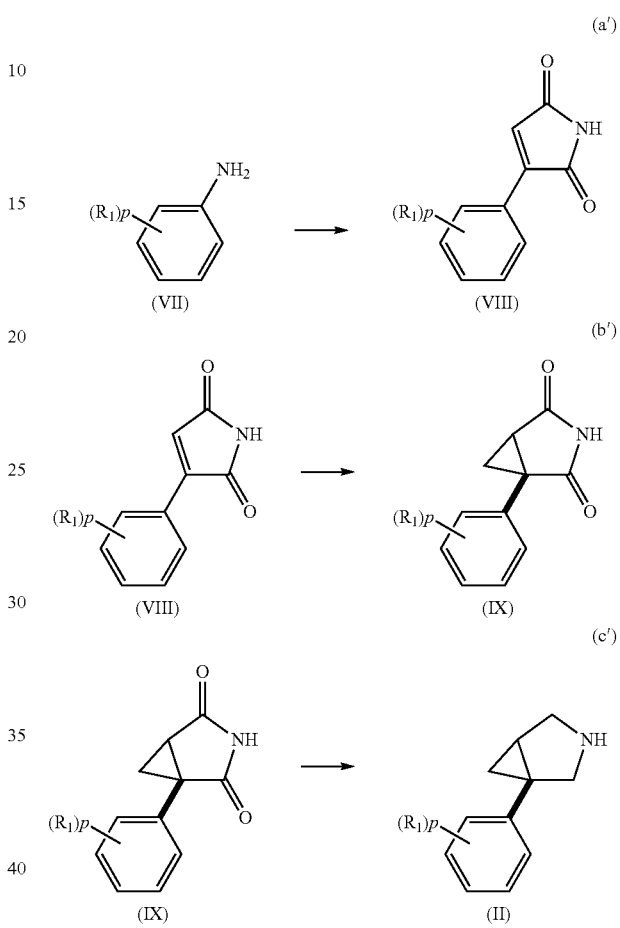

wherein:
step (a') means diazotation of an aniline (VII) followed by reaction with maleimide to give 3-arylmaleimide (VIII);
step (b') means cycloropanation of (VIII) to provide bicyclic imide (IX);
step (c') means reduction of imide (IX) to give compounds of formula (II).

Step (a') may be effected using conventional methods for the Meerwein reaction (e.g. *J. Am. Chem. Soc.* 1955, 77, 2313 describes the formation of arylmaleimides using this approach). Alternatively, in many cases this step is suitably performed applying a procedure where to a mixture of maleimide, an appropriate copper (II) salt such as anhydrous $CuCl_2$, and a suitable organonitrite, such as tert-butyl nitrite, in a compatible solvent, such as acetonitrile, is slowly added a solution of a compound of formula (VII). This is followed by allowing time to react as appropriate and a suitabe workup. Preparation 37 exemplifies this process.

Step (b') consists of slow addition of a solution of purified compound of formula (VIII), or mixtures containing a compound of formula (VIII), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitabe workup. Preparation 37 exemplifies this process.

Step (c') can be performed using a suitable reducing agent in a compatible solvent, such as borane in tetrahydrofuran or Red-Al® in toluene at an appropriate temperature, such as for example 65° C. in the case of borane as the reducing agent. This is followed by a suitabe workup. Preparation 38 exemplifies this process.

In another aspect of the present invention an alternative synthetic process for the preparation of compounds of formula (II), or generally of formula (XIII), is provided. This process comprises the following steps:

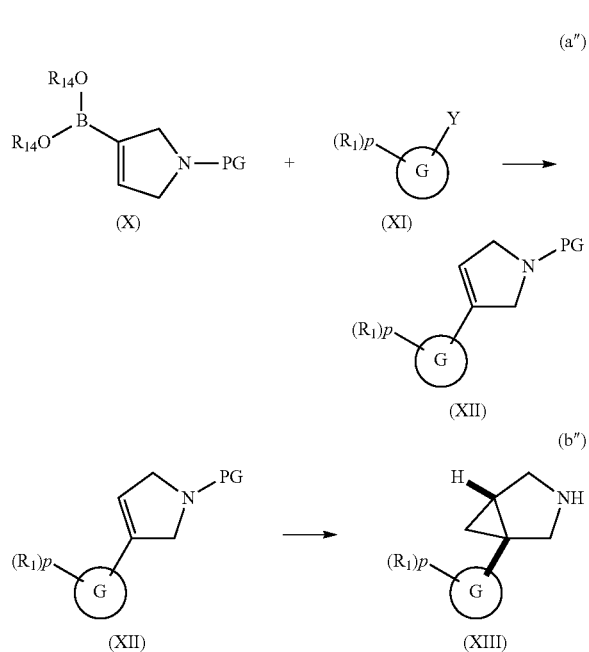

wherein:
$R_1$, p and G are as defined for formula (I), $R_{14}O$ is a suitable alkoxy group, PG is an appropriate protecting group and Y may be halogen such as bromine, or a sulfonyloxy group such as trifluoromethylsulfonyloxy and comprising the following steps:
  step (a″) means coupling reaction of a (2,5-dihydro-1H-pyrrol-3-yl)boronate (X) with the aromatic halogen or sulfonyloxy derivative (XI);
  step (b″) means cycloropanation of (XII) followed by, if appropriate, deprotection to provide bicyclic amine (XIII).

Step (a″) may be effected using conventional methods for the Suzuki coupling, e.g. using tetrakis(triphenylphosphine) palladium(0) as the source of catalytic palladium(0) in the presence of cesium fluoride in an appropriate solvent such as tetrahydrofuran at a suitable temperature. $(R_{14}O)_2B$ may suitably be 4,4,5,5-tetramethyl-1,3,2-dioxaborolan-2-yl and PG benzyl, representing a compound of structure (X) as reported in *Synlett* 2002, 5, 829-831. Preparation 50 exemplifies this process.

Step (b″) consists of a cyclopropanation reaction effected for example using the reagent generated from trimethylsulfoxonium iodide and a suitable base such as sodium hydride, in a compatible solvent, for example dimethylsulfoxide. Preparation 52 exemplifies this process. This is followed by a deprotection reaction as exemplified in Preparation 54.

A compound of formula (III) may itself be prepared by reacting a compound of formula (V):

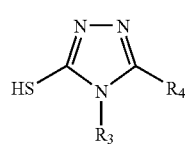

(V)

wherein $R_3$ and $R_4$ are as hereinbefore defined; with a compound of formula (VI):

L(CHR$_2$)(CH$_2$)$_2$X (VI)

wherein X is defined as for formula (I) and L is a leaving group, e.g., a bromine atom. For typical reaction conditions, see Preparation 13 hereinafter.

Compounds of formula (I) where $R_1$, $R_2$, $R_3$, $R_4$, G and p are as above defined may be prepared by reacting a compound of formula (XIV):

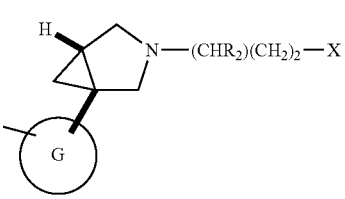

(XIV)

wherein $R_1$, $R_2$, G and p are as defined for formula (I) and X is a leaving group, with a compound of formula (V):

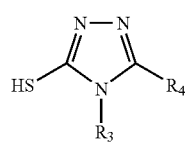

(V)

wherein $R_3$ and $R_4$ are as hereinbefore defined. For typical reaction conditions when X is chlorine see Example 35 or alternatively Examples 41-52.

A compound of formula (XIV) wherein $R_1$, G and p are as defined for formula (I), X is a leaving group and $R_2$ is H (hydrogen) can be prepared by alkylation of a compound of formula (XIII) in the presence of a suitable base such as a tertiary amine, for example diisopropylethylamine, with a propyl derivative carrying two leaving groups of preferrably differential reactivity in positions 1 and 3, for example 1-bromo-3-chloropropane. Typical reaction conditions for this transformation are given in Preparation 40.

A compound of formula (XIV) wherein $R_1$, G and p are as defined for formula (I), X is a leaving group and $R_2$ is $C_{1-4}$alkyl can be prepared by the reaction between a beta-hydroxy ketone, for example 4-hydroxy-2-butanone if $R_2$ is methyl, with a compound of formula (XIII) in the presence of a suitable borohydride source such as NaBH(OAc)$_3$, followed by conversion of the hydroxyl group into a leaving group by methods known to the person skilled in the art, for example by the action of thionyl chloride. Typical reaction conditions for these transformations are given in Preparations 19 and 20.

Interconversion reactions between compounds of formula (I) and salts thereof may be performed using methods well known in the art. Examples include:

(i) converting one or more of $R_1$ from alkoxy (e.g. methoxy) to hydroxy, (ii) converting one or more of $R_1$ from hydroxy to sulfonyloxy, such as alkylsulfonyloxy or haloalkylsulfonyloxy, e.g. methanesulfonyloxy or alkylsulfonyloxy or trifluoro-methanesulfonyloxy, (iii) converting one or more of $R_1$ from halogen or perfluoroalkylsulfonyloxy to cyano; and optionally thereafter forming a salt of formula (I).

Compounds of formula (I) have been found to exhibit affinity for dopamine receptors, in particular the $D_3$ receptor, and are expected to be useful in the treatment of disease states which require modulation of such receptors, such as psychotic conditions.

Such affinity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In the context of the present invention pKi (corresponding to the antilogarithm of Ki) is used instead of Ki and the compounds of the present invention typically show pKi greater than 7. In one aspect the present invention provides compounds of formula (I) having a pKi comprised between 7 and 8. In another aspect the present invention provides compounds of formula (I) having a pKi comprised between 8 and 9. In a further aspect the present invention provides compounds of formula (I) having a pKi greater than 9.

Many of the compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of the present invention are provided which have higher (e.g. $\geq 10\times$ or $\geq 100\times$ higher) affinity for dopamine $D_3$ than dopamine $D_2$ receptors (such affinity can be measured using standard methodology for example using cloned dopamine receptors—see herein). Said compounds may suitably be used as selective modulators of $D_3$ receptors.

From the localisation of $D_3$ receptors, it could also be envisaged that the compounds could also have utility for the treatment of substance abuse where it has been suggested that $D_3$ receptors are involved (e.g. see Levant, 1997, Pharmacol. Rev., 49, 231-252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, sexual dysfunction, sleep disorders, emesis, movement disorders, obsessive-compulsive disorders, amnesia, aggression, autism, vertigo, dementia, circadian rhythm disorders and gastric motility disorders e.g. IBS.

Compounds of formula (I) may be used for treatment of all aspects of drug dependency including withdrawal symptoms from drugs of abuse such as alcohol, cocaine, opiates, nicotine, benzodiazepines and inhibition of tolerance induced by opioids. In addition, compounds of formula (I) and pharmaceutically acceptable salts and solvates thereof may be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242).

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "psychotic disorder" includes:—

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

Within the context of the present invention, the term "substance-related disorder" includes:—

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

In a further aspect therefore the present invention provides a method of treating a condition for which modulation (especially antagonism/inhibition) of dopamine receptors (especially dopamine $D_3$ receptors) is beneficial, which comprises administering to a mammal (e.g. human) in need thereof an effective amount of a compound of formula (I) or a pharmaceutically (i.e physiologically) acceptable salt thereof. Such conditions in particular include psychoses/psychotic conditions such as schizophrenia, and substance abuse.

The invention also provides the use of a compound of formula (I) or a pharmaceutically acceptable salt thereof in the manufacture of a medicament for the treatment of a condition in a mammal for which modulation (especially antagonism/inhibition) of dopamine receptors (especially dopamine $D_3$ receptors) is beneficial.

The invention also provides a compound of formula (I) or a pharmaceutically acceptable salt thereof for use in the treatment of a condition in a mammal for which modulation (especially antagonism/inhibition) of dopamine receptors (especially dopamine $D_3$ receptors) is beneficial.

In one embodiment, $D_3$ antagonists according to the present invention are used in the treatment of psychoses such as schizophrenia or in the treatment of substance abuse.

Thus, a still further aspect the invention provides a method of treating a psychotic condition (e.g. schizophrenia) or substance abuse which comprises administering to a mammal (e.g. human) in need thereof an effective amount of a compound of formula (I) as herein defined or a pharmaceutically acceptable salt thereof.

Also provided is the use of a compound of formula (I) or a pharmaceutically acceptable salt thereof in the manufacture of a medicament for the treatment of a psychotic condition (e.g. schizophrenia) or substance abuse in a mammal.

Also provided is a compound of formula (I) or a pharmaceutically acceptable salt thereof for use in the treatment of a psychotic condition (e.g. schizophrenia) or substance abuse in a mammal.

Also provided is a compound of formula (I) or a pharmaceutically acceptable salt thereof for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil.

Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochloro-hydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

Biological Test Methods

Functional potency and intrinsic activity of compounds of this invention can be measured by the following GTPγS scintillation proximity assay (GTPγS-SPA). Cells used in the study are Chinese Hamster Ovary (CHO) Cells.

Cell Line

CHO_D2

CHO_D3

Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$10^{-6}$M Leupeptin (Sigma L2884)–5000×stock=5 mg/ml in buffer 25 ug/ml Bacitracin (Sigma B0125)–1000×stock=25 mg/ml in buffer 1 mM PMSF–1000×stock=17 mg/ml in 100% ethanol $2\times10^{-6}$M Pepstain A–1000×stock=2 mM in 100% DMSO The cells are homogenised by 2×15 second bursts in a 1 litre Glass Waring blender in a class two biohazard cabinet. The resulting suspension is spun at 500 g for 20 mins (Beckman T21 centrifuge: 1550 rpm). The supernatant is withdrawn with a 25 ml pipette, aliquotted into pre-chilled centrifuge tubes and spun at 48,000 g to pellet membrane fragments (Beckman T1270: 23,000 rpm for 30 mins). The final 48,000 g pellet is resuspended in Homogenisation Buffer, (4× the volume of the original cell pellet). The 48,000 g pellet is resuspended by vortexing for 5 seconds and homogenized in a dounce homogenizer 10-15 stokes. The prep is distributed into appropriate sized aliquots, (200-1000 ul), in polypropylene tubes and store at −80° C. Protein content in the membrane preparations is evaluated with the Bradford protein assay.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 90 mins at 4° C.) membranes, 5

μg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM $MgCl_2$, 60 μg/ml saponin and 30 μM GDP is added. The third addition was a 20% TAV addition of either buffer, (agonist format) or $EC_{80}$ final assay concentration of agonist, Quinelorane, prepared in assay buffer (antagonist format). The assay was started by the addition of 29% TAV of GTPγ[$^{35}$S] 0.38 nM final (37 MBq/ml, 1160 Ci/mmol, Amersham). After all additions assay plates are spun down for 1 min at 1,000 rpm. Assay plates are counted on a Viewlux, 613/55 filter, for 5 min., between 2-6 hours after the final addition.

The effect of the test drug over the basal generates $EC_{50}$ value by an iterative least squares curve fitting programme, expressed in the table as $pEC_{50}$ (i.e. $-\log EC_{50}$). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the $IC_{50}$ generated by "antagonist format" experiment, using Cheng & Prusoff equation: $fKi=IC_{50}/1+([A]/EC_{50})$ where: [A] is the concentration of the agonist 5-HT in the assay and $EC_{50}$ is the 5-HT $EC_{50}$ value obtained in the same experiment. fpKi is defined as $-\log fKi$.

The compounds of the invention listed above have pKi values within the range of 7.0-10.5 at the dopamine D3 receptor. pKi results are only estimated to be accurate to about ±0.3-0.5.

The compounds of the invention listed above have a selectivity over D2 greater than 30.

EXAMPLES

The invention is further illustrated by the following non-limiting examples. Preparations 1 to 5 were carried out in analogy to the synthetic route described in *J. Med. Chem.* 1981, 24, 481-490.

All temperatures refer to ° C. Infrared spectra were measured on a FT-IR instrument. Compounds were analysed by direct infusion of the sample dissolved in acetonitrile into a mass spectra operated in positive electro spray (ES+) ionisation mode. Proton Magnetic Resonance ($^1$H-NMR) spectra were recorded at 400 MHz, chemical shifts are reported in ppm downfield (d) from $Me_4Si$, used as internal standard, and are assigned as singlets (s), broad singlets (bs), doublets (d), doublets of doublets (dd), triplets (t), quartets (q) or multiplets (m).

Experimental vibrational circular dichroism (VCD) spectra were measured using a Chirall® VCD spectrometer operating in the 2000-800 cm-1 frequency range. Spectra were measured at room temperature (23° C.) using a sealed transmission cell with barium fluoride windows and a path length of 100 microns. (Scan times varied from 60 to 120 minutes per isomer.) Sample solutions were typically prepared by dissolving 10 milligrams of each enantiomer in 100 microliters of deutero-chloroform ($CDCl_3$). For ab initio assignments, VCD and unpolarized IR spectra were calculated using the Gaussian 98 software package.1.

Optical rotations were measured using a (Perkin Elmer Model 241) polarimeter operating at 589 nm (Sodium source). Measurements were made using a 1 decimeter microcell thermostated at 23° C. Concentrations were typically 10 mg/ml (c=0.01). For ab initio OR assignments, the Dalton Quantum Chemistry Program was used.

Column chromatography was carried out over silica gel (Merck AG Darmstaadt, Germany). The following abbreviations are used in the text: NBS=N-bromosuccinimide, Vitride="Red-Al®", HOBt=1-hydroxybenzotriazole EtOAc=ethyl acetate, $Et_2O$=dietyl ether, DMF=N,N'-dimethylformamide, MeOH=methanol, TFA=trifluoroacetic acid, tetrahydrofuran=tetrahydrofuran, IPA=isopropanol, TEA=triethylamine, DCC=1,3-dicyclohexylcarbodiimide, SCX=strong cation exchanger, Tlc refers to thin layer chromatography on silica plates, and dried refers to a solution dried over anhydrous sodium sulphate, r.t. (RT) refers to room temperature, Rt=retention time, DMSO=dimethyl sulfoxide.

Preparation 1: Methyl bromo(4-methoxyphenyl)acetate

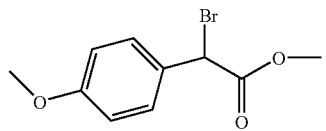

To a mixture of methyl 4-methoxyphenylacetate (20 g, 0.11 mol) and NBS (0.11 mol) in $CCl_4$ (0.2 l) were added 3 drops of 48% HBr and this mixture was heated to reflux for 8 h. The cooled solution was filtered through a pad of silica gel and the filtrate was evaporated in vacuo to give 29 g of the title compound as pale yellow oil, which was used in the subsequent step without further purification.

NMR ($^1$H, $CDCl_3$): δ 7.3 (d, 2H), 6.8 (d, 2H), 5.1 (s, 1H), 3.8 (s, 3H), 3.5 (s, 3H).

Preparation 2: Dimethyl 1-(4-methoxyphenyl)-1,2-cyclopropanedicarboxylate

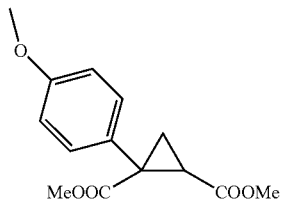

To a stirred slurry of NaH (4.4 g, 60% in mineral oil) in anhydrous $Et_2O$ (0.3 l) was added methanol (10.3 mL) followed by a solution of bromo ester obtained in Prep. 1 methyl bromo(4-methoxyphenyl)acetate (29 g) in methyl acrylate (19.8 mL) (for examples starting from an ethyl phenylacetate derivative ethanol and ethyl acrylate were used, respectively) and methanol (3 mL) at 0° C., over a 30 min. The mixture was stirred at 25° C. for 24 h and then unreacted NaH was decomposed with 3 mL methanol. Water was added (75 mL), the organic phase separated, dried over $Na_2SO_4$ and filtered. Volatiles were evaporated in vacuo to give 31.5 g of the title compound as an oil, which was used in the subsequent step without further purification.

NMR (¹H, CDCl₃): δ 7.3 (d, 2H), 6.8 (d, 2H), 3.77 (s, 3H), 3.73 (s, 3H), 3.64 (s, 3H), 2.18 (dd, 1H), 2.05 (dd, 1H), 1.46 (dd, 1H). MS (m/z): 265.4 [MH]⁺.

Preparation 3:
1-(4-Methoxyphenyl)-1,2-cyclopropanedicarboxylic acid

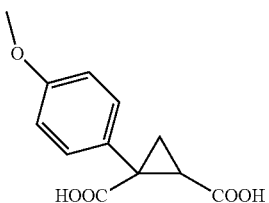

A mixture of diester obtained in Prep. 2 (31.5 g) and KOH (13.5 g) in 1:1 EtOH:H₂O (240 mL) was heated at reflux for 6 h and then concentrated to half the original volume. The aqueous solution was extracted with Et₂O, chilled in ice, and then made acidic with 25 mL of 12N HCl. White crystalline product was collected by filtration and dried under vacuo to give 12.8 of the title compound (overall yield from methyl bromo(4-methoxyphenyl)acetate: 50%).

NMR (¹H, DMSO): δ 12.5 (bs, 2H), 7.25 (d, 2H), 6.85 (d, 2H), 3.7 (s, 3H), 2.0 (dd, 1H), 1.85 (dd, 1H), 1.38 (dd, 1H). MS (m/z): 235.0 [M-H]⁻.

Preparation 4: (1R,5S/1S,5R)-1-[4-(Methoxy)phenyl]-3-azabicyclo[3.1.0]hexane-2,4-dione

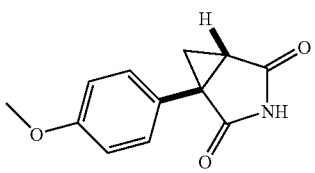

A mixture of 12.8 g of the diacid obtained in Preparation 3 and 6.5 g of urea in 300 mL of m-xylene was heated at reflux for 8 h and then concentrated to dryness in vacuo. The crude was purified by column chromatography (AcOEt:cyclohexane=1 (?):10 to 4:6) to give 5.5 g of the title compound (y=46%).
MS (m/z): 218.1 [MH]⁺.

Preparation 5: (1R,5S/1S,5R)-[4-(Methoxy)phenyl]-3-azabicyclo[3.1.0]hexane

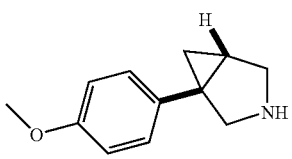

To a stirred slurry of 5.5 g of the imide obtained in Preparation 4 in 170 mL of toluene was slowly added 45 mL of Vitride (3.4 M in toluene) under N₂. This solution was stirred at reflux for 2 h. To the cooled solution was cautiously added aqueous NaOH (10 M, 40 mL) and the organic layer was washed with two portions of water and dried over Na₂SO₄. This solution was filtered, and the filtrate was evaporated in vacuo to give 4.8 g of the title compound (y=100%).

NMR (¹H, CDCl₃): δ 7.10 (d, 2H), 6.82 (d, 2H), 3.77 (s, 3H), 3.35-2.98 (m, 4H), 2.58 (dd, 1H), 0.87 (dd, 1H), 0.78 (dd, 1H), NH not observed. MS (m/z): 190.1 [MH]⁺.

Preparation 6: (1R,5S/1S,5R)-1-(4-Bromophenyl)-3-azabicyclo[3.1.0]hexane

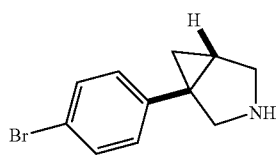

To 20 mL of 1M BH₃-tetrahydrofuran, stirred at 0° C. under N₂, was slowly added a solution of 1.32 g (5 mmol) of (1R,5S/1S,5R)-1-(4-bromophenyl)-3-azabicyclo[3.1.0]hexane-2,4-dione, prepared in analogy to Preparation 4, in 20 mL of dry tetrahydrofuran. This solution was stirred at room temperature for 15 min and then warmed on a steam bath for 1 h. The solution was then cooled in an ice bath, 2.5 mL of 6 M HCl was added cautiously, and the solvent was removed in vacuo. The residual material was combined with 12.5 mL of 5 M NaOH and the mixture was extracted with ether. The ether extract was washed twice with water, dried over Na₂SO₄ and filtered to give 1.19 g of the title compound (y=100%).

NMR (¹H, CDCl₃): δ 7.35 (d, 2H), 7.02 (d, 2H), 3.25-2.96 (m, 4H), 1.63 (dd, 1H), 1.55 (dd, 1H), 1.30 (dd, 1H), NH not observed. MS (m/z): 238.1 [MH]⁺, 1Br.

Preparation 7: (1R,5S/1S,5R)-4-[3-(Trifluoroacetyl)-3-azabicyclo[3.1.0]hex-1-yl]benzonitrile

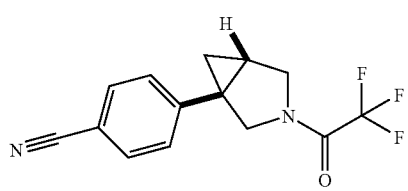

Trifluoroacetic anhydride (0.21 mL) was added to a solution of 4-[3-azabicyclo[3.1.0]hex-1-yl]benzonitrile (280 mg, prepared in analogy to the method described in Preparation 5), and triethylamine (0.25 mL) in dichloromethane (15 mL) at 0° C. The reaction mixture was allowed to warm to room temperature over 2 h, then washed with saturated NaHCO₃, the organic layer dried and evaporated to give 269 mg of the title compound.
MS (m/z): 281.2 [MH]⁺.

Preparation 8: (1R,5S/1S,5R)-4-[3-(Trifluoroacetyl)-3-azabicyclo[3.1.0]hex-1-yl]benzaldehyde

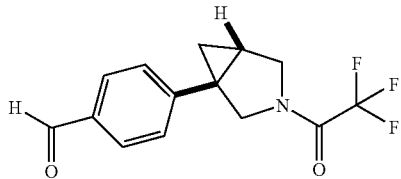

A mixture of 4-[3-(trifluoroacetyl)-azabicyclo[3.1.0]hex-1-yl]benzonitrile (283 mg), Ni—Al alloy (450 mg), formic acid (3.9 mL) and water (1.1 mL) was stirred at 80° C. for 3 h. The reaction mixture was cooled to room temperature and filtered. The filtrate was extracted with ethyl acetate and the organic phase washed with NaHCO$_3$, dried over Na$_2$SO$_4$ and evaporated in vacuo to give 195 mg of the title compound as yellow oil.

MS (m/z): 284.2 [MH]$^+$.

Preparation 9: (1R,5S/1S,5R)-4-[3-(Trifluoroacetyl)-3-azabicyclo[3.1.0]hex-1-yl]benzaldehyde oxime

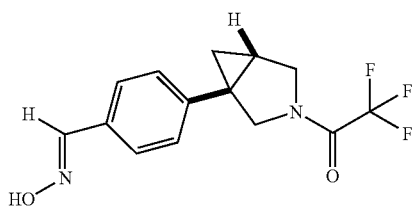

To a solution of 4-[3-(trifluoroacetyl)-3-azabicyclo[3.1.0]hex-1-yl]benzaldehyde (195 mg) in 5 mL of pyridine was added hydroxylamine hydrochloride (57.5 mg) and the mixture was stirred for 3 h at room temperature. The solvent was evaporated, the crude dissolved in ethyl acetate and the organic phase washed with 10% aqueous Na$_2$CO$_3$ and brine, dried over Na$_2$SO$_4$ and evaporated in vacuo to give 225 mg of the title compound as yellow oil.

MS (m/z): 299.2 [MH]$^+$.

Preparation 10: (1R,5S/1S,5R)-4-[3-(Trifluoroacetyl)-3-azabicyclo[3.1.0]hex-1-yl]-N-hydroxybenzenecarboximidoyl chloride

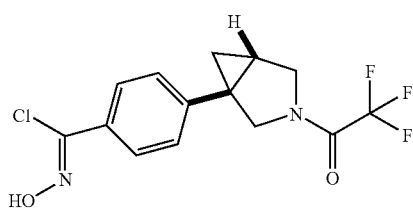

To a solution of 4-[3-(trifluoroacetyl)-(3-azabicyclo[3.1.0]hex-1-y]benzaldehyde oxime (0.69 mmol) in 3.5 mL of dimethylformamide was added portion wise N-chlorosuccinimide (97 mg) at 0° C. After stirring for 1.5 h at 40° C. the solvent was evaporated. The crude product was dissolved in diethyl ether/dichloromethane (4/1) and the organic phase washed with water, dried over Na$_2$SO$_4$ and concentrated in vacuo to give 243 mg of the title compound as a brown oil.

Preparation 11: (1R,5S/1S,5R)-1-[4-(5-Methyl-3-isoxazolyl)phenyl]-3-(trifluoroacetyl)-3-azabicyclo[3.1.0]hexane

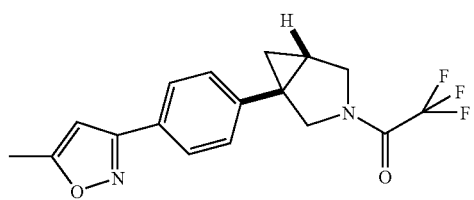

To a solution of 4-[3-(trifluoroacetyl)-3-azabicyclo[3.1.0]hex-1-yl)-N-hydroxybenzenecarboximidoyl chloride (0.69 mmol) in 6 mL of chloroform triethylamine (0.24 mL) and 2-chloro propene (0.29 mL) were added and the reaction stirred for 18 h at room temperature. The solution was washed with water, dried over Na$_2$SO$_4$ and volatiles evaporated in vacuo. The crude was purified by column chromatography (AcOEt:cyclohexane=1:10 to 4:6) to give 180 mg of the title compound.

MS (m/z): 337.2 [MH]$^+$.

Preparation 12: (1R,5S/1S,5R)-1-[4-(5-Methyl-3-isoxazolyl)phenyl]-3-azabicyclo[3.1.0]hexane

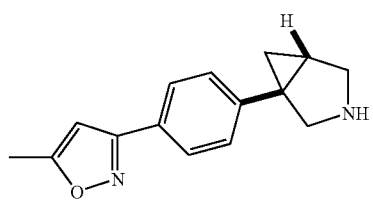

A mixture of 1-[4-(5-methyl-3-isoxazolyl)phenyl]-3-(trifluoroacetyl)-3-azabicyclo[3.1.0]hexane (0.54 mmol) and K$_2$CO$_3$ (296 mg) in methanol (5 mL) and water (5 mL) was stirred for 4 h at 50° C. The solvent was evaporated in vacuo and the product treated with dichloromethane/isopropanol 1/1 and filtered. The filtrate was dried over Na$_2$SO$_4$ and volatiles evaporated in vacuo to give 105 mg of the title compound (y=81%).

MS (m/z): 241.2 [MH]$^+$.

Preparation 13: 5-{5-[(3-Chloropropyl)thio]-4-methyl-4H-1,2,4-triazol-3-yl}-2-methylquinoline

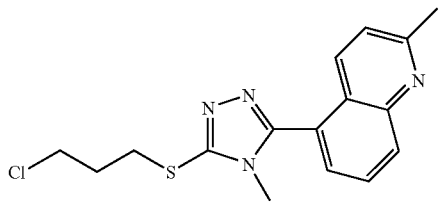

To 4-methyl-5-(2-methyl-5-quinolinyl)-2,4-dihydro-3H-1,2,4-triazole-3-thione (3.6 g, prepared in analogy to the method described in WO200240471) in ethanol (60 mL) containing 1-bromo-3-chloropropane (2.0 mL) was carefully added with stirring sodium hydride (0.60 g, 60% in petrolium). The mixture was heated at reflux for 45 min. Volatiles were evaporated in vacuo and the residue submitted to column chromatography (EtOAc—acetone gradient). The material thus obtained was precipitated from hot EtOAc (20 mL) by adding petroleum ether (40-60, 50 mL), cooled and collected by filtration to provide the title compound as colourless crystals (2.1 g).

NMR ($^1$H, CDCl$_3$): δ 8.18 (d, 1H), 8.12 (d, 1H), 7.76 (t, 1H), 7.55 (d, 1H), 7.30 (d, 1H), 3.75 (t, 2H), 3.50 (t, 2H), 3.40 (s, 3H), 2.76 (s, 3H), 2.37 (m, 2H).

Preparation 14: 3-[(3-Chloropropyl)thio]-4-methyl-5-(4-methyl-1,3-oxazol-5-yl)-4H-1,2,4-triazole

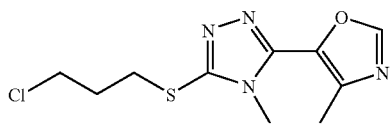

Ethyl-2-chloroacetoacetate (1 wt; 1 eq., 1000 g) was aged with formamide (0.68 vol; ca. 2.8 eq.) and the resulting solution was heated to 120° C. After 5 hours the mixture was allowed to cool to room temperature and allowed to age under nitrogen over night. The mixture was treated with NaOH (3 M, 6 vol, reaction moderately exothermic) and stirred at room temperature for 4 hours. Ethyl acetate (6 vol) was added and the phases allowed to separate. The organic layer was discarded while the aqueous was acidified with conc. (32%) aqueous HCl to pH 2 (ca. 2.0 vol). A precipitate started to form. The suspension was treated with AcOEt (8 vol) and vigorously stirred until the bulk of the precipitate had dissolved. The aqueous phase was further extracted with AcOEt twice (6 vol each) and the combined organic layers distilled to low volume (again a suspension was observed at low volume). Fresh AcOEt (8 vol) was added and the mixture evaporated to dryness. The collected solid was placed in the oven at 40° C. over night under reduced pressure to give 4-methyl-1,3-oxazole-5-carboxylic acid (498 g, 64.5%).

This material (498 g, 1 wt) was dissolved in dry tetrahydrofuran (5 vol), under nitrogen, cooled to 0° C. DCC (1.62 wt, 1 eq) was added portionwise followed by HOBt (1.07 wt, 1 eq). The mixture was warmed to 25±2° C. and stirred for 30 min. 4-Methyl-3-thiosemicarbazide (0.83 wt, 1 eq) was then added and the mixture further stirred for 2 h at 25±2° C. The mixture was filtered and the cake was washed with fresh tetrahydrofuran (1 vol) and dried on the filter for a few hours. The cake was suspended in 1 M aqueous NaOH (13 vol) and heated to 70° C. for 30 min. After this time, the mixture was cooled to 25±2° C. and a solid was removed by filtration. The cake was washed with 1 M aqueous NaOH (10 vol). The combined mother liquors were cooled to 0° C. and acidified to ca. pH 5 with HCl (aqueous, 16%; NOTE: keep temperature while adding HCl below +10° C.). The suspended product was isolated by filtration washing with water (2×3 vol). The cake was dried at 40° C. for 18 h in high vacuum to obtain 4-methyl-5-(4-methyl-1,3-oxazol-5-yl)-2,4-dihydro-3H-1,2,4-triazole-3-thione (respectively a tautomeric form thereof; 290 g, 37%). NaOEt (21% solution in EtOH, 2.08 vol, 1.1 eq) was added to EtOH (20 vol) under nitrogen atmosphere. 4-Methyl-5-(4-methyl-1,3-oxazol-5-yl)-2,4-dihydro-3H-1,2,4-triazole-3-thione (respectively a tautomeric form thereof; 290 g, 1 wt) was added in one portion and the resulting mixture stirred at 25±2° C. until a clear solution was obtained. Then 1-bromo-3-chloropropane (0.54 vol, 1.1 eq) was added and the solution stirred at 40° C. for 24 h then cooled to 25° C. After filtration water (20 vol) was added and the ethanolic phase was removed by vacuum distillation (internal temperature ~40° C.). The mixture was extracted with EtOAc (41 vol). The aqueous layer was removed and the organic phase was evaporated to dryness. Dichloromethane (4 vol) was added. The organic solution is purified through a short silica gel column (18 wt of silica), eluting with EtOAc (200 vol) to give the title compound as a solid foam (267.64 g, 66%).

NMR ($^1$H, CDCl$_3$): δ 7.90 (s, 1H), 3.70 (s, 5H), 3.40 (t, 2H), 2.52 (s, 3H), 2.30 (m, 2H).

Preparation 15: 3-[4-(Trifluoromethyl)phenyl]-1H-pyrrole-2,5-dione

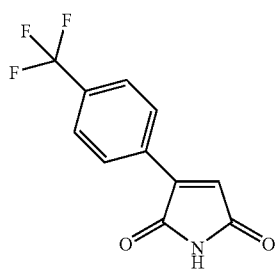

A mixture of hydrochloric acid (37%, 285 mL) and water (190 mL) was added to 4-(trifluoromethyl)aniline (150 g, 116 mL) at room temperature with vigorous stirring and the formed precipitate was allowed to stir for further 30 minutes. Temperature was reduced to 0° C. and sodium nitrite (70.6 g) in 180 mL of water was added dropwise to the stirred suspension. At the end of diazotisation, a clear yellow solution was obtained. Maleimide (180 g) in acetone (1.1 l) was added dropwise at 0° C. and then the pH of the solution was adjusted to 3-3.5 by adding sodium acetate. Copper (II) chloride (18.8 g) was added to the vigorously stirred mixture. After a few minutes a gas started to develop (conspicuous foaming). The reaction mixture was allowed to stir at 0° C. for 1 h and overnight at room temperature.

Acetone was removed in vacuo, the residue was filtered and dried overnight in vacuo to give the title compound (155 g) as a light brown solid (y=63%).

MS (m/z): 242.2 [MH]$^+$.

Preparation 16: (1R,5S/1S,5R)-1-[4-(Trifluoromethyl)phenyl]-3-azabicyclo[3.1.0]-hexane-2,4-dione

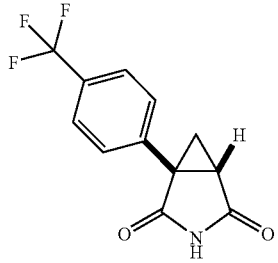

Milled sodium hydroxide (40 g) was added in small portions to a stirred solution of trimethylsulfoxonium iodide (219 g) in DMSO (anhydrous, 2 l). The resulting mixture was allowed to stir at room temperature for 1.5 h.

3-[4-(Trifluoromethyl)phenyl]-1H-pyrrole-2,5-dione (Preparation 15, 120 g) dissolved in DMSO (anhydrous, 0.5 l) was then added dropwise and the resulting mixture was allowed to stir at room temperature for 20 minutes. Temperature was then reduced to 0° C. and NH$_4$Cl (aqueous saturated solution, 2 l) was slowly added, followed by Et$_2$O (1 l). After separation of the two phases, the aqueous layer was repeatedly extracted with Et$_2$O (3×1 l). Combined organic layers were washed with brine (2×1 l) and then dried over Na$_2$SO$_4$. Evaporation of the solvent gave a light brown solid which was suspended in 1 l of dichloromethane and 1 l of cyclohexane. The mixture was allowed to stir at room temperature for 45 minutes and then filtered to give the title compound (116 g) as white solid (y=71%).

MS (m/z): 256.1 [MH]$^+$.

Preparation 17: (1R,5S/1S,5R)-1-[4-(Trifluoromethyl)phenyl]-3-azabicyclo[3.1.0]-hexane

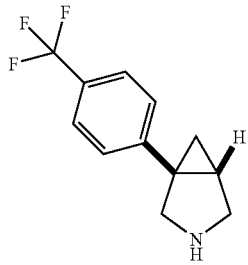

Borane (1M in tetrahydrofuran, 1.4 l) was charged into a 5 l reactor under N$_2$ and cooled at 0° C. (1R,5S/1S,5R)-1-[4-(Trifluoromethyl)phenyl]-3-azabicyclo[3.1.0]hexane-2,4-dione (Preparation 16, 101 g) dissolved in tetrahydrofuran (anhydrous, 1 l) was then added dropwise with vigorous stirring whereby the temperature was constantly kept below 5° C. and gas evolution was monitored. At the end of the addition the resulting mixture was allowed to stir at 0° C. for 1 h and then at room temperature overnight.

The mixture was then cooled to 0° C. and methanol (200 mL) followed by hydrochloric acid (6 M solution, 0.8 l) were cautiously added monitoring gas evolution. tetrahydrofuran was then removed in vacuo, the residue was cooled to 0° C. and sodium hydroxide (5 M solution) was added until pH 9-10 had been reached. The aqueous layer was extracted with Et$_2$O (3×1 l). Removal of solvent in vacuo gave the title compound (140 g) as colorless oil.

MS (m/z): 228.1 [MH]$^+$.

Preparation 18: (1S,5R)-1-[4-(Trifluoromethyl)phenyl]-3-azabicyclo[3.1.0]hexane

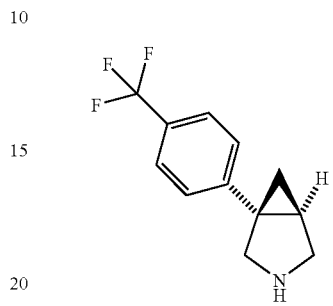

(S)-(+)-Mandelic acid (94 g) was added in portions to a stirred solution of (1R,5S/1S,5R)-1-[4-(trifluoromethyl)phenyl]-3-azabicyclo[3.1.0]hexane (Preparation 17, 140 g) in 1.4 l of tetrahydrofuran. The resulting mixture was stirred at room temperature for 2 h until a white precipitate was formed. The mixture was then warmed up to reflux temperature, stirred for 45 minutes and then slowly cooled down to room temperature. The white solid was collected by filtration and dried in vacuo. This material was recrystallised 4 times from tetrahydrofuran (10 volumes) to give 32.5 g of a white solid. This material was then suspended in sodium hydroxide (1M solution, 400 mL) and Et$_2$O (400 mL) and allowed to stir at room temperature until complete dissolution. After separation of the two phases, the aqueous layer was extracted again with Et$_2$O (3×250 mL). Combined organic layers were washed with sodium hydroxide (1M solution, 3×200 mL) and then dried over Na$_2$SO$_4$. Evaporation of solvent in vacuo gave the title compound (19 g) as white solid (y=37%).

The absolute configuration of the optical isomers was assigned using comparative VCD (vibrational circular dichroism) and OR (optical rotation) analyses.

The configuration of the title compound was assigned by comparing its experimental VCD spectrum and observed specific rotation to the data observed for (1S,5R)-1-(3,4-dichlorophenyl)-3-azabicyclo[3.1.0]hexane (see Preparation 48) as the reference sample. The assignment of the absolute configuration of the title compound was confirmed by a single crystal X-ray structure obtained from a crystal of (1S,5R)-1-[4-(trifluoromethyl)phenyl]-3-azabicyclo[3.1.0]hexane, (S)-(+)-mandelic acid salt. Both, analysis based on the known configuration of the (S)(+)-mandelic acid and on the basis of anomalous dispersion effects confirmed the assignment of the title compound as being (1S,5R)-1-[4-(trifluoromethyl)phenyl]-3-azabicyclo[3.1.0]hexane.

NMR ($^1$H, CDCl$_3$): δ 7.51 (d, 2H), 7.25 (d, 2H), 3.20 (d, 1H), 3.0-3.1 (m, 3H), 1.69 (m, 1H), 0.8-1.0 (m, 2H), NH not observed. MS (m/z): 228.1 [MH]$^+$.

Analytical Chromatography

Column: chiralcel OD 10 um, 250×4.6 mm

Mobile phase: A: n-Hexane; B: Isopropanol+0.1% Isopropyl amine

Gradient: isocratic 2% B

Flow rate: 1 mL/min

UV wavelength range: 200-400 nm
Analysis time 25 min
ret. time (min) % a/a
16.5 0.4 (1R,5S)-1-[4-(trifluoromethyl)phenyl]-3-azabicyclo[3.1.0]hexane
21.7 99.6 title compound
Specific Optical Rotation: [α]$_D$=−10° (CDCl$_3$, T=20° C., c≅0.004 g/0.8 mL).

Preparation 19: 3-{(1S,5R)-1-[4-(Trifluoromethyl)phenyl]-3-azabicyclo[3.1.0]hex-3-yl}-1-butanol

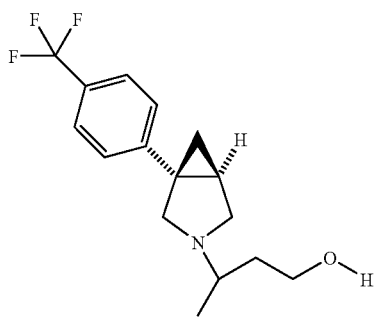

To a suspension of (1S,5R)-[4-(trifluoromethyl)phenyl]-3-azabicyclo[3.1.0]hexane (Preparation 18, 100 mg) in tetrahydrofuran (1.1 mL), 4-hydroxy-2-butanone (0.66 mmol), acetic acid (0.66 mmol) and NaBH(OAc)$_3$ (0.88 mmol) were added. The mixture was stirred at room temperature for 2 h. After addition of NaOH (1M), the solvent was eliminated under vacuo, the residue was dissolved in ethyl acetate and the organic layer was washed with H$_2$O and dried over Na$_2$SO$_4$. This solution was concentrated in vacuo to give 130 mg of the title compound which was used without further purification.
MS (m/z): 300 [MH]$^+$.

Preparation 20: (1S,5R)-3-(3-Chloro-1-methylpropyl)-1-[4-(trifluoromethyl)phenyl]-3-azabicyclo[3.1.0]hexane

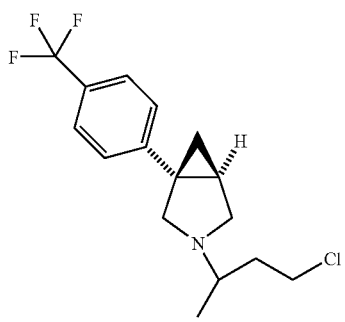

To a solution of 3-{(1S,5R)-1-[4-(trifluoromethyl)phenyl]-3-azabicyclo[3.1.0]hex-3-yl}-1-butanol (Preparation 19, 130 mg) in chloroform (4 mL), thionyl chloride (0.87 mmol) was added and the mixture was stirred at room temperature for 6 h. After addition of NaOH (1 M), dichloromethane was added and the organic layer was washed with Brine and dried over Na$_2$SO$_4$. The solution was concentrated in vacuo and the crude product purified by flash chromatography (ethyl acetate:cyclohexane=5:95) to give 106 mg of the title compound.
MS (m/z): 318 [MH]$^+$.

Preparation 21: 1-{5-[(1S,5R/1R,5S)-3-Azabicyclo[3.1.0]hex-1-yl)-2-(methyloxy)phenyl}ethanone

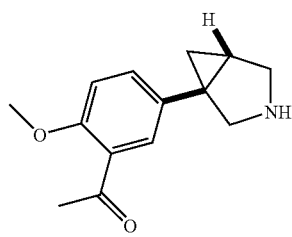

The title compound was prepared in 32 mg yield from 1-[4-(methyloxy)phenyl]-3-(trifluoroacetyl)-3-azabicyclo[3.1.0]hexane (94 mg) as described for preparation 34.
MS (m/z): 232 [MH]+. HPLC: condition 1, Rt=3.393 min.

Preparation 22: (1S,5R/1R,5S)-1-(4-Chlorophenyl)-3-azabicyclo[3.1.0]hexane

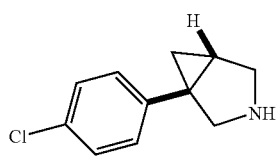

The title compound was prepared in 230 mg yield from commercially available methyl 4-chlorophenylacetate (1 g, 5.5 mmol) following the methods described in preparations 1, 2, 3, 4, 6.
MS (m/z): 194 [MH]+.

Preparation 23: (1S,5R/1R,5S)-1-(4-Fluorophenyl)-3-azabicyclo[3.1.0]hexane

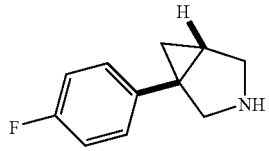

The title compound was prepared in 160 mg yield from commercially available methyl 4-fluorophenylacetate (1 g, 6 mmol) following the methods described in preparations 1, 2, 3, 4, 6.
MS (m/z): 178 [MH]+.

Preparation 24: (1S,5R/1R,5S)-1-(3-Chlorophenyl)-3-azabicyclo[3.1.]hexane

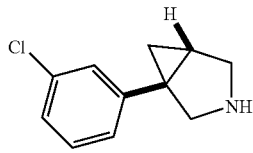

The title compound was prepared in 1.25 g yield from commercially available methyl 3-chlorophenylacetate (5 g, 27 mmol) following the methods described in preparations 1, 2, 3, 4, 5.

MS (m/z): 194 [MH]+. HPLC: condition 1, Rt=3.469 min.

Preparation 25: (1S,5R/1R,5S)-1-(3-Fluorophenyl)-3-azabicyclo[3.1.0]hexane

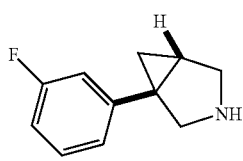

The title compound was prepared in 1.97 g yield from commercially available methyl 3-fluorophenylacetate (5 g, 29.7 mmol) following the methods described in preparations 1, 2, 3, 4, 5.

MS (m/z): 178 [MH]+.

Preparation 26: (1S,5R/1R,5S)-1-[3-(Methyloxy)phenyl]-3-azabicyclo[3.1.0]hexane

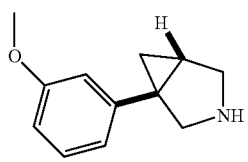

The title compound was prepared in 1.2 g yield from commercially available methyl 3-methoxyphenylacetate (5 g, 27.7 mmol) following the methods described in preparations 1, 2, 3, 4, 5.

MS (m/z): 190 [MH]+. HPLC: condition 1, Rt=3.219 min.

Preparation 27: (1S,5R/1R,5S)-1-[2-Methyl-4-(trifluoromethyl)phenyl]-3-azabicyclo[3.1.0]hexane

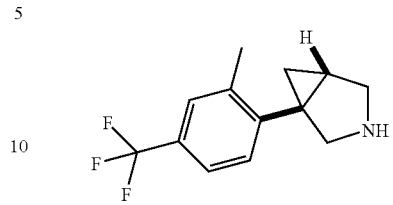

The title compound was prepared in 71 mg yield from commercially available 2-methyl-4-(trifluoromethyl)aniline (1 g, 5.7 mmol) following the methods described in preparations 15, 16, 17.

MS (m/z): 242 [MH]+.

Preparation 28: Methyl bromo{4-[(trifluoromethyl)oxy]phenyl}acetate

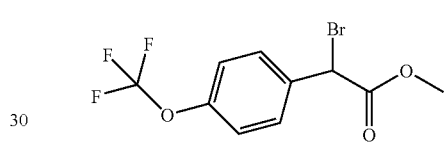

To a solution of 4-trifluoromethoxyphenylacetic acid (5 g, 23 mmol) in carbon tetrachloride oxalyl chloride (25 mmol) and two drops of DMF were added at 0° C. After stirring the solution at room temperature for 1 h, NBS (25 mmol) and few drops of 48% HBr were added and the mixture was heated to reflux for 4 h. The solution was allowed to cool, MeOH (5 mL) was added and the mixture was stirred at room temperature for 1 h.

After filtration through a pad of silica gel, the filtrate was evaporated in vacuo to give 7.2 g of the title compound as yellow foam, which was used in the subsequent step without further purification.

MS (m/z): 314 [MH]+.

Preparation 29: (1S,5R/1R,5S)-1-{4-[(Trifluoromethyl)oxy]phenyl}-3-azabicyclo[3.1.0]hexane

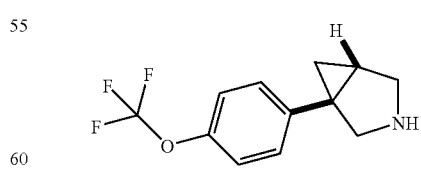

The title compound was prepared in 1.2 g yield from methyl 3-trifluoromethoxyphenylacetate (Preparation M, 23 mmol) following the methods described in preparations 2, 3, 4, 5.

MS (m/z): 244 [MH]+. HPLC: condition 1, Rt=3.942 min.

Preparation 30: (1S,5R/1R,5S)-1-[3-(Trifluoromethyl)phenyl]-3-azabicyclo[3.1.0]hexane

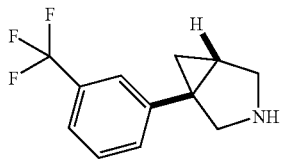

The title compound was prepared in 1.5 g yield from commercially available 3-trifluoromethylphenylacetic acid (5 g, 24.5 mmol), following the methods described in preparations 28, 2, 3, 4, 5.

MS (m/z): 228 [MH]+. HPLC: condition 1, Rt=3.665 min.

Preparation 31: (1R,5S/1S,5R)-1-(3-Bromophenyl)-3-azabicyclo[3.1.0]hexane

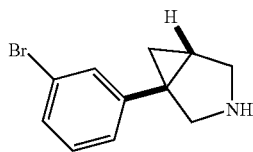

The title compound was prepared in 1.6 g yield from commercially available 3-bromophenylacetic acid (5 g, 23.2 mmol), following the methods described in preparations 28, 2, 3, 4, 6.

MS (m/z): 239 [MH]+. HPLC: condition 1, Rt=3.528 min.

Preparation 32: (1S,5R)-1-(4-Bromophenyl)-3-azabicyclo[3.1.0]hexane

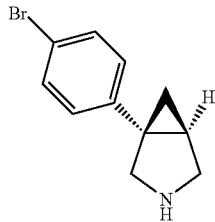

(S)(+)-Acetyl mandelic acid (3.22 g) was added in portions to a stirred solution of (1R,5S/1S,5R)-1-[4-bromophenyl]-3-azabicyclo[3.1.0]hexane (Preparation 6, 3.96 g) in 80 mL of IPA. The resulting mixture was stirred at room temperature for 2 h until a white precipitate was formed. The mixture was then warmed up to reflux temperature, stirred for 45 minutes and then slowly allowed to cool to room temperature. The white solid was collected by filtration and dried in vacuo. This material was recrystallised 4 times from IPA (10 volumes) to give 2.3 g of a white solid.

This material was then suspended in sodium hydroxide (1M aqueous solution, 400 mL) and Et$_2$O (400 mL) and allowed to stir at room temperature until complete dissolution. After separation of the two phases, the aqueous layer was extracted again with Et$_2$O (3×250 mL). Combined organic layers were washed with sodium hydroxide (1M solution, 3×200 mL) and then dried over Na$_2$SO$_4$. Evaporation of solvent in vacuo gave the title compound (1.24 g) as white solid.

The absolute configuration of the optical isomers was assigned as described for Preparation 18.

The assignment of the absolute configuration of the title compound was confirmed by a single crystal X-ray structure obtained from a crystal of (1S,5R)-1-(4-bromophenyl)-3-azabicyclo[3.1.0]hexane, (S)-(+)-O-acetyl mandelic acid salt. Both, analysis based on the known configuration of the (S)(+)-acetyl mandelic acid and on the basis of anomalous dispersion effects confirmed the assignment of the title compound as being (1S,5R)-1-(4-bromophenyl)-3-azabicyclo[3.1.0]hexane.

NMR ($^1$H, CDCl$_3$): δ 7.43 (d, 2H), 7.09 (d, 2H), 3.25 (d, 1H), 3.15 (m, 2H), 3.06 (d, 1H), 1.71 (m, 1H), 0.95 (dd, 1H), 0.89 (t, 1H), NH not observed. MS (m/z): 239 [MH]$^+$.

Analytical Chromatography
Column: chiralcel OD 5 μm, 250×4.6 mm
Mobile phase: A: n-Hexane; B: Isopropanol+0.1% Isopropyl amine
Gradient: isocratic 2% B
Flow rate: 1 mL/min
UV wavelength range: 200-400 nm
Analysis time 25 min
Ret. time 22.3 min, purity >99% a/a
Specific Optical Rotation: [α]$_D$=−86° (CDCl$_3$, T=20° C., c=0.0053 g/0.8 mL).

Preparation 33: (1R,5S/1S,5R)-1-[2-(Trifluoromethyl)phenyl]-3-azabicyclo[3.1.0]hexane

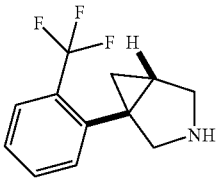

The title compound was prepared in 53 mg yield from commercially available methyl [2-(trifluoromethyl)phenyl] acetate (944 mg) following the methods described in preparations 1, 2, 3, 4 and 5.

MS (m/z): 228 [MH]$^+$.

Preparation 34: 1-[4-[(1R,5S/1S,5R)-3-Azabicyclo[3.1.0]hex-1-yl]-2-(methyloxy)phenyl]ethanone

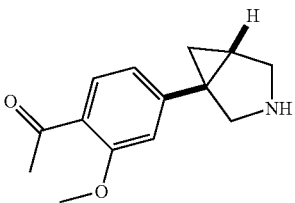

To a mixture of AlCl$_3$ (2 eq) in 1,2-dichloroethane (anhydrous, 9 mL) at 0° C. was added acetyl chloride (1.05 eq). The reaction mixture was stirred at 0° C. for 15 min and a solution of 1-[3-(methyloxy)phenyl]-3-(trifluoroacetyl)-3-azabicyclo[3.1.0]hexane (1.1 g, obtained in analogy to the method described in preparation 7 from 1-[3-(methyloxy)phenyl]-3-azabicyclo[3.1.0]hexane) in 1,2-dichloroethane (anhydrous, 9 mL) was added. The reaction mixture was stirred at RT for 1.5 h. HCl (1 M, 4 mL) was added followed by water (20 mL) and the mixture was extracted with dichloromethane. The organic layer was washed with saturated aqueous NaHCO$_3$ and dried over Na$_2$SO$_4$. The solution was filtered and the filtrate was concentrated in vacuo. The crude product was purified by flash chromatography (cyclohexanes:EtOAc 6:4) to give 593 mg as a colourless liquid of the protected amine. 143 mg of the protected amine was dissolved in MeOH:H$_2$O (3 mL:3 mL) and K$_2$CO$_3$ (4 eq) was added stirring the mixture at 50° C. for 2.5 h. The reaction mixture was extracted with dichloromethane and the organic layer was washed with saturated aqueous NaHCO$_3$ and dried over Na$_2$SO$_4$. The solution was filtered and the filtrate was concentrated in vacuo to give the title compound as a white solid (88 mg).

MS (m/z): 232 [MH]$^+$.

HPLC: Conditions 1

Analytical

Column: Supelcosil ABZ+Plus 33×4.6 mm, 3 μm

Mobile phase: A: H2O+0.1% HCOOH, B: CH3CN

Gradient: 0% (B) for 1 min, from 0% (B) to 95% (B) in 5 min, 95% (B) for 2 min

Flow rate: 1 mL/min

UV wavelength: 285 nm, band width 130 nm

Mass range: 100-1000 amu

Ionization: ES+

R$_t$ 2.971 min

Preparation 35: 1-[4-[(1R,5S/1S,5R)-3-Azabicyclo[3.1.0]hex-1-yl)-2-(methyloxy)phenyl]-1-propaone

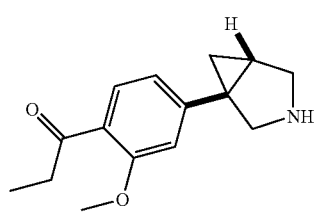

The title compound was prepared using propionyl chloride in place of acetyl chloride, in 106 mg yield from 147 mg of protected amine obtained in 705 mg from 1-[3-(methyloxy)phenyl]-3-(trifluoroacetyl)-3-azabicyclo[3.1.0]hexane (1.07 g) as described for preparation 34.

MS (m/z): 246 [MH]$^+$.

HPLC: Conditions 1

R$_t$ 3.249 min

Preparation 36: 1(1R,5S/1S,5R)-[2-Fluoro-5-(trifluoromethyl)phenyl]-3-azabicyclo[3.1.0]hexane

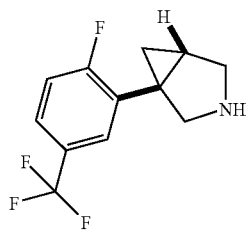

The title compound was prepared in 112 mg yield from 2-fluoro-5-(trifluoromethyl)aniline (1.09 g) following the procedures reported for preparations 37 and 6.

NMR ($^1$H, CDCl$_3$): δ 7.45 (m, 2H), 7.1 (m, 1H), 3.2 (m, 2H), 3.05 (m, 2H), 1.7 (m, 1H), 0.95 (m, 1H), 0.9 (m, 1H), NH not observed. MS (m/z): 246 [MH]$^+$.

Preparation 37: 1(1R,5S/1S,5R)-[2-Fluoro-4-(trifluoromethyl)phenyl]-3 azabicyclo[3.1.0]hexane-2,4-dione

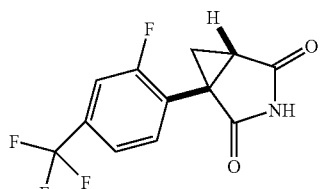

To a slurry of maleimide (1.7 eq), anhydrous CuCl$_2$ (1.2 eq) and tert-butyl nitrite (1.5 eq) in CH$_3$CN (35 mL) at 0° C. a solution of 2-fluoro-4-(trifluoromethyl)aniline (16.3 g) in CH$_3$CN (6.5 mL) was added dropwise. The reaction mixture was stirred at room temperature for 1 h and HCl (10%, aqueous, 196 mL) was added. The mixture was extracted with EtOAc, the organic layer was washed with saturated aqueous NaCl and dried over Na$_2$SO$_4$. The solution was filtered and the filtrate was concentrated in vacuo. By NMR analysis the crude mixture resulted a 1:4 mixture of the arylated maleimide hydrogen chloride adduct (component A) and unreacted maleimide (component B).

A DMSO (140 mL) solution of this crude product was added dropwise to a preformed solution of trimethylsulfoxonium iodide (2 eq with respect to component A plus 2 eq with respect to component B) in anhydrous DMSO (412 mL) to which NaH (3 eq with respect to component A plus 2 eq with respect to component B) had been added portionwise. The reaction mixture was stirred for 30 min and AcOH (2 eq) was added followed by water. The reaction mixture was extracted with Et$_2$O and then with EtOAc, the combined organic layers were washed with saturated aqueous NaCl and dried over Na$_2$SO$_4$. The solution was filtered and the filtrate was concentrated in vacuo. The crude product obtained was triturated with water and then with cyclohexanes to give the title compound as light brown solid (5.98 g).

NMR (¹H, CDCl₃): δ 7.55-7.3 (m, 3H), 2.8-2.7 (m, 1H), 2.1 (m, 1H), 2.0 (m, 1H), NH not observed. MS (m/z): 274 [MH]⁺.

Preparation 38 (1R,5S/1S,5R)-1-[2-Fluoro-4-(trifluoromethyl)phenyl]-3-azabicyclo[3.1.0]hexane

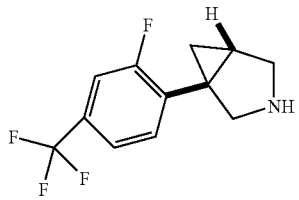

To a solution of (1R,5S/1S,5R)-1-[2-fluoro-4-(trifluoromethyl)phenyl]-3-azabicyclo-[3.1.0]hexane-2,4-dione (2.6 g) in anhydrous tetrahydrofuran (56 mL), BH₃ in tetrahydrofuran (1 M, 4 eq) was added at 0° C. The reaction mixture was stirred at 65° C. for 24 h, cooled to RT and MeOH was added until gas evolution ceased. Solvent was removed in vacuo, MeOH was added (200 mL) p-tolueneulfonic acid (3 eq) was added and the reaction mixture was stirred at 65° C. for 6 h, the reaction mixture was cooled to room temperature and a saturated solution of K₂CO₃ (1.7 eq) was added. The mixture was extracted with dichloromethane, the organic layer was washed with saturated aqueous NaCl and dried over Na₂SO₄. The solution was filtered and the filtrate was concentrated in vacuo to give the title compound as colourless oil (2.1 g).

NMR (¹H, CDCl₃): δ 7.2-7.4 (m, 3H), 3.2 (m, 2H), 3.1 (m, 2H), 1.8 (m, 1H), 0.8 (m, 2H), NH not observed. MS (m/z): 246 [MH]⁺.

Preparation 39: (1S,5R)-1-[2-Fluoro-4-(trifluoromethyl)phenyl]-3-azabicyclo[3.1.0]hexane

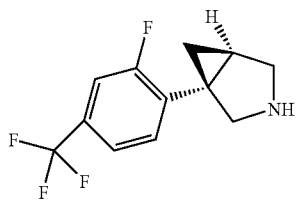

(1R)-(−)-10-Camphorsulfonic acid (4.19 g) was added in portions to a stirred solution of (1R,5S/1S,5R)-1-[2-fluoro-4-(trifluoromethyl)phenyl]-3-azabicyclo[3.1.0]hexane (4.4 g) in CH₃CN (44 mL). The resulting mixture was stirred at room temperature for 20 min until a white precipitate formed. The mixture was then warmed up to reflux temperature, stirred for 45 minutes and then slowly allowed to cool to room temperature. The white solid was collected by filtration and dried in vacuo. This material was recrystallised 2 times from CH₃CN (25 mL per g solid) to give 1.57 g of a white solid.

This material was then suspended in sodium hydroxide (1M solution, 1.1 eq) and dichloromethane (100 mL) and allowed to stir at room temperature until complete dissolution. After separation of the two phases, the aqueous layer was extracted again with dichloromethane. The combined organic layers were washed with sodium hydroxide and then dried over Na₂SO₄. Evaporation of solvent in vacuo gave the title compound (874 mg) as colorless liquid.

Analytical Chromatography
Column: chiralcel OD 10 μm, 250×4.6 mm
Mobile phase: A: n-Hexane; B: Isopropanol+0.1% Isopropyl amine
Gradient: isocratic 2% B
Flow rate: 0.8 mL/min
UV wavelength range: 200-400 nm
Analysis
ret. time (min) % a/a
17.18 >99.5 (1S,5R)-1-[2-fluoro-4-(trifluoromethyl)phenyl]-3-azabicyclo[3.1.0]hexane Preparation 40: (1S,5R)-3-(3-Chloropropyl)-1-[4-(trifluoromethyl)phenyl]-3-azabicyclo[3.1.0]hexane

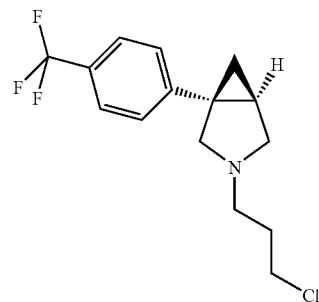

To a solution of (1S,5R)-1-[4-(trifluoromethyl)phenyl]-3-azabicyclo[3.1.0]hexane (1.00 g) in dry tetrahydrofuran (5 mL), diisopropylethylamine (2.4 mL) and 1-bromo-3-chloropropane (3.7 mL) were added and the resulting mixture was heated at reflux for 3 hours. After cooling at room temperature it was diluted with ethyl acetate (30 mL) washed twice with a saturated solution of NH₄Cl in water (20 mL) and once with a saturated solution of NaHCO₃ in water (20 mL), dried over anhydrous Na₂SO₄ and concentrated under reduced pressure. The crude product was purified by silica gel chromatography eluting with cyclohexane/EtOAc 7:3 to give the title compound as a colourless oil (1.26 g).

NMR (¹H, CDCl₃): δ 7.50 (d, 2H) 7.19 (d, 2H), 3.59 (t, 2H), 3.33 (d, 1H), 3.09 (d, 1H), 2.58 (m, 2H), 2.66 (dd, 1H), 2.46 (dd, 1H), 1.92 (m, 2H), 1.74 (m, 1H), 1.67 (t, 1H), 0.81 (dd, 1H). MS (m/z): 304 [MH]⁺.

Preparation 41: (1S,5R)-3-(3-Chloropropyl)-1-[2-fluoro-4-(trifluoromethyl)phenyl]-3-azabicyclo[3.1.0]hexane

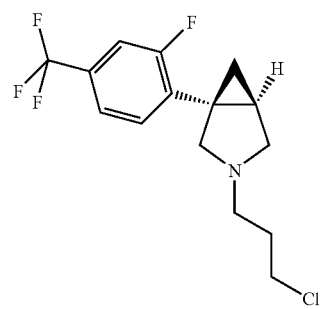

To a solution of (1S,5R)-1-[2-fluoro-4-(trifluoromethyl) phenyl]-3-azabicyclo[3.1.0]hexane (300 mg) in dry tetrahydrofuran (3 mL), diisopropylethylamine (0.65 mL) and 1-bromo-3-chloropropane (1.01 mL) were added and the resulting mixture was refluxed for 3 hours.

After cooling at room temperature it was diluted with ethyl acetate (15 mL) washed twice with a saturated solution of NH₄Cl in water (10 mL) and once with a saturated solution of NaHCO₃ in water (10 mL), dried over anhydrous Na₂SO₄ and concentrated under reduced pressure. The crude product was purified by chromatography (silica gel) eluting with cyclohexane/EtOAc 6:4 to give the title compound as yellow oil (345 mg).

NMR (¹H, CDCl₃): δ 7.24 (d, 2H), 7.16 (t, 1H), 3.51 (t, 2H), 3.18 (dd, 1H), 3.03 (d, 1H), 2.54 (t, 2H), 2.48 (dd, 1H), 2.37 (d, 1H), 1.83 (m, 2H), 1.69 (m, 1H), 1.34 (t, 1H), 0.70 (dd, 1H). MS (m/z): 322 [MH]⁺.

Preparation 42: (1R,5S/1S,5R)-1-[3-Fluoro-4-(trifluoromethyl)phenyl]-3-azabicyclo[3.1.0]hexane

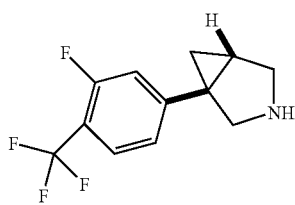

The title compound was prepared in 338 mg yield from 3-fluoro-4-(trifluoromethyl)aniline (2 g) following the procedures reported for Preparations 37 and 6.

NMR (¹H, CDCl₃): δ 7.5 (m, 1H), 6.9 (m, 2H), 3.3-3.0 (m, 4H), 1.7 (m, 1H), 0.95 (m, 2H), NH not observed. MS (m/z): 246 [MH]⁺.

Preparation 43: (1R,5S/1S,5R)-1-[4-(Methyloxy) phenyl]-3-(trifluoroacetyl)-3-azabicyclo[3.1.0]hexane

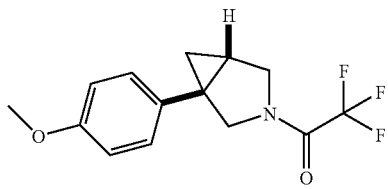

The title compound was prepared in 1.80 g yield (95%) as a colorless oil from (1R,5S/1S,5R)-1-[4-(methoxy)phenyl]-3-azabicyclo[3.1.0]hexane (1.25 g) in analogy to the method described in Preparation 7.

MS (m/z): 286 [MH]⁺.

Preparation 44: 1-{2-(Methyloxy)-5-[(1R,5S/1S,5R)-3-(trifluoroacetyl)-3-azabicyclo[3.1.0]hex-1-yl] phenyl}ethan one and 1-{2-hydroxy-5-[(1R,5S/1S, 5R)-3-(trifluoroacetyl)-3-azabicyclo[3.1.0]hex-1-yl] phenyl}ethanone

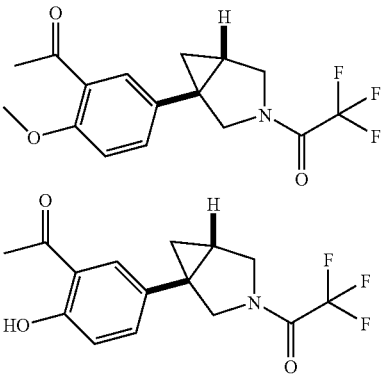

To a suspension of AlCl₃ (12.6 mmol) in dry 1,2-dichloroethane (16 mL) at 0° C. acetyl chloride (6.6 mmol) was added and the mixture was stirred at this temperature for 15 min. A solution of (1R,5S/1S,5R)-1-[4-(methyloxy)phenyl]-3-(trifluoroacetyl)-3-azabicyclo[3.1.0]hexane (1.81 g, 6.3 mmol) in 1,2-dichloroethane (16 mL) was then added. The reaction mixture was allowed to stir at 0° C. for 15 min and overnight at room temperature. 1 M aqueous HCl was then added and the mixture was extracted with dichloromethane. The organic phase was washed with 5% NaHCO₃ and water, dried over Na₂SO₄ and concentrated in vacuo. The two products were separated by flash chromatography (cyclohexane/ethyl acetate from 95/5 to 80/20) to give 965 mg of 1-{2-(methyloxy)-5-[(1R,5S/1S,5R)-3-(trifluoroacetyl)-3-azabicyclo [3.1.0]hex-1-yl]phenyl}ethanone (48%) and 266 mg of 1-{2-hydroxy-5-[(1R,5S/1S,5R)-3-(trifluoroacetyl)-3-azabicyclo [3.1.0]hex-1-yl]phenyl}ethanone (18%) as yellow oils.

MS (m/z): 328 [MH]⁺, 1-{2-(methyloxy)-5-[(1R,5S/1S, 5R)-3-(trifluoroacetyl)-3-azabicyclo[3.1.0]hex-1-yl] phenyl}ethanone; 312 [M-H]⁻, 1-{2-hydroxy-5-[(1R,5S/1S, 5R)-3-(trifluoroacetyl)-3-azabicyclo[3.1.0]hex-1-yl] phenyl}ethanone.

Preparation 45: 1-[5-[(1R,5S/1S,5R)-3-Azabicyclo [3.1.0]hex-1-yl]-2-(methyloxy)phenyl]ethanone

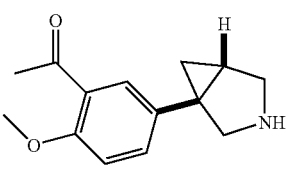

The title compound was prepared in 624 mg yield (91%) as a colorless oil from 1-{2-(methyloxy)-5-[(1R,5S/1S,5R)-3-(trifluoroacetyl)-3-azabicyclo[3.1.0]hex-1-yl] phenyl}ethanone (965 mg) in analogy to the method described in Preparation 12.

MS (m/z): 232 [MH]⁺.

Preparation 46: 1-{5-[(1R,5S/1S,5R)-3-Azabicyclo[3.1.0]hex-1-yl]-2-hydroxyphenyl}ethanone

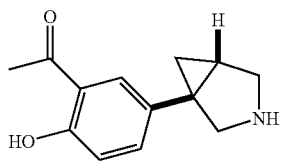

The title compound was prepared in 151 mg yield (82%) as a colorless oil from 1-{2-hydroxy-5-[(1R,5S/1S,5R)-3-(trifluoroacetyl)-3-azabicyclo[3.1.0]hex-1-yl]phenyl}ethanone (266 mg) in analogy to the method described in Preparation 12.

MS (m/z): 216 [M-H]−.

Preparation 47: (1S,5R/1R,5S)-1-(4-Bromophenyl)-3-(3-chloropropyl)-3-azabicyclo[3.1.0]hexane

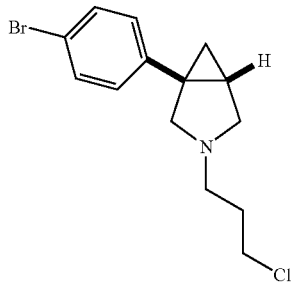

To a solution of racemic (1S,5R/1R,5S)-1-(4-bromophenyl)-3-azabicyclo[3.1.0]hexane (0.12 g) in dry tetrahydrofuran (2 mL), diisopropylethylamine (0.22 mL) and 1-bromo-3-chloropropane (0.062 mL) were added and the resulting mixture was heated at reflux for 3 hours. After cooling to room temperature the solvent was removed in vacuo and the resulting crude oil was taken up in dichloromethane (10 mL). This solution was then washed twice with a saturated solution of NH$_4$Cl in water (5 mL), dried over anhydrous Na$_2$SO$_4$ and concentrated under reduced pressure. The crude product was purified passing the sample through a 2 g silica cartridge (Varian) with a gradient elution from cyclohexane to cyclohexane/EtOAc 7:3, to give the title compound as a colourless oil (0.10 g).

NMR ($^1$H, DMSO): δ 7.45 (d, 2H), 7.10 (d, 2H), 3.65 (t, 2H), 3.30 (d, 1H), 3.00 (d, 1H), 2.55 (t, 2H), 2.45 (m, 1H), 2.40 (dd, 1H), 1.85 (m, 2H), 1.80 (m, 1H), 1.30 (t, 1H), 0.70 (m, 1H). MS (m/z): 314, 316, 318 [MH]+.

Preparation 48: (1R,5S/1S,5R)-1-(3,4-Dichlorophenyl)-3-azabicyclo[3.1.0]hexane

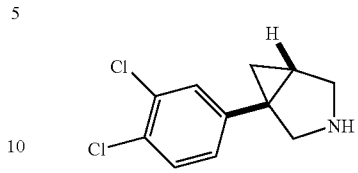

The crude title compound was prepared in 0.36 g yield from commercially available methyl 3,4-dichlorophenylacetate (1 g, 4.57 mmol) following the methods described in preparations 1, 2, 3, 4, 6.

The title compound was separated to give the separated enantiomers by preparative chromatography using a chiral column chiralcel AD 10 um, 250×21 mm, eluent A: n-hexane; B: isopropanol+0.1% isopropyl amine, gradient isocratic 2% B, flow rate 7 mL/min, detection UV at 200-400 nm. Retention times given were obtained using an analytical HPLC using a chiral column chiralcel AD 5 um, 250×4.6 mm, eluent A: n-hexane; B: isopropanol+0.1% Isopropyl amine, gradient isocratic 2% B, flow rate 1.2 mL/min, detection UV at 200-400 nm.

Enantiomer 1, (1R,5S)-1-(3,4-dichlorophenyl)-3-azabicyclo[3.1.0]hexane, was recovered in 20 mg yield as white solid from the racemate (60 mg). Rt.=41 min.

Enantiomer 2, (1S,5R)-1-(3,4-dichlorophenyl)-3-azabicyclo[3.1.0]hexane, was recovered in 28 mg yield as white solid from the racemate (60 mg). Rt.=43.4 min.

The absolute configuration of (1S,5R)-1-(3,4-dichlorophenyl)-3-azabicyclo[3.1.0]hexane was assigned using ab initio VCD and ab initio OR analyses.

Specific Optical Rotation of (1S,5R)-1-(3,4-dichlorophenyl)-3-azabicyclo[3.1.0]hexane: [α]$_D$=−67.9° (CDCl$_3$, T=20° C., c≈0.01 g/mL).

NMR ($^1$H, CDCl$_3$): δ 7.35 (d, 1H), 7.27 (s, 1H), 7.02 (dd, 1H), 3.25 (d, 1H), 3.13 (bm, 2H), 3.06 (d, 1H), 1.71 (m, 1H), 0.93 (m, 2H), NH not observed. MS (m/z): 228 [MH]+.

Preparation 49: 1-(Phenylmethyl)-3-(4,4,5,5-tetramethyl-1,3,2-dioxaborolan-2-yl)-2,5-dihydro-1H-pyrrole

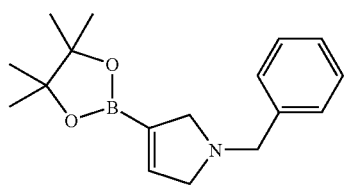

Diisopinocampheylborane was prepared following the procedure reported in *J. Org. Chem.* 1984, 49, 945-947. 2-[(1Z)-3-Chloro-1-(chloromethyl)-1-propen-1-yl]-4,4,5,5-tetramethyl-1,3,2-dioxaborolane (previously described in *Tetrahedron Lett.* 1993, 34, 4827-4828) was prepared following the general procedure reported in *Tetrahedron Lett.* 1989, 30, 2929, using 1,4-dichloro-2-butyne. The material thus obtained was further converted following the procedure reported in Synlett 2002, 5, 829-831. This latter procedure was modified in that isolation of the title product was achieved (rather than by distillation) by extraction of a solution of the crude reaction products in acetonitrile with cyclohexane, to provide the title compound (containing ˜10% in moles of benzylamine) after evaporation of the volatiles from the cyclohexane phase.

Preparation 50: 2-[1-(Phenylmethyl)-2,5-dihydro-1H-pyrrol-3-yl]-5-(trifluoromethyl)pyridine

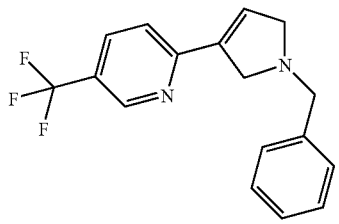

To a solution of 2-bromo-5-(trifluoromethyl)pyridine (4.42 mmol) in dry tetrahydrofuran (45 mL) 1-(phenylmethyl)-3-(4,4,5,5-tetramethyl-1,3,2-dioxaborolan-2-yl)-2,5-dihydro-1H-pyrrole (3.4 mmol), tetrakis(triphenylphosphine)palladium(0) (0.196 mmol) and cesium fluoride (13.2 mmol) were added at room temperature. The resulting mixture was stirred at 80° C. for 1.5 hours. After cooling solvent was evaporated under reduced pressure and the residue was partitioned between dichloromethane (25 mL) and sodium hydroxyde (15 mL, 1M). The organic phase was evaporated under reduced pressure. The crude product was purified by silica gel column chromatography (AcOEt:cyclohexane=1: 10 to 4:6) to give 0.33 g of the title compound (y=24%).

NMR ($^1$H, CDCl$_3$): δ 9.8 (s, 1H), 7.85 (dd, 1H), 7.5-7.2 (m, 6H), 6.7 (s, 1H), 3.95 (m, 2H), 3.9 (s, 2H), 3.75 (m, 2H). MS (m/z): 305 [MH]$^+$.

Preparation 51: 2-[1-(Phenylmethyl)-2,5-dihydro-1H-pyrrol-3-yl]-6-(trifluoromethyl)pyridine

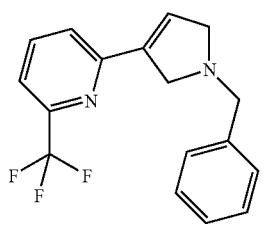

2-[1-(Phenylmethyl)-2,5-dihydro-1H-pyrrol-3-yl]-6-(trifluoromethyl)pyridine was prepared in analogy to the method described in Preparation 50 in 0.56 g (y=42%) as an oil.

NMR ($^1$H, CDCl$_3$): δ 7.7 (t, 1H), 7.85 (dd, 1H), 7.4-7.1 (m, 6H), 6.5 (s, 1H), 3.90 (sb, 2H), 3.8 (s, 2H), 3.6 (m, 2H). MS (m/z): 305 [MH]$^+$.

Preparation 52: 3-(Phenylmethyl)-1-[5-(trifluoromethyl)-2-pyridinyl]-3-azabicyclo[3.1.0]hexane

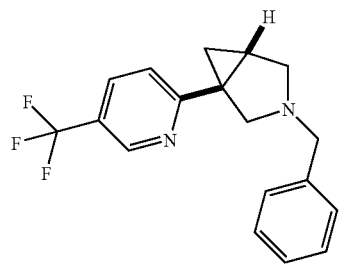

To a slurry of sodium hydride (83 mg) and trimethylsulfoxonium iodide (0.46 g) DMSO (anhydrous, 3 mL) was added dropwise (gas evolution). The resulting mixture was allowed to stir at room temperature for 0.5 h. A solution of 2-[1-(phenylmethyl)-2,5-dihydro-1H-pyrrol-3-yl]-5-(trifluoromethyl)pyridine (330 mg) in DMSO (anhydrous, 6 mL) was added at room temperature. After 1 h a saturated solution of ammonium chloride (4 mL) was added and the mixture extracted with dichloromethane (2×10 mL). Volatiles from the organic phase were evaporated under reduced pressure, the residue charged onto an SCX column and eluted with MeOH followed by MeOH/NH$_3$ 0.25 M. The methanole/ammonia fractions were concentrated under reduced pressure to give 0.31 g of the title compound (y=89%).

NMR ($^1$H, CDCl$_3$): δ 8.78 (s, 1H), 8.03 (dd, 1H), 7.32 (m, 5H), 7.25 (m, 1H), 3.66 (dd, 2H), 3.25 (d, 1H), 2.96 (d, 1H), 2.80 (d, 1H), 2.46 (sb, 1H), 2.05 (q, 1H), 1.58 (m, 1H), 1.22 (m, 1H). MS (m/z): 317 [MH]$^+$.

Preparation 53: 3-(Phenylmethyl)-1-[6-(trifluoromethyl)-2-pyridinyl]-3-azabicyclo[3.1.0]hexane

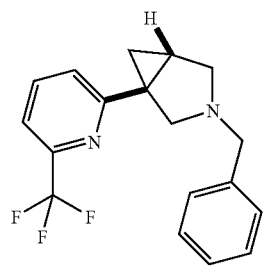

3-(Phenylmethyl)-1-[6-(trifluoromethyl)-2-pyridinyl]-3-azabicyclo[3.1.0]hexane was prepared in analogy to the method described in Preparation 52 (0.46 g, 79%) as an oil.

NMR ($^1$H, CDCl$_3$): δ 7.7 (t, 1H), 7.4 (d, 1H), 7.35 (m, 5H), 7.2 (d, 1H), 3.7 (s, 2H), 3.4 (d, 1H), 3.1 (d, 1H), 2.85 (d, 1H), 2.55 (m, 1H), 2.1 (m, 1H), 1.7 (m, 1H), 1.3 (m, 1H). MS (m/z): 317 [MH]$^+$.

Preparation 54: 1-[5-(Trifluoromethyl)-2-pyridinyl]-3-azabicyclo[3.1.0]hexane

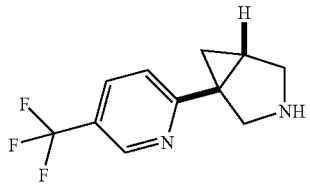

3-(Phenylmethyl)-1-[5-(trifluoromethyl)-2-pyridinyl]-3-azabicyclo[3.1.0]hexane was dissolved in ethanol (15 mL), hydrochloric acid (3M, 0.76 mL) was added followed, in inert atmosphere, by Pd/C 10% w/w (120 mg). After 20 h under a hydrogen atmosphere (1 atm) the mixture was filtered. Solvent was removed under reduced pressure. A saturated solution of sodium bicarbonate was added (10 mL) and the mixture extracted with diethyl ether (2×10 mL) to provide the title compound (0.14 g, 81%) after evaporation of volatiles.

NMR ($^1$H, DMSO-d$^6$): δ 8.7 (s, 1H), 7.8 (d, 1H), 7.15 (d, 1H), 3.4-3.2 (dd, 2H), 3.1 (m, 2H), 2.05 (m, 1H), 1.4 (m, 1H), 1.05 (t, 1H).

Preparation 55: 2-Fluoro-4-[1-(phenylmethyl)-2,5-dihydro-1H-pyrrol-3-yl]benzonitrile

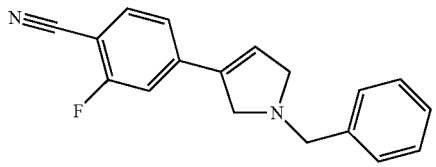

The title compound was prepared in analogy to the method described in Preparation 50 in 0.44 g (y=31%) as an oil.

NMR ($^1$H, CDCl$_3$): δ 7.55 (t, 1H), 7.4-7.2 (m, 5H), 7.2 (d, 1H), 7.1 (d, 1H), 6.4 (bs, 1H), 3.9 (s, 2H), 3.8 (m, 2H), 3.75 (m, 2H). MS (m/z): 279 [MH]$^+$.

Preparation 56: 2-Fluoro-4-[3-(phenylmethyl)-3-azabicyclo[3.1.0]hex-1-yl]benzonitrile

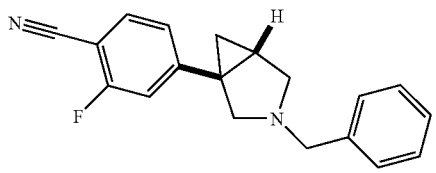

The title compound was prepared in analogy to the method described in Preparation 52 in 0.39 g (y=84%) as an oil.

NMR ($^1$H, CDCl$_3$): δ 7.41 (t, 1H), 7.25-7.15 (m, 5H), 6.85-6.8 (dd, 2H), 3.64-3.56 (dd, 2H), 3.19 (dd, 1H), 3.01 (dd, 1H), 2.53 (dd, 1H), 2.47 (dd, 1H), 1.73 (q, 1H), 1.67 (m, 1H), 0.81 (m, 1H). MS (m/z): 293 [MH]$^+$.

Preparation 57: 1-[3-Fluoro-4-(1H-pyrrol-1-ylmethyl)phenyl]-3-azabicyclo[3.1.0]hexane

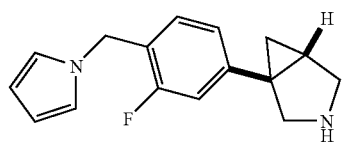

To a solution of {[4-(3-azabicyclo[3.1.0]hex-1-yl)-2-fluorophenyl]methyl}amine dihydrochloride in methanol/tetrahydrofuran (anhydrous, 1/1, 5 mL), which was prepared in analogy to the method described in Preparation 54 starting from 1.1 mmol of 2-fluoro-4-[3-(phenylmethyl)-3-azabicyclo[3.1.0]hex-1-yl]benzonitrile and used without further purification, a solution of 2,5-bis(methyloxy)tetrahydrofuran (2.53 mmol), H$_2$SO$_4$ (4.4 mmol) in methanol/tetrahydrofuran (anhydrous, 1/1, 5 mL) was added dropwise over 5 min at room temperature. After standing over night at room temperature a saturated solution of NaHCO$_3$ was slowly added, extraction with 2×15 mL of dichloromethane followed by preparative HPLC purification provided 14 mg of titled compound as an oil (y=5%).

NMR ($^1$H, CDCl$_3$): δ 6.88-6.82 (m, 3H), 6.67 (t, 2H), 6.14 (t, 2H), 5.04 (s, 2H), 3.21 (d, 1H), 3.1 (d, 1H), 3.09 (d, 1H), 3.01 (d, 1H), 1.67 (m, 1H), 0.88 (m, 2H). MS (m/z): 257 [MH]$^+$.

Preparation 58: (1R,5S/1S,5R)-3-(3-Chloropropyl)-1-[6-(trifluoromethyl)-3-pyridinyl]-3-azabicyclo[3.1.0]hexane

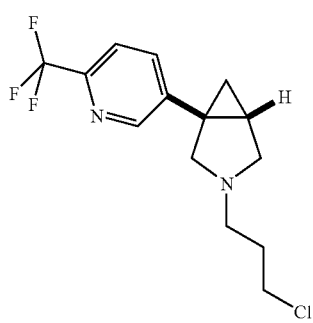

The title compound was prepared in 522 mg yield (84%) as a colorless oil from (1R,5S/1S,5R)-1-[6-(trifluoromethyl)-3-pyridinyl]-3-azabicyclo[3.1.0]hexane (584 mg) in analogy to the method described in Preparation 40.

NMR ($^1$H, CDCl$_3$): δ 8.47 (s, 1H), 7.55 (m, 2H), 3.59 (t, 2H), 3.33 (d, 1H), 3.09 (d, 1H), 2.6 (m, 3H), 2.52 (dd, 1H), 1.92 (m, 2H), 1.78 (m, 1H), 0.85 (m, 1H), 0.81 (dd, 1H). MS (m/z): 305 [MH]$^+$.

Preparation 59: 5-[(1R,5S/1S,5R)-3-(3-Chloropropyl)-3-azabicyclo[3.1.0]hex-1-yl]-2-methyl-1,3-benzothiazole

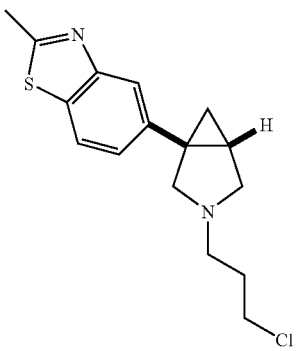

The title compound was prepared in 480 mg yield (84%) as a colorless oil from 5-[(1R,5S/1S,5R5)-3-azabicyclo[3.1.0]hex-1-yl]-2-methyl-1,3-benzothiazole (374 mg) in analogy to the method described in Preparation 40.

NMR ($^1$H, CDCl$_3$): δ 7.70 (m, 2H), 7.11 (d, 1H), 3.59 (t, 2H), 3.38 (d, 1H), 3.09 (d, 1H), 2.8 (s, 3H), 2.66 (m, 3H), 2.53 (dd, 1H), 1.95 (m, 2H), 1.74 (m, 1H), 1.44 (t, 1H), 0.83 (dd, 1H).

MS (m/z): 307 [MH]$^+$.

Preparation 60: 1(1R,5S/1S,5R)-[3-Fluoro-5-(trifluoromethyl)phenyl]-3-azabicyclo[3.1.0]hexane-2,4-dione

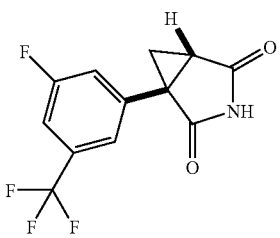

To a slurry of maleimide (1.8 eq), anhydrous CuCl$_2$ (1.2 eq) and tert-butyl nitrite (1.5 eq) in CH$_3$CN (5 mL) at 0° C. a solution of 3-fluoro-5-(trifluoromethyl)aniline (2.2 g) in CH$_3$CN (4 mL) was added dropwise. The reaction mixture was stirred at room temperature for 2 h and HCl (aqueous 6 M, 30 mL) was added. The mixture was extracted with EtOAc, the organic layer dried over Na$_2$SO$_4$. The solution was filtered and the filtrate was concentrated in vacuo. The filtered was triturated with water and dried in vacuo A DMSO (10 mL) solution of this crude product was added dropwise to a preformed solution of trimethylsulfoxonium iodide (2 eq) in anhydrous DMSO (20 mL) to which NaH (15 eq) had been added portionwise. The reaction mixture was stirred for 30 min and water was added followed by a satured solution of NH$_4$Cl (until pH 6.5). The reaction mixture was extracted with Et$_2$O, the combined organic layers were washed with saturated aqueous NaCl and dried over Na$_2$SO$_4$. The solution was filtered and the filtrate was concentrated in vacuo. The crude product obtained was triturated with cyclohexane to give the title compound as light green solid (1.02 g).

NMR ($^1$H, CDCl$_3$): δ 7.4-7.20 (m, 3H), 2.85-2.75 (m, 1H), 2.0 (m, 1H), 1.85 (m, 1H), NH not observed. MS (m/z): 274 [MH]$^+$.

Preparation 61: (1R,5S/1S,5R)-1-[3-Fluoro-5-(trifluoromethyl)phenyl]-3-azabicyclo[3.1.0]hexane

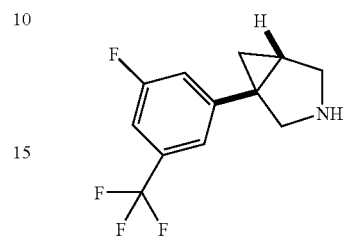

The title compound was prepared in 650 mg yield from (1R,5S/1S,5R)-1-[3-fluoro-5-(trifluoromethyl)phenyl]-3-azabicyclo[3.1.0]hexane-2,4-dione following the procedure reported for Preparation 38.

NMR ($^1$H, CDCl$_3$): δ 7.05-7.40 (m, 3H), 3.1-3.3 (m, 4H), 1.7 (m, 1H), 0.9 (m, 2H), NH not observed. MS (m/z): 246 [MH]$^+$.

Preparation 62: (1R,5S/1S,5R)-1-[2-Fluoro-3-(trifluoromethyl)phenyl]-3-azabicyclo[3.1.0]hexane

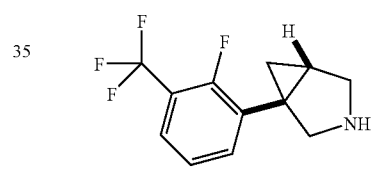

The title compound was prepared in 947 mg yield from 2-fluoro-3-(trifluoromethyl)aniline (3 g) following the procedures reported for Preparations 60 and 38.

NMR ($^1$H, CDCl$_3$): δ 7.2 (m, 2H), 6.9 (m, 1H), 3.0-2.7 (m, 4H), 1.6 (m, 1H), 0.7 (m, 2H);

MS (m/z): 246 [MH]$^+$.

Preparation 63: (1R,5S/1S,5R)-1-[4-(Methyloxy)-5-(trifluoromethyl)phenyl]-3-azabicyclo[3.1.0]hexane

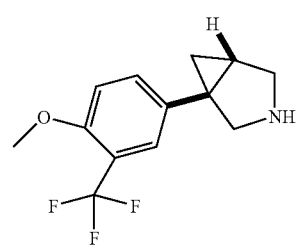

The title compound was prepared in 430 mg yield from 4-(methyloxy)-5-(trifluoromethyl)aniline (2.2 g) following the procedures reported for Preparations 60 and 38.

Preparation 64: (1R,5S/1S,5R)-1-(4-Chloro-2-fluorophenyl)-3-azabicyclo[3.1.0]hexane

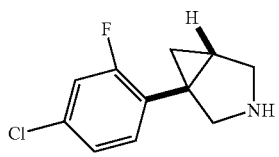

The title compound was prepared in 360 mg yield from 4-chloro-2-fluoro aniline (1.87 g) following the procedures reported for Preparations 60 and 38.

NMR ($^1$H, CDCl$_3$): δ 7.2-7.0 (m, 3H), 3.2-3.0 (m, 4H), 2.0 (s, 1H), 1.75 (m, 1H), 0.8 (m, 2H). MS (m/z): 212 [MH]$^+$.

Preparation 65: (1R,5S/1S,5R)-1-{3-[(Trifluoromethyl)oxy]phenyl}-3-azabicyclo[3.1.0]hexane

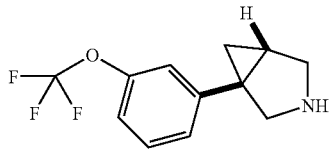

The title compound was prepared in 600 mg yield from 3-trifluoromethyloxy aniline (2.65 g) following the procedures reported for Preparations 60 and 38.

NMR ($^1$H, CDCl$_3$): δ 7.3-7 (m, 4H), 3.3-3.0 (m, 4H), 1.8 (s, 1H), 1.75 (m, 1H), 0.95 (m, 2H); MS (m/z): 212 [MH]$^+$.

Preparation 66: (1R,5S/1S,5R)-1-(2-Fluoro-4-methylphenyl)-3-azabicyclo[3.1.0]hexane

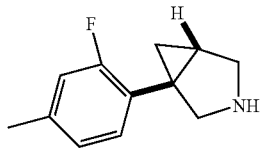

The title compound was prepared in 148 mg yield from 2-fluoro-4-methyl aniline (2.18 g) following the procedures reported for Preparations 60 and 38.

NMR ($^1$H, CDCl$_3$): δ 7.2 (m, 1H), 6.85 (m, 2H), 3.2-2.9 (m, 4H), 2.25 (s, 3H), 1.75 (s, 1H), 1.65 (m, 1H), 0.9 (m, 2H); MS (m/z): 192 [MH]$^+$.

Preparation 67: (1R,5S/1S,5R)-1-[3-Chloro-4-(methyloxy)phenyl]-3-azabicyclo[3.1.0]hexane

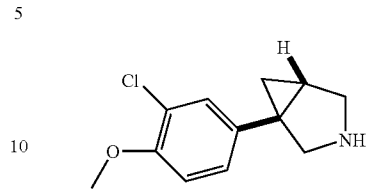

The title compound was prepared in 60 mg yield from 2-chloro-4-methyl aniline (2.36 g) following the procedures reported for Preparations 60 and 38.

NMR ($^1$H, CDCl$_3$): δ 7.15-7 (m, 2H), 6.85 (m, 1H), 3.85 (s, 3H), 3.2-2.9 (m, 4H), 1.8-1.6 (m, 2H), 0.75 (m, 2H); MS (m/z): 224 [MH]$^+$.

Preparation 68: (1R,5S/1S,5R)-1,1-Dimethylethyl 1-(4-bromophenyl)-3-azabicyclo[3.1.0]hexane-3-carboxylate

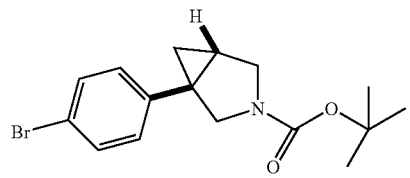

To a stirred solution of (1R,5S/1S,5R)-1-(4-bromophenyl)-3-azabicyclo[3.1.0]hexane (Preparation 6, 1.3 g) in dichloromethane (20 mL) at room temperature, triethylamine (0.99 mL) and bis(1,1-dimethylethyl)dicarbonate were added. Stirring was continued over 6 h, then the reaction mixture was concentrated under vacuum and the crude product treated with diethyl ether and water. The organic phase was washed with saturated ammonium chloride solution, dried over sodium sulphate and the solvent evaporated under vacuum to give a crude product that was purified by chromatography over silica gel (cyclohexane/ETOAC 9/1) affording the title compound (1.68 g, 91%).

MS (m/z): 282.1 [MH-C$_4$H$_8$]$^+$, 1Br.

Preparation 69: (1R,5S/1S,5R)-1,1-Dimethylethyl 1-[4-(4,4,5,5-tetramethyl-1,3,2-dioxaborolan-2-yl)phenyl]-3-azabicyclo[3.1.0]hexane-3-carboxylate

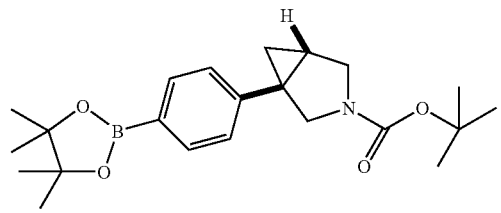

To a stirred solution of (1R,5S/1S,5R)-1,1-dimethylethyl 1-(4-bromophenyl)-3-azabicyclo[3.1.0]hexane-3-carboxylate (2 g) in DMF (30 mL), at RT, bis(pinacolate)di boron (2.25 g), potassium acetate (1.75 g) and PdCl$_2$(dppf) (0.15 g) were subsequently added. The reaction mixture was heated at 85° C. for 1.5 h, poured into water and extracted twice with diethylether, and the organic phase was washed with brine and dried over sodium sulphate. The solvent was evaporated under vacuum and the crude product purified by chromatography over silica gel (cyclohexane/ETOAC 9/1) affording the title compound as a white solid (2.1 g, 92%).

MS (m/z): 330.3 [MH-C$_4$H$_8$]$^+$, 1Br.

Preparation 70: (1R,5S/1S,5R)-1,1-Dimethylethyl 1-(3-bromophenyl)-3-azabicyclo[3.1.0]hexane-3-carboxylate

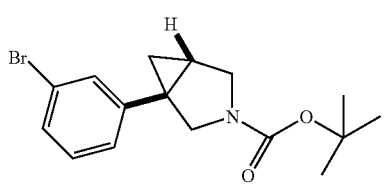

The title compound was prepared in 94% yield as a white solid in analogy to the method described for Preparation 68 starting from (1R,5S/1S,5R)-1-(3-bromophenyl)-3-azabicyclo[3.1.0]hexane (7.4 g).

MS (m/z): 282.1 [MH-C$_4$H$_8$]$^+$, 1Br.

Preparation 71: (1R,5S/1S,5R)-1,1-Dimethylethyl 1-[3-(4,4,5,5-tetramethyl-1,3,2-dioxaborolan-2-yl)phenyl]-3-azabicyclo[3.1.0]hexane-3-carboxylate

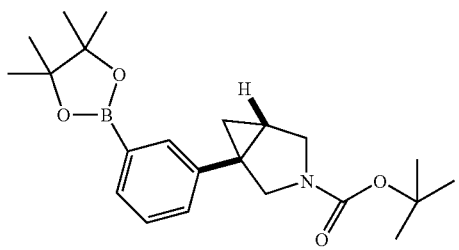

The title compound was prepared in 84% yield as a white solid in analogy to the method described for Preparation 69 starting from (1R,5S/1S,5R)-1,1-dimethylethyl 1-(3-bromophenyl)-3-azabicyclo[3.1.0]hexane-3-carboxylate (2.5 g).

MS (m/z): 330.3 [MH-C$_4$H$_8$]$^+$, 1Br.

Preparation 72: (1R,5S/1S,5R)-1-[4-(2,4-Dimethyl-1,3-thiazol-5-yl)phenyl]-3-azabicyclo[3.1.0]hexane

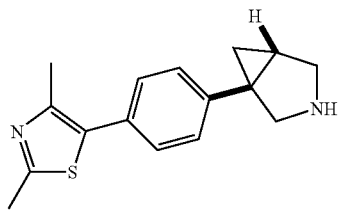

To a stirred solution of (1R,5S/1S,5R)-1,1-dimethylethyl 1-[4-(4,4,5,5-tetramethyl-1,3,2-dioxaborolan-2-yl)phenyl]-3-azabicyclo[3.1.0]hexane-3-carboxylate (0.3 g) in tetrahydrofuran (12 mL), at RT and under a nitrogen atmosphere, 5-bromo-2,4-dimethyl-1,3-thiazole (0.22 g), cesium fluoride (0.47 g) and tetrakis-(triphenylphosphin)-palladium(0) (0.06 g) were subsequently added. The reaction mixture was heated at 80° C. for 4 h and the solvent evaporated under vacuum. The crude product was treated with diethyl ether and saturated aqueous ammonium chloride solution, the organic phase was washed with brine, dried over sodium sulphate and concentrated under vacuum. The crude product was purified by chromatography over silica gel (cyclohexane/ETOAC 8/1). The purified product was then dissolved in CH$_2$Cl$_2$ (10 mL) and trifluoroacetic acid was added (4 mL). After 2 h the reaction mixture was treated with solid sodium carbonate and the solvent evaporated. The residue was treated with water and extracted with CH$_2$Cl$_2$, the organic phase washed with brine, dried over sodium sulphate and evaporated to give the title compound (0.1 g, 34%).

MS (m/z): 271.2 [MH]$^+$.

Preparation 73: (1R,5S/1S,5R)-1-{4-[6-(Trifluoromethyl)-2-pyridinyl]phenyl}-3-azabicyclo[3.1.0]hexane

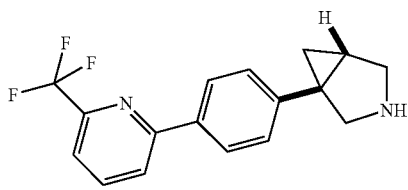

The title compound was prepared in analogy to the method described for Preparation 72 (using 2-bromo-6-(trifluoromethyl)pyridine) in 60% yield.

MS (m/z): 305.3 [MH]$^+$.

Preparation 74: (1R,5S/1S,5R)-1-[4-(3,5-Dimethyl-4-isoxazolyl)phenyl]-3-azabicyclo[3.1.0]hexane

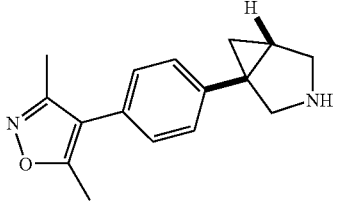

To a stirred solution of (1R,5S/1S,5R)-1,1-dimethylethyl 1-(4-bromophenyl)-3-azabicyclo[3.1.0]hexane-3-carboxylate (0.37 g) in toluene (5 mL) and ethyl alcohol (2 mL), at RT and under a nitrogen atmosphere, (3,5-dimethyl-4-ixazolyl) boronic acid (0.25 g), tetrakis-(triphenylphosphin)-palladium(0) (0.03 g) and a saturated solution of potassium carbonate (2 mL) were subsequently added. The reaction mixture was heated at 88° C. for 2 h, and the solvents evaporated under vacuum. The crude product was treated with diethyl ether and water, the organic phase washed with brine, dried over sodium sulphate, concentrated under vacuum and extracted twice with ether. The solvent was evaporated and the crude product purified by chromatography over silica gel (cyclohexane/ETOAC 8/1). The recovered product was then dissolved in $CH_2Cl_2$ (10 mL) and trifluoroacetic acid was added (4 mL). After 3 h the reaction mixture was treated with solid sodium carbonate and the solvent evaporated. The residue was treated with water and extracted with $CH_2Cl_2$, the organic phase washed with brine, dried over sodium sulphate and evaporated to give the title compound (0.12 g, 45%).

MS (m/z): 255.2 $[MH]^+$.

Preparation 75: (1R,5S/1S,5R)-1-[3-(2,4-Dimethyl-1,3-thiazol-5-yl)phenyl]-3-azabicyclo[3.1.0]hexane

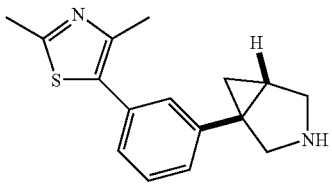

The title compound was prepared in analogy to the method described for Preparation 72, using (1R,5S/1S,5R)-1,1-dimethylethyl 1-[3-(4,4,5,5-tetramethyl-1,3,2-dioxaborolan-2-yl)phenyl]-3-azabicyclo[3.1.0]hexane-3-carboxylate intermediate 4), in 50% yield.

MS (m/z): 271.3 $[MH]^+$.

Preparation 76: (1R,5S/1S,5R)-1-[3-(5-Methyl-2-thienyl)phenyl]-3-azabicyclo[3.1.0]hexane

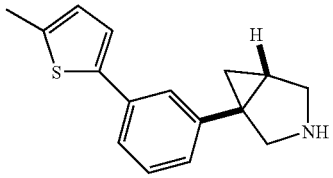

The title compound was prepared in analogy to the method described for Preparation 72, using (1R,5S/1S,5R)-1,1-dimethylethyl 1-[3-(4,4,5,5-tetramethyl-1,3,2-dioxaborolan-2-yl)phenyl]-3-azabicyclo[3.1.0]hexane-3-carboxylate intermediate 4), in 55% yield.

MS (m/z): 256.2 $[MH]^+$.

Preparation 77: 5-(2,4-Dimethyl-1,3-oxazol-5-yl)-4-methyl-2,4-dihydro-3H-1,2,4-triazole-3-thione

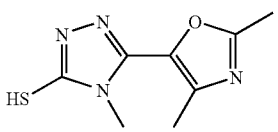

2,4-Dimethyl-1,3-oxazole-5-carboxylic acid (0.8 g), N-methylhydrazinecarboxamide (0.6 g), 1-(3-Dimethylaminopropyl)-3-ethyl carbodiimide hydrochloride (1.09 g), HOBt (0.038 g) and triethylamine (0.86 ml) were dissolved, under nitrogen, in dry DMF (15 ml) at room temperature. The mixture was stirred overnight, then DMF was removed under vacuum. NaOH (0.75M, 10 ml) was added and mixture was heated at 80° C. for 3 h. The reaction mixture was cooled to 0° C. and acidified to ca. pH 5 with HCl (aqueous, 37%). The suspended product was isolated by filtration, washing with water (2×3 ml). The cake was dried at room temperature overnight under vacuum to give the title compound in a 3:2 mixture with 2,4-dimethyl-1,3-oxazole-5-carboxylic acid as a solid foam (0.68 g, 57% yield).

NMR ($^1$H, CDCl$_3$): δ 3.80 (s, 3H), 2.60 (s, 3H), 2.40 (s, 3H), NH/SH not observed.

Preparation 78: 3-[(3-Chloropropyl)thio]-5-(2,4-dimethyl-1,3-oxazol-5-yl)-4-methyl-4H-1,2,4-triazole

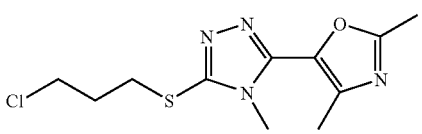

The product mixture from Preparation 77 was suspended in EtOH (10 ml). NaOEt (21% solution in EtOH, 1.14 ml) was added followed by 1-bromo-3-chloropropane (0.41 ml), the solution stirred at 90° C. for 45 min, then cooled to 25° C. Acetic acid (0.1 eq.) was added than solvent was removed under vacuum. The solid was purified by silica gel column chromatography, eluting with cyclohexane/EtOAc to give the title compound as a solid foam (0.44 g, 54% yield).

NMR ($^1$H, CDCl$_3$): δ 3.70 (t+s, 5H), 3.35 (t, 2H), 2.50 (s, 3H), 2.4 (s, 3H), 2.30 (m, 2H).

MS (m/z): 287 [MH]$^+$.

Example 1

5-[5-({3-[(1R,5S/1S,5R)-1-(4-Methoxyphenyl)-3-azabicyclo[3.1.0]hex-3-yl]propyl}thio)-4-methyl-4H-1,2,4-triazol-3-yl]-2-mthylquinoline hydrochloride

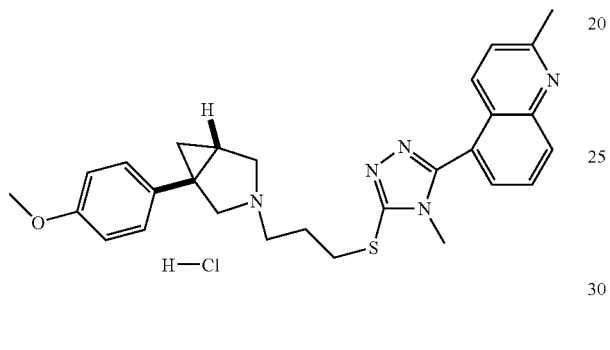

A mixture of (1R,5S/1S,5R)-1-[4-(methoxy)phenyl]-3-azabicyclo[3.1.0]hexane (Preparation 5, 42 mg), 5-{5-[(3-chloropropyl)thio]-4-methyl-4H-1,2,4-triazol-3-yl}-2-methylquinoline (0.26 mmol), Na$_2$CO$_3$ (0.44 mmol) and NaI (0.22 mmol) in DMF (anhydrous, 0.4 mL) was heated at 60° C. for 24 h. After elimination of the solvent under vacuo, the residue was dissolved in ethyl acetate and the organic layer was washed with saturated aqueous NaHCO$_3$ and dried over Na$_2$SO$_4$. This solution was filtered and the filtrate was concentrated in vacuo. The crude was purified by flash chromatography (dichloromethane to 10% MeOH in dichloromethane) to give 65 mg of the free base of the title compound. To a solution of this material in dichloromethane (0.2 mL) was added 0.14 mmol of HCl (1M in Et$_2$O), the solvent evaporated under vacuo and the material thus obtained triturated with Et$_2$O to give 69 mg of the title compound as a white slightly hygroscopic solid (59% yield).

[The procedure may in analogy be adapted to other combinations of 1-substituted 3-azabicyclo[3.1.0]hexanes and 3-substituted 5-[(3-chloropropyl)thio]-4-methyl-4H-1,2,4-triazols. An equivalent molar amount of K$_2$CO$_3$ may be used to replace Na$_2$CO$_3$.]

NMR ($^1$H, DMSO): δ 10.57 (bs, 1H), 8.28 (bs, 1H), 8.2 (d, 1H), 7.94 (t, 1H), 7.82 (d, 1H), 7.56 (d, 1H), 7.25 (d, 2H), 6.91 (d, 2H), 4.01 (dd, 1H), 3.7 (m, 1H), 3.74 (s, 3H), 3.6-3.2 (m, 6H), 3.42 (s, 3H), 2.75 (s, 3H), 2.24 (quint, 2H), 2.08 (quint, 1H), 1.62/1.05 (t/t, 2H). MS (m/z): 486.3 [MH]$^+$.

Example 1 was separated to give the separated enantiomers by semipreparative Supercritical Fluid Chromatography (Gilson) using a chiral column Chiralpak AD-H, 25×2.1 cm, eluent CO$_2$ containing 20% (ethanol+0.1% isopropanol), flow rate 25 mL/min, P 194 bar, T 35° C., detection UV at 220 nm, loop 1 mL. Retention times given were obtained using an analytical Supercritical Fluid Chromatography (Gilson) using a chiral column Chiralpak AD-H, 25×0.46 cm, eluent CO$_2$ containing 20% (ethanol+0.1% isopropanol), flow rate 2.5 mL/min, P 194 bar, T 35° C., detection UV at 220 nm.

Enantiomer 1 was recovered in 15 mg yield as white solid (y=27%) from the racemate (60 mg). Rt.=39.2 min.

Enantiomer 2 was recovered in 17 mg yield as white solid (y=30%) from the racemate (60 mg). Rt.=43.4 min.

Enantiomer 1 showed fpKi (D3)>1 log-unit higher than Enantiomer 2.

Example 2

5-[5-({3-[(1R,5S/1S,5R)-1-(4-Bromophenyl)-3-azabicyclo[3.1.0]hex-3-yl]propyl}thio)-4-methyl-4H-1,2,4-triazol-3-yl]-2-methylquinoline hydrochloride

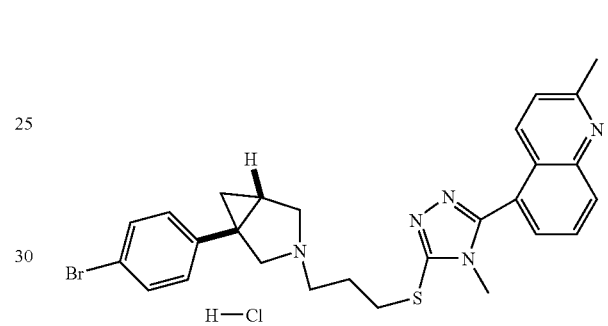

The title compound was prepared in analogy to the method described in Example 1 in 39 mg yield as a white slightly hygroscopic solid (y=40%) from (1R,5S/1S,5R)-1-(4-bromophenyl)-3-azabicyclo[3.1.0]hexane (40 mg).

NMR ($^1$H, DMSO): δ 10.28 (bs, 1H), 8.16 (dd, 2H), 7.89 (dd, 1H), 7.76 (d, 1H), 7.55 (d, 2H), 7.49 (d, 1H), 7.28 (d, 2H), 4.06 (bm, 1H), 3.77 (bm, 1H), 3.6 (bm, 2H), 3.44 (s, 3H), 3.5-3.2 (bm, 4H), 2.71 (s, 3H), 2.23 (m, 3H), 1.58/1.14 (t/m, 2H). MS (m/z): 534.1 [MH]$^+$, 1 Br.

Example 2 was separated to give the separated enantiomers by semipreparative Supercritical Fluid Chromatography (Gilson) using a chiral column Chiralcel OJ-H, 25×2.1 cm, eluent CO$_2$ containing 12% (ethanol+0.1% isopropylamine), flow rate 2.5 mL/min, P 196 bar, T 36° C., detection UV at 220 nm, loop 1 mL. Retention times given were obtained using an analytical Supercritical Fluid Chromatography (Gilson) using a chiral column Chiralcel OJ-H, 25×0.46 cm, eluent CO$_2$ containing 10% (ethanol+0.1% isopropylamine), flow rate 2.5 mL/min, P 196 bar, T 35° C., detection UV at 220 nm.

Enantiomer 1 was recovered in 7 mg yield as white solid, hydrochloride salt from the racemate (39 mg). Rt.=56.8 min. Purity >99% a/a by UV.

Enantiomer 2 was recovered in 7 mg yield as white solid, hydrochloride salt from the racemate (39 mg). Rt.=62.5 min. Purity >99% a/a by UV.

The absolute configuration of Enantiomer 1 was assigned using comparative VCD and comparative OR analyses of the corresponding free base to be 5-[5-({3-[(1R,5S)-1-(4-bromophenyl)-3-azabicyclo[3.1.0]hex-3-yl]propyl}thio)-4-methyl-4H-1,2,4-triazol-3-yl]-2-methylquinoline. (1S,5R)-1-

(3,4-dichlorophenyl)-3-azabicyclo[3.1.0]hexane (see Preparation 48) was used as the reference.

The absolute configuration of Enantiomer 2 was assigned as described for Enantiomer 1 to be 5-[5-({3-[(1S,5R)-1-(4-bromophenyl)-3-azabicyclo[3.1.0]hex-3-yl]propyl}thio)-4-methyl-4H-1,2,4-triazol-3-yl]-2-methylquinoline.

Enantiomer 1: Specific Optical Rotation of the corresponding free base: $[\alpha]_D$=+47° (CHCl$_3$, T=20° C., c=0.066 g/mL).

Enantiomer 2: Specific Optical Rotation of the corresponding free base: $[\alpha]_D$=−42° (CHCl$_3$, T=20° C., c=0.065 g/mL).

Enantiomer 2 showed fpKi (D3)>1 log-unit higher than Enantiomer 1.

Example 3

2-Methyl-5-[4-methyl-5-({3-[(1R,5S/1S,5R)-1-phenyl-3-azabicyclo[3.1.0]hex-3-yl]propyl}thio)-4H-1,2,4-triazol-3-yl]quinoline hydrochloride

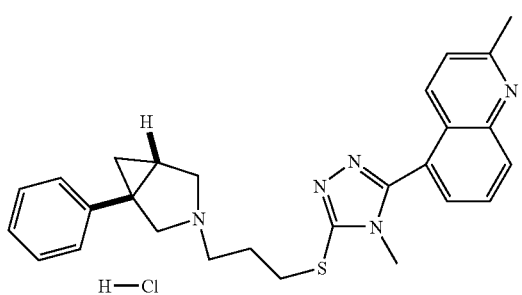

The title compound was prepared in analogy to the method described in Example 1 in 74 mg yield as a white slightly hygroscopic solid (y=59%) from (1R,5S/1S,5R)-1-phenyl-3-azabicyclo[3.1.0]hexane (40 mg).

NMR ($^1$H, DMSO): δ 10.4 (bs, 1H), 8.3 (bs, 1H), 8.2 (d, 1H), 7.9 (t, 1H), 7.8 (d, 1H), 7.6 (bd, 1H), 7.4-7.3 (m, 5H), 4.0-3.5 (m/m, 2H), 3.7-3.45 (m/m, 2H), 3.5-3.3 (m, 7H), 2.73 (s, 3H), 2.3 (m, 3H), 1.60, 1.1 (t, t 2H). MS (m/z): 456.3 [MH]$^+$.

Example 3 was separated to give the separated enantiomers by semi-preparative HPLC using a chiral column Chiralcel OD 10 µm, 250×20 mm, eluent A: n-hexane; B: isopropanol, gradient isocratic 35% B, flow rate 7 mL/min, detection UV at 200-400 nm, CD 230 nm. Retention times given were obtained using an analytical HPLC using a chiral column Chiralcel OD 5 µm, 250×4.6 mm, eluent A: n-hexane; B: isopropanol, gradient isocratic 25% B, flow rate 1 mL/min, detection UV at 200-400 nm.

Enantiomer 1 was recovered in 15 mg yield as white solid (y=27%) from the racemate (60 mg). Rt.=39.2 min.

Enantiomer 2 was recovered in 17 mg yield as white solid (y=30%) from the racemate (60 mg). Rt.=43.4 min.

Enantiomer 2 showed fpKi (D3)>1 log-unit higher than Enantiomer 1.

Example 4

5-[5-({3-[(1R,5S/1S,5R)-1-(3,4-Dichlorophenyl)-3-azabicyclo[3.1.0]hex-3-yl]propyl}thio)-4-methyl-4H-1,2,4-triazol-3-yl]-2-methylquinoline hydrochloride The title compound was prepared in analogy to the method described in Example 1 in 65 mg yield as a white slightly hygroscopic solid (y=52%) from (1R,5S/1S,5R)-1-(3,4-dichlorophenyl)-3-azabicyclo[3.1.0]hexane (50 mg).

NMR ($^1$H, DMSO): δ 10.6 (s, 1H), 8.32 (bs, 1H), 8.21 (d, 1H), 7.96 (d, 1H), 7.84 (d, 1H), 7.66 (d, 1H), 7.61 (d, 1H), 7.6 (d, 1H), 7.31 (dd, 1H), 4.06 (m, 2H), 3.74 (m, 2H), 3.7-3.2 (m, 4H), 3.36 (s, 3H), 2.76 (s, 3H), 2.25 (m, 4H), 1.69 (m, 1H), 1.2 (m, 1H). MS (m/z): 524.3 [MH]$^+$, 2Cl.

Example 4 was separated to give the separated enantiomers by semipreparative Supercritical Fluid Chromatography (Gilson) as described in Example 1.

Enantiomer 1 was recovered in 19 mg yield as white solid (y=36%) from the racemate (56 mg). Rt.=26.9 min.

The absolute configuration of Enantiomer 1 was assigned using comparative VCD and comparative OR analyses of the corresponding free base to be 5-[5-({3-[(1S,5R)-1-(3,4-dichlorophenyl)-3-azabicyclo[3.1.0]hex-3-yl]propyl}thio)-4-methyl-4H-1,2,4-triazol-3-yl]-2-methylquinoline. (1S,5R)-1-(3,4-dichlorophenyl)-3-azabicyclo[3.1.0]hexane (see Preparation 48) was used as the reference.

The absolute configuration of Enantiomer 2 was assigned as described for Enantiomer 1 to be 5-[5-({3-[(1R,5S)-1-(3,4-dichlorophenyl)-3-azabicyclo[3.1.0]hex-3-yl]propyl}thio)-4-methyl-4H-1,2,4-triazol-3-yl]-2-methylquinoline.

Enantiomer 1: Specific Optical Rotation of the corresponding free base: $[\alpha]_D$=−38.4° (CDCl$_3$, T=20° C., c=0.010 g/mL).

Enantiomer 2 was recovered in 14 mg yield as white solid (y=26%) from the racemate (56 mg). Rt.=31.4 min.

Enantiomer 2: Specific Optical Rotation of the corresponding free base: $[\alpha]_D$=+34.4° (CDCl$_3$, T=20° C., c=0.010 g/mL).

Enantiomer 1 showed fpKi (D3)>0.6 log-unit higher than Enantiomer 2.

Example 5

5-[5-({3-[(1R,5S/1S,5R)-1-(4-tert-Butylphenyl)-3-azabicyclo[3.1.0]hex-3-yl]propyl}thio)-4-methyl-4H-1,2,4-triazol-3-yl]-2-methylquinoline hydrochloride

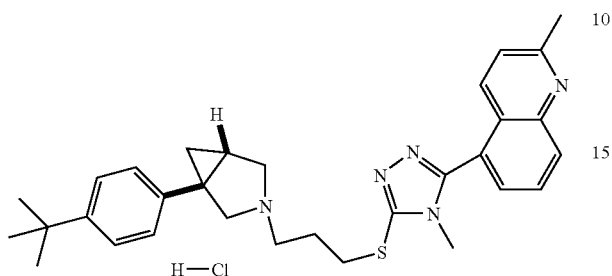

The title compound was prepared in analogy to the method described in Example 1 in 38 mg yield as a white slightly hygroscopic solid (y=51%) from (1R,5S/1S,5R)-1-(4-tert-butylphenyl)-3-azabicyclo[3.1.0]hexane (29 mg).

NMR ($^1$H, DMSO): δ 10.16 (bs, 1H), 8.15 (dd, 2H), 7.89 (t, 1H), 7.76 (d, 1H), 7.49 (d, 1H), 7.36 (d, 2H), 7.23 (d, 2H), 4.05 (dd, 1H), 3.77 (dd, 1H), 3.58 (m, 2H), 3.44 (s, 3H), 2.7 (bm, 4H), 2.34 (s, 3H), 2.23 (t, 2H), 2.15 (t, 1H), 1.51 (t, 1H), 1.27 (s, 9H), 1.14 (m, 1H). MS (m/z): 512.4 [MH]$^+$.

Example 5 was separated to give the separated enantiomers by semipreparative Supercritical Fluid Chromatography (Gilson) as described in Example 1 but applying a pressure of 200 bar instead of 194 bar.

Enantiomer 1 was recovered in 6.5 mg yield as white solid (y=30%) from the racemate (23 mg). Rt.=7.0 min.

Enantiomer 2 was recovered in 5 mg yield as white solid (y=23%) from the racemate (23 mg). Rt.=7.8 min.

Enantiomer 2 showed fpKi (D3)>0.9 log-unit higher than Enantiomer 1.

Example 6

4-[(1R,5S/1S,5R)-3-(3-{[4-Methyl-5-(2-methylquinolin-5-yl)-4H-1,2,4-triazol-3-yl]thio}propyl)-3-azabicyclo[3.1.0]hex-1-yl]benzonitrile hydrochloride

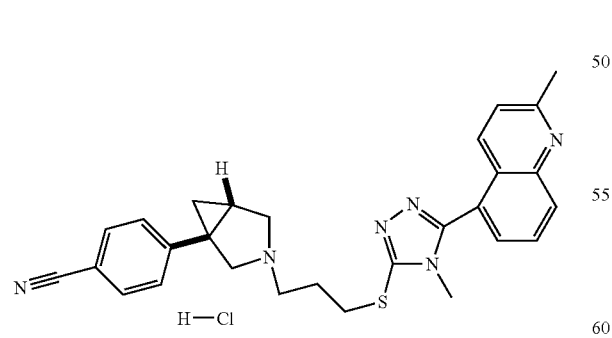

The title compound was prepared in analogy to the method described in Example 1 in 19 mg yield as a white slightly hygroscopic solid (y=27%) from (1R,5S/1S,5R)-1-(4-cyanophenyl)-3-azabicyclo[3.1.0]hexane (25 mg).

NMR ($^1$H, DMSO): δ 10.45 (bs, 1H), 8.26 (bd, 1H), 8.17 (d, 1H), 7.93 (t, 1H), 7.8 (d/d, 3H), 7.5 (d, 1H), 7.46 (d, 2H), 4.09 (d, 1H), 3.76 (d, 1H), 3.67 (t, 1H), 3.6-3.2 (bm, 5H), 3.43 (s, 3H), 2.73 (s, 3H), 2.34 (m, 1H), 2.25 (quint., 2H), 1.71/1.22 (dt, 2H).

Example 7

4-[(1R,5S/1S,5R)-3-(3-{[4-Methyl-5-(2-methylquinolin-5-yl)-4H-1,2,4-triazol-3-yl]thio}propyl)-3-azabicyclo[3.1.0]hex-1-yl]phenol hydrochloride

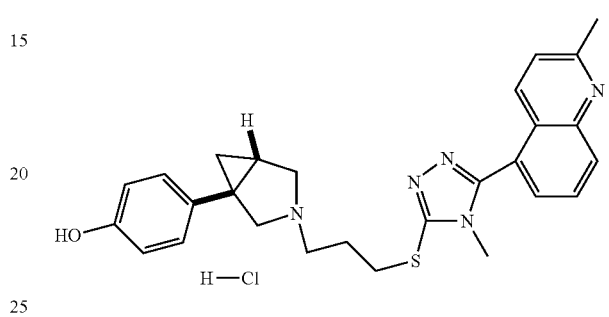

The title compound was prepared in analogy to the method described in Example 1 in 10 mg yield as a white slightly hygroscopic solid (y=11%) from (1R,5S/1S,5R)-1-(4-hydroxyphenyl)-3-azabicyclo[3.1.0]hexane (38 mg).

NMR ($^1$H, DMSO): δ 10.17 (bs, 1H), 9.4 (s, 1H), 8.15 (bd, 2H), 7.89 (d, 1H), 7.75 (d, 1H), 7.48 (d, 1H), 7.12 (d, 2H), 6.73 (d, 2H), 3.98 (dd, 1H), 3.74 (m, 1H), 3.5 (bm, 2H), 3.44 (s, 3H), 3.5-3.2 (bm, 4H), 2.7 (s, 3H), 2.22 (bquint. 2H), 2.03 (m, 1H), 1.46/1.03 (dm, 2H). MS (m/z): 486.2 [MH]$^+$.

Example 8

(1R,5S/1S,5R)-3-(3-{[4-methyl-5-(4-methyl-1,3-oxazol-5-yl)-4H-1,2,4-triazol-3-yl]thio}propyl)-1-phenyl-3-azabicyclo[3.1.0]hexane hydrochloride

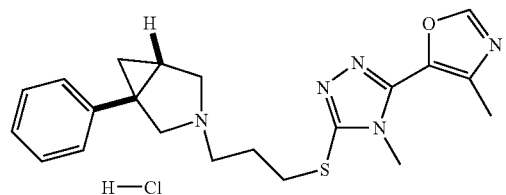

The title compound was prepared in analogy to the method described in Example 1 in 75 mg yield as a white slightly hygroscopic solid (y=70%) from (1R,5S/1S,5R)-1-phenyl-3-azabicyclo[3.1.0]hexane (40 mg).

NMR ($^1$H, DMSO): δ 10.46 (bs, 1H), 8.58 (s, 1H), 7.4-7.2 (m, 5H), 4.04 (dd, 1H), 3.73 (m, 1H), 3.7 (s, 3H), 3.7-3.4 (m, 2H), 3.4-3.2 (m+t, 4H), 2.39 (s, 3H), 2.17 (m, 3H), 1.64, 1.1 (2t, 2H).

Example 9

(1R,5S/1S,5R)-1-(4-Bromophenyl)-3-(3-({[4-methyl-5-(4-methyl-1,3-oxazol-5-yl)-4H-1,2,4-triazol-3-yl]thio}propyl)-3-azabicyclo[3.1.0]hexane hydrochloride

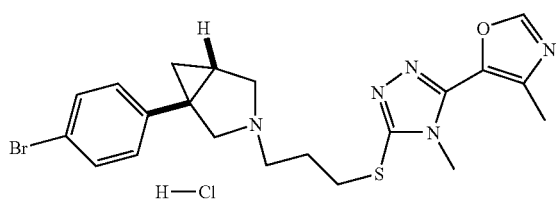

The title compound was prepared in analogy to the method described in Example 1 in 24 mg yield as a white slightly hygroscopic solid (y=28%) from (1R,5S/1S,5R)-1-(4-bromophenyl)-3-azabicyclo[3.1.0]hexane (40 mg).

NMR ($^1$H, DMSO): δ 10.29 (bs, 1H), 8.58 (s, 1H), 7.55 (dd, 2H), 7.27 (dd, 2H), 4.03 (dd, 1H), 3.73 (dd, 1H), 3.7 (s, 3H), 3.55 (m, 2H), 3.5-3.2/3.28 (m+t, 4H), 2.39 (s, 3H), 2.19 (m, 3H), 1.59/1.12 (2t, 2H). MS (m/z): 474.1 [MH]$^+$.

Example 9 was separated to give the separated enantiomers by semipreparative Supercritical Fluid Chromatography (Gilson) using a chiral column Chiralcel AS-H, 25×2.1 cm, eluent CO$_2$ containing 11% (ethanol+0.1% isopropylamine), flow rate 22 mL/min, P 192 bar, T 36° C., detection UV at 220 nm, loop 2 mL. Retention times given were obtained using an analytical Supercritical Fluid Chromatography (Gilson) using a chiral column Chiralpak AS-H, 25×0.46 cm, eluent CO$_2$ containing 10% (ethanol+0.1% isopropyilamine), flow rate 2.5 mL/min, P 199 bar, T 35° C., detection UV at 220 nm.

Enantiomer 1 was recovered in 59 mg yield as white solid, hydrochloride salt from the racemate (138 mg). Rt.=22.2 min. Purity >99% a/a by UV Enantiomer 2 was recovered in 50 mg yield as white solid, hydrochloride salt from the racemate (138 mg). Rt.=30.8 min. Purity >99% a/a by UV The absolute configuration of Enantiomer 1 was assigned using comparative VCD and comparative OR analyses of the corresponding free base to be (1S,5R)-1-(4-bromophenyl)-3-(3-{[4-methyl-5-(4-methyl-1,3-oxazol-5-yl)-4H-1,2,4-triazol-3-yl]thio}propyl)-3-azabicyclo[3.1.0]hexane. (1R,5S)-1-(4-Bromophenyl)-3-azabicyclo[3.1.0]hexane (compare Preparation 32) was used as the reference.

The absolute configuration of Enantiomer 2 was assigned as described for Enantiomer 1 to be (1R,5S)-1-(4-bromophenyl)-3-(3-{[4-methyl-5-(4-methyl-1,3-oxazol-5-yl)-4H-1,2,4-triazol-3-yl]thio}propyl)-3-azabicyclo[3.1.0]hexane.

Enantiomer 1: Specific Optical Rotation of the corresponding free base: [α]$_D$=−51° (CHCl$_3$, T=20° C., c=0.00913 g/mL).

Enantiomer 2: Specific Optical Rotation of the corresponding free base: [α]$_D$=+27° (CHCl$_3$, T=20° C., c=0.0113 g/mL).

Enantiomer 1 showed fpKi (D3)>1 log-unit higher than Enantiomer 2.

Example 10

(1R,5S/1S,5R)-1-(4-tert-Butylphenyl)-3-(3-{[4-methyl-5-(4-methyl-1,3-oxazol-5-yl)-4H-1,2,4-triazol-3-yl]thio}propyl)-3-azabicyclo[3.1.0]hexane hydrochloride

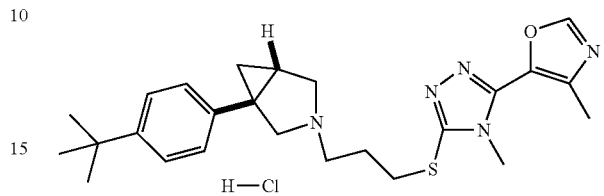

The title compound was prepared in analogy to the method described in Example 1 in 52 mg yield as a white slightly hygroscopic solid (y=57%) from (1R,5S/1S,5R)-1-(4-tert-butylphenyl)-3-azabicyclo[3.1.0]hexane (40 mg).

NMR ($^1$H, CD3OD): δ 8.4 (s, 1H), 7.42 (d, 2H), 7.28 (d, 2H), 4.11 (d, 1H), 3.88 (d, 1H), 3.8 (s, 3H), 3.65 (m, 2H), 3.43 (t, 2H), 3.39 (t, 2H), 2.47 (s, 3H), 2.29 (m, 2H), 2.21 (m, 1H), 1.44 (m, 1H), 1.33 (s, 9H), 1.3 (m, 1H). MS (m/z): 452.3 [MH]$^+$.

Example 11

(1R,5S/1S,5R)-1-(3,4-Dichlorophenyl)-3-(3-{[4-methyl-5-(4-methyl-1,3-oxazol-5-yl)-4H-1,2,4-triazol-3-yl]thio}propyl)-3-azabicyclo[3.1.0]hexane hydrochloride

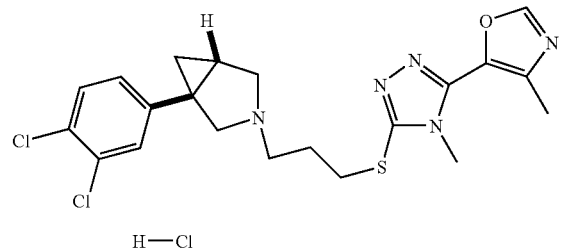

The title compound was prepared in analogy to the method described in Example 1 in 35 mg yield as a white slightly hygroscopic solid (y=32%) from (1R,5S/1S,5R)-1-(3,4-dichlorophenyl)-3-azabicyclo[3.1.0]hexane (50 mg).

NMR ($^1$H, DMSO): δ 10.11 (vbs, 1H), 8.58 (s, 1H), 7.6 (d+d, 2H), 6.29 (dd, 1H), 4.04/3.74 (2 dd, 2H), 3.7 (s, 3H), 3.6-3.2 (m, 4H), 3.28 (t, 2H), 2.39 (s, 3H), 2.26 (quint, 1H), 2.15 (quint., 2H), 1.53/1.2 (2t, 2H). MS (m/z): 464.1 [MH]$^+$, 2Cl.

Example 11 was separated to give the separated enantiomers by semipreparative Supercritical Fluid Chromatography (Gilson) using a chiral column Chiralpak AS-H, 25×2.1 cm, eluent CO$_2$ containing 8% (ethanol+0.1% isopropylamine), flow rate 22 mL/min, P 194 bar, T 36° C., detection UV at 220 nm, loop 1 mL. Retention times given were obtained using an analytical Supercritical Fluid Chromatography (Gilson) using a chiral column Chiralpak AS-H,

Example 12

(1R,5S/1S,5R)-1-(4-methoxyphenyl)-3-(3-{[4-methyl-5-(4-methyl-1,3-oxazol-5-yl)-4H-1,2,4-triazol-3-yl]thio}propyl)-3-azabicyclo[3.1.0]hexane hydrochloride

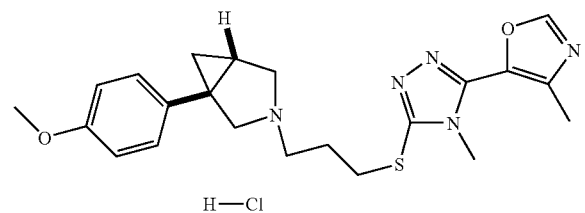

The title compound was prepared in analogy to the method described in Example 1 in 38 mg yield as a white slightly hygroscopic solid (y=39%) from (1R,5S/1S,5R)-1-(4-methoxyphenyl)-3-azabicyclo[3.1.0]hexane (40 mg).

NMR (¹H, DMSO): δ 10.18 (bs, 1H), 8.58 (s, 1H), 7.24 (d, 2H), 6.91 (d, 2H), 3.97 (dd, 1H), 3.74 (s, 3H), 3.7 (s, 3H), 3.7 (m, 1H), 3.6-3.2 (m, 4H), 3.27 (t, 2H), 2.39 (s, 3H), 2.15 (quint, 2H), 2.07 (quint., 1H), 1.49/1.05 (2t, 2H). MS (m/z): 426.2 [MH]⁺.

Example 12 was separated to give the separated enantiomers by semipreparative Supercritical Fluid Chromatography (Gilson) using a chiral column Chiralpak AS-H, 25×2.1 cm, eluent CO₂ containing 9% (ethanol+0.1% isopropylamine), flow rate 22 mL/min, P 192 bar, T 36° C., detection UV at 220 nm, loop 1 mL. Retention times given were obtained using an analytical Supercritical Fluid Chromatography (Gilson) using a chiral column Chiralpak AS-H, 25×0.46 cm, eluent CO₂ containing 8% (ethanol+0.1% isopropylamine), flow rate 2.5 mL/min, P 190 bar, T 35° C., detection UV at 220 nm.

Enantiomer 1 was recovered in 5 mg yield as white solid, hydrochloride salt from the racemate (30 mg). Rt.=28.7 min. Purity >99% a/a by UV.

Enantiomer 2 was recovered in 12.5 mg yield as white solid, hydrochloride salt from the racemate (30 mg). Rt.=36.4 min. Purity >99% a/a by UV.

Enantiomer 1 showed fpKi (D3)>1 log-unit higher than Enantiomer 2.

25×0.46 cm, eluent CO₂ containing 8% (ethanol+0.1% isopropylamine), flow rate 2.5 mL/min, P 190 bar, T 35° C., detection UV at 220 nm.

Enantiomer 1 was recovered in 12.5 mg yield as white solid, hydrochloride salt from the racemate (29 mg). Rt.=38.0 min. Purity 98.6% a/a by UV.

Enantiomer 2 was recovered in 12.5 mg yield as white solid, hydrochloride salt from the racemate (29 mg). Rt.=40.8 min. Purity 98.6% a/a by UV.

Enantiomer 1 showed fpKi (D3)>0.5 log-units higher than Enantiomer 2.

Example 13

(1R,5S/1S,5R)-1-[4-(5-methyl-3-isoxazolyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane hydrochloride

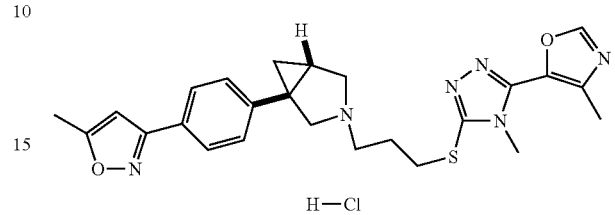

The title compound was prepared in analogy to the method described in Example 1 in 30 mg yield as a white slightly hygroscopic solid (y=25%) from (1R,5S/1S,5R)-1-[4-(5-methyl-3-isoxazolyl)phenyl]-3-azabicyclo[3.1.0]hexane (55 mg).

NMR (¹H, CD₃OD): δ 8.37 (s, 1H), 7.8 (d, 2H), 7.43 (d, 2H), 6.55 (s, 1H), 4.16/3.88 (2d, 2H), 3.78 (s, 3H), 3.7 (m, 2H), 3.48-3.4 (2t, 4H), 2.48 (s, 3H), 2.45 (s, 3H), 2.29 (m, 3H), 1.51/1.37 (2t, 2H). MS (m/z): 477.2 [MH]⁺.

Example 14

(1S,5R)-3-(3-{[4-Methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane

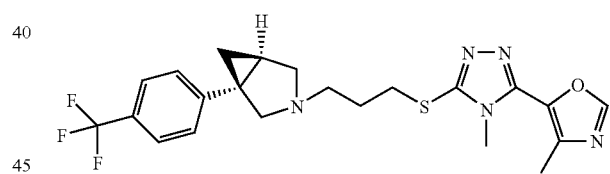

A mixture of (1S,5R)-1-[4-(trifluoromethyl)phenyl]-3-azabicyclo[3.1.0]hexane (Preparation 18, 10.4 g), 3-[(3-chloropropyl)thio]-4-methyl-5-(4-methyl-1,3-oxazol-5-yl)-4H-1,2,4-triazole (Preparation 14, 15.0 g), K₂CO₃ (7.5 g) and NaI (8.23 g) in DMF (anhydrous, 100 mL) were heated at 60° C. for 15 h. The mixture was then allowed to cool to room temperature, diluted with Et₂O (250 mL) and water (200 mL). After separation of the two phases, the aqueous layer was extracted again with Et₂O (2×200 mL). The combined organic layers were washed with water (2×150 mL) and then dried over Na₂SO₄. After evaporation of the solvent in vacuo, the crude product was purified by flash chromatography (dichloromethane to 10% MeOH in dichloromethane) to give 16.5 g of a yellow solid. The material thus obtained was triturated with Et₂O to provide the title compound (13 g) as white solid (y=61%).

Assignment of the configuration of the title compound is based on two lines of evidence: The fact that it was prepared from (1S,5R)-1-[4-(trifluoromethyl)phenyl]-3-azabicyclo[3.1.0]hexane (of known configuration, see Preparation 14)

and by comparison with the spectroscopic data obtained for (1S,5R)-1-[4-(trifluoromethyl)-phenyl]-3-azabicyclo[3.1.0] hexane: Bands in the VCD spectrum of the title compound are coincident with the corresponding bands in the spectrum of (1S,5R)-1-[4-(trifluoromethyl)phenyl]-3-azabicyclo[3.1.0] hexane, additionally the sign of the specific rotation is the same for both compounds.

NMR ($^1$H, CDCl$_3$): δ 7.89 (m, 1H), 7.49 (d, 2H), 7.18 (d, 2H), 3.67 (s, 3H), 3.31 (m, 2H), 3.30 (d, 1H), 3.09 (d, 1H), 2.61 (m, 2H), 2.56 (d, 1H), 2.5 (s, 3H), 2.45 (d, 1H), 1.97 (m, 2H), 1.73 (m, 1H), 1.47 (t, 1H), 0.8 (dd, 1H). MS (m/z): 464 [MH]$^+$.

Example 15

(1S,5R)-3-(3-{[4-Methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane hydrochloride

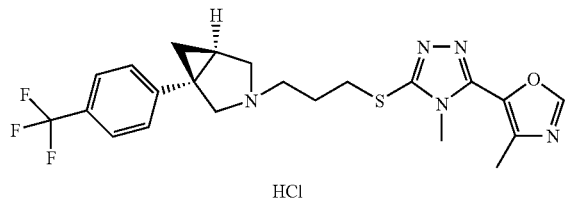

Hydrochloric acid (1M solution in Et$_2$O, 19.4 mL) was added dropwise under N$_2$ to a solution of (1S,5R)-3-(3-{[4-methyl-5-(4-methyl-1,3-oxazol-5-yl)-4H-1,2,4-triazol-3-yl] thio}propyl)-1-[4-(trifluoromethyl)phenyl]-3-azabicyclo [3.1.0]hexane (Example 14, 9 g) in Et$_2$O (anhydrous, 135 mL). The resulting suspension was allowed to stir at room temperature for 2 h. The solid was then filtered, washed with Et$_2$O and dried in vacuo overnight to provide the title compound (8.9 g) as off white solid (y=92%).

NMR ($^1$H, DMSO): δ 10.16 (bs, 1H), 8.58 (s, 1H), 7.72 (d, 2H), 7.51 (d, 2H), 4.1 (dd, 1H), 3.78 (dd, 1H), 3.70 (s, 3H), 3.66 (m, 2H), 3.29 (t, 2H), 2.5 (bm, 2H), 2.39 (s, 3H), 2.33 (quint, 2H), 2.19 (m, 1H), 1.62/1.23 (t/t, 2H). MS (m/z): 464 [MH]$^+$.

Example 16

(1R,5S/1S,5R)-1-[2-Fluoro-4-(trifluoromethyl)phenyl]-3-(3-{[4-methyl-5-(4-methyl-1,3-oxazol-5-yl)-4H-1,2,4-triazol-3-yl]thio}propyl)-3-azabicyclo [3.1.0]-hexane hydrochloride

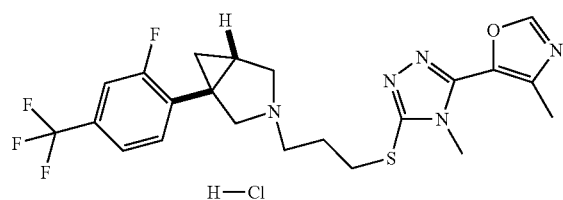

A mixture of (1R,5S/1S,5R)-1-[2-Fluoro-4-(trifluoromethyl)phenyl]-3-azabicyclo-[3.1.0]hexane (Preparation 38, 700 mg, 2.8 mmol), 3-[(3-Chloropropyl)thio]-4-methyl-5-(4-methyl-1,3-oxazol-5-yl)-4H-1,2,4-triazole (Preparation 14, 3.4 mmol), Na$_2$CO$_3$ (3.4 mmol) and NaI (3.4 mmol) in DMF (anhydrous, 6 mL) was heated at 60° C. for 24 h. After elimination of the solvent under vacuo, the residue was dissolved in ethyl acetate and the organic layer was washed with saturated aqueous NaHCO$_3$ and dried over Na$_2$SO$_4$. This solution was filtered and the filtrate was concentrated in vacuo. The crude was purified by flash chromatography (dichloromethane to 10% MeOH in dichloromethane) to give 503 mg of the free base of the title compound.

NMR ($^1$H, CDCl$_3$): δ 7.89 (s, 1H), 7.32-7.2 (m, 3H), 3.70 (s, 3H), 3.30 (t, 2H), 3.26 (dd, 1H), 3.10 (dd, 1H), 2.60 (t, 2H), 2.52 (dd, 1H), 2.51 (s, 3H), 2.43 (dd, 1H), 1.94 (m, 2H), 1.74 (m, 1H), 1.40 (t, 1H), 0.76 (dd, 1H). MS (m/z): 482.2 [MH]$^+$.

The title compound was obtained as a white solid following the method described for Example 15.

NMR ($^1$H, DMSO): δ 10.28 (bs, 1H), 8.58 (s, 1H), 7.73 (d, 1H), 7.6 (m, 2H), 4/3.57 (d/m, 2H), 3.79 (d, 1H), 3.69 (s, 3H), 3.5-3.2 (vbm, 1H), 3.27 (t, 2H), 2.5 (m, 2H), 2.4 (m, 1H), 2.38 (s, 3H), 2.14 (quint., 2H), 1.62/1.16 (2t, 2H). MS (m/z): 481 [MH]$^+$.

Example 16 was separated to give the separated enantiomers by semi-preparative HPLC using a chiral column Chiralpak AD 10 μm, 250×21 mm, eluent A: n-hexane; B: isopropanol+0.1% isopropyl amine, gradient isocratic 9% B, flow rate 7 mL/min, detection UV at 200-400 nm. Retention times given were obtained using an analytical HPLC using a chiral column Chiralpak AD-H 5 μm, 250×4.6 mm, eluent A: n-hexane; B: isopropanol, gradient isocratic 15% B, flow rate 0.8 mL/min, detection UV at 200-400 nm. Enantiomer 1 was recovered as white solid, Rt.=15.4 min.

Enantiomer 2 was recovered as white solid, Rt.=16.3 min.
Enantiomer 2 showed fpKi (D3)>1 log-unit higher than Enantiomer 1.

Example 17

(1R,5S/1S,5R)-3-(3-{[4-Methyl-5-(4-methyl-1,3-oxazol-5-yl)-4H-1,2,4-triazol-3-yl]thio}propyl)-1-[3-(trifluoromethyl)phenyl]-3-azabicyclo[3.1.0]hexane hydrochloride

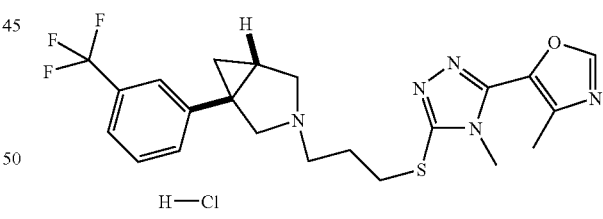

(1R,5S/1S,5R)-1-[3-(Trifluoromethyl)phenyl]-3-azabicyclo[3.1.0]hexane was prepared in analogy to the method described in Preparations 15, 16 and 17. From this material the title compound was obtained as a white slightly hygroscopic solid following the method described for Examples 14 and 15.

NMR ($^1$H, DMSO): δ 10.5 (bs, 1H), 8.58 (s, 1H), 7.7-7.5 (m, 4H), 4.09 (m, 1H), 3.8-3.2 (m, 8H), 3.29 (t, 2H), 2.39 (s, 3H), 2.3 (m, 1H), 2.18 (m, 2H), 1.68 (t, 1H), 1.21 (t, 1H). MS (m/z): 464 [MH]$^+$.

Example 17 was separated to give the separated enantiomers by semipreparative Supercritical Fluid Chromatography (Gilson) using a chiral column Chiralpak AD-H, 25×0.46 cm, eluent CO$_2$ containing 10% (ethanol+0.1% isopropanol),

Example 18

(1R,5S/1S,5R)-1-[4-Fluoro-3-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]-hexane hydrochloride

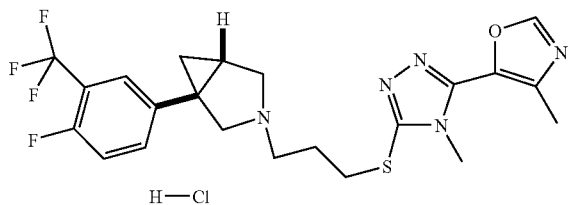

(1R,5S/1S,5R)-1-[4-Fluoro-3-(trifluoromethyl)phenyl]-3-azabicyclo[3.1.0]hexane was prepared in analogy to the method described in Preparations 15, 16 and 17. From this material the title compound was obtained as a white slightly hygroscopic solid following the method described for Examples 14 and 15.

NMR ($^1$H, DMSO): δ 10.2 (bs, 1H), 8.58 (s, 1H), 7.75 (dm, 1H), 7.72 (m, 1H), 7.53 (t, 1H), 4.06 (dd, 1H), 3.74 (dd, 1H), 3.7 (s, 3H), 3.6 (m, 2H), 3.4 (m, 2H), 3.28 (t, 2H), 2.39 (s, 3H), 2.26 (m, 1H), 2.18 (m, 2H), 1.54 (t, 1H), 1.22 (dd, 1H). MS (m/z): 481 [MH]$^+$.

Example 19

1-[5-[(1S,5R/1R,5S)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]ethanone hydrochloride

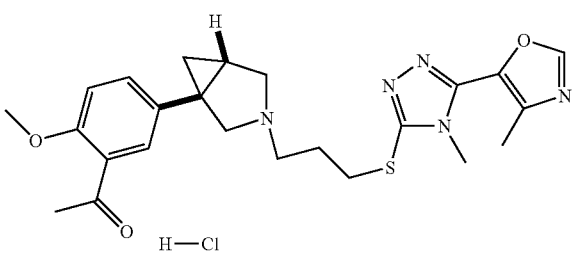

The title compound was prepared in analogy to the method described in Example 1 in 25 mg yield as a white slightly hygroscopic solid from (1R,5S/1S,5R)-1-[5-(3-azabicyclo[3.1.0]hex-1-yl]-2-(methyloxy)phenyl]ethanone (32 mg).

NMR ($^1$H, DMSO): δ 10.31 (bs, 1H), 8.58 (s, 1H), 7.52 (d, 1H), 7.49 (dd, 1H), 7.16 (d, 1H), 3.98 (dd, 1H), 3.89 (s, 3H), 3.7 (m, 4H), 3.6-3.2 (bm, 4H), 3.27 (t, 2H), 2.5 (m, 3H), 2.39 (s, 3H), 2.15 (quint, 2H), 2.09 (quint, 1H), 1.54-1.08 (2t, 2H). MS (m/z): 468 [MH]$^+$.

Example 19 was separated to give the separated enantiomers by semipreparative Supercritical Fluid Chromatography (Gilson) using a chiral column Chiralpak AS-H, 25×2.1 cm, eluent CO$_2$ containing 15% (ethanol+0.1% isopropylamine), flow rate 22 mL/min, P 196 bar, T 36° C., detection UV at 220 nm, loop 1 mL. Retention times given were obtained using an analytical Supercritical Fluid Chromatography (Gilson) using a chiral column Chiralpak AS-H, 25×0.46 cm, eluent CO$_2$ containing 15% (ethanol+0.1% isopropylamine), flow rate 2.5 mL/min, P 190 bar, T 35° C., detection UV at 220 nm.

Enantiomer 1 was recovered in 14 mg yield as white solid, hydrochloride salt from the racemate (40 mg). Rt.=12.5 min. Purity >99% a/a by UV Enantiomer 2 was recovered in 16 mg yield as white solid, hydrochloride salt from the racemate (40 mg). Rt.=16.8 min. Purity >99% a/a by UV Enantiomer 1 showed fpKi (D3)>1 log-unit higher than Enantiomer 2.

Example 20

(1S,5R/1R,5S)-1-(4-Chlorophenyl)-3-(3-{[4-methyl-5-(4-methyl-1,3-oxazol-5-yl)-4H-1,2,4-triazol-3-yl]thio}propyl)-3-azabicyclo[3.1.0]hexane hydrochloride

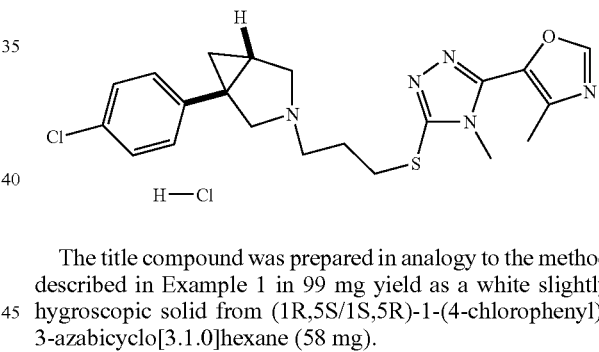

The title compound was prepared in analogy to the method described in Example 1 in 99 mg yield as a white slightly hygroscopic solid from (1R,5S/1S,5R)-1-(4-chlorophenyl)-3-azabicyclo[3.1.0]hexane (58 mg).

NMR ($^1$H, DMSO): δ 9.93 (bs, 1H), 8.58 (s, 1H), 7.42 (d, 2H), 7.33 (d, 2H), 4.04 (dd, 1H), 3.75 (dd, 1H), 3.7 (s, 3H), 3.5 (m, 2H), 3.3 (bm, 4H), 2.39 (s, 3H), 2.2 (m, 1H), 2.15 (m, 2H), 1.47-1.14 (2t, 2H). MS (m/z): 431 [MH]$^+$.

Example 20 was separated to give the separated enantiomers by semipreparative Supercritical Fluid Chromatography (Gilson) using a chiral column Chiralpak AS-H, 25×2.1 cm, eluent CO$_2$ containing 15% (ethanol+0.1% isopropylamine), flow rate 22 mL/min, P 192 bar, T 36° C., detection UV at 220 nm, loop 1 mL. Retention times given were obtained using an analytical Supercritical Fluid Chromatography (Gilson) using a chiral column Chiralpak AS-H, 25×0.46 cm, eluent CO$_2$ containing 15% (ethanol+0.1% isopropylamine), flow rate 2.5 mL/min, P 190 bar, T 35° C., detection UV at 220 nm.

Enantiomer 1 was recovered in 17 mg yield as white solid, hydrochloride salt from the racemate (40 mg). Rt.=7.8 min. Purity >99% a/a by UV Enantiomer 2 was recovered in 17 mg yield as white solid, hydrochloride salt from the racemate (40 mg). Rt.=9.7 min. Purity >99% a/a by UV The absolute configuration of Enantiomer 1 was assigned using comparative VCD and comparative OR analyses of the corresponding free base to be (1S,5R)-1-(4-chlorophenyl)-3-(3-{[4-methyl-5-(4-methyl-1,3-oxazol-5-yl)-4H-1,2,4-triazol-3-yl]thio}propyl)-3-azabicyclo[3.1.0]hexane. 5-[5-({3-[(1R,5S)-1-(4-Bromophenyl)-3-azabicyclo[3.1.0]hex-3-yl]propyl}thio)-4-methyl-4H-1,2,4-triazol-3-yl]-2-methylquinoline (compare Example 2) was used as the reference.

The absolute configuration of Enantiomer 2 was assigned as described for Enantiomer 1 to be (1R,5S)-1-(4-chlorophenyl)-3-(3-{[4-methyl-5-(4-methyl-1,3-oxazol-5-yl)-4H-1,2,4-triazol-3-yl]thio}propyl)-3-azabicyclo[3.1.0]hexane.

Enantiomer 1: Specific Optical Rotation of the corresponding free base: $[\alpha]_D = -25°$ (CHCl$_3$, T=20° C., c=0.0066 g/mL).

Enantiomer 2: Specific Optical Rotation of the corresponding free base: $[\alpha]_D = +29°$ (CHCl$_3$, T=20° C., c=0.0068 g/mL).

Enantiomer 1 showed fpKi (D3)>1 log-unit higher than Enantiomer 2.

Example 21

(1S,5R/1R,5S)-1-(4-Fluorophenyl)-3-(3-{[4-methyl-5-(4-methyl-1,3-oxazol-5-yl)-4H-1,2,4-triazol-3-yl]thio}propyl)-3-azabicyclo[3.1.0]hexane hydrochloride

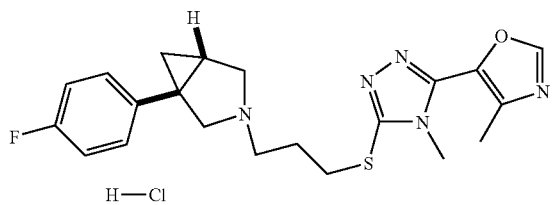

The title compound was prepared in analogy to the method described in Example 1 in 78 mg yield as a white slightly hygroscopic solid from (1R,5S/1S,5R)-1-(4-florophenyl)-3-azabicyclo[3.1.0]hexane (49 mg).

NMR ($^1$H, DMSO): δ 10.06 (bs, 1H), 8.58 (s, 1H), 7.36 (dd, 2H), 7.19 (t, 2H), 4.02 (dd, 1H), 3.74 (dd, 1H), 3.7 (s, 3H), 3.55 (m, 2H), 3.5-3.2 (bm, 4H), 2.39 (s, 3H), 2.15 (m, 3H), 1.49-1.1 (2t, 2H). MS (m/z): 414 [MH]$^+$.

Example 21 was separated to give the separated enantiomers by semipreparative Supercritical Fluid Chromatography (Gilson) using a chiral column Chiralpak AS-H, 25×2.1 cm, eluent CO$_2$ containing 7% (ethanol+0.1% isopropylamine), flow rate 22 mL/min, P 196 bar, T 36° C., detection UV at 220 nm, loop 1 mL. Retention times given were obtained using an analytical Supercritical Fluid Chromatography (Gilson) using a chiral column Chiralpak AS-H, 25×0.46 cm, eluent CO$_2$ containing 6% (ethanol+0.1% isopropylamine), flow rate 2.5 mL/min, P 190 bar, T 35° C., detection UV at 220 nm.

Enantiomer 1 was recovered in 14 mg yield as white solid, hydrochloride salt from the racemate (40 mg). Rt.=26.2 min. Purity >99% a/a by UV Enantiomer 2 was recovered in 16 mg yield as white solid, hydrochloride salt from the racemate (40 mg). Rt.=32.4 min. Purity >99% a/a by UV Enantiomer 1 showed fpKi (D3)>1 log-unit higher than Enantiomer 2.

Example 22

(1S,5R/1R,5S)-1-(3-Chlorophenyl)-5-methyl-3-(3-({[4-methyl-5-(4-methyl-1,3-oxazol-5-yl)-4H-1,2,4-triazol-3-yl]thio}propyl)-3-azabicyclo[3.1.0]hexane hydrochloride

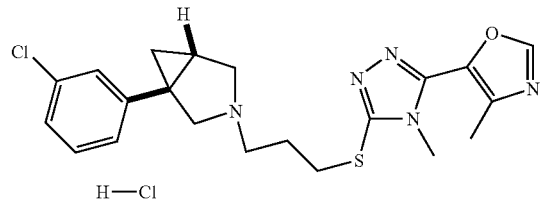

The title compound was prepared in analogy to the method described in Example 1 in 184 mg yield as a white slightly hygroscopic solid from (1R,5S/1S,5R)-1-(3-chlorophenyl)-3-azabicyclo[3.1.0]hexane (116 mg).

NMR ($^1$H, DMSO): δ 9.88 (bs, 1H), 8.58 (s, 1H), 7.43 (d, 1H), 7.4-7.2 (m, 3H), 4.06 (dd, 1H), 3.75 (dd, 1H), 3.7 (s, 3H), 3.62-3.54 (t/m, 2H), 3.5-3.3 (bm, 4H), 2.39 (s, 3H), 2.25 (m, 1H), 2.15 (m, 2H), 1.46-1.19 (2m, 2H). MS (m/z): 431 [MH]$^+$.

Example 22 was separated to give the separated enantiomers by semipreparative Supercritical Fluid Chromatography (Gilson) using a chiral column Chiralpak AD-H, 25×0.46 cm, eluent CO$_2$ containing 15% (ethanol+0.1% isopropylamine), flow rate 22 mL/min, P 192 bar, T 36° C., detection UV at 220 nm, loop 1 mL. Retention times given were obtained using an analytical Supercritical Fluid Chromatography (Berger) using a chiral column Chiralpak AD-H, 25×0.46 cm, eluent CO$_2$ containing 15% (ethanol+0.1% isopropylamine), flow rate 2.5 mL/min, P 180 bar, T 35° C., detection UV at 220 nm.

Enantiomer 1 was recovered in 18 mg yield as white solid, hydrochloride salt from the racemate (40 mg). Rt.=29.6 min. Purity 100% a/a by UV.

Enantiomer 2 was recovered in 16 mg yield as white solid, hydrochloride salt from the racemate (40 mg). Rt.=32.0 min. Purity 100% a/a by UV Enantiomer 1 showed fpKi (D3)>1 log-unit higher than Enantiomer 2.

Example 23

(1S,5R/1R,5S)-1-(3-Fluorophenyl)-3-(3-{[4-methyl-5-(4-methyl-1,3-oxazol-5-yl)-4H-1,2,4-triazol-3-yl]thio}propyl)-3-azabicyclo[3.1.0]hexane hydrochloride

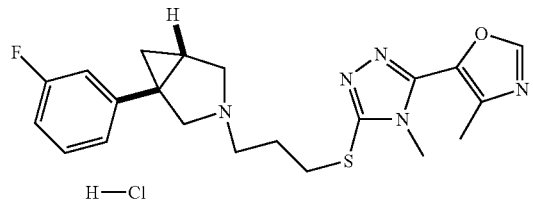

The title compound was prepared in analogy to the method described in Example 1 in 150 mg yield as a white slightly hygroscopic solid from (1R,5S/1S,5R)-1-(3-fluorophenyl)-3-azabicyclo[3.1.0]hexane (116 mg).

NMR ($^1$H, DMSO): δ 10.21 (bs, 1H), 8.58 (d, 1H), 7.4 (m, 1H), 7.2-7.0 (m, 3H), 4.03 (dd, 1H), 3.75 (dd, 1H), 3.7 (s, 3H), 3.61 (t/m, 1H), 3.52 (m, 1H), 3.3 (m, 2H), 3.28 (t, 2H), 2.38 (s, 3H), 2.25 (m, 1H), 2.16 (m, 2H), 1.57-1.17 (t/m, 2H). MS (m/z): 414 [MH]$^+$.

Example 23 was separated to give the separated enantiomers by semipreparative Supercritical Fluid Chromatography (Gilson) using a chiral column Chiralpak AS-H, 25×2.1 cm, eluent $CO_2$ containing 7% (ethanol+0.1% isopropylamine), flow rate 22 mL/min, P 192 bar, T 36° C., detection UV at 220 nm, loop 1 mL. Retention times given were obtained using an analytical Supercritical Fluid Chromatography (Gilson) using a chiral column Chiralpak AS-H, 25×0.46 cm, eluent $CO_2$ containing 6% (ethanol+0.1% isopropylamine), flow rate 2.5 mL/min, P 190 bar, T 35° C., detection UV at 220 nm.

Enantiomer 1 was recovered in 12 mg yield as white solid, hydrochloride salt from the racemate (40 mg). Rt.=24.6 min. Purity >99% a/a by UV Enantiomer 2 was recovered in 14.5 mg yield as white solid, hydrochloride salt from the racemate (40 mg). Rt.=26.0 min. Purity >99% a/a by UV Enantiomer 1 showed fpKi (D3)>1 log-unit higher than Enantiomer 2.

Example 24

(1S,5R/1R,5S)-3-(3-{[4-methyl-5-(4-methyl-1,3-oxazol-5-yl)-4H-1,2,4-triazol-3-yl]thio}propyl)-1-[3-(methyloxy)phenyl]-3-azabicyclo[3.1.0]hexane hydrochloride

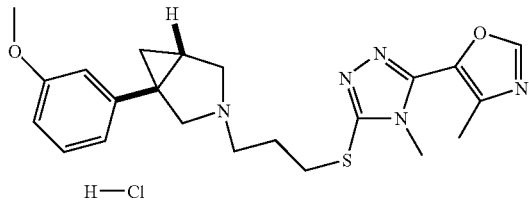

The title compound was prepared in analogy to the method described in Example 1 in 140 mg yield as a white slightly hygroscopic solid from (1R,5S/1S,5R)-1-(3-methoxyphenyl)-3-azabicyclo[3.1.0]hexane (116 mg).

NMR ($^1$H, DMSO): δ 10.16 (bs, 1H), 8.58 (d, 1H), 7.26 (dd, 1H), 6.85 (m, 3H), 4.03 (dd, 1H), 3.77 (s, 3H), 3.72 (dd, 1H), 3.7 (s, 3H), 3.6-3.3 (bm, 4H), 3.28 (t/m, 2H), 2.39 (s, 3H), 2.18 (m, 3H), 1.53-1.1 (t/m, 2H). MS (m/z): 426 [MH]$^+$.

Example 24 was separated to give the separated enantiomers by semipreparative Supercritical Fluid Chromatography (Gilson) using a chiral column Chiralcel OJ-H, 25×2.1 cm, eluent $CO_2$ containing 13% (2-propanol+0.1% isopropylamine), flow rate 22 mL/min, P 200 bar, T 36° C., detection UV at 220 nm. Retention times given were obtained using an analytical Supercritical Fluid Chromatography (Berger) using a chiral column Chiralcel OJ-H, 25×0.46 cm, eluent $CO_2$ containing 13% (2-propanol+0.1% isopropylamine), flow rate 2.5 mL/min, P 180 bar, T 35° C., detection UV at 220 nm.

Enantiomer 1 was recovered in 13.5 mg yield as white solid, hydrochloride salt from the racemate (40 mg). Rt.=24.2 min. Purity >99% a/a by UV.

Enantiomer 2 was recovered in 13.5 mg yield as white solid, hydrochloride salt from the racemate (40 mg). Rt.=26.8 min. Purity >99% a/a by UV.

Enantiomer 1 showed fpKi (D3)>1 log-unit higher than Enantiomer 2.

Example 25

(1S,5R)-1-(4-Bromophenyl)-3-(3-{[4-methyl-5-(tetrahydro-2H-pyran-4-yl)-4H-1,2,4-triazol-3-yl]thio}propyl)-3-azabicyclo[3.1.0]hexane hydrochloride

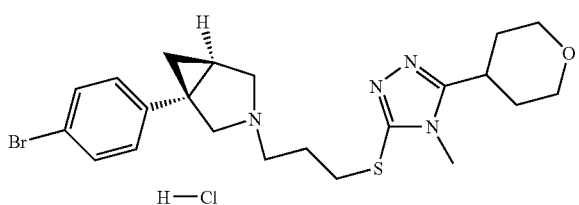

The title compound was prepared in analogy to the method described in Example 1 in 33 mg yield as a white slightly hygroscopic solid from (1S,5R)-1-(4-bromophenyl)-3-azabicyclo[3.1.0]hexane (Preparation 32, 30 mg).

NMR ($^1$H, CD3OD): δ 7.54 (d, 2H), 7.28 (d, 2H), 4.08 (m, 3H), 3.8-3.6 (m, 2H), 3.72 (s, 3H), 3.65 (m, 3H), 3.47 (t, 2H), 3.3 (m, 3H), 2.25 (m, 3H), 1.93 (m, 4H), 1.48-1.34 (2m, 2H). MS (m/z): 478 [MH]$^+$.

Example 26

(1S,5R)-1-(4-Bromophenyl)-3-[3-({4-methyl-5-[4-(trifluoromethyl)phenyl]-4H-1,2,4-triazol-3-yl}thio)propyl]-3-azabicyclo[3.1.0]hexane hydrochloride

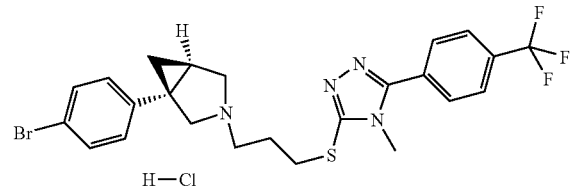

The title compound was prepared in analogy to the method described in Example 1 in 36 mg yield as a white slightly hygroscopic solid from (1S,5R)-1-(4-bromophenyl)-3-azabicyclo[3.1.0]hexane (Preparation 32, 30 mg).

NMR (¹H, CD3OD): δ 7.96 (m, 4H), 7.54 (d, 2H), 7.29 (t, 2H), 4.14 (d, 1H), 3.90 (m, 1H), 3.75 (s, 3H), 3.66 (m, 2H), 3.50 (m, 2H), 3.43 (t, 2H), 2.30 (m, 3H), 1.50 (m, 1H), 1.34 (t, 1H). MS (m/z): 578 [MH]+.

Example 27

(1S,5R)-1-(4-Bromophenyl)-3-(3-{[4-methyl-5-(3-pyridinyl)-4H-1,2,4-triazol-3-yl]thio}propyl)-3-azabicyclo[3.1.0]hexane hydrochloride

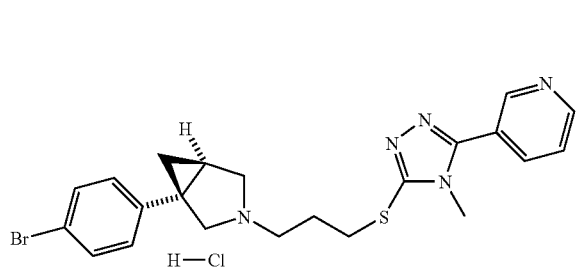

The title compound was prepared in analogy to the method described in Example 1 in 49 mg yield as a white slightly hygroscopic solid from (1S,5R)-1-(4-bromophenyl)-3-azabicyclo[3.1.0]hexane (Preparation 32, 30 mg).

NMR (¹H, CD3OD): δ 8.97 (m, 1H), 8.82 (m, 1H), 8.31 (m, 1H), 7.75 (m, 1H), 7.53 (d, 2H), 7.29 (t, 2H), 4.15 (d, 1H), 3.90 (d, 1H), 3.75 (s, 3H), 3.67 (m, 2H), 3.50 (m, 2H), 3.42 (t, 2H), 2.29 (m, 3H), 1.51 (m, 1H), 1.34 (t, 1H). MS (m/z): 471 [MH]+.

Example 28

(1S,5R)-1-(4-Bromophenyl)-3-(3-{[5-(3,4-difluorophenyl)-4-methyl-4H-1,2,4-triazol-3-yl]thio}propyl)-3-azabicyclo[3.1.0]hexane hydrochloride

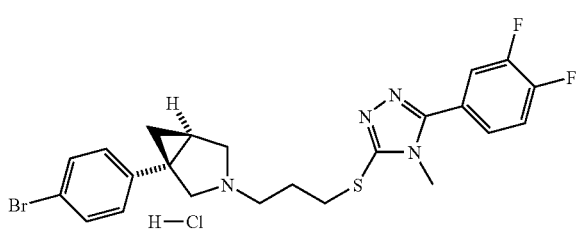

The title compound was prepared in analogy to the method described in Example 1 in 26 mg yield as a white slightly hygroscopic solid from (1S,5R)-1-(4-bromophenyl)-3-azabicyclo[3.1.0]hexane (Preparation 32, 30 mg).

NMR (¹H, CD3OD): δ 7.72 (m, 1H), 7.55 (m, 4H), 7.28 (d, 2H), 4.13 (d, 1H), 3.89 (d, 1H), 3.7 (s, 3H), 3.64 (m, 2H), 3.43 (t, 2H), 3.38 (m, 2H), 2.29 (m, 3H), 1.48 (m, 1H), 1.34 (t, 1H). MS (m/z): 506 [MH]+.

Example 29

6-[5-({3-[(1S,5R/1R,5S)-1-(4-Chlorophenyl)-3-azabicyclo[3.1.0]hex-3-yl]propyl}thio)-4-methyl-4H-1,2,4-triazol-3-yl]-2-methylquinoline hydrochloride

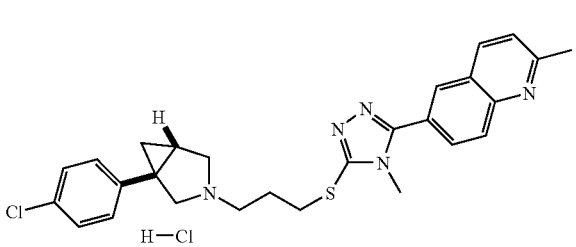

The title compound was prepared in analogy to the method described in Example 1 in 110 mg yield as a white slightly hygroscopic solid from (1R,5S/1S,5R)-1-(4-chlorophenyl)-3-azabicyclo[3.1.0]hexane (87 mg).

NMR (¹H, CD3OD): δ 8.95 (d, 1H), 8.39 (d, 1H), 8.28 (t, 1H), 8.13 (d, 1H), 7.96 (d, 1H), 7.37 (m, 4H), 4.17 (d, 1H), 3.93 (d, 1H), 3.71 (m, 2H), 3.62 (s, 3H), 3.5 (2m, 4H), 3.04 (s, 3H), 2.37 (m, 2H), 2.27 (m, 1H), 1.55 (m, 1H), 1.31 (m, 1H). MS (m/z): 490 [MH]+.

Example 29 was separated to give the separated enantiomers by semipreparative Supercritical Fluid Chromatography (Gilson) using a chiral column Chiralpak AD-H, 25×0.46 cm, eluent CO₂ containing 25% (ethanol+0.1% isopropylamine), flow rate 22 mL/min, P 199 bar, T 36° C., detection UV at 220 nm. Retention times given were obtained using an analytical Supercritical Fluid Chromatography (Berger) using a chiral column Chiralpak AD-H, 25×0.46 cm, eluent CO₂ containing 25% (ethanol+0.1% isopropylamine), flow rate 2.5 mL/min, P 180 bar, T 35° C., detection UV at 220 nm.

Enantiomer 1 was recovered in 13.5 mg yield as white solid, hydrochloride salt from the racemate (40 mg). Rt.=24.3 min. Purity 87.6% a/a by UV.

Enantiomer 2 was recovered in 5 mg yield as white solid, hydrochloride salt from the racemate (40 mg). Rt.=26.5 min. Purity 100% a/a by UV.

Enantiomer 1 showed fpKi (D3)>1 log-unit higher than Enantiomer 2.

Example 30

(1S,5R/1R,5S)-3-(3-{[4-Methyl-5-(4-methyl-1,3-oxazol-5-yl)-4H-1,2,4-triazol-3-yl]thio}propyl)-1-{4-[(trifluoromethyl)oxy]phenyl}-3-azabicyclo[3.1.0]hexane hydrochloride

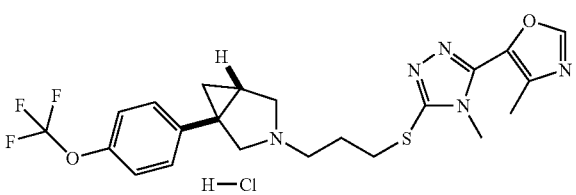

The title compound was prepared in analogy to the method described in Example 1 in 246 mg yield as a white slightly hygroscopic solid from (1R,5S/1S,5R)-1-{4-[(trifluoromethyl)oxy]phenyl}-3-azabicyclo[3.1.0]hexane (205 mg).

NMR ($^1$H, DMSO): δ 10.33 (bs, 1H), 8.58 (s, 1H), 7.43 (d, 2H), 7.36 (d, 2H), 4.04 (dd, 1H), 3.73 (dd, 1H), 3.7 (s, 3H), 3.6-3.2 (bm, 6H), 2.39 (s, 3H), 2.2 (m, 3H), 1.61-1.16 (2t, 2H). MS (m/z): 480 [MH]$^+$.

Example 30 was separated to give the separated enantiomers by semi-preparative HPLC using a chiral column Chirapak AS-H, 25×2 cm, eluent A: n-hexane; B: isopropanol, gradient isocratic 15% B v/v, flow rate 7 mL/min, detection UV at 220 nm. Retention times given were obtained using chiral column Chiracel OD, 25×0.46 cm, eluent A: n-hexane; B: isopropanol, gradient isocratic 10% B v/v, flow rate 1 mL/min, detection UV at 220 nm.

Enantiomer 1 was recovered in 15 mg yield as white solid, hydrochloride salt from the racemate (40 mg). Rt.=28.3 min. Purity >99% a/a by UV.

Enantiomer 2 was recovered in 16 mg yield as white solid, hydrochloride salt from the racemate (40 mg). Rt.=50.6 min. Purity >99% a/a by UV.

Enantiomer 1 showed fpKi (D3)>1 log-unit higher than Enantiomer 2.

Example 31

(1S,5R/1R,5S)-3-(3-{[4-Methyl-5-(4-methyl-1,3-oxazol-5-yl)-4H-1,2,4-triazol-3-yl]thio}propyl)-1-[2-methyl-4-(trifluoromethyl)phenyl]-3-azabicyclo[3.1.0]hexane hydrochloride

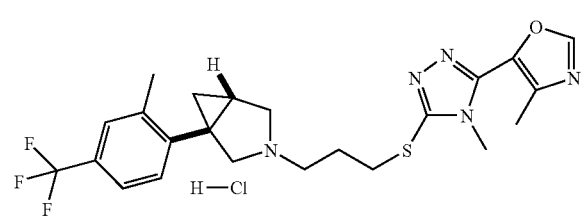

The title compound was prepared in analogy to the method described in Example 1 in 46 mg yield as a white slightly hygroscopic solid from (1R,5S/1S,5R)-1-[2-methyl-4-(trifluoromethyl)phenyl]-3-azabicyclo[3.1.0]hexane (71.5 mg).

NMR ($^1$H, DMSO): δ 10.25 (bs, 1H), 8.58 (s, 1H), 7.6 (m, 3H), 3.97-3.7 (dd/m, 2H), 3.79/3.4 (dd/m, 2H), 3.69 (s, 3H), 3.27 (t, 2H), 2.5 (m, 2H), 2.48 (s, 3H), 2.38 (s, 3H), 2.2 (m, 1H), 2.13 (quint., 2H), 1.61-1.01 (2t, 2H). MS (m/z): 478 [MH]$^+$.

Example 32 not used

Example 33

(1S,5R/1R,5S)-3-(3-{[4-Methyl-5-(tetrahydro-2H-pyran-4-yl)-4H-1,2,4-triazol-3-yl]thio}propyl)-1-{4-[(trifluoromethyl)oxy]phenyl}-3-azabicyclo[3.1.0] hexane hydrochloride

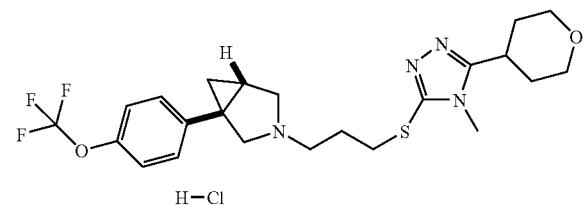

The title compound was prepared in analogy to the method described in Example 1 in 72 mg yield as a white slightly hygroscopic solid from (1R,5S/1S,5R)-1-{4-[(trifluoromethyl)oxy]phenyl}-3-azabicyclo[3.1.0]hexane (100 mg).

NMR ($^1$H, DMSO): δ 10.45 (bs, 1H), 7.44 (d, 2H), 7.36 (d, 2H), 4.04 (bm, 1H), 3.94 (dm, 2H), 3.73 (bm, 1H), 3.55 (s, 3H), 3.6-3.3 (bm, 6H), 3.22 (t, 2H), 3.13 (m, 1H), 2.23 (m, 1H), 2.21 (m, 2H), 1.9-1.7 (m, 4H), 1.63-1.16 (2t, 2H). MS (m/z): 483 [MH]$^+$.

Example 33 was separated to give the separated enantiomers by semipreparative Supercritical Fluid Chromatography (Gilson) using a chiral column Chiralpak AS-H, 25×2.1 cm, eluent $CO_2$ containing 8% (2-propanol+0.1% isopropylamine), flow rate 22 mL/min, P 200 bar, T 36° C., detection UV at 220 nm. Retention times given were obtained using an analytical Supercritical Fluid Chromatography (Berger) using a chiral column Chiralpak AS-H, 25×0.46 cm, eluent $CO_2$ containing 8% (2-propanol+0.1% isopropylamine), flow rate 2.5 mL/min, P 180 bar, T 35° C., detection UV at 220 nm.

Enantiomer 1 was recovered in 15 mg yield as white solid, hydrochloride salt from the racemate (65 mg). Rt.=23.2 min. Purity 100% a/a by UV.

Enantiomer 2 was recovered in 12 mg yield as white solid, hydrochloride salt from the racemate (65 mg). Rt.=24.6 min. Purity 100% a/a by UV.

Enantiomer 1 showed fpKi (D3)>1 log-unit higher than Enantiomer 2.

Example 34

(1R,5S/1S,5R)-1-(3-Bromophenyl)-3-(3-{[4-methyl-5-(4-methyl-1,3-oxazol-5-yl)-4H-1,2,4-triazol-3-yl] thio}propyl)-3-azabicyclo[3.1.0]hexane hydrochloride

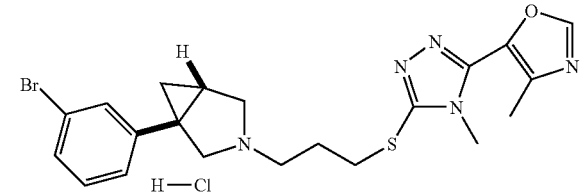

The title compound was prepared in 23 mg yield as a white slightly hygroscopic solid from (1R,5S/1S,5R)-1-(3-bromophenyl)-3-azabicyclo[3.1.0]hexane (140 mg) in analogy to the method described in Example 1 and purifying the free base of the title compound by preparative HPLC using a column X Terra MS C18 5 µm, 100×19 mm, eluent A: H$_2$O+ 0.1% TFA; B: CH$_3$CN+0.1% TFA, gradient 10% (B) for 1 min, from 10% (B) to 35% (B) in 12 min, flow rate 17 mL/min, detection UV at 200-400 nm. Retention times given were obtained using column X Terra MS C18 5 µm, 50×4.6 mm, eluent A: H$_2$O+0.1% TFA; B: CH$_3$CN+0.1% TFA, gradient isocratic 25% B v/v, flow rate 1 mL/min, detection UV at 200-400 nm. Rt.=6.26 min. Purity 96.4% a/a by UV.

NMR (1H, DMSO): δ 9.9 (bs, 1H), 8.58 (s, 1H), 7.57 (s, 1H), 7.47 (m, 1H), 7.3 (m, 2H), 4.04 (m, 1H), 3.75 (dd, 1H), 3.7-3.2 (m, 6H), 3.7 (s, 3H), 2.39 (s, 3H), 2.23 (m, 1H), 2.15 (m, 2H), 1.47 (t, 1H), 1.2 (t, 1H). MS (m/z): 512 [MH]$^+$.

Example 35

(1S,5R)-3-(1-Methyl-3-{[4-methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane hydrochloride

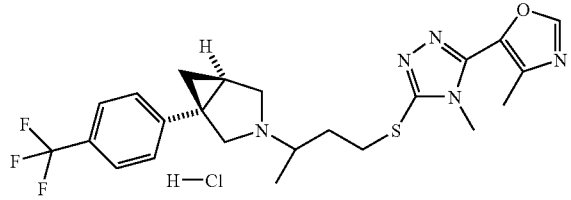

A mixture of (1S,5R)-3-(3-chloro-1-methylpropyl)-1-[4-(trifluoromethyl)phenyl]-3-azabicyclo[3.1.0]hexane hexane (Preparation 20, 105 mg), 4-methyl-5-(4-methyl-1,3-oxazol-5-yl)-2,4-dihydro-3H-1,2,4-triazole-3-thione (0.43 mmol), TEA (0.46 mmol) and NaI (0.43 mmol) in DMF (anhydrous, 1.6 mL) was heated at 60° C. for 12 h. After elimination of the solvent under vacuo, the residue was dissolved in ethyl acetate and the organic layer was washed with H$_2$O and dried over Na$_2$SO$_4$. This solution was concentrated in vacuo, treated with cyclohexane and filtered to give 125 mg of the free base of the title compound. To a solution of this material in dichloromethane (0.2 mL) was added 0.34 mmol of HCl (1M in Et$_2$O), the solvent evaporated under vacuo and the material thus obtained triturated with Et$_2$O to give 105 mg of the title compound as a white slightly hygroscopic solid.

MS (m/z): 478 [MH]$^+$.

Example 35 was separated to give the separated diastereoisomers by semi-preparative HPLC using a chiral column Chirapak AD, 25×2 cm, eluent A: n-hexane; B: ethanol+0.1% isopropylamine, gradient isocratic 15% B v/v, flow rate 7 mL/min, UV wavelength range 220-400 nm. Retention times given were obtained using a chiral column Chiralpak AD-H, 25×0.46 cm, eluent A: n-hexane; B: ethanol+0.1% isopropylamine, gradient isocratic 17% B v/v, flow rate 1 mL/min, UV wavelength range 200-400 nm. Diastereoisomer 1 was recovered in 30 mg yield as a white solid, hydrochloride salt from the diastereomeric mixture (105 mg). Rt.=17.9 min. Purity 99.4% a/a by UV NMR ($^1$H, DMSO): δ 10.33 (bs, 1H), 8.58 (s, 1H), 7.71 (d, 2H), 7.53 (d, 2H), 4.07 (dd, 1H), 3.78 (dd, 1H), 3.7 (s, 3H), 3.7 (m, 1H), 3.56 (bs, 2H), 3.4 (m, 1H), 3.18 (m, 1H), 2.4 (s, 3H), 2.4-2.3 (m, 1H), 2.26-2.09 (m, 2H), 1.72 (m, 1H), 1.42 (d, 3H), 1.2 (m, 1H). MS (m/z): 478 [MH]$^+$.

Diastereoisomer 2 was recovered in 46 mg yield as white solid, hydrochloride salt from the diastereomeric mixture (105 mg). Rt.=21.2 min. Purity >99% a/a by UV NMR ($^1$H, DMSO): δ 10.26 (bs, 1H), 8.58 (s, 1H), 7.7 (d, 2H), 7.51 (d, 2H), 4.14 (dd, 1H), 3.8-3.6 (m, 3H), 3.7 (s, 3H), 3.53 (bs, 1H), 3.4 (m, 1H), 3.18 (m, 1H), 2.38 (s, 3H), 2.4-2.25 (m, 2H), 2.1 (m, 1H), 1.69 (m, 1H), 1.39 (d, 3H), 1.2 (m, 1H). MS (m/z): 478 [MH]$^+$.

Example 36

(1R,5S/1S,5R)-1-[2-Fluoro-5-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane hydrochloride

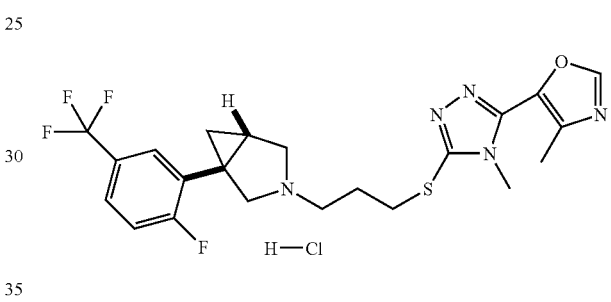

The title compound was prepared in analogy to the method described in Example 1 in 144 mg yield as a white slightly hygroscopic solid from 1(1R,5S/1S,5R)-[2-fluoro-5-(trifluoromethyl)phenyl]-3-azabicyclo[3.1.0]hexane (109 mg).

NMR ($^1$H, CD$_3$OD): δ 8.41 (s, 1H), 7.8 (m, 1H), 7.74 (m, 1H), 7.39 (t, 1H), 4.13 (d, 1H), 3.95 (d, 1H), 3.81 (s, 3H), 3.73 (bd, 1H), 3.54 (d, 1H), 3.48 (m, 2H), 3.41 (m, 2H), 2.48 (s, 3H), 2.39 (m, 1H), 2.28 (q, 2H), 1.58 (m, 1H), 1.35 (m, 1H). MS (m/z): 482 [MH]$^+$.

Example 36 was separated to give the separated enantiomers by semi-preparative HPLC using a chiral column Chirapak AS-H, 25×2 cm, eluent A: n-hexane; B: isopropanol+0.1% isopropylamine, gradient isocratic 10% B v/v, flow rate 7 mL/min, detection UV at 220 nm. Retention times given were obtained using an analytical Supercritical Fluid Chromatography (Berger) using a chiral column Chiralpak AD-H, 25×0.46 cm, eluent CO$_2$ containing 7% (ethanol+ 0.1% isopropylamine), flow rate 2.5 mL/min, P 180 bar, T 35° C., detection UV at 220 nm.

Enantiomer 1 was recovered in 48 mg yield as a white solid, hydrochloride salt from the racemate (138 mg). Rt.=21.2 min. Purity 100% a/a by UV Enantiomer 2 was recovered in 46 mg yield as white solid, hydrochloride salt from the racemate (138 mg). Rt.=22.7 min. Purity 99% a/a by UV Enantiomer 2 showed fpKi (D3)>1 log-unit higher than Enantiomer 1.

Example 37

1-[4-[(1R,5S/1S,5R)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]ethanone hydrochloride

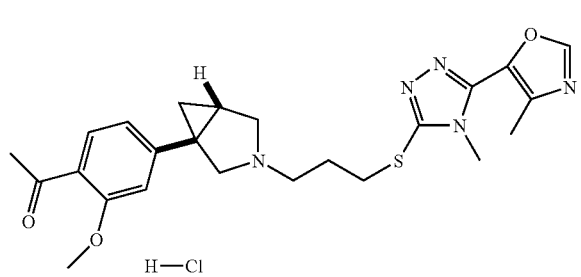

The title compound was prepared in analogy to the method described in Example 1 in 70 mg yield as a white slightly hygroscopic solid from 1-[4-[(1S,5R/1R,5S)-3-azabicyclo[3.1.0]hex-1-yl]-2-(methyloxy)phenyl]ethanone (87 mg).

NMR ($^1$H, CDCl$_3$) of the corresponding free base: δ 8.0 (s, 1H), 7.7 (d, 1H), 6.7-6.8 (m, 2H), 3.9 (s, 3H), 3.7 (s, 3H), 3.35 (m, 4H), 3.1 (d, 1H), 2.6 (m, 3H), 2.55 (s, 3H), 2.5 (s, 3H), 2.45 (m, 1H), 2.0 (m, 2H), 1.75 (m, 1H), 0.8 (m, 1H). MS (m/z): 468 [MH]$^+$.

Example 38

1-[4-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]-1-propanone hydrochloride

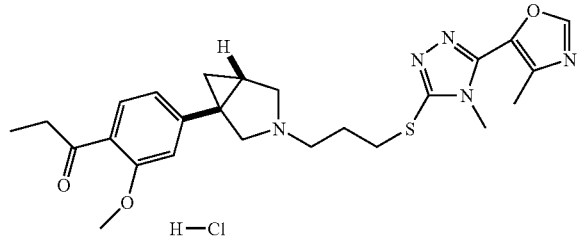

The title compound was prepared in analogy to the method described in Example 1 in 75 mg yield as a white slightly hygroscopic solid from 1-[(1S,5R/1R,5S)-3-azabicyclo[3.1.0]hex-1-yl]-2-(methyloxy)phenyl]-1-propanone (106 mg).

Free base NMR ($^1$H, CDCl$_3$): δ 7.9 (s, 1H), 6.65 (d, 1H), 6.7 (m, 2H), 3.9 (s, 3H), 3.7 (s, 3H), 3.35 (m, 3H), 3.1 (d, 1H), 2.9 (m, 2H), 2.6 (m, 3H), 2.5 (s, 3H), 2.45 (m, 1H), 2.0 (m, 2H), 1.8 (m, 1H), 1.1 (m, 3H), 0.8 (m, 1H). MS (m/z): 482 [MH]$^+$.

Example 39

(1R,5S/1S,5R)-3-(3-{[4-Methyl-5-(4-methyl-1,3-oxazol-5-yl)-4H-1,2,4-triazol-3-yl]thio}propyl)-1-[2-(trifluoromethyl)phenyl]-3-azabicyclo[3.1.0]hexane hydrochloride

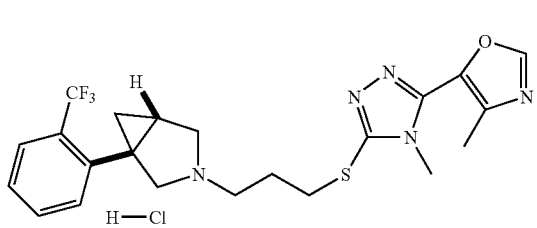

The title compound was prepared in analogy to the method described in Example 1 in 7 mg yield as a white slightly hygroscopic solid from (1R,5S/1S,5R)-1-[2-(trifluoromethyl)phenyl]-3-azabicyclo[3.1.0]hexane (53 mg).

NMR ($^1$H, DMSO): δ 10.48 (bs, 1H), 8.55 (s, 1H), 7.9-7.6 (m, 4H), 3.9-3.1 (bm, 8H), 3.68 (s, 3H), 2.36 (s, 3H), 2.13 (m, 2H), 1.66 (m, 1H), 1.2 (m, 1H), 1.1 (m, 1H). MS (m/z): 464 [MH]$^+$.

Example 40

(1S,5R)-1-[2-Fluoro-4-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane hydrochloride

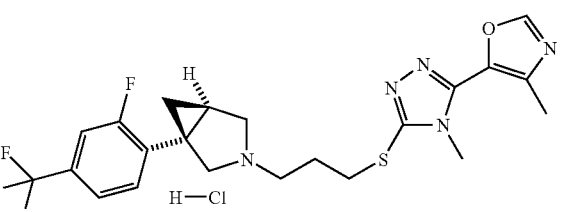

The free base of the title compound was prepared in analogy to the method described in Example 1 from (1S,5R)-1-[2-fluoro-4-(trifluoromethyl)phenyl]-3-azabicyclo[3.1.0]hexane. A mixture of (1S,5R)-1-[2-fluoro-4-(trifluoromethyl)phenyl]-3-azabicyclo[3.1.0]hexane (Preparation 39, 727 mg, 2.97 mmol), 3-[(3-Chloropropyl)thio]-4-methyl-5-(4-methyl-1,3-oxazol-5-yl)-4H-1,2,4-triazole (Preparation 14, 3.6 mmol.), K$_2$CO$_3$ (3.6 mmol.) and NaI (2.97 mmol) in DMF anhydrous was heated at 60° C. for 24 h. After elimination of the solvent under vacuo, the residue was dissolved in ethyl acetate and the organic layer was washed with saturated aqueous NaHCO$_3$ and dried over Na$_2$SO$_4$. This solution was filtered and the filtrate was concentrated in vacuo. The crude was purified by flash chromatography (dichloromethane to 10% MeOH in dichloromethane) to give 940 mg of the free base of the title compound.

This free base (886 mg) was converted to the hydrochloride salt (847 mg) according to the method described in Example 1. The title compound was obtained as a white solid. Analytical Chiral HPLC confirmed the product to be identical to Enantiomer 2 of Example 16.

NMR and MS data corresponded to those reported for Example 16.

The absolute configuration of the title compound was confirmed using comparative VCD and comparative OR analyses of the corresponding free base to be (1S,5R)-1-[2-fluoro-4-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane. (1S,5R)-3-(3-{[4-Methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane (see Example 14) was used as the reference.

Specific Optical Rotation of the corresponding free base: $[\alpha]_D = -42°$ (CDCl$_3$, T=25° C., c≅0.005 g/0.8 mL).

Examples 41-52

To a solution of the respective 3-thio-5-aryl-1,2,4-triazole (prepared in analogy to the method described in Preparation 13, 0.131 mmol) in dry acetonitrile (2 mL) 2-tert-butylimino-2-diethylamino-1,3-dimethyl-perhydro-1,3,2-diaza-phosphorine on polystyrene (90 mg, 2.2 mmol/g) was added and the resulting mixture was shaken for 30 minutes at room temperature. (1S,5R)-3-(3-Chloropropyl)-1-[4-(trifluoromethyl)phenyl]-3-azabicyclo[3.1.0]hexane (40 mg) was added and the resulting mixture was shaken at 70° C. for three hours. After cooling the resin was removed by filtration, washed with methanol (2 mL), and then the solvent was removed under reduced pressure. Purifications were carried out using mass directed HPLC using a Waters XTerra Prep MS C18 10 µm, 30×150 mm column using the following conditions:

|  | Time | Flow | % A | % B |
|---|---|---|---|---|
| Prerun | 0 | 40 ml/min | 99 | 1 |
|  | 1 | 40 ml/min | 99 | 1 |
| Run | 0 | 40 ml/min | 99 | 1 |
|  | 10 | 40 ml/min | 75 | 25 |
|  | 14.5 | 40 ml/min | 10 | 90 |
|  | 15 | 40 ml/min | 0 | 100 |
| Postrun | 0 | 40 ml/min | 0 | 100 |
|  | 0.2 | 45 ml/min | 0 | 100 |
|  | 1.5 | 45 ml/min | 0 | 100 |
|  | 2 | 40 ml/min | 0 | 100 |

A = H2O + 0.1% formic acid
B = ACN + 0.1% formic acid

Then solvent was removed under reduced pressure to give the respective compounds as formate salts. The residues were taken up with methanol (1 mL) and loaded on SCX SPE cartridges (1 g), washed with methanol (3 mL) and eluted with a 2 M ammonia solution in methanol (3 mL), then the solvent was removed under reduced pressure. The residues were taken up with dichloromethane (1 mL) and a 1.0 M HCl solution in diethylether was added (0.131 mmol), then the solvent was removed under reduced pressure to give product compounds summarised in TABLE 1 as hydrochloride salts.
Analytical Chromatographic Conditions:
Column: X Terra MS C18 5 mm, 50×4.6 mm
Mobile phase: A: NH4HCO3 sol. 10 mM, pH10; B: CH3CN
Gradient: 10% (B) for 1 min, from 10% (B) to 95% (B) in 12 min, 95% (B) for 3 min
Flow rate: 1 mL/min
UV wavelength range: 210-350 nm
Mass range: 100-900 amu
Ionization: ES+

TABLE 1

| EX | Name and Structure | R (min) | Analytical data |
|---|---|---|---|
| 41 | (1S,5R)-3-(3-{[4-Methyl-5-(2-methyl-3-pyridinyl)-4H-1,2,4-triazol-3-yl]thio}propyl)-1-{4-(trifluoromethyl)phenyl]-3-azabicyclo[3.1.0]hexane hydrochloride | 9.35 | NMR ($^1$H, DMSO): δ 10.84(bs, HCl), 8.77(dd, 1H), 8.19(bd, 1H), 7.71(d, 2H), 7.66(m, 1H), 7.51(d, 2H), 4.08(dd, 1H), ca 3.8(s, 3H), 3.8-3.3(m, 7H), 2.54 (s, 3H), 2.30(m ,1H), 2.22(m, 2H), 1.83(m, 1H), 1.20(m, 1H). NMR ($^{19}$F, DMSO): δ −60.8. MS (m/z): 474 [MH]$^+$. |

TABLE 1-continued

| EX | Name and Structure | R (min) | Analytical data |
|---|---|---|---|
| 42 | (1S,5R)-3-(3-{[4-Methyl-5-(4-pyridazinyl)-4H-1,2,4-triazol-3-yl]thio}propyl)-1-[4-(trifluoromethyl)phenyl]-3-azabicyclo-[3.1.0]hexane hydrochloride | 8.84 | NMR ($^1$H, DMSO): δ 10.24(bs, HCl), 9.56(m, 1H), 9.39(m, 1H), 8.01(s, 1H), 7.64(m, 2H), 7.44(m, 2H), 4.08(m, 1H), 3.68 (s, 3H), 3.58(bm, 1H), 3.7-3.3 (m, 6H), 2.26(m, 1H), 2.13(m, 2H), 1.58(t, 1H), 1.14(t, 1H). MS (m/z): 461 [MH]$^+$ |
| 43 | (1S,5R)-3-(3-{[5-(1,5-Dimethyl-1H-pyrazol-4-yl)-4-methyl-4H-1,2,4-triazol-3-yl]thio}propyl)-1-[4-(trifluoromethyl)phenyl]-3-azabicyclo[3.1.0]hexane hydrochloride | 9.27 | MS (m/z): 477 [MH]$^+$ |
| 44 | (1S,5R)-3-(3-{[4-Methyl-5-(5-pyrimidinyl)-4H-1,2,4-triazol-3-yl]thio}propyl)-1-[4-(trifluoromethyl)phenyl]-3-azabicyclo-[3.1.0]hexane hydrochloride | 8.92 | MS (m/z): 461 [MH]$^+$ |

TABLE 1-continued

| EX | Name and Structure | R (min) | Analytical data |
|---|---|---|---|
| 45 | (1S,5R)-3-(3-{[4-Methyl-5-(3-methyl-2-furanyl)-4H-1,2,4-triazol-3-yl]thio}propyl)-1-[4-(trifluoromethyl)phenyl]-3-azabicyclo[3.1.0]hexane hydrochloride | 10.72 | NMR ($^1$H, DMSO): δ 10.56(bs, HCl), 7.85(d, 1H), 7.71(d, 2H), 7.51(d, 2H), 6.64(d, 1H), 4.08 (dd, 1H), 3.75(dd, 1H), 3.71(s, 3H), 3.7-3.3(m, 4H), 3.27(t, 2H), 2.31(m, 1H), 2.28(s, 3H), 2.18(m, 2H), 1.74(t, 1H), 1.21 (t, 1H).<br>MS (m/z): 463 [MH]$^+$. |
| 46 | (1S,5R)-3-(3-{[4-Methyl-5-(6-methyl-3-pyridinyl)-4H-1,2,4-triazol-3-yl]thio}-propyl)-1-[4-(trifluoromethyl)phenyl]-3-azabicyclo[3.1.0]hexane hydrochloride | 9.47 | MS (m/z): 474 [MH]$^+$ |
| 47 | (1S,5R)-3-(3-{[5-[2,4-Dimethyl-1,3-thiazol-5-yl)-4-methyl-4H-1,2,4-triazol-3-yl]thio}propyl)-1-[4-(trifluoromethyl)-phenyl]-3-azabicyclo[3.1.0]hexane hydrochloride | 9.79 | MS (m/z): 494 [MH]$^+$ |

TABLE 1-continued

| EX | Name and Structure | R (min) | Analytical data |
|---|---|---|---|
| 4 | (1S,5R)-3-(3-{[4-Methyl-5-(5-methyl-2-pyrazinyl)-4H-1,2,4-triazol-3-yl]thio}propyl)-1-[4-(trifluoromethyl)phenyl]-3-azabicyclo[3.1.0]hexane hydrochloride | 10.15 | NMR (¹H, DMSO): δ 10.41(bs, HCl), 9.11(bs, 1H), 8.63(bs, 1H), 7.66(d, 2H), 7.44(d, 2H), 4.02(dd, 1H), 3.83(s, 3H), 3.68 (d, 1H), 3.6-3.2(m, 6H), 2.54(s, 3H), 2.25(m, 1H), 2.14(m, 2H), 1.65(m, 1H), 1.14(m, 1H). MS (m/z): 475 [MH]⁺. |
| 49 | (1S,5R)-3-(3-{[4-Methyl-5-(tetrahydro-2H-pyran-4-yl)-4H-1,2,4-triazol-3-yl]thio}-propyl)-1-[4-(trifluoromethyl)phenyl]-3-azabicyclo[3.1.0]hexane hydrochloride | 9.15 | MS (m/z): 467 [MH]⁺ |
| 50 | 2-Methyl-6-{4-methyl-5-[(3-{(1S,5R)-1-[4-(trifluoromethyl)phenyl]-3-azabicyclo[3.1.0]hex-3-yl}propyl)thio]-4H-1,2,4-triazol-3-yl)quinoline hydrochloride | 10.17 | NMR (¹H, DMSO): δ 10.41(bs, HCl), 8.67(bs, 1H), 8.47(s, 1H), 8.2(s, 2H), 7.72(m, 1H), 7.68(m, 2H), 7.49(m, 2H), 4.07 (m, 1H), 3.74(dd, 1H), 3.72(s, 3H), 3.64(dd, 1H), 3.51(m, 1H), 3.3(m, 4H), 2.81(s, 3H), 2.28 (m, 1H), 2.19(m, 2H), 1.72(t, 1H), 1.19(t, 1H). MS (m/z): 524 [MH]⁺. |

TABLE 1-continued

| EX | Name and Structure | R (min) | Analytical data |
|---|---|---|---|
| 51 | 8-Fluoro-2-methyl-5-{4-methyl-5-[(3-{(1S,5R)-1-[4-(trifluoromethyl)phenyl]-3-azabicyclo[3.1.0]hex-3-yl}propyl)thio]-4H-1,2,4-triazol-3-yl}quinoline hydrochloride | 10.14 | MS (m/z): 542 [MH]+ |
| 52 | 2-Methyl-5-{4-methyl-5-[(3-{(1S,5R)-1-[4-(trifluoromethyl)phenyl]-3-azabicyclo-[3.1.0]hex-3-yl}propyl)thio]-4H-1,2,4-triazol-3-yl}quinoline hydrochloride | 10.12 | MS (m/z): 524 [MH]+ |

Examples 53-58

To a solution of the respective 3-thio-5-aryl-1,2,4-triazole (0.124 mmol) in dry acetonitrile (2 mL) 2-tert-butylimino-2-diethylamino-1,3-dimethyl-perhydro-1,3,2-diaza-phosphorine on polystyrene (85 mg, 2.2 mmol/g) was added and the resulting mixture was shaken for 30 minutes at room temperature, then (1S,5R)-3-(3-chloropropyl)-1-[2-fluoro-4-(trifluoromethyl)phenyl]-3-azabicyclo[3.1.0]hexane (40 mg) was added and the resulting mixture was shaken at 50° C. overnight. After cooling the resin was removed by filtration, washed with methanol (2 mL) and then the solvent was removed under reduced pressure. Purifications were carried out using mass directed HPLC:

Preparative Chromatographic Conditions (Prep. HPLC of 6 Out of 6 Compounds)
Column: X Terra MS C18 5 mm, 100×19 mm
Mobile phase: A: NH4HCO3 sol. 10 mM, pH10; B: CH3CN
Gradient: 30% (B) for 1 min, from 30% (B) to 95% (B) in 9 min, 95% (B) for 3 min
Flow rate: 17 mL/min
UV wavelength range: 210-350 nm
Mass range: 100-900 amu
Ionization: ES+

Then solvent was removed under reduced pressure to give compounds as free bases. The residues were taken up with dichloromethane (2 mL) and a 1.0 M HCl solution in diethylether was added (0.124 mmol) then solvent was removed under reduced pressure to give to give product compounds summarised in TABLE 2 as hydrochloride salts.

Analytical Chromatographic Conditions
Column: X Terra MS C18 5 mm, 50×4.6 mm
Mobile phase: A: NH4HCO3 sol. 10 mM, pH10; B: CH3CN
Gradient: 30% (B) for 1 min, from 30% (B) to 95% (B) in 9 min, 95% (B) for 3 min
Flow rate: 1 mL/min
UV wavelength range: 210-350 nm
Mass range: 100-900 amu
Ionization: ES+

TABLE 2

| Example | Name and Structure | R (min) | Analytical data |
|---|---|---|---|
| 53 | (1S,5R)-1-[2-Fluoro-4-(trifluoromethyl)-phenyl]-3-(3-{[4-methyl-5-(2-methyl-3-pyridinyl)-4H-1,2,4-triazol-3-yl]thio}propyl)-3-azabicyclo[3.1.0]hexane hydrochloride | 6.58 | NMR ($^1$H, DMSO): δ 10.64(bs, HCl), 8.72(dd, 1H), 8.05(d, 1H), 7.73(d, 1H), 7.67(t, 1H), 7.62(d, 1H), 7.56(dd, 1H), 4.01 (d, 1H), 3.79(d, 1H), 3.7-3.3(m, 5H), 3.5-3.3(2 × t, 4H), 2.57(s, 3H), 2.46(m, 1H), 2.18(m, 2H), 1.73(t, 1H), 1.15(t, 1H). MS (m/z): 492 [MH |
| 54 | (1S,5R)-1-[2-Fluoro-4-(trifluoromethyl)-phenyl]-3-(3-{[4-methyl-5-(4-pyridazinyl)-4H-1,2,4-triazol-3-yl]thio}propyl)-3-azabicyclo-[3.1.0]hexane hydrochloride | 6.09 | NMR ($^1$H, DMSO): δ 10.66(bs, HCl), 9.63(m, 1H), 9.47(dd, 1H), 8.09(dd, 1H), 7.73(d, 1H), 7.67(t, 1H), 7.62(d, 1H), 3.99 (d, 1H), 3.78(d, 1H), 3.75(s, 3H), 3.7-3.4(m, 2H), 3.32(m, 4H), 2.36(m, 1H), 2.17(m, 2H), 1.74(t, 1H), 1.14(t, 1H). MS (m/z): 479[M |
| 55 | (1S,5R)-1-[2-Fluoro-4-(trifluoromethyl)-phenyl]-3-(3-{[4-methyl-5-(5-pyrimidinyl)-4H-1,2,4-triazol-3-yl]thio}propyl)-3-azabicyclo-[3.1.0]hexane hydrochloride | 6.22 | NMR ($^1$H, DMSO): δ 10.05(bs, HCl), 9.38(s, 1H), 9.19(s, 2H), 7.74(d, 1H), 7.67(t, 1H), 7.62 (d, 1H), 4.02(bd, 1H), 3.81(bd, 1H), 3.69(t, 3H), 3.58(m, 1H), 3.5-3.2(m, 5H), 2.38(m ,1H), 2.16(m, 2H), 1.55(t, 1H), 1.17 (t, 1H). MS (m/z): 479 [MH]$^+$. |

TABLE 2-continued

| Example | Name and Structure | R (min) | Analytical data |
|---|---|---|---|
| 56 | (1S,5R)-3-(3-{[5-[2,4-Dimethyl-1,3-thiazol-5-yl)-4-methyl-4H-1,2,4-triazol-3-yl]thio}propyl)-1-[2-fluoro-4-(trifluoromethyl)phenyl]-3-azabicyclo[3.1.0]hexane hydrochloride | 7.17 | NMR ($^1$H, DMSO): δ 10.45(bs, HCl), 7.73(d, 1H), 7.67(t, 1H), 7.62(d, 1H), 4.01(d, 1H), 3.79 (d, 1H), 3.6-3.3(m, 5H), 3.5-3.3 (t, 2H), 3.28(t, 2H), 2.70(s, 3H), 2.37(m, 1H), 2.34(s, 3H), 2.16 (m, 2H), 1.67(t, 1H), 1.55(t, 1H). MS (m/z): 512 [MH]$^+$ |
| 57 | (1S,5R)-1-[2-Fluoro-4-(trifluoromethyl)-phenyl]-3-(3-{[4-methyl-5-(5-methyl-2-pyrazinyl)-4H-1,2,4-triazol-3-yl]thio}propyl)-3-azabicyclo[3.1.0]hexane hydrochloride | 7.7 | NMR ($^1$H, DMSO): δ 10.23(bs, HCl), 9.17(s, 1H), 8.70(s, 1H), 7.73(d, 1H), 7.67(t, 1H), 7.61 (d, 1H), 4.01(d, 1H), 3.89(s, 3H), 3.8(d, 1H), 3.6-3.3(m, 2H), 3.5-3.2(bm, 4H), 2.61(s, 3H), 2.37(m, 1H), 2.16(m, 2H), 1.61 (t, 1H), 1.16(t, 1H). MS (m/z): 493 [MH |
| 58 | (1S,5R)-1-[2-Fluoro-4-(trifluoromethyl)-phenyl]-3-[3-({4-methyl-5-[4-(trifluoromethyl)-phenyl]-4H-1,2,4-triazol-3-yl}thio)propyl]-3-azabicyclo[3.1.0]hexane hydrochloride | 8.92 | NMR ($^1$H, DMSO): δ 10.64(bs, HCl), 7.98(d, 2H), 7.95(d, 2H), 7.73(d, 1H), 7.70(t, 1H), 7.61 (d, 1H), 4.00(d, 1H), 3.79(d, 1H), 3.67(s, 3H), 3.55(d, 1H), 3.45(d, 1H), 3.34(bm, 2H), 3.29 (t, 2H), 2.35(m, 1H), 2.17(m, 2H), 1.73(t, 1H), 1.14(t, 1H). MS (m/z): 545 [MH |

Example 59

1-{4-[(1R,5S/1S,5R)-3-(3-{[4-Methyl-5-(2-methyl-5-quinolinyl)-4H-1,2,4-triazol-3-yl]thio}propyl)-3-azabicyclo[3.1.0]hex-1-yl]phenyl}-2-pyrrolidinone hydrochloride

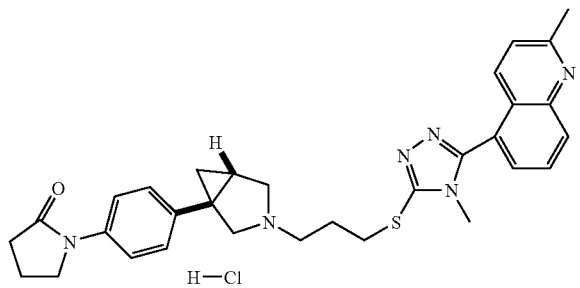

A Schlenk tube was charged with 5-[5-({3-[(1R,5S/1S,5R)-1-(4-bromophenyl)-3-azabicyclo[3.1.0]hex-3-yl]propyl}thio)-4-methyl-4H-1,2,4-triazol-3-yl]-2-methylquinoline (cf. Example 2; 0.15 g), 2-pyrrolidinone (32 mg), tris(dibenzylideneacetone)-dipalladium(0) (6 mg), 4,5-bis(diphenylphosphino)-9,9-dimethylxanthene (10 mg), cesium carbonate (130 mg) and 1,4-dioxane (2 mL). The Schlenk tube was sealed with a teflon screwcap and the reaction mixture was stirred at 100° C. for 12 h. The reaction mixture was allowed to cool to room temperature, diluted with dichloromethane (10 mL), filtered and concentrated in vacuo. The crude product was purified by flash chromatography (dichloromethane to 10% MeOH in dichloromethane) to give 60 mg of the free base of the title compound. To a solution of this material in dichloromethane (0.4 mL) was added HCl (0.11 mL, 1M in Et$_2$O), the solvent evaporated in vacuo and the material thus obtained triturated with Et$_2$O to give 64 mg of the title compound as a white solid.

NMR ($^1$H, DMSO): δ 10.48 (bs, 1H), 8.24 (bd, 1H), 8.18 (d, 1H), 7.93 (t, 1H), 7.81 (d, 1H), 7.62 (d, 2H), 7.54 (d, 1H), 7.31 (d, 2H), 4.04 (dd, 1H), 3.82 (t, 2H), 3.76 (dd, 1H), 3.70/3.10 (bm, 8H), 3.45 (s, 3H), 2.74 (s, 3H), 2.25 (m, 2H), 2.16 (m, 1H), 2.07 (m, 2H), 1.63/1.10 (t/t, 2H). MS (m/z): 539 [MH]$^+$.

Example 60

5-{5-[(3-{(1R,5S/1S,5R)-1-[4-(1,1-Dioxido-2-isothiazolidinyl)phenyl]-3-azabicyclo[3.1.0]hex-3-yl}propyl)thio]-4-methyl-4H-1,2,4-triazol-3-yl}-2-methylquinoline hydrochloride

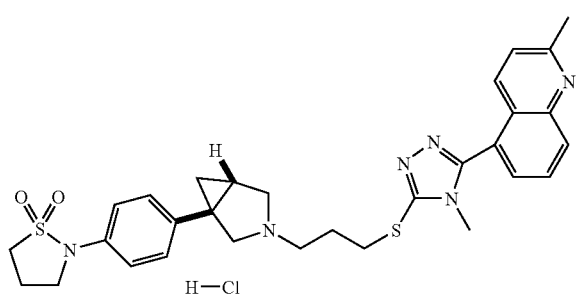

A Schlenk tube was charged with 5-[5-({3-[(1R,5S/1S,5R)-1-(4-bromophenyl)-3-azabicyclo[3.1.0]hex-3-yl]propyl}thio)-4-methyl-4H-1,2,4-triazol-3-yl]-2-methylquinoline (cf. Example 2; 0.15 g), isothiazolidine 1,1-dioxide (46 mg), tris(dibenzylideneacetone)-dipalladium(0) (6 mg), 4,5-bis(diphenylphosphino)-9,9-dimethylxanthene (10 mg), cesium carbonate (130 mg) and 1,4-dioxane (2 mL). The Schlenk tube was sealed with a teflon screwcap and the reaction mixture was stirred at 100° C. for 12 h. The reaction mixture was allowed to cool to room temperature, diluted with dichloromethane (10 mL), filtered and concentrated in vacuo. The crude product was purified by flash chromatography (dichloromethane to 10% MeOH in dichloromethane) to give 50 mg of the free base of the title compound. To a solution of this material in dichloromethane (0.3 mL) was added HCl (0.087 mL, 1M in Et$_2$O), the solvent evaporated in vacuo and the material thus obtained triturated with Et$_2$O to give 52 mg of the title compound as a white solid.

NMR ($^1$H, DMSO): δ 10.57 (bs, 1H), 8.27 (bd, 1H), 8.19 (d, 1H), 7.94 (t, 1H), 7.82 (d, 1H), 7.55 (d, 1H), 7.32 (d, 2H), 7.18 (d, 2H), 4.03 (dd, 1H), 3.72 (m, 3H), 3.60/3.20 (bm, 8H), 3.45 (s, 3H), 2.75 (s, 3H), 2.41 (m, 2H), 2.25 (m, 2H), 2.14 (m, 1H), 1.66/1.10 (t/m, 2H). MS (m/z): 575 [MH]$^+$.

Example 61

(1R,5S/1S,5R)-1-[3-Fluoro-4-(trifluoromethyl)phenyl]-5-methyl-3-(3-{[4-methyl-5-(4-methyl-1,3-oxazol-5-yl)-4H-1,2,4-triazol-3-yl]thio}propyl)-3-azabicyclo[3.1.0]hexane hydrochloride

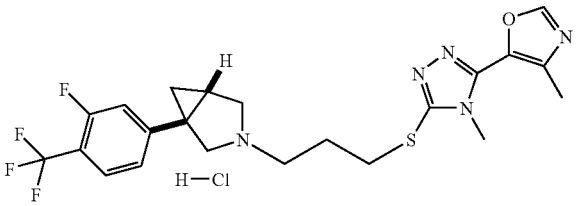

The title compound was prepared in analogy to the method described in Example 1 in 247 mg yield as a white slightly hygroscopic solid from (1R,5S/1S,5R)-1-[3-fluoro-4-(trifluoromethyl)phenyl]-3-azabicyclo[3.1.0]hexane (338 mg).

NMR ($^1$H, CD3OD): δ 8.4 (s, 1H), 7.55 (t, 1H), 7.37 (d, 1H), 7.32 (d, 1H), 4.2 (d, 1H), 3.91 (d, 1H), 3.81 (s, 3H), 3.76 (d, 1H), 3.67 (d, 1H), 3.51 (t, 2H), 3.43 (t, 2H), 2.47 (s, 3H), 2.41 (m, 1H), 2.31 (m, 2H), 1.61 (t, 1H), 1.45 (t, 1H). MS (m/z): 496 [MH]$^+$.

Example 61 was separated to give the separated enantiomers by semipreparative Supercritical Fluid Chromatography (Gilson) using a chiral column Chiralpak AD-H, 25×2.1 cm, eluent CO$_2$ containing 12% (Ethanol+0.1% isopropylamine), flow rate 22 mL/min, P 194 bar, T 36° C., detection UV at 220 nm. Retention times given were obtained using an analytical Supercritical Fluid Chromatography (Berger) using a chiral column Chiralpak AD-H, 25×0.46 cm, eluent CO$_2$ containing 10% (ethanol+0.1% isopropylamine), flow rate 2.5 mL/min, P 180 bar, T 35° C., detection UV at 220 nm.

Enantiomer 1 was recovered in 42 mg yield as white solid, hydrochloride salt from the racemate (100 mg). Rt.=27.1 min. Purity 100% a/a by UV.

Enantiomer 2 was recovered in 34 mg yield as white solid, hydrochloride salt from the racemate (100 mg). Rt.=31.0 min. Purity 100% a/a by UV. Enantiomer 1 showed fpKi (D3)>2 log-unit higher than Enantiomer 2.

Example 62

1-(2-(Methyloxy)-5-{(1R,5S/1S,5R)-3-[3-({4-methyl-5-[4-(trifluoromethyl)phenyl]-4H-1,2,4-triazol-3-yl}thio)propyl]-3-azabicyclo[3.1.0]hex-1-yl}phenyl)ethanone hydrochloride

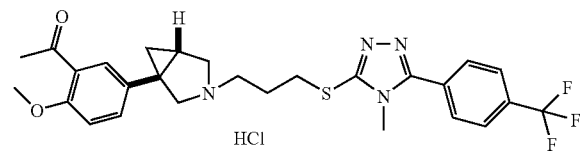

The title compound was prepared in analogy to the method described in Example 1 in 51 mg yield as a white solid (y=60%) from 1-[5-[(1R,5S/1S,5R)-3-azabicyclo[3.1.0]hex-1-yl]-2-(methyloxy)phenyl]ethanone (35 mg) and 3-[(3-chloropropyl)thio]-4-methyl-5-[4-(trifluoromethyl)phenyl]-4H-1,2,4-triazole (60 mg, prepared in analogy to the method described in Preparation 13).

NMR ($^1$H, CDCl$_3$, free base): δ 7.80-7.70 (m, 4H), 7.50 (s, 1H), 7.27-7.20 (m, 1H), 6.85 (d, 1H), 3.86 (s, 3H), 3.62 (s, 3H), 3.40-3.24 (m, 3H), 3.15 (d, 1H), 2.58 (s, 3H), 2.65-2.55 (m, 2H), 2.54-2.45 (m, 2H), 2.10-1.90 (quint, 2H), 1.65-1.57 (m, 1H), 1.35 (m, 1H), 0.75 (m, 1H). MS (m/z): 531 [MH]$^+$.

Example 63

1-[5-[(1R,5S/1S,5R)-3-(3-{[5-(3,4-Difluorophenyl)-4-methyl-4H-1,2,4-triazol-3-yl]thio}propyl)-3-azabicyclo[3.1.0]hex-1-yl]-2-(methyloxy)phenyl]ethanone hydrochloride

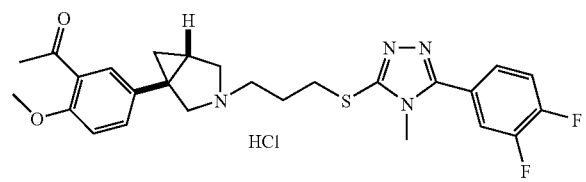

The title compound was prepared in analogy to the method described in Example 1 in 40 mg yield as a white solid (y=50%) from 1-[5-[(1R,5S/1S,5R)-3-azabicyclo[3.1.0]hex-1-yl]-2-(methyloxy)phenyl]ethanone (35 mg) and 3-[(3-chloropropyl)thio]-5-(3,4-difluorophenyl)-4-methyl-4H-1,2,4-triazole (54 mg, prepared in analogy to the method described in Preparation 13).

NMR ($^1$H, CDCl$_3$, free base): δ 7.56-7.19 (m, 5H), 6.84 (d, 1H), 3.86 (s, 3H), 3.62 (s, 3H), 3.38-3.24 (m, 3H), 3.10 (d, 1H), 2.58 (s, 3H), 2.65-2.42 (m, 4H), 2.10-1.90 (quint, 2H), 1.65-1.57 (m, 1H), 1.35 (m, 1H), 0.75 (m, 1H). MS (m/z): 499 [MH]$^+$.

Example 64

1-{2-(Methyloxy)-5-[(1R,5S/1S,5R)-3-(3-{[4-methyl-5-(3-pyridinyl)-4H-1,2,4-triazol-3-yl]thio}propyl)-3-azabicyclo[3.1.0]hex-1-yl]phenyl}ethanone hydrochloride The title compound was prepared in analogy to the method described in Example 1 in 32 mg yield as a yellow solid (y=42%) from 1-[5-[(1R,5S/1S,5R)-3-azabicyclo[3.1.0]hex-1-yl]-2-(methyloxy)phenyl]ethanone (35 mg) and 3-{5-[(3-chloropropyl)thio]-4-methyl-4H-1,2,4-triazol-3-yl}pyridine (48 mg, prepared in analogy to the method described in Preparation 13).

NMR ($^1$H, CDCl$_3$, free base): δ 8.87 (s, 1H), 8.70 (d, 1H), 8.0 (d, 1H), 7.48 (s, 1H), 7.43 (m, 1H), 7.23 (m, 1H), 6.84 (d, 1H), 3.86 (s, 3H), 3.62 (s, 3H), 3.40-3.25 (m, 3H), 3.10 (d, 1H), 2.58 (s, 3H), 2.67-2.42 (m, 4H), 2.10-1.90 (quint, 2H), 1.65-1.57 (m, 1H), 1.35 (m, 1H), 0.75 (m, 1H). MS (m/z): 464 [MH]$^+$.

Example 65

1-[5-[(1R,5S/1S,5R)-3-(3-{[4-Methyl-5-(2-methyl-5-quinolinyl)-4H-1,2,4-triazol-3-yl]thio}propyl)-3-azabicyclo[3.1.0]hex-1-yl]-2-(methyloxy)phenyl]ethanone hydrochloride The title compound was prepared in analogy to the method described in Example 1 in 50 mg yield as a yellow solid (y=60%) from 1-[5-[(1R,5S/1S,5R)-3-azabicyclo[3.1.0]hex-1-yl]-2-(methyloxy)phenyl]ethanone (35 mg) and 5-{5-[(3-chloropropyl)thio]-4-methyl-4H-1,2,4-triazol-3-yl}-2-methylquinoline (60 mg).

NMR ($^1$H, DMSO): δ 10.38 (bs, 1H), 8.2 (m, 2H), 7.91 (t, 1H), 7.78 (d, 1H), 7.5 (m, 3H), 7.17 (d, 1H), 4.02 (d, 1H), 3.89 (s, 3H), 3.74 (dd, 1H), 3.6-3.2 (m, 6H), 3.45 (s, 3H), 2.72 (s, 3H), 2.5 (s, 3H), 2.23 (quint, 2H), 2.11 (quint, 1H), 1.57 (t, 1H), 1.1 (t, 1H). MS (m/z): 528 [MH]$^+$.

Example 66

1-{2-(Methyloxy)-5-[(1R,5S/1S,5R)-3-(3-{[4-methyl-5-(tetrahydro-2H-pyra-4-yl)-4H-1,2,4-triazol-3-yl]thio}propyl)-3-azabicyclo[3.1.0]hex-1-yl]phenyl}ethanone hydrochloride

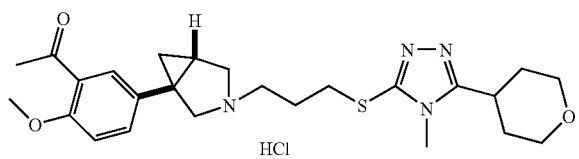

The title compound was prepared in analogy to the method described in Example 1 in 24 mg yield as a white solid (y=32%) from 1-[5-[(1R,5S/1S,5R)-3-azabicyclo[3.1.0]hex-1-yl]-2-(methyloxy)phenyl]ethanone (35 mg) and 3-[(3-chloropropyl)thio]-4-methyl-5-(tetrahydro-2H-pyran-4-yl)-4H-1,2,4-triazole (50 mg, prepared in analogy to the method described in Preparation 13).

NMR ($^1$H, CDCl$_3$, free base): δ 7.49 (s, 1H), 7.24 (m, 1H), 6.85 (d, 1H), 4.14-4.05 (m, 2H), 3.86 (s, 3H), 3.62 (s, 3H), 3.57-3.40 (m, 2H), 3.29-3.15 (m, 3H), 3.05 (d, 1H), 2.82-2.95 (m, 1H), 2.63-2.40 (m, 4H), 2.58 (s, 3H), 2.15-1.77 (m, 6H), 1.62 (m, 1H), 1.32 (m, 1H), 0.70 (m, 1H). MS (m/z): 471 [MH]$^+$.

Example 67

1-(2-Hydroxy-5-{(1R,5S/1S,5R)-3-[3-({4-methyl-5-[4-(trifluoromethyl)phenyl]-4H-1,2,4-triazol-3-yl}thio)propyl]-3-azabicyclo[3.1.0]hex-1-yl}phenyl)ethanone hydrochloride

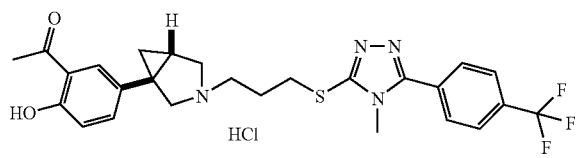

The title compound was prepared in analogy to the method described in Example 1 in 35 mg yield as a white solid (y=33%) from 1-{5-[(1R,5S/1S,5R)-3-azabicyclo[3.1.0]hex-1-yl]2-hydroxyphenyl}ethanone (43 mg) and 3-[(3-chloropropyl)thio]-4-methyl-5-[4-(trifluoromethyl)phenyl]-4H-1,2,4-triazole (80 mg, prepared in analogy to the method described in Preparation 13).

NMR ($^1$H, CDCl$_3$, free base): δ 12.2 (s, 1H), 7.80-7.70 (m, 4H), 7.50 (s, 1H), 7.30 (m, 1H), 6.88 (d, 1H), 3.86 (s, 3H), 3.40-3.25 (m, 3H), 3.10 (d, 1H), 2.58 (s, 3H), 2.65-2.35 (m, 4H), 2.0 (quint, 2H), 1.58 (m, 1H), 1.35 (m, 1H), 0.70 (m, 1H). MS (m/z): 517 [MH]$^+$.

Example 68

1-{5-[(1R,5S/1S,5R)-3-(3-{[5-(3,4-Difluorophenyl)-4-methyl-4H-1,2,4-triazol-3-yl]thio}propyl)-3-azabicyclo[3.1.0]hex-1-yl]-2-hydroxyphenyl}ethanone hydrochloride

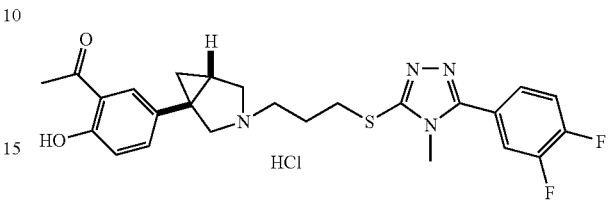

The title compound was prepared in analogy to the method described in Example 1 in 27 mg yield as a white solid (y=29%) from 1-{5-[(1R,5S/1S,5R)-3-azabicyclo[3.1.0]hex-1-yl]-2-hydroxyphenyl}ethanone (40 mg) and 3-[(3-chloropropyl)thio]-5-(3,4-difluorophenyl)-4-methyl-4H-1,2,4-triazole (67 mg, prepared in analogy to the method described in Preparation 13).

NMR ($^1$H, DMSO): δ 11.82 (s, 1H), 10.26 (bs, 1H), 7.85 (m, 1H), 7.76 (d, 1H), 7.67 (m, 1H), 7.61 (m, 1H), 7.51 (dd, 1H), 6.97 (d, 1H), 4.02 (dd, 1H), 3.74 (dd, 1H), 3.64 (s, 3H), 3.55 (m, 2H), 3.3 (m, 4H), 2.67 (s, 3H), 2.15 (m, 3H), 1.52 (t, 1H), 1.13 (t, 1H). MS (m/z): 485 [MH]$^+$.

Example 69

1-{2-Hydroxy-5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]phenyl}ethanone hydrochloride

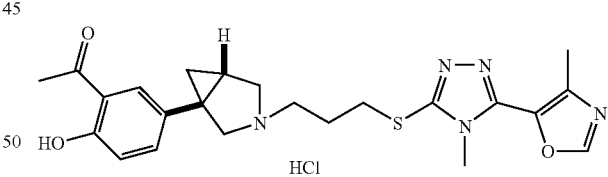

The title compound was prepared in analogy to the method described in Example 1 in 36 mg yield as a white solid (y=43%) from 1-{5-[(1R,5S/1S,5R)-3-azabicyclo[3.1.0]hex-1-yl]-2-hydroxyphenyl}ethanone (38 mg) and 3-[(3-chloropropyl)thio]-4-methyl-5-(4-methyl-1,3-oxazol-5-yl)-4H-1,2,4-triazole (57 mg).

NMR ($^1$H, CDCl$_3$, free base): δ 12.2 (s, 1H), 7.88 (s, 1H), 7.50 (s, 1H), 7.24 (m, 1H), 6.58 (d, 1H), 3.68 (s, 3H), 3.32 (m, 3H), 3.10 (d, 1H), 2.58-2.47 (m, 4H), 2.58 (s, 3H), 2.47 (s, 3H), 2.0 (m, 2H), 1.62 (m, 1H), 1.35 (m, 1H), 0.68 (m, 1H). MS (m/z): 454 [MH]$^+$.

Example 70

1-{2-Hydroxy-5-[(1R,5S/1S,5R)-3-(3-{[4-methyl-5-(2-methyl-5-quinolinyl)-4H-1,2,4-triazol-3-yl]thio}propyl)-3-azabicyclo[3.1.0]hex-1-yl]phenyl}ethanone hydrochloride

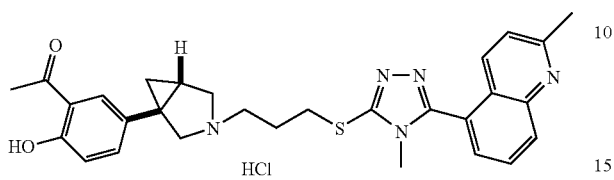

The title compound was prepared in analogy to the method described in Example 1 in 24 mg yield as a yellow solid (y=32%) from 1-{5-[(1R,5S/1S,5R)-3-azabicyclo[3.1.0]hex-1-yl]-2-hydroxyphenyl}ethanone (30 mg) and 5-{5-[(3-Chloropropyl)thio]-4-methyl-4H-1,2,4-triazol-3-yl}-2-methylquinoline (55 mg).

NMR ($^1$H, CDCl$_3$, free base): δ 12.1 (s, 1H), 8.10 (dd, 2H), 7.67 (t, 1H), 7.50 (m, 2H), 7.23 (m, 2H), 6.85 (d, 1H), 3.45-3.23 (m, 3H), 3.40 (s, 3H), 3.08 (d, 1H), 2.67 (s, 3H), 2.65-2.41 (m, 4H), 2.55 (s, 3H), 2.02 (m, 2H), 1.58 (m, 1H), 1.32 (m, 1H), 0.64 (m, 1H). MS (m/z): 514 [MH]$^+$.

Example 71

1-[5-[(1R,5S/1S,5R)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]-1-propanone hydrochloride

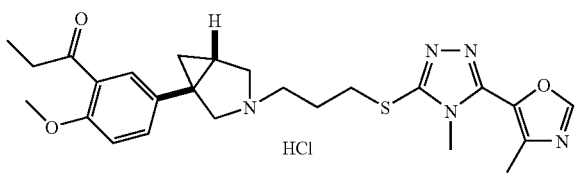

The title compound was prepared in analogy to the method described in Example 1 in 51 mg yield as a white solid (y=47%) from 1-[5-[(1R,5S)-3-azabicyclo[3.1.0]hex-1-yl]-2-(methyloxy)phenyl]-1-propanone (52 mg, prepared in analogy to the method described in Preparations 43-45) and 3-[(3-chloropropyl)thio]-4-methyl-5-(4-methyl-1,3-oxazol-5-yl)-4H-1,2,4-triazole (69 mg).

NMR ($^1$H, DMSO): δ 10.24 (bs, 1H), 8.52 (m, 1H), 7.42 (d, 1H), 7.40 (dd, 1H), 7.08 (d, 1H), 3.93 (dd, 1H), 3.81 (s, 3H), 3.67 (dd, 1H), 3.64 (s, 3H), 3.48 (m, 2H), 3.28 (m, 2H), 3.22 (t, 2H), 2.86 (q, 2H), 2.33 (s, 3H), 2.1 (m, 2H), 2.03 (m, 1H), 1.48 (t, 1H), 1.0 (t, 1H), 1.04 (t, 3H). MS (m/z): 482 [MH]$^+$.

The title compound was separated to give the separated enantiomers by semi-preparative HPLC using a chiral column chiralpak AS-H 5 μm, 250×21 mm, eluent A: n-hexane; B: ethanol+0.1% isopropylamine, gradient isocratic 40% B, flow rate 7 mL/min, detection UV at 200-400 nm. Retention times given were obtained using an analytical HPLC using a chiral column chiralpak AS-H 5 μm, 250×4.6 mm, eluent A: n-hexane; B: ethanol+0.1% isopropylamine, gradient isocratic 40% B, flow rate 0.8 mL/min, detection UV at 200-400 nm.

Enantiomer 1 was recovered in 10 mg yield as white solid (y=30%) from the racemate (66 mg). Rt.=17.2 min.
Enantiomer 2 was recovered in 10 mg yield as white solid (y=30%) from the racemate (66 mg). Rt.=19.1 min.
Enantiomer 1 showed fpKi (D3)>1 log-unit higher than Enantiomer 2.

Example 72

2-Methyl-5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole hydrochloride

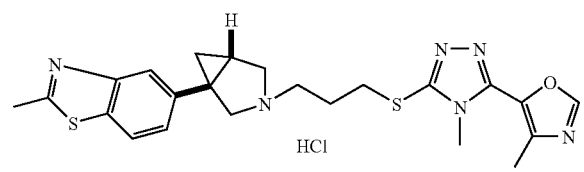

5-[(1R,5S)-3-Azabicyclo[3.1.0]hex-1-yl]-2-methyl-1,3-benzothiazole was prepared from 2-methyl-1,3-benzothiazol-5-amine dihydrochloride in analogy to the method described in Preparations 15, 16 and 17. From this material the title compound was obtained as a yellow solid following the method described for Examples 14 and 15.

NMR ($^1$H, DMSO): δ 10.54 (bs, 1H), 8.58 (m, 1H), 8.0 (d, 1H), 7.9 (d, 1H), 7.34 (dd, 1H), 4.0 (dd, 1H), 3.75 (dd, 1H), 3.70 (s, 3H), 3.65 (m, 1H), 3.57 (m, 1H), 3.35 (m, 2H), 3.30 (t, 2H), 2.8 (s, 3H), 2.39 (s, 3H), 2.27 (m, 1H), 2.19 (m, 2H), 1.7 (t, 1H), 1.19 (t, 1H). MS (m/z): 467 [MH]$^+$.

The title compound was separated to give the separated enantiomers by semi-preparative HPLC using a chiral column chiralpak AS-H 5 μm, 250×21 mm, eluent A: n-hexane; B: ethanol+0.1% isopropylamine, gradient isocratic 13% B, flow rate 7 mL/min, detection UV at 200-400 nm. Retention times given were obtained using an analytical HPLC using a chiral column chiralpak AS-H 5 μm, 250×4.6 mm, eluent A: n-hexane; B: ethanol+0.1% isopropylamine, gradient isocratic 13% B, flow rate 1 mL/min, detection UV at 200-400 nm.

Enantiomer 1 was recovered in 17 mg yield as white solid (y=62%) from the racemate (55 mg). Rt.=17.1 min.
Enantiomer 2 was recovered in 18 mg yield as white solid (y=65%) from the racemate (55 mg). Rt.=19.3 min.
Enantiomer 1 showed fpKi (D3)>1 log-unit higher than Enantiomer 2.

Example 73

2-Methyl-6-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole hydrochloride

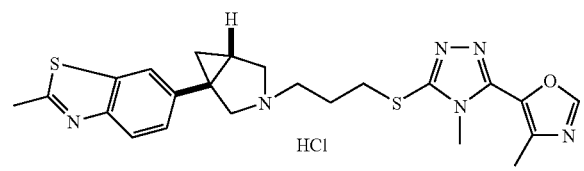

6-[(1R,5S/1S,5R)-3-Azabicyclo[3.1.0]hex-1-yl]-2-methyl-1,3-benzothiazole was prepared from 2-methyl-1,3-benzothiazol-6-amine in analogy to the method described in Preparations 15, 16 and 5. From this material the title compound was obtained as a yellow solid following the method described for Examples 14 and 15.

NMR (¹H, CD₃OD): δ 8.39 (s, 1H), 7.98 (d, 1H), 7.89 (d, 1H), 7.5 (dd, 1H), 4.19 (d, 1H), 3.92 (d, 1H), 3.8 (s, 3H), 3.72 (d, 2H), 3.52 (t, 2H), 3.42 (t, 2H), 2.85 (s, 3H), 2.47 (s, 3H), 2.31 (m, 3H), 1.54 (t, 1H), 1.41 (t, 1H). MS (m/z): 467 [MH]⁺.

Example 74

1-Methyl-5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1H-indazole hydrochloride

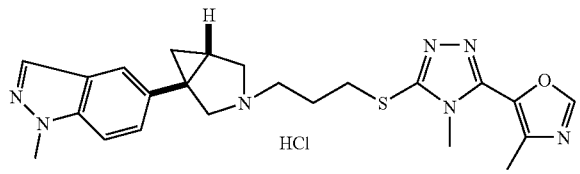

5-[(1R,5S/1S,5R)-3-Azabicyclo[3.1.0]hex-1-yl]-1-methyl-1H-indazole was prepared from 1-methyl-1H-indazol-5-amine in analogy to the method described in Preparations 15, 16 and 5. From this material the title compound was obtained as a yellow solid following the method described for Examples 14 and 15.

NMR (¹H, DMSO): δ 10.4 (bs, 1H), 8.58 (m, 1H), 8.01 (s, 1H), 7.70 (d, 1H), 7.63 (d, 1H), 7.39 (dd, 1H), 4.05 (m, 1H), 4.04 (s, 3H), 3.75 (d, 1H), 3.70 (s, 3H), 3.59 (m, 2H), 3.39 (t, 2H), 3.26 (t, 2H), 2.39 (s, 3H), 2.18 (m, 3H), 1.61 (t, 1H), 1.14 (t, 1H). MS (m/z): 450 [MH]⁺.

The title compound was separated to give the separated enantiomers by semi-preparative SFC (Gilson) using a chiral column chiralpak AS-H, 250×21 mm, modifier: ethanol+0.1% isopropylamine 12%, flow rate 22 mL/min, P 200 bar, T 36° C., detection UV at 220 nm. Retention times given were obtained using an analytical SFC (Berger) using a chiral column chiralpak AS-H 5 μm, 250×46 mm, modifier: ethanol+0.1% isopropylamine 12%, flow rate 2.5 mL/min, P 180 bar, T 35° C., detection UV at 220 nm.

Enantiomer 1 was recovered in 25 mg yield as white solid (y=62%) from the racemate (80 mg). Rt.=19.5 min.

Enantiomer 2 was recovered in 28 mg yield as white solid (y=70%) from the racemate (80 mg). Rt.=22.8 min.

Enantiomer 1 showed fpKi (D3)>1 log-unit higher than Enantiomer 2.

Example 75

(1R,5S/1S,5R)-3-(3-{[4-Methyl-5-(4-methyl-1,3-oxazol-5-yl)-4H-1,2,4-triazol-3-yl]thio}propyl)-1-[6-(trifluoromethyl)-3-pyridinyl]-3-azabicyclo[3.1.0]hexane hydrochloride

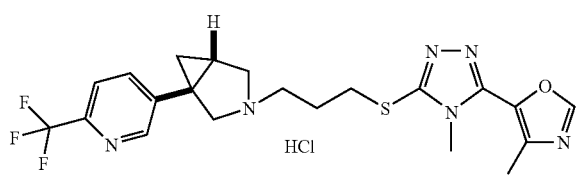

(1R,5S/1S,5R)-1-[6-(Trifluoromethyl)-3-pyridinyl]-3-azabicyclo[3.1.0]hexane was prepared from 6-(trifluoromethyl)-3-pyridinamine in analogy to the method described in Preparations 37 and 5. From this material the title compound was obtained as a yellow solid following the method described for Examples 14 and 15.

NMR (¹H, DMSO): δ 10.46 (bs, 1H), 8.73 (bs, 1H), 8.58 (m, 1H), 8.0 (dd, 1H), 7.90 (d, 1H), 4.12 (m, 1H), 3.78 (d, 1H), 3.70 (s, 3H), 3.7 (m, 1H), 3.54 (m, 1H), 3.39 (t, 2H), 3.29 (s, 2H), 2.39 (m, 3H), 2.47 (m, 1H), 2.18 (m, 2H), 1.71 (m, 1H), 1.33 (m, 1H). NMR (¹⁹F, DMSO): δ −66.2 (s). MS (m/z): 465 [MH]⁺.

Examples 76-94

To a solution of the respective 3-thio-5-aryl-1,2,4-triazole (prepared in analogy to the method described in Preparation 13, 0.063 mmol) in dry acetonitrile (2 mL) 2-tert-butylimino-2-diethylamino-1,3-dimethyl-perhydro-1,3,2-diaza-phosphorine on polystyrene (43 mg, 2.2 mmol/g) was added and the resulting mixture was shaken for 1 h at room temperature, then (1R,5S/1S,5R)-1-(4-bromophenyl)-3-(3-chloropropyl)-3-azabicycle-[3.1.0]hexane (20 mg) was added and the resulting mixture was shaken at 70° C. for 3.5 hours. After cooling the resin was removed by filtration, washed with dichloromethane (2 mL) and methanol (2 mL) and the collected liquid phase was evaporated under reduced pressure. Two isomers were formed by S- and N-alkylation, the major isomer being the desired S-alkylated. Those isomers were separated using mass directed HPLC using a Waters XTerra Prep MS C18 10 μm. 30×150 mm column using the following conditions:

|  | Time | Flow | % A | % B |
| --- | --- | --- | --- | --- |
| Prerun | 0 | 40 ml/min | 99 | 1 |
|  | 1 | 40 ml/min | 99 | 1 |
| Run | 0 | 40 ml/min | 99 | 1 |
|  | 10 | 40 ml/min | 75 | 25 |
|  | 14.5 | 40 ml/min | 10 | 90 |
|  | 15 | 40 ml/min | 0 | 100 |
| Postrun | 0 | 40 ml/min | 0 | 100 |
|  | 0.2 | 45 ml/min | 0 | 100 |
|  | 1.5 | 45 ml/min | 0 | 100 |
|  | 2 | 40 ml/min | 0 | 100 |

A = H2O + 0.1% formic acid
B = acetonitrile + 0.1% formic acid

Then solvent was removed under reduced pressure to give title compounds as formate salts.

In the case of Examples 93 and 94 the isomers were separated by silica gel flash chromatography. The S-alkylated isomers were dissolved in dry diethyl ether and cooled at 0° C. 1.2 eq of HCl (as 1.0 M solution in diethyl ether) were slowly added. The resulting precipitate was decanted, washed with pentane and filtered, yielding the products as the hydrochloride salts.

Analytical Conditions

Examples 76-90

| | |
|---|---|
| Column | X-Terra MS C18 5 um, 50 × 4.6 mm |
| Mobile Phase | A: H20 + 0.1% TFA; B: CH3CN + 0.1% TFA |
| Gradient | 10% (B) for 1 min; from 10% (B) to 90% (B) in 12 min; 90% (B) for 3 min |
| Flow rate | 1 mL/min |
| UV wavelength range | 200-400 nm |
| Mass range | 100-900 amu |
| Ionisation | ES+ |

Example 91

| | |
|---|---|
| Column | X-Terra MS C18 5 um, 50 × 4.6 mm |
| Mobile Phase | A: H20 + 0.2% HCOOH; B: CH3CN + 0.2% HCOOH |
| Gradient | 10% (B) for 1 min; from 10% (B) to 95% (B) in 12 min; 95% (B) for 3 min |
| Flow rate | 1 mL/min |
| UV wavelength range | 210-400 nm |
| Mass range | 100-900 amu |
| Ionisation | ES+ |

Example 93

| | |
|---|---|
| Analytical Column | ZORBAX SB C18, 50 mm, 4.6 mm i.d.; 1.8 um |
| Mobile phase | Amm.Acet., 5 mM/Acetonitrile + 0.1% Formic Acid |
| Gradient | 97/3 > 36/64 v/v in 3.5 min >0/100 v/v in 3.5 min |
| Flow rate | 2 mL/min |
| Detection | DAD, 210-350 nm |
| MS | ES+ |
| Retention time | 2.42 min |
| [M + H]+ | 484/486 (1Br pattern) |
| Assay | 98.17% a/a (by DAD) |

Example 94

| | |
|---|---|
| Analytical Column | ZORBAX SB C18, 50 mm, 4.6 mm i.d.; 1.8 um |
| Mobile phase | Amm.Acet., 5 mM/Acetonitrile + 0.1% Formic Acid |
| Gradient | 97/3 > 36/64 v/v in 3.5 min >0/100 v/v in 3.5 min |
| Flow rate | 2 mL/min |
| Detection | DAD, 210-350 nm |
| MS | ES+ |
| Retention time | 3.02 min |
| [M + H]+ | 552/554 (1Br pattern) |
| Assay | 99.51% a/a (by DAD) |

| Example | Name and Structure | R (min) | Analytical data |
|---|---|---|---|
| 76 | (1R,5S/1S,5R)-1-(4-Bromophenyl)-3-(3-{[4-methyl-5-(2-methyl-3-pyridinyl)-4H-1,2,4-triazol-3-yl]thio}propyl)-3-azabicyclo[3.1.0]hexane formate | 5.92 | NMR ($^1$H, DMSO): δ 8.6(d, 1H), 8.2(s, HCOOH), 7.9(d, 1H), 7.5 (d, 2H), 7.4(dd, 1H), 7.1(d, 2H), 3.4(s, 3H), 3.4(m, 1H + water), 3.25(t, 2H), 3.05(d, 1H), 2.6(m, 1H), 2.5(m, 2H + DMSO), 2.4(m, 1H), 2.4(s, 3H), 1.9(m, 2H), 1.8 (m, 1H), 1.4(m, 1H), 0.8(m, 1H). MS (m/z): 484, 486 [MH]$^+$. |

| Example | Name and Structure | R (min) | Analytical data |
|---|---|---|---|
| 77 | (1R,5S/1S,5R)-1-(4-Bromophenyl)-3-(3-{[4-methyl-5-(4-pyridazinyl)-4H-1,2,4-triazol-3-yl]thio}propyl)-3-azabicyclo[3.1.0]hexane formate | 6.42 | NMR (¹H, DMSO): δ 9.6(d, 1H), 8.2(s, HCOOH), 9.4(dd, 1H), 8.1 (d, 1H), 7.45(d, 2H), 7.1(d, 2H), 3.75(s, 3H), 3.3(m, 1H), 2.25(t, 2H), 3.05(d, 1H), 2.6(t, 2H), 2.5 (d, 1H + DMSO), 2.4(m, 1H), 1.9 (m, 2H), 1.8(m, 1H), 1.4(m, 1H), 0.75(m, 1H).<br>MS (m/z): 471, 473 [MH]⁺. |
| 78 | (1R,5S/1S,5R)-1-(4-Bromophenyl)-3-(3-{[5-(5-chloro-1-methyl-1H-pyrazol-4-yl)-4-methyl-4H-1,2,4-triazol-3-yl]thio}propyl)-3-azabicyclo[3.1.0]hexane formate | 6.94 | NMR (¹H, DMSO): δ 8.2(s, HCOOH), 8.0(s, 1H), 7.45(d, 2H), 7.1(d, 2H), 3.9(s, 3H), 3.55 (s, 3H), 3.3(m, 1H + water), 3.2 (t, 2H), 3.0(m, 1H), 2.6(t, 2H), 2.5(m, 1H), 2.4(m, 1H), 2.85(m, 2H), 2.8(m, 1H), 1.4(m, 1H), 0.75(m, 1H).<br>MS (m/z): 507, 509 [MH]⁺. |
| 79 | (1R,5S/1S,5R)-1-(4-Bromophenyl)-3-(3-{[4-methyl-5-(1-methyl-1H-1,2,3-triazol-4-yl)-4H-1,2,4-triazol-3-yl]thio}propyl)-3-azabicyclo[3.1.0]hexane formate | 6.64 | NMR (¹H, DMSO): δ 8.7(s, 1H), 8.2(s, HCOOH), 7.45(d, 2H), 7.1 (d, 2H), 4.2(s, 3H), 3.85(s, 3H), 3.3(m, 1H), 3.2(t, 2H), 3.05(m, 1H), 2.6(t, 2H), 2.45(m, 1H), 2.4 (m, 1H), 2.9(m, 2H), 2.8(m, 1H), 1.35(m, 1H), 0.75(m, 1H).<br>MS (m/z): 474, 476 [MH]⁺. |

-continued

| Example | Name and Structure | R (min) | Analytical data |
|---|---|---|---|
| 80 | (1R,5S/1S,5R)-1-(4-Bromophenyl)-3-(3-{[5-(1,5-dimethyl-1H-pyrazol-4-yl)-4-methyl-4H-1,2,4-triazol-3-yl]thio}propyl)-3-azabicyclo[3.1.0]hexane formate | 6.62 | NMR ($^1$H, DMSO): δ 8.2(s, HCOOH), 7.8(s, 1H), 7.45(d, 2H), 7.1(d, 2H), 3.85(s, 3H), 3.6 (s, 3H), 3.3(m, 1H + DMSO), 3.2 (t, 2H), 3.0(d, 1H), 2.6(t, 2H), 2.5 (m, 1H), 2.4(s, 3H), 2.4(m, 1H), 1.85(m, 3H), 1.4(m, 1H), 0.75 (m, 1H). MS (m/z): 487, 489 [MH]. |
| 81 | (1R,5S/1S,5R)-1-(4-Bromophenyl)-3-(3-{[4-methyl-5-(5-pyrimidinyl)-4H-1,2,4-triazol-3-yl]thio}propyl)-3-azabicyclo[3.1.0]hexane formate | 6.39 | NMR ($^1$H, DMSO): δ 9.4(d, 1H), 9.2(d, 2H), 8.2(s, HCOOH), 7.45 (d, 2H), 7.1(d, 2H), 3.7(s, 3H), 3.3(m, 1H + DMSO), 3.2(t, 2H), 3.1(m, 1H), 2.6(t, 2H), 2.5 (m, 1H), 2.4(m, 1H), 1.9(t, 2H), 1.8(m, 1H), 1.4(m, 1H), 0.75(m, 1H). MS (m/s): 471, 473 [M]$^+$. |
| 82 | (1R,5S/1S,5R)-1-(4-Bromophenyl)-3-[3-({4-methyl-5-[1-methyl-3-(trifluoromethyl)-1H-pyrazol-4-yl]-4H-1,2,4-triazol-3-yl}thio)propyl]-3-azabicyclo[3.1.0]hexane formate | 7.67 | NMR ($^1$H, DMSO): δ 8.4(s, 1H), 8.2(s, HCOOH), 7.45(d, 2H), 7.1 (d, 2H), 4.05(s, 3H), 3.45(s, 3H), 3.3(m, 1H + water), 3.2(t, 2H), 3.0(m, 1H), 2.6(m ,2H), 2.45(m, 1H), 2.4(m, 1H), 2.85(m, 3H), 1.4(m, 1H), 0.75(m, 1H). MS (m/z): 541, 543 [MH]$^+$. |

| Example | Name and Structure | R (min) | Analytical data |
|---|---|---|---|
| 83 | (1R,5S/1S,5R)-1-(4-Bromophenyl)--3-(3-{[4-methyl-5-(3-methyl-2-furanyl)-4H-1,2,4-triazol-3-yl]thio}propyl)-3-azabicyclo[3.1.0]hexane formate | 7.82 | NMR ($^1$H, DMSO): δ 8.2(s, HCOOH), 7.85(d, 1H), 7.45(d, 2H), 7.1(d, 2H), 6.6(d, 1h), 3.7 (s, 3H), 3.3(m, 1H + water), 3.2 (t, 2H), 3.1(m, 1H), 2.6(m, 2H), 2.5(m, 1H), 2.4(m, 1H), 2.3(s, 3H), 1.9(m, 3H), 1.4(m, 1H), 0.8 (m, 1H). MS (m/z): 473, 475 [MH]$^+$. |
| 84 | (1R,5S/1S,5R)-1-(4-Bromophenyl)-3-(3-{[4-methyl-5-(3-methyl-5-isoxazolyl)-4H-1,2,4-triazol-3-yl]thio}propyl)-3-azabicyclo[3.1.0]hexane formate | 7.22 | NMR ($^1$H, DMSO): δ 8.2(s, HCOOH), 7.45(d, 2H), 7.1(d, 2H), 7.0(s, 1H), 3.8(s, 3H), 3.3 (m, 1H + water), 3.2(t, 2H), 3.0 (m, 1H), 2.6(t, 2H), 2.5(m, 1H), 2.4(m, 1H), 2.4(s, 3H), 1.9(m, 2H), 1.8(m, 1H), 1.35(m, 1H), 0.75(m, 1H). MS (m/z): 474, 476 [MH]$^+$. |
| 85 | (1R,5S/1S,5R)-1-(4-Bromophenyl)-3-(3-{[4-methyl-5-(6-methyl-3-pyridinyl)-4H-1,2,4-triazol-3-yl]thio}propyl)-3-azabicyclo[3.1.0]hexane formate | 5.94 | NMR ($^1$H, DMSO): δ 8.8(d, 1H), 8.2(s, HCOOH), 8.0(dd, 1H), 7.45(d, 2H), 7.45(d, 1H), 7.1(d, 2H), 3.6(s, 3H), 3.3(m, 1H + water), 3.2(t, 2H), 3.05(m, 1H), 2.6(m, 2H), 2.6(s, 3H), 2.5(m, 1H + DMSO), 2.4(m, 1H), 1.9(m, 2H), 1.8(m, 1H), 1.4(m, 1H), 0.75(m, 1H). MS (m/z): 484, 484 [MH]$^+$. |

-continued

| Example | Name and Structure | R (min) | Analytical data |
|---|---|---|---|
| 86 | (1R,5S/1S,5R)-1-(4-Bromophenyl)-3-(3-{[4-methyl-5-(1-methyl-1H-pyrazol-5-yl)-4H-1,2,4-triazol-3-yl]thio}propyl)-3-azabicyclo[3.1.0]hexane formate | 6.87 | NMR ($^1$H, DMSO): δ 8.2(s, HCOOH), 7.6(d, 1H), 7.45(d, 2H), 7.1(d, 2H), 6.8(d, 2H), 4.0 (s, 3H), 3.6(s, 3H) 3.3(m, 1H + water), 3.2(t, 2H), 3.1(m ,1H), 2.6(t, 2H), 2.5(m, 1H + DMSO), 2.4(m, 1H), 1.9(m, 2H), 1.8(m, 1H), 1.4(m, 1H), 0.75(m, 1H). MS (m/z): 473, 475 [MH]$^+$. |
| 87 | (1R,5S/1S,5R)-1-(4-Bromophenyl)-3-(3-{[4-methyl-5-(5-methyl-3-pyridinyl)-4H-1,2,4-triazol-3-yl]thio}propyl)-3-azabicyclo[3.1.0]hexane formate | 6.09 | NMR ($^1$H, DMSO): δ 8.75(dd, 1H), 8.6(dd, 1H), 8.2(s, HCOOH), 8.0(dd, 1H), 7.45(d, 2H), 7.1(d, 2H), 3.6(s, 3H), 3.3 (m, 1H + water), 3.2(t, 2H), 3.05 (m, 1H), 2.6(t, 2H) ,2.5(m, 1H), 2.4(m, 1H), 2.4(s, 3H), 1.9(m, 2H), 1.8(m, 1H), 1.4(m, 1H), 0.75(m, 1H). MS (m/z): 484, 486 [MH$^+$]. |
| 88 | (1R,5S/1S,5R)-1-(4-Bromophenyl)-3-[3-({4-methyl-5-[2-methyl-5-(trifluoromethyl)-1,3-oxazol-4-yl]-4H-1,2,4-triazol-3-yl}thio)propyl]-3-azabicyclo[3.1.0]hexane formate | 8.12 | NMR ($^1$H, DMSO): δ 8.2(s, HCOOH), 7.45(d, 2H), 7.1(d, 2H), 3.7(s, 3H), 3.3(m, 1H), 3.2 (t, 2H), 3.05(m, 1H), 2.65(t, 3H), 2.6(t, 2H), 2.5(m, 1H), 2.4(m, 1H), 1.9(m, 2H), 1.8(m, 1H), 1.35(m, 1H), 0.75(m, 1H). MS (m/z): 542, 544 [MH]$^+$. |

| Example | Name and Structure | R (min) | Analytical data |
|---|---|---|---|
| 89 | (1R,5S/1S,5R)-1-(4-Bromophenyl)-3-(3-{[4-methyl-5-(3-methyl-2-pyridinyl)-4H-1,2,4-triazol-3-yl]thio}propyl)-3-azabicyclo[3.1.0]hexane formate 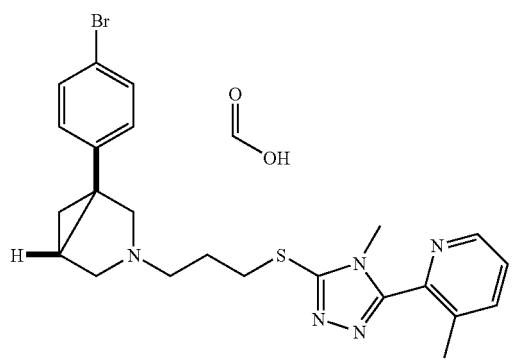 | 7.17 | NMR ($^1$H, DMSO): δ 9.6(dd, 1H), 8.2(s, HCOOH), 7.9(dd, 1H), 7.45(dd, 1H), 7.45(d, 2H), 7.1(d, 2H), 3.6(s, 3H), 3.3(m, 1H), 3.2(t, 2H), 3.05(m, 1H), 2.6(t, 2H), 2.5(m, 1H), 2.5(s, 3H), 2.4, m, 1H), 1.9(m, 2H), 1.8(m, 1H), 1.4(m, 1H), 0.75(m, 1H). MS (m/z): 484, 486 [MH]$^+$. |
| 90 | (1R,5S/1S,5R)-1-(4-Bromophenyl)-3-(3-{[5-(2,4-dimethyl-1,3-thiazol-5-yl)-4-methyl-4H-1,2,4-triazol-3-yl]thio}propyl)-3-azabicyclo[3.1.0]hexane formate 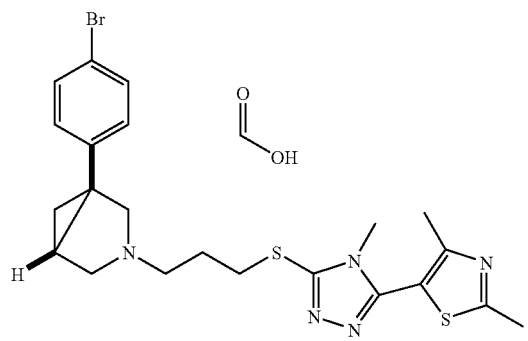 | 6.96 | NMR ($^1$H, DMSO): δ 8.2(s, HCOOH), 7.45(d, 2H), 7.1(d, 2H), 3.5(s, 3H), 3.3(m, 1H + water), 3.2(t, 2H), 3.0(m, 1H), 2.75(s, 3H), 2.6(t, 2H), 2.5(m, 1H), 2.4(m, 1H), 2.3(s, 3H), 1.9(m, 2H), 1.8(m, 1H), 1.35(m, 1H), 0.75(m, 1H). MS (m/z): 504, 506 [M$^+$. |
| 91 | (1R,5S/1S,5R)-1-(4-Bromophenyl)-3-(3-{[5-(2,5-dimethyl-3-furanyl)-4-methyl-4H-1,2,4-triazol-3-yl]thio}propyl)-3-azabicyclo[3.1.0]hexane formate 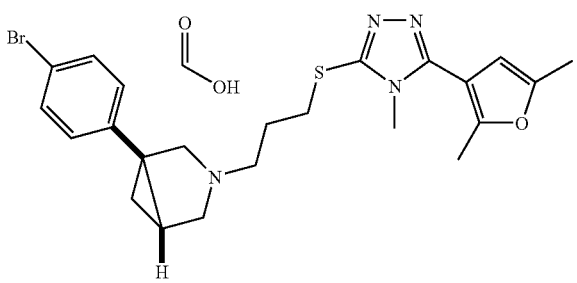 | 8.33 | NMR ($^1$H, DMSO): δ 8.2(s, HCOOH), 7.45(d, 2H), 7.1(d, 2H), 6.4(s, 1H), 3.5(s, 3H), 3.3(m, 1H), 3.2(t, 2H), 3.1(m, 1H), 2.6(t, 2H), 2.5(m, 1H), 2.4(m, 1H), 2.4(s, 3H), 2.3(s, 3H), 1.85(m, 3H), 1.3(m, 1H), 0.75(m, 1H). MS (m/z): 487, 489 [MH]$^+$. |

| Example | Name and Structure | R (min) | Analytical data |
|---|---|---|---|
| 92 | (1R,5S/1S,5R)-1-(4-Bromophenyl)-3-(3-{-[5-(5-chloro-2-thienyl)-4-methyl-4H-1,2,4-triazol-3-yl]thio}propyl)-3-azabicyclo[3.1.0]hexane hydrochloride | n.d. | NMR ($^1$H, CD$_3$OD): δ 7.54(m, 3H), 7.29(d, 2H), 7.23(d, 1H), 4.12(dd, 1H), 3.88(dd, 1H), 3.82 (s, 3H), 3.65(m, 2H), 3.50(t, 2H), 3.40(t, 2H), 2.3(m, 3H), 1.50-1.3(2t, 2H). |
| 93 | (1R,5S/1S,5R)-1-(4-Bromophenyl)-3-(3-{[4-ethyl-5-(3-pyridinyl)-4H-1,2,4-triazol-3-yl]thio}propyl)-3-azabicyclo[3.1.0]hexane hydrochloride | 2.42 | NMR ($^1$H, DMSO): δ 10.45(bs, HCl), 8.85(dd, 1H), 8.75(dd, 1H), 8.1(dt, 1H), 7.6(dd, 1H), 7.45(d, 2H), 7.1(d, 2H), 4.0(m, 2H), 3.6(m, 2H + water), 3.35(m, 4H), 2.5(m, 2H + DMSO), 2.2(m, 3H), 1.6(m, 1H), 1.2(t, 3H), 1.1 (m, 1H). <br> MS (m/z): 484, 486 [MH]$^+$ |
| 94 | (1R,5S/1S,5R)-1-(4-Bromophenyl)-3-[3-({4-methyl-5-[2-methyl-6-(trifluoromethyl)-3-pyridinyl]-4H-1,2,4-triazol-3-yl}thio)propyl]-3-azabicyclo[3.1.0]hexane hydrochloride | 3.02 | NMR ($^1$H, DMSO): δ 10.45(bs, HCl), 8.2(d, 1H), 7.9(d, 1H), 7.55(d, 2H), 7.25(d, 2H), 4.05 (m, 1H), 3.7(m, 1H), 3.5(m, 1H + water), 3.4(s, 3H), 3.3(m, 4H), 2.5(s, 3H + DMSO), 2.2(m, 3H), 1.6(m, 1H), 1.2(m, 1H), 1.1(m, 1H). <br> MS (m/z): 552, 554 [MH]$^+$. |

| Example | Name and Structure | R (min) | Analytical data |
|---|---|---|---|
| 95 | 5-[5-({3-[(1R,5S/1S,5R)-1-(4-Bromophenyl)-3-azabicyclo[3.1.0]hex-3-yl]propyl}thio)-4-methyl-4H-1,2,4-triazol-3-yl]-1-methyl-3-(trifluoromethyl)-1H-thieno[2,3-c]pyrazole hydrochloride<br />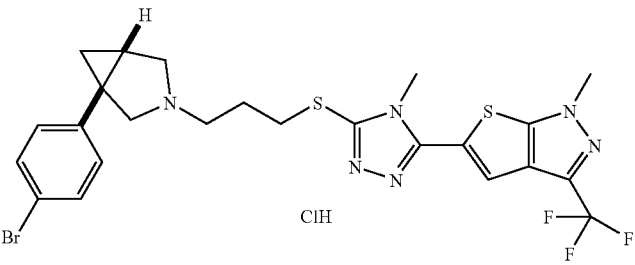 | n.d. | NMR (¹H, DMSO): 10.6 (broad s, 1H, HCl), 7.65(s, 1H), 7.5(d, 2H), 7.25(d, 2H), 4.1(s, 3H), 4.0 (m, 1H), 3.8(s, 3H + water), 3.7 (m, 1H), 3.5(m, 2H), 3.25(m, 4H), 2.2(m, 3H), 1.65(m, 1H), 1.1(m, 1H)<br />MS (m/z): 597, 599. |

Example 96

3-(3-{[4-Methyl-5-(4-methyl-1,3-oxazol-5-yl)-4H-1,2,4-triazol-3-yl]thio}propyl)-(1R,5R/1S,5S)-1-[5-(trifluoromethyl)-2-pyridinyl]-3-azabicyclo[3.1.0]hexane hydrochloride

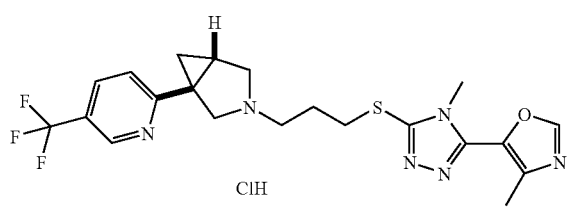

The title compound was prepared in analogy to the method described in Example 1 as a white slightly hygroscopic solid (70 mg, 45%), from 1-[5-(trifluoromethyl)-2-pyridinyl]-3-azabicyclo[3.1.0]hexane.

NMR (corresponding free base, ¹H, CD₃OD): δ 8.71 (s, 1H), 7.93 (s, 1H), 7.78 (dd, 1H), 7.15 (d, 1H), 3.72 (s, 3H), 3.41 (d, 1H), 3.36 (t, 2H), 3.13 (d, 1H), 2.8 (d, 1H), 2.68 (m, 2H), 2.54 (s, 3H), 2.48 (dd, 1H), 2.04 (m, 3H), 1.6 (m, 1H), 1.26 (dd, 1H). MS (m/z): 465 [MH]⁺.

Example 96 was separated to give the separated enantiomers by semi-preparative HPLC using a chiral column Chirapak AD-H 5 μm, 250×4.6 mm, eluent A: n-hexane; B: Ethanol+0.1% isopropylamine, gradient isocratic 30% B v/v, flow rate 6 mL/min, detection UV at 270 nm. Retention times given were obtained using a chiral column Chirapak AD-H 5 μm, 250×4.6 mm, eluent A: n-hexane; B: Ethanol, gradient isocratic 30% B v/v, flow rate 0.8 mL/min, detection UV at 200-400 nm.

Enantiomer 1 was recovered in 18 mg yield as a white solid, hydrochloride salt from the racemate (70 mg). Rt.=19.09 min. Purity 100% a/a by UV Enantiomer 2 was recovered in 18 mg yield as white solid, hydrochloride salt from the racemate (70 mg). Rt.=21.6 min. Purity 99% a/a by UV.

Enantiomer 2 showed fpKi (D3)>1 log-unit higher than Enantiomer 1.

Example 97

3-(3-{[4-methyl-5-(4-methyl-1,3-oxazol-5-yl)-4H-1,2,4-triazol-3-yl]thio}propyl)-(1R,5R/1S,5S)-1-[6-(trifluoromethyl)-2-pyridinyl]-3-azabicyclo[3.1.0]hexane dihydrochloride

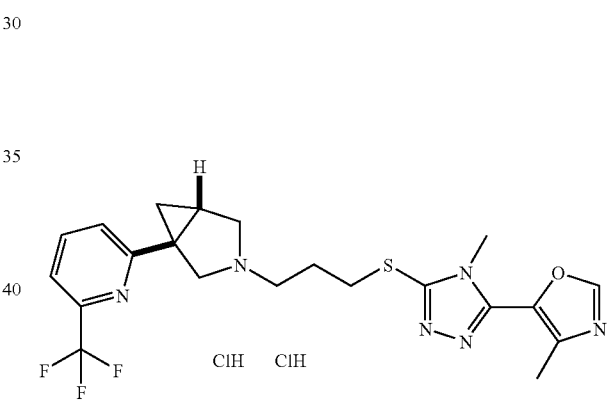

3-(Phenylmethyl)-1-[5-(trifluoromethyl)-2-pyridinyl]-3-azabicyclo[3.1.0]hexane (0.19 mmol) was dissolved in 1,2-dichloroethane (1 mL) and 1-chloroethyl chloridocarbonate was added (0.21 mmol). After two microwave cycles (5 min at 120° C. and 10 min at 140° C.) the solvent was removed at reduced pressure. Methanol (2 mL) was added and the solution was submitted to an additional microwave cycle (10 min, 120° C.). The solvent was removed at reduced pressure to give 47 mg of intermediate which was used without further purification and treated in analogy to the method described in Example 1 to give the title compound (5 mg, 5%) as a white slightly hygroscopic solid.

NMR (¹H, CD₃OD): δ 8.38 (s, 1H), 7.99 (dd, 1H), 7.67 (dd, 1H), 7.48 (dd, 1H), 4.18 (d, 1H), 4.06 (d, 1H), 3.88 (d, 1H), 3.79 (s, 3H), 3.63 (dd, 1H), 3.50 (m, 2H), 3.41 (t, 2H), 2.49 (m, 1H), 2.44 (s, 3H), 2.31 (m, 2H), 1.69 (m, 1H), 1.65 (dd, 1H). MS (m/z): 465 [MH]⁺.

Example 98

(1R,5S/1S,5R)-1-[3-Fluoro-4-(1H-pyrrol-1-ylm-ethyl)phenyl]-3-(3-{[4-methyl-5-(4-methyl-1,3-ox-azol-5-yl)-4H-1,2,4-triazol-3-yl]thio}propyl)-3-azabicyclo[3.1.0]hexane hydrochloride

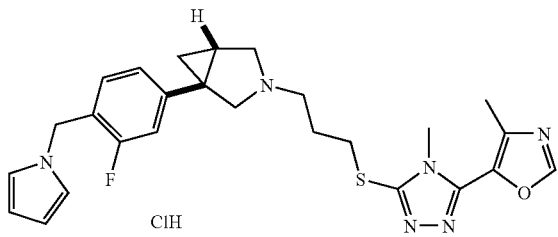

The title compound was prepared in analogy to the method described in Example 1 as a white slightly hygroscopic solid (5.4 mg, yield=19%), from 1-[3-fluoro-4-(1H-pyrrol-1-ylm-ethyl)phenyl]-3-azabicyclo[3.1.0]hexane (Preparation 57).

NMR (as formate salt) (1H, CDCl3): δ 7.9 (s, 1H), 6.8 (m, 4H), 6.65 (s, 2H), 6.15 (s, 2H), 5.05 (s, 2H), 3.66 (s, 3H), 3.4 (d, 1H), 3.25 (t, 2H), 3.2 (d, 1H), 2.75 (t, 2H), 2.6 (d, 1H), 2.55 (m, 1H), 2.5 (s, 3H), 2.0 (m, 2H), 1.7 (m, 1H), 1.45 (t, 1H), 0.8 (m, 1H); acidic proton not observed. MS (hydrochloride salt) (m/z): 475 [MH]$^+$.

Examples 99-104

Examples 99-104 were prepared as white slightly hygroscopic solids from (1R,5S/1S,5R)-3-(3-chloropropyl)-1-[6-(trifluoromethyl)-3-pyridinyl]-3-azabicyclo[3.1.0]hexane (40 mg) in analogy to the method described for Examples 53-58.

| Example | Name and Structure | R (min) | Analytical data |
|---|---|---|---|
| 99 | (1S,5R/1R,5S)-3-(3-{[4-Methyl-5-(5-methyl-2-pyrazinyl)-4H-1,2,4-triazol-3-yl]thio}propyl)-1-[6-(trifluoromethyl)-3-pyridinyl]-3-azabicyclo[3.1.0]hexane hydrochloride | 5.82 | MS (m/z): 477 [MH]$^+$. |
| 100 | (1S,5R/1R,5S)-3-(3-{[4-Methyl-5-(6-methyl-3-pyridinyl)-4H-1,2,4-triazol-3-yl]thio}propyl)-1-[6-(trifluoromethyl)-3-pyridinyl]-3-azabicyclo[3.1.0]hexane hydrochloride | 5.05 | NMR ($^1$H, DMSO): δ 9.11(d, 1H), 8.76(dd, 1H), 8.73(bs, 1H), 8.08(d, 1H), 8.01(bdd, 1H), 7.83(d, 1H), 4.25(d, 1H), 3.95(d, 1H), 3.81(s, 3H), 3.79(d, 1H), 3.71(dd, 1H), 3.54(t, 2H), 3.45(t, 2H), 2.89(s, 3H), 2.46(m, 1H), 2.33(m, 2H), 1.69(dd, 1H), 1.47(t, 1H). Acidic proton not observed. MS (m/z): 476 [MH]$^+$. |

-continued

| Example | Name and Structure | R (min) | Analytical data |
|---------|--------------------|---------|-----------------|
| 101 | (1S,5R/1R,5S)-3-(3-{[4-Methyl-5-(2-methyl-3-pyridinyl)-4H-1,2,4-triazol-3-yl]thio}propyl)-1-[6-(trifluoromethyl)-3-pyridinyl]-3-azabicyclo[3.1.0]hexane hydrochloride | 4.82 | MS (m/z): 476 [MH]$^+$ |
| 102 | (1S,5R/1R,5S)-3-(3-[(4-Methyl-5-phenyl-4H-1,2,4-triazol-3-yl)thio]propyl}-1-[6-(trifluoromethyl)-3-pyridinyl]-3-azabicyclo[3.1.0]hexane hydrochloride | 6.27 | MS (m/z): 461 [MH]$^+$ |
| 103 | (1S,5R/1R,5S)--3-(3-{[5-(2,4-Dimethyl-1,3-thiazol-5-yl)-4-methyl-4H-1,2,4-triazol-3-yl]thio}propyl)-1-[6-(trifluoromethyl)-3-pyridinyl]-3-azabicyclo[3.1.0]hexane hydrochloride | 5.40 | MS (m/z): 496 [MH]$^+$ |

| Example | Name and Structure | R (min) | Analytical data |
|---|---|---|---|
| 104 | (1S,5R/1R,5S)-3-[3-({4-Methyl-5-[4-(trifluoromethyl)phenyl]-4H-1,2,4-triazol-3-yl}thio)propyl]-1-[6-(trifluoromethyl)-3-pyridinyl]-3-azabicyclo[3.1.0]hexane hydrochloride 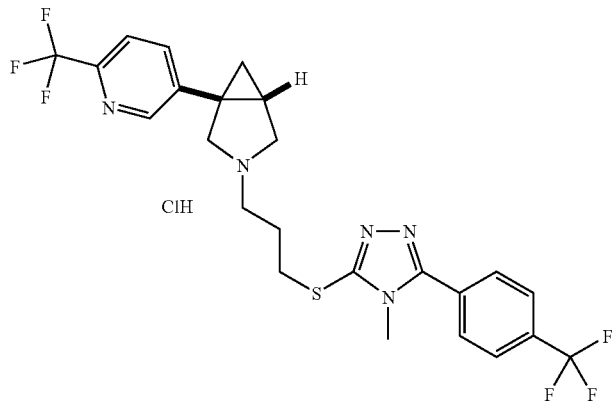 | 7.36 | MS (m/z): 528 [MH]+. |

Examples 105-109

Examples 105-109 were prepared as white slightly hygroscopic solids from 5-[(1R,5S/1S,5R)-3-(3-chloropropyl)-3-azabicyclo[3.1.0]hex-1-yl]-2-methyl-1,3-benzothiazole (40 mg) in analogy to the method described in Example 53-58.

| Example | Name | R (min) | Analytical data |
|---|---|---|---|
| 105 | (1S,5R/1R,5S)-2-Methyl-5-[3-(3-{[4-methyl-5-(5-methyl-2-pyrazinyl)-4H-1,2,4-triazol-3-yl]thio}propyl)-3-azabicyclo[3.1.0]hex-1-yl]-1,3-benzothiazole hydrochloride 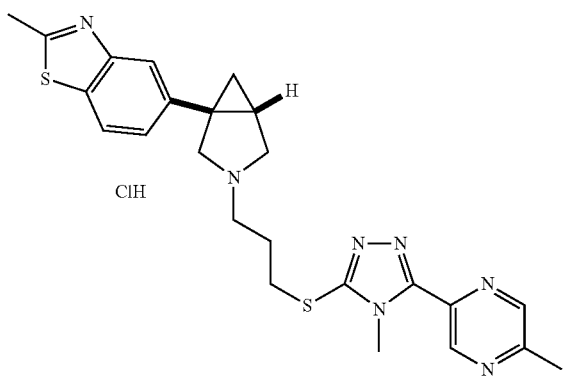 | 5.83 | MS (m/z): 478 [MH]+. |

| Example | Name | R (min) | Analytical data |
|---|---|---|---|
| 106 | (1S,5R/1R,5S)-2-Methyl-5-[3-(3-{[4-methyl-5-(6-methyl-3-pyridinyl)-4H-1,2,4-triazol-3-yl]thio}propyl)-3-azabicyclo[3.1.0]hex-1-yl]-1,3-benzothiazole hydrochloride | 5.04 | MS (m/z): 477 [MH]+. |
| 107 | (1S,5R/1R,5S)-2-Methyl-5-(3-{3-[(4-methyl-5-phenyl-4H-1,2,4-triazol-3-yl)thio]propyl}-3-azabicyclo[3.1.0]hex-1-yl)-1,3-benzothiazole hydrochloride | 6.28 | MS (m/z): 462 [MH]+ |
| 108 | (1S,5R/1R,5S)-5-[3-(3-{[5-(2,4-Dimethyl-1,3-thiazol-5-yl)-4-methyl-4H-1,2,4-triazol-3-yl]thio}propyl)-3-azabicyclo[3.1.0]hex-1-yl]-2-methyl-1,3-benzothiazole hydrochloride | 5.35 | MS (m/z): 497 [MH]+ |

| Example | Name | R (min) | Analytical data |
|---|---|---|---|
| 109 | (1S,5R/1R,5S)-2-Methyl-5-{3-[3-({4-methyl-5-[4-(trifluoromethyl)phenyl]-4H-1,2,4-triazol-3-yl}thio)propyl]-3-azabicyclo[3.1.0]hex-1-yl}-1,3-benzothiazole hydrochloride | 7.43 | NMR (¹H, DMSO): δ 7.98-8.03(m, 4H), 7.97(d, 1H), 7.89(s, 1H), 7.45(d, 1H), 4.2 (d, 1H), 3.91(d, 1H), 3.78(s, 3H), 3.73(d, 2H), 3.49(m, 4H), 2.88(s, 3H), 2.36(m, 3H), 1.6(t, 1H), 1.37(t, 1H). MS (m/z): 530 [MH]⁺. |

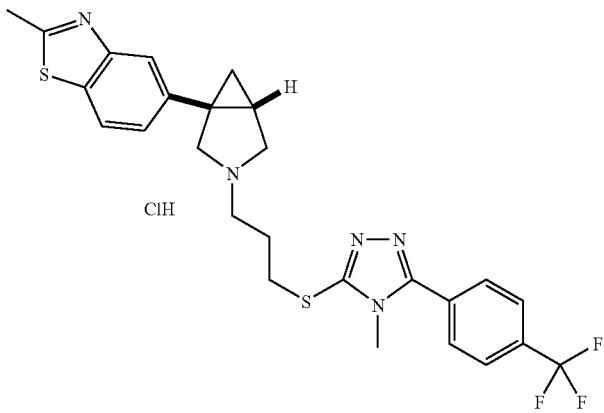

Example 110

(1R,5S/1S,5R)-1-[3-Fluoro-5-(trifluoromethyl)phenyl]-3-(3-({[4-methyl-5-(4-methyl-1,3-oxazol-5-yl)-4H-1,2,4-triazol-3-yl]thio}propyl)-azabicyclo[3.1.0]hexane hydrochloride

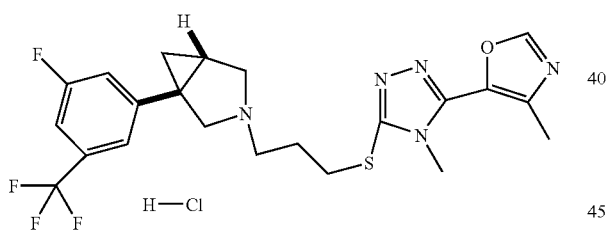

The title compound was prepared in analogy to the method described in Example 1 in 383 mg yield as a white slightly hygroscopic solid (y=46%) from (1R,5S/1S,5R)-1-[3-fluoro-5-(trifluoromethyl)phenyl]-3-azabicyclo[3.1.0]hexane (400 mg).

NMR (¹H, CD3OD): δ 8.46 (s, 1H), 7.54 (bs, 1H), 7.47 (bd, 1H), 7.41 (bd, 1H), 4.19 (d, 1H), 3.09 (d, 1H), 3.87 (s, 3H), 3.71 (m, 2H), 3.51 (t, 2H), 3.46 (t, 2H), 2.49 (s, 3H), 2.33 (m, 3H), 1.67 (m, 1H), 1.39 (m, 1H). MS (m/z): 482 [MH]⁺.

(1R,5S/1S,5R)-1-[3-Fluoro-5-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane hydrochloride was separated to give the separated enantiomers by semipreparative Supercritical Fluid Chromatography (Gilson) using a chiral column Chiralcel AD-H, 25×2.1 cm, eluent CO₂ containing 9% (ethanol+0.1% isopropylamine), flow rate 22 mL/min, P 192 bar, T 36° C., detection UV at 220 nm, loop 2 mL. Retention times given were obtained using an analytical Supercritical Fluid Chromatography (Gilson) using a chiral column Chiralpak AD-H, 25×0.46 cm, eluent CO₂ containing 10% (ethanol+0.1% isopropylamine), flow rate 2.5 mL/min, P 180 bar, T 35° C., detection UV at 220 nm.

Enantiomer 1 was recovered in 19.4 mg yield as white solid, hydrochloride salt from the racemate (100 mg). Rt.=12.6 min. Purity >99% a/a by UV Enantiomer 2 was recovered in 18.3 mg yield as white solid, hydrochloride salt from the racemate (100 mg). Rt.=14.7 min. Purity >99% a/a by UV Enantiomer 1 showed fpKi (D3)>1 log-unit higher than Enantiomer 2.

Example 110

(1R,5S/1S,5R)-1-[3-Fluoro-5-(trifluoromethyl)phenyl]-3-(3-({[4-methyl-5-(4-methyl-1,3-oxazol-5-yl)-4H-1,2,4-triazol-3-yl]thio}propyl)-azabicyclo[3.1.0]hexane hydrochloride

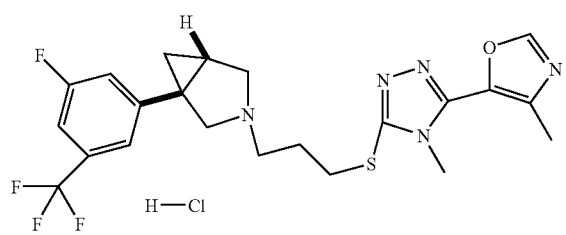

The title compound was prepared in analogy to the method described in Example 1 in 383 mg yield as a white slightly hygroscopic solid (y=46%) from (1R,5S/1S,5R)-1-[3-fluoro-5-(trifluoromethyl)phenyl]-3-azabicyclo[3.1.0]hexane (400 mg).

NMR (¹H, CD3OD): δ 8.46 (s, 1H), 7.54 (bs, 1H), 7.47 (bd, 1H), 7.41 (bd, 1H), 4.19 (d, 1H), 3.09 (d, 1H), 3.87 (s, 3H), 3.71 (m, 2H), 3.51 (t, 2H), 3.46 (t, 2H), 2.49 (s, 3H), 2.33 (m, 3H), 1.67 (m, 1H), 1.39 (m, 1H). MS (m/z): 481 [MH]⁺.

(1R,5S/1S,5R)-1-[3-Fluoro-5-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane hydrochloride was separated to give the separated enantiomers by semipreparative Supercritical Fluid Chromatography (Gilson) using a chiral column Chiralcel AD-H, 25×2.1 cm, eluent CO2 containing 9% (ethanol+0.1% isopropylamine), flow rate 22 mL/min, P 192 bar, T 36° C., detection UV at 220 nm, loop 2 mL. Retention times given were obtained using an analytical Supercritical Fluid Chromatography (Gilson) using a chiral column Chiralpak AD-H, 25×0.46 cm, eluent CO2 containing 10% (ethanol+0.1% isopropyilamine), flow rate 2.5 mL/min, P 180 bar, T 35° C., detection UV at 220 nm.

Enantiomer 1 was recovered in 19.4 mg yield as white solid, hydrochloride salt from the racemate (100 mg). Rt.=12.6 min. Purity >99% a/a by UV Enantiomer 2 was recovered in 18.3 mg yield as white solid, hydrochloride salt from the racemate (100 mg). Rt.=14.7 min. Purity >99% a/a by UV Enantiomer 1 showed fpKi (D3)>1 log-unit higher than Enantiomer 2.

Example 111

(1R,5S/1S,5R)-1-[2-Fluoro-3-(trifluoromethyl)phenyl]-3-(3-({[4-methyl-5-(4-methyl-1,3-oxazol-5-yl)-4H-1,2,4-triazol-3-yl]thio}propyl)-azabicyclo[3.1.0]hexane hydrochloride

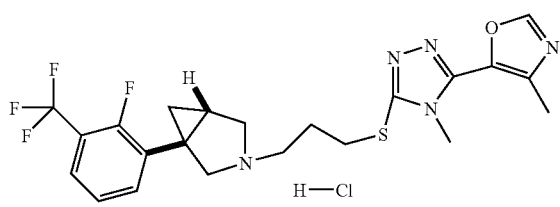

The title compound was prepared in analogy to the method described in Example 1 in 349 mg yield as a white slightly hygroscopic solid (y=45%) from (1R,5S/1S,5R)-1-[2-fluoro-3-(trifluoromethyl)phenyl]-3-azabicyclo[3.1.0]hexane (400 mg).

NMR ($^1$H, CD3OD): δ 8.46 (s, 1H), 7.75-7.65 (m, 2H), 7.38 (t, 1H), 4.1 (d, 1H), 3.93 (d, 1H), 3.78 (s, 3H), 3.71 (d, 1H), 3.54 (d, 1H), 3.48 (t, 2H), 3.38 (t, 2H), 2.45 (s, 3H), 2.36 (m, 1H), 2.25 (m, 2H), 1.54 (m, 1H), 1.34 (m, 1H). MS (m/z): 481 [MH]$^+$.

(1R,5S/1S,5R)-1-[2-Fluoro-3-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane hydrochloride was separated to give the separated enantiomers by semipreparative Supercritical Fluid Chromatography (Gilson) using a chiral column Chiralpak AD-H, 250×4.6 mm, eluent n-Hexane/Ethanol 88/12 (isocratic), flow rate 1 mL/min, P 200-400 bar, T 36° C., detection UV at 200-400 nm, loop 2 mL. Retention times given were obtained using an analytical Supercritical Fluid Chromatography (Gilson) using a chiral column Chiralpak AD-H, 250×4.6 mm, eluent n-Hexane/Ethanol 88/12 (isocratic), flow rate 1 mL/min, P 200-400 bar, T 36° C., detection UV at 200-400 nm.

Enantiomer 1 was recovered in 37 mg yield as white solid, hydrochloride salt from the racemate (98 mg). Rt.=20.4 min. Purity 98.5% a/a by UV Enantiomer 2 was recovered in 35 mg yield as white solid, hydrochloride salt from the racemate (98 mg). Rt.=23.0 min. Purity 99.5% a/a by UV Enantiomer 2 showed fpKi (D3)>1 log-unit higher than Enantiomer 1.

Example 112

(1R,5S/1S,5R)-1-[4-(Methyloxy)-5-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane hydrochloride

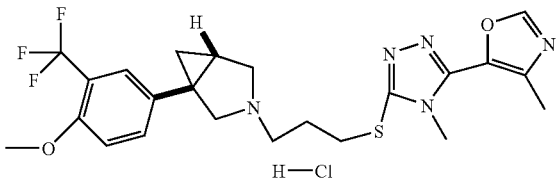

The title compound was prepared in analogy to the method described in Example 1 in 658 mg yield as a white slightly hygroscopic solid (y=76%) from (1R,5S/1S,5R)-1-[4-(methyloxy)-5-(trifluoromethyl)phenyl]-3-azabicyclo[3.1.0]hexane (430 mg).

NMR ($^1$H, CD3OD): δ 8.37 (s, 1H), 7.57 (m, 2H), 7.17 (d, 1H) 3.9 (m, 4H), 3.77 (s, 3H), 3.74 (m, 1H), 3.65-3.30 (m, 6H), 2.44 (s, 3H), 2.21 (m, 2H), 2.13 (m, 1H), 1.43 (t, 1H), 1.24 (m, 1H). MS (m/z): 494 [MH]$^+$.

(1R,5S/1S,5R)-1-[4-(Methyloxy)-5-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane hydrochloride was separated to give the separated enantiomers by semipreparative Supercritical Fluid Chromatography (Gilson) using a chiral column Chiralpak AD-H, 250×4.6 mm, eluent n-Hexane/Ethanol+0.1% isopropylamine 70/30 (isocratic), flow rate 6 mL/min, detection UV at 270 nm, loop 2 mL. Retention times given were obtained using an analytical Supercritical Fluid Chromatography (Gilson) using a chiral column Chiralpak AD-H, 250×4.6 mm, eluent n-Hexane/Ethanol 70/30 (isocratic), flow rate 0.8 mL/min, detection UV at 200-400 nm.

Enantiomer 1 was recovered in 18.3 mg yield as white solid, hydrochloride salt from the racemate (100 mg). Rt.=15.5 min. Purity >99% a/a by UV Enantiomer 2 was recovered in 22.2 mg yield as white solid, hydrochloride salt from the racemate (100 mg). Rt.=17.5 min. Purity >99% a/a by UV Enantiomer 2 showed fpKi (D3)>2 log-units higher than Enantiomer 1.

Example 113

(1R,5S/1S,5R)-1-[4-(4-Chloro-2-fluorophenyl]-3-(3-({[4-methyl-5-(4-methyl-1,3-oxazol-5-yl)-4H-1,2,4-triazol-3-yl]thio}propyl)-azabicyclo[3.1.0]hexane hydrochloride

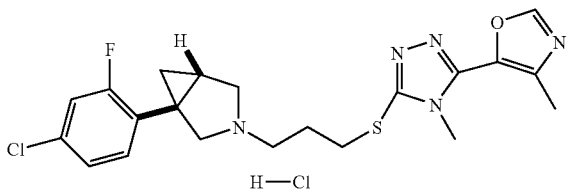

The title compound was prepared in analogy to the method described in Example 1 in 112 mg yield as a white slightly hygroscopic solid from (1R,5S/1S,5R)-1-[4-chloro-2-fluorophenyl]-3-azabicyclo[3.1.0]hexane (130 mg).

NMR ($^1$H, CD3OD): δ 8.27 (s, 1H), 7.3 (t, 1H), 7.1 (m, 2H), 3.95 (d, 1H), 3.8 (d, 1H), 3.67 (s, 3H), 3.56 (dd, 1H), 3.4-3.2 (m, 5H), 2.34 (s, 3H), 2.15 (m, 3H), 1.4 (t, 1H), 1.18 (t, 1H). MS (m/z): 448 [MH]$^+$.

Example 114

(1R,5S/1S,5R)-1-[3-(2-{[4-Methyl-5-(4-methyl-1,3-oxazol-5-yl)-4H-1,2,4-triazol-3-yl]thio}propyl)-1-{3-[(trifluoromethyl)oxy]phenyl}-3-azabicyclo[3.1.0]hexane hydrochloride

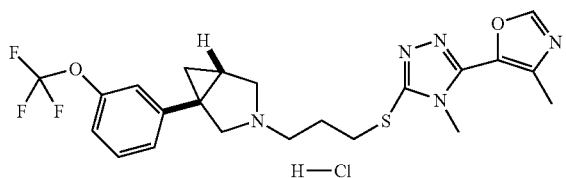

The title compound was prepared in analogy to the method described in Example 1 in 160 mg yield as a white slightly hygroscopic solid from 1-{3-[(trifluoromethyl)oxy]phenyl}-3-azabicyclo[3.1.0]hexane (150 mg).

NMR ($^1$H, CD3OD): δ 8.41 (s, 1H), 7.49 (t, 1H), 7.3 (s, 1H), 7.37 (d, 1H), 7.24 (m, 1H), 4.17 (d, 1H), 3.9 (d, 1H), 3.8 (s, 3H), 3.69 (d, 2H), 3.51 (t, 2H), 3.42 (t, 2H), 2.47 (s, 3H), 2.3 (m, 3H), 1.57 (dd, 1H), 1.36 (t, 1H). MS (m/z): 480 [MH]$^+$.

Example 115

(1R,5S/1S,5R)-1-(2-fluoro-4-methylphenyl)-3-(3-{[4-methyl-5-(4-methyl-1,3-oxazol-5-yl)-4H-1,2,4-triazol-3-yl]thio}propyl)-3-azabicyclo[3.1.0]hexane hydrochloride

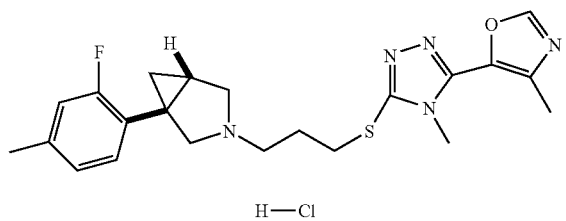

The title compound was prepared in analogy to the method described in Example 1 in 60 mg yield as a white slightly hygroscopic solid from 1-(2-fluoro-4-methylphenyl)-3-azabicyclo[3.1.0]hexane (148 mg).

NMR ($^1$H, CD3OD): δ 8.39 (s, 1H), 7.26 (t, 1H), 7.01 (m, 2H), 3.93 (m, 1H), 3.77 (m, 4H), 3.61 (m, 1H), 3.41-3.38 (m, 5H), 2.47 (s, 3H), 2.36 (s, 3H), 2.23 (m, 2H), 2.19 (m, 1H), 1.45 (t, 1H), 1.21 (t, 1H). MS (m/z): 428 [MH]$^+$.

Example 116

(1R,5S/1S,5R)-1-[3-Chloro-4-(methyloxy)phenyl]-3-(2-{[4-methyl-5-(4-methyl-1,3-oxazol-5-yl)-4H-1,2,4-triazol-3-yl]thio}propyl)-3-azabicyclo[3.1.0]hexane hydrochloride

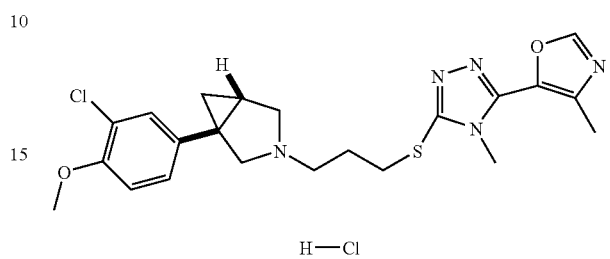

The title compound was prepared in analogy to the method described in Example 1 in 56 mg yield as a white slightly hygroscopic solid from 1-[3-chloro-4-(methyloxy)phenyl]-3-azabicyclo[3.1.0]hexane (60 mg).

NMR ($^1$H, CD3OD): δ 8.4 (s, 1H), 7.35 (m, 1H), 7.1 (m, 2H), 4.01 (m, 1H), 3.89 (m, 4H), 3.8 (s, 3H), 3.6-3.3 (m, 6H), 2.47 (s, 3H), 2.23 (m, 2H), 2.19 (m, 1H), 1.4 (m, 1H), 1.2 (m, 1H). MS (m/z): 460 [MH]$^+$.

Example 117

(1R,5S/1S,5R)-1-[4-(2,4-Dimethyl-1,3-thiazol-5-yl)phenyl]-3-(3-{[4-methyl-5-(4-methyl-1,3-oxazol-5-yl)-4H-1,2,4-triazol-3-yl]thio}propyl)-3-azabicyclo[3.1.0]hexane hydrochloride

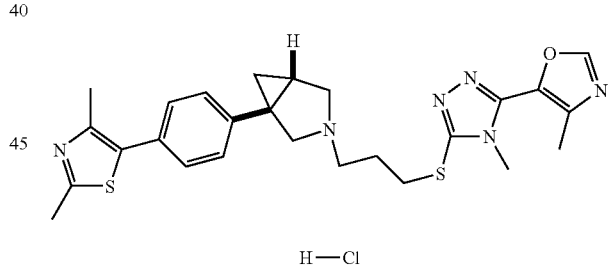

A mixture of (1R,5S/1S,5R)-1-[4-(2,4-dimethyl-1,3-thiazol-5-yl)phenyl]-3-aza-bicyclo[3.1.0]hexane (70 mg), 3-[(3-chloropropyl)thio]-4-methyl-5-(4-methyl-1,3-oxazol-5-yl)-4H-1,2,4-triazole (85 mg), potassium carbonate (43 mg), Na$_2$CO$_3$ and sodium iodide (45 mg) in anhydrous DMF (0.6 mL) was heated at 60° C. for 24 h. After elimination of the solvent in vacuo the residue was dissolved in ethyl acetate and the organic phase was washed with saturated aqueous sodium bicarbonate, dried over sodium sulphate and concentrated in vacuo. The crude was purified by flash chromatography (dichloromethane to 10% MeOH in dichloromethane) to give 65 mg of the free base of the title compound. To a solution of this material in dichloromethane (1 mL) was added HCl (1 M in Et$_2$O, 0.13 mL), the solvent evaporated under vacuo and the material thus obtained triturated with Et$_2$O to give 69 mg of the title compound as a white solid (50% yield).

NMR (¹H, DMSO): δ 10.39 (bs, 1H), 8.56 (s, 1H), 7.39 (d, 2H), 7.35 (d, 2H), 4.02 (m, 1H), 3.72 (m, 1H), 3.68 (s, 3H), 3.60 (t, 1H), 3.51 (bm, 1H), 3.27 (m, 4H), 2.60 (s, 3H), 2.37 (s, 3H), 2.35 (s, 3H), 2.19 (m, 1H), 2.16 (m, 2H), 1.62 (m, 1H), 1.15 (m, 1H); MS (m/z): 507.2 [MH]⁺.

Example 118

(1R,5S/1S,5R)-3-(3-{[4-Methyl-5-(4-methyl-1,3-oxazol-5-yl)-4H-1,2,4-triazol-3-yl]thio}propyl)-1-{4-[6-(trifluoromethyl)-2-pyridinyl]phenyl}-3-azabicyclo[3.1.0]hexane hydrochloride

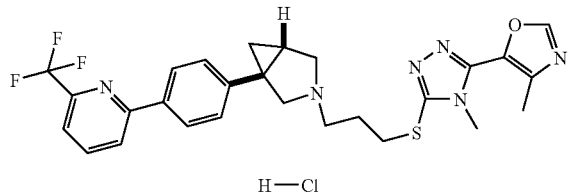

The title compound was prepared in analogy to the method described in Example 117 (using (1R,5S/1S,5R)-1-{4-[6-(trifluoromethyl)-2-pyridinyl]phenyl}-3-azabicyclo[3.1.0]-hexane) in 55% yield as a white solid.

NMR (¹H, CDCl₃): δ 10.44 (bs, 1H), 8.56 (s, 1H), 8.29 (d, 1H), 8.17 (t, 1H), 8.09 (d, 2H), 7.84 (d, 1H), 7.43 (d, 2H), 4.08 (m, 1H), 3.75 (m, 1H), 3.68 (s, 3H), 3.64 (t, 1H), 3.53 (bm, 1H), 3.28 (m, 4H), 2.37 (s, 3H), 2.27 (m, 1H), 2.17 (m, 2H), 1.68 (m, 1H), 1.17 (m, 1H); MS (m/z): 541.2 [MH]⁺.

Example 119

(1R,5S/1S,5R)-1-[3-(2,4-Dimethyl-1,3-thiazol-5-yl)phenyl]-3-(3-({[4-methyl-5-(4-methyl-1,3-oxazol-5-yl)-4H-1,2,4-triazol-3-yl]thio}propyl)-3-azabicyclo[3.1.0]hexane hydrochloride

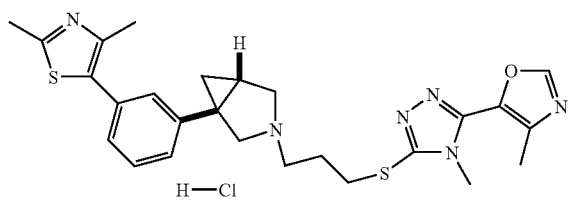

The title compound was prepared in analogy to the method described in Example 117 (using (1R,5S/1S,5R)-1-[3-(2,4-dimethyl-1,3-thiazol-5-yl)phenyl]-3-azabicyclo[3.1.0]-hexane) in 53% yield as a white solid.

NMR (¹H, CDCl₃): δ 10.53 (b, 1H), 8.58 (s, 1H), 7.43 (d, 1H), 7.28-7.38 (m, 3H), 4.07 (dd, 1H), 3.73 (dd, 1H), 3.70 (s, 3H), 3.61 (t, 1H), 3.53 (m, 1H), 3.34 (m, 2H), 3.29 (t, 2H), 2.64 (s, 3H), 2.39 (s, 3H), 2.73 (s, 3H), 2.23 (m, 1H), 2.20 (m, 2H), 1.68 (t, 1H), 1.16 (t, 1H); MS (m/z): 507.1 [MH]⁺.

Example 120

(1R,5S/1S,5R)-3-(3-{[4-Methyl-5-(4-methyl-1,3-oxazol-5-yl)-4H-1,2,4-triazol-3-yl]thio}propyl)-1-[3-(5-methyl-2-thienyl)phenyl]-3-azabicyclo[3.1.0]hexane hydrochloride

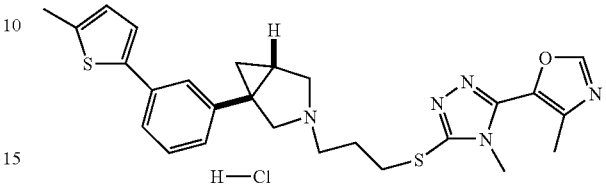

The title compound was prepared in analogy to the method described in Example 117 (using (1R,5S/1S,5R)-1-[3-(5-methyl-2-thienyl)phenyl]-3-azabicyclo[3.1.0]hexane) in 51% yield as a white solid.

NMR (¹H, CDCl₃): δ 10.44 (b, 1H), 8.58 (s, 1H), 7.49 (d, 1H), 7.45 (dt, 1H), 7.37 (t, 2H), 7.18 (dt, 1H), 6.84 (t, 1H), 4.08 (dd, 1H), 3.76 (dd, 1H), 3.70 (s, 3H), 3.62 (t, 1H), 3.54 (tm, 1H), 3.28 (t, 4H), 2.48 (s, 3H), 2.39 (s, 3H), 2.24 (m, 1H), 2.19 (t, 2H), 1.65 (t, 1H), 1.16 (t, 1H); MS (m/z): 472.0 [MH]⁺.

Example 121

(1R,5S/1S,5R)-1-[4-(3,5-Dimethyl-4-isoxazolyl)phenyl]-3-(3-({[4-methyl-5-(4-methyl-1,3-oxazol-5-yl)-4H-1,2,4-triazol-3-yl]thio}propyl)-3-azabicyclo[3.1.0]hexane

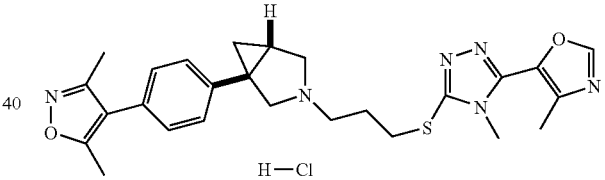

The title compound was prepared in analogy to the method described in Example 117 (using (1R,5S/1S,5R)-1-[4-(3,5-dimethyl-4-isoxazolyl)phenyl]-3-azabicyclo[3.1.0]hexane), in 55% yield as a white solid.

MS (m/z): 491.2 [MH]⁺.

Example 122

(1S,5R)-3-(3-{[5-(2,4-Dimethyl-1,3-oxazol-5-yl)-4-methyl-4H-1,2,4-triazol-3-yl]thio}propyl)-1-[2-fluoro-4-(trifluoromethyl)phenyl]-3-azabicyclo[3.1.0]-hexane hydrochloride

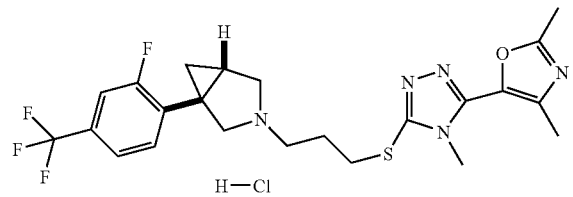

A mixture of (1S,5R)-1-[4-(trifluoromethyl)phenyl]-3-azabicyclo[3.1.0]hexane (Preparation 18, 60 mg), 3-[(3-chloropropyl)thio]-5-(2,4-dimethyl-1,3-oxazol-5-yl)-4-methyl-4H-1,2,4-triazole (Preparation 78, 78 mg), 2-tert-butylimino-2-diethylamino-1,3-dimethyl-perhydro-1,3,2-diazaphosphorine on polystyrene (2.2 mmol/g, 140 mg) and a catalytic amount of NaI in acetonitrile dry (3 ml) was heated at 70° C. for 4 h, then overnight at 55° C. The resin was removed by filtration and washed with acetonitrile (2×3 ml). The solvent was removed under vacuum, the remaining solid dissolved in DMF dry (0.5 ml), 3-[(3-chloropropyl)thio]-5-(2,4-dimethyl-1,3-oxazol-5-yl)-4-methyl-4H-1,2,4-triazole (Preparation 78, 60 mg) was added followed by potassium carbonate (118 mg). The resulting suspension was heated at 60° C. overnight. At room temperature a saturated solution of sodium bicarbonate was added (4 ml) and the suspension was extracted with DCM (2×6 ml). The resulting solution was charged onto a SCX column and eluted with MeOH followed by MeOH/NH$_3$ 0.25 M. The resulting material was purified by preparative HPLC and then converted to the hydrochloride salt following the method described for Example 15 to give the title compound as a white slightly hygroscopic solid (37 mg, 27% yield).

NMR ($^1$H, DMSO): δ 10.38 (b, 1H), 7.71 (d, 1H), 7.64 (t, 1H), 7.59 (d, 1H), 3.98 (bd, 1H), 3.76 (bd, 1H), 3.65 (s, 3H), 3.54 (b, 1H), 3.44 (bt, 1H), 3.31 (b, 2H), 3.24 (t, 2H), 2.47 (s, 3H), 2.35 (m, 1H), 2.29 (s, 3H), 2.11 (m, 2H), 1.63 (t, 1H), 1.13 (t, 1H). MS (m/z): 496 [MH]$^+$.

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

The invention claimed is:
1. A compound of formula (I) or a salt thereof,

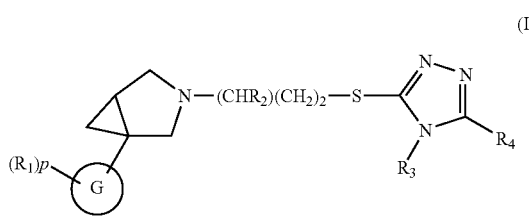

(I)

wherein
G is selected from a group consisting of: phenyl, pyridyl, benzothiazolyl, and indazolyl;
p is an integer ranging from 0 to 5;
R$_1$ is independently selected from a group consisting of: halogen, hydroxy, cyano, C$_{1-4}$alkyl, haloC$_{1-4}$alkyl, C$_{1-4}$alkoxy, haloC$_{1-4}$alkoxy, and C$_{1-4}$alkanoyl; or is R$_5$;
R$_2$ is hydrogen or C$_{1-4}$alkyl;
R$_3$ is C$_{1-4}$alkyl;
R$_4$ is hydrogen, or a phenyl group, a heterocyclyl group, a 5- or 6-membered heteroaromatic group, or a 8- to 11-membered bicyclic group, any of which groups is unsubstituted or substituted by 1, 2, 3 or 4 substituents selected from the group consisting of: halogen, cyano, C$_{1-4}$alkyl, haloC$_{1-4}$alkyl, C$_{1-4}$alkoxy, and C$_{1-4}$alkanoyl;
R$_5$ is a moiety selected from the group consisting of: isoxazolyl, —CH$_2$—N-pyrrolyl, 1,1-dioxido-2-isothiazolidinyl, thienyl, thiazolyl, pyridyl, and 2-pyrrolidinonyl, and such a group is unsubstituted or substituted by one or two substituents selected from: halogen, cyano, C$_{1-4}$alkyl, haloC$_{1-4}$alkyl, C$_{1-4}$alkoxy, and C$_{1-4}$alkanoyl;
and when R$_1$ is chlorine and p is 1, such R$_1$ is not present in the ortho position with respect to the linking bond to the rest of the molecule; and when R$_1$ corresponds to R$_5$, p is 1.

2. A compound of formula (I), according to claim 1, or a salt thereof,

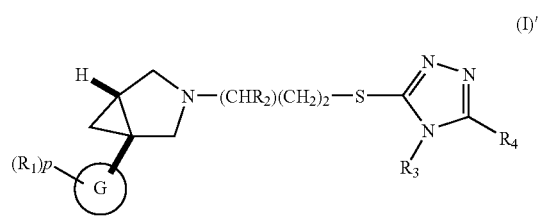

(I)' wherein G, p, R$_1$, R$_2$, R$_3$, R$_4$, and R$_5$ are defined as in claim 1.

3. A compound according to claim 1 wherein R$_1$ is bromo, fluoro, trifluoromethoxy, cyano, hydroxy, chloro, methoxy, tert-butyl, or trifluoromethyl; and R$_5$ is isoxazolyl, 2-pyrrolidinonyl, —CH$_2$—N-pyrrolyl, 1,1-dioxido-2-isothiazolidinyl, 2-thienyl, 2-pyridyl, or 2-thiazolyl; or a salt thereof.

4. A compound as claimed in claim 1 wherein p is 1 or 2; or a salt thereof.

5. A compound as claimed in claim 1 wherein R$_2$ is hydrogen; or a salt thereof.

6. A compound as claimed in claim 1, wherein R$_4$ is unsubstituted or substituted phenyl, quinolinyl, pyranyl, pyridinyl, pyrazolyl, pyrimidyl, pyridazinyl, pyrazinyl, furanyl, thienyl, oxazolyl, isoxazolyl, thiazolyl, or triazolyl; or a salt thereof.

7. A compound according to claim 1 having the structure of formula (IB) or a salt thereof wherein R$_1$, p, R$_3$ and R$_4$ are as defined in claim 1

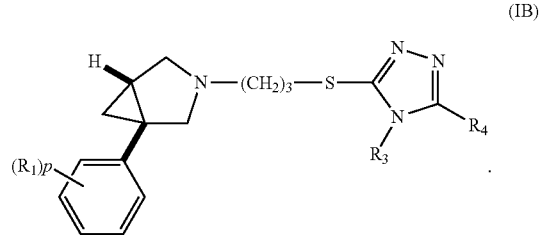

(IB)

8. A compound according to claim 1 having the structure of formula (IC) or a salt thereof wherein $R_1$, p, $R_3$ and $R_4$ are as defined in claim 1; or a salt thereof

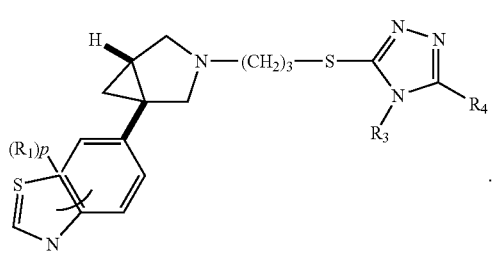

(IC)

9. A compound according to claim 1 having the structure of formula (ID) or a salt thereof wherein $R_1$, p, $R_3$ and $R_4$ are as defined in claim 1

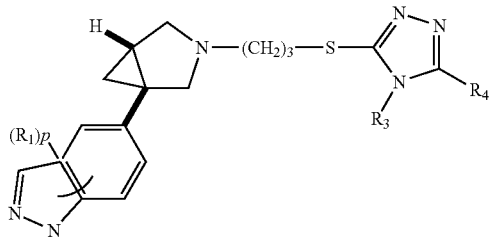

(ID)

10. A compound according to claim 1 having the structure of formula (IE) or a salt thereof wherein G is 2-pyridyl or 3-pyridyl and $R_1$, p, $R_3$ and $R_4$ are as defined in claim 1

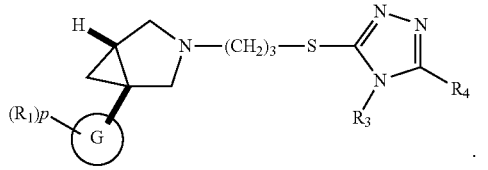

(IE)

11. A compound according to claim 1 having the structure of formula (IF) or a salt thereof wherein $R_1$, p, $R_3$ and $R_4$ are as defined in claim 1

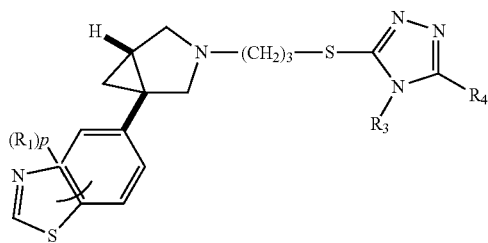

(IF)

12. A compound according to claim 1 which is a stereochemical isomer enriched in the (1S,5R) configuration of formula (IA) or a salt thereof and $R_1$, p, $R_3$ and $R_4$ are as defined in claim 1

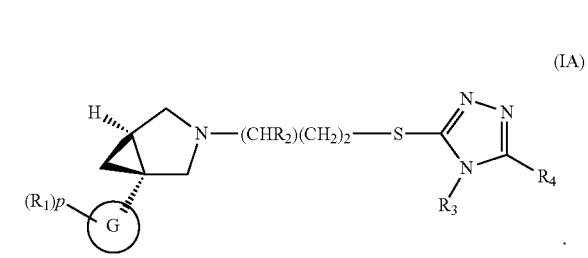

(IA)

13. A compound according to claim 12 which is a stereochemical isomer enriched in the (1S,5R) configuration of formula (IB)' or a salt thereof and $R_1$, p, $R_3$ and $R_4$ are as defined in claim 12

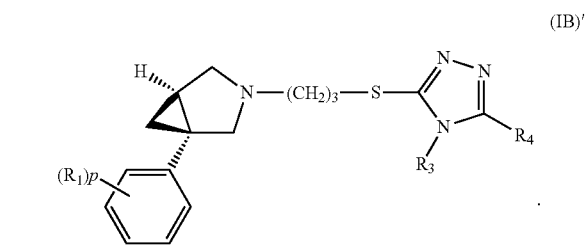

(IB)'

14. A compound according to claim 12 which is a stereochemical isomer enriched in the (1S,5R) configuration of formula (IC)' or a salt thereof and $R_1$, p, $R_3$ and $R_4$ are as defined in claim 12

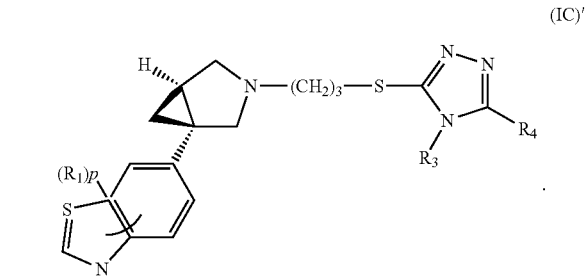

(IC)'

15. A compound according to claim 12 which is a stereochemical isomer enriched in the (1S,5R) configuration of formula (ID)' or a salt thereof and $R_1$, p, $R_3$ and $R_4$ are as defined in claim 12

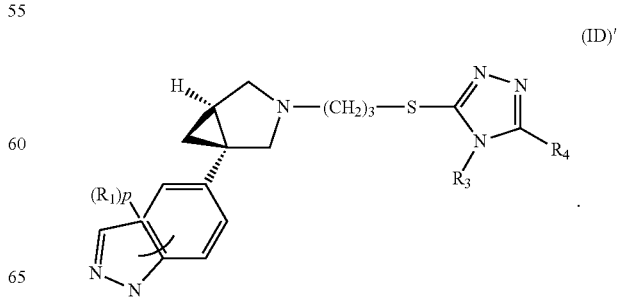

(ID)'

16. A compound according to claim 12 which is a stereochemical isomer enriched in the (1S,5R) configuration or (1R,5R) configuration of formula (IE)' or a salt thereof, wherein G is 2-pyridyl or 3-pyridyl and R₁, p, R₃ and R₄ are as defined in claim 12

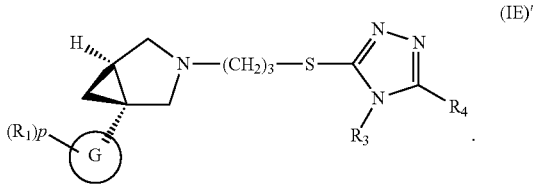

(IE)'

17. A compound according to claim 12 which is a stereochemical isomer is enriched in the (1S,5R) configuration of formula (IF)' or a salt thereof, wherein R₁, p, R₃ and R₄ are as defined in claim 1

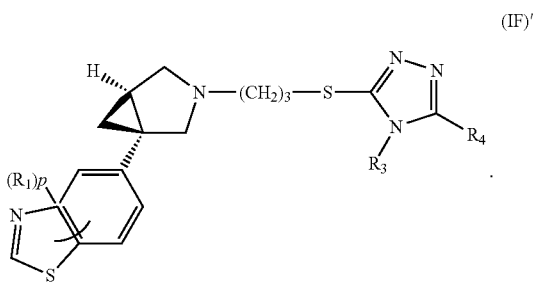

(IF)'

18. A compound according to claim 12 which is a stereochemical isomer enriched in the (1R,5S) configuration selected from the group consisting of:
5-[5-({3-[(1R,5S)-1-(4-methoxyphenyl)-3-azabicyclo[3.1.0]hex-3-yl]propyl}thio)-4-methyl-4H-1,2,4-triazol-3-yl]-2-methylquinoline, enantiomer 2;
5-[5-({3-[(1R,5S)-1-(4-bromophenyl)-3-azabicyclo[3.1.0]hex-3-yl]propyl}thio)-4-methyl-4H-1,2,4-triazol-3-yl]-2-methylquinoline, enantiomer 1;
5-[5-({3-[(1R,5S)-1-(4-tert-butylphenyl)-3-azabicyclo[3.1.0]hex-3-yl]propyl}thio)-4-methyl-4H-1,2,4-triazol-3-yl]-2-methylquinoline, enantiomer 1;
(1R,5S)-3-(3-{[4-methyl-5-(4-methyl-1,3-oxazol-5-yl)-4H-1,2,4-triazol-3-yl]thio}propyl)-1-[3-(trifluoromethyl)phenyl]-3-azabicyclo[3.1.0]hexane, enantiomer 2;
(1R,5S)-1-(3-chlorophenyl)-5-methyl-3-(3-{[4-methyl-5-(4-methyl-1,3-oxazol-5-yl)-4H-1,2,4-triazol-3-yl]thio}propyl)-3-azabicyclo[3.1.0]hexane, enantiomer
1-[5-[(1R,5S)-3-(3-{[4-methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]-1-propanone, enantiomer 2;
2-methyl-5-[(1R,5S)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole, enantiomer 2;
or a salt thereof.
19. A compound according to claim 1 selected from the group consisting of:
5-[5-({3-[(1R,5S/1S,5R)-1-(4-methoxyphenyl)-3-azabicyclo[3.1.0]hex-3-yl]propyl}-thio)-4-methyl-4H-1,2,4-triazol-3-yl]-2-methylquinoline;
5-[5-({3-[(1S,5R)-1-(4-methoxyphenyl)-3-azabicyclo[3.1.0]hex-3-yl]propyl}thio)-4-methyl-4H-1,2,4-triazol-3-yl]-2-methylquinoline, enantiomer 1;
5-[5-({3-[(1R,5S/1S,5R)-1-(4-bromophenyl)-3-azabicyclo[3.1.0]hex-3-yl]propyl}thio)-4-methyl-4H-1,2,4-triazol-3-yl]-2-methylquinoline;
5-[5-({3-[(1S,5R)-1-(4-bromophenyl)-3-azabicyclo[3.1.0]hex-3-yl]propyl}thio)-4-methyl-4H-1,2,4-triazol-3-yl]-2-methylquinoline, enantiomer 2;
2-methyl-5-[4-methyl-5-({3-[(1R,5S/1S,5R)-1-phenyl-3-azabicyclo[3.1.0]hex-3-yl]propyl}thio)-4H-1,2,4-triazol-3-yl]quinoline;
2-methyl-5-[4-methyl-5-({3-[(1S,5R)-1-phenyl-3-azabicyclo[3.1.0]hex-3-yl]propyl}thio)-4H-1,2,4-triazol-3-yl]quinoline, enantiomer 2;
5-[5-({3-[(1R,5S/1S,5R)-1-(3,4-dichlorophenyl)-3-azabicyclo[3.1.0]hex-3-yl]propyl}thio)-4-methyl-4H-1,2,4-triazol-3-yl]-2-methylquinoline;
5-[5-({3-[(1S,5R)-1-(3,4-dichlorophenyl)-3-azabicyclo[3.1.0]hex-3-yl]propyl}thio)-4-methyl-4H-1,2,4-triazol-3-yl]-2-methylquinoline, enantiomer 1;
5-[5-({3-[(1R,5S/1S,5R)-1-(4-tert-butylphenyl)-3-azabicyclo[3.1.0]hex-3-yl]propyl}thio)-4-methyl-4H-1,2,4-triazol-3-yl]-2-methylquinoline;
5-[5-({3-[(1S,5R)-1-(4-tert-Butylphenyl)-3-azabicyclo[3.1.0]hex-3-yl]propyl}thio)-4-methyl-4H-1,2,4-triazol-3-yl]-2-methylquinoline, enantiomer 2;
4-[(1R,5S/1S,5R)-3-(3-{[4-methyl-5-(2-methylquinolin-5-yl)-4H-1,2,4-triazol-3-yl]thio}propyl)-3-azabicyclo[3.1.0]hex-1-yl]benzonitrile;
4-[(1R,5S/1S,5R)-3-(3-{[4-methyl-5-(2-methylquinolin-5-yl)-4H-1,2,4-triazol-3-yl]thio}propyl)-3-azabicyclo[3.1.0]hex-1-yl]phenol;
(1R,5S/1S,5R)-3-(3-{[4-methyl-5-(4-methyl-1,3-oxazol-5-yl)-4H-1,2,4-triazol-3-yl]thio}propyl)-1-phenyl-3-azabicyclo[3.1.0]hexane;
(1R,5S/1S,5R)-1-(4-bromophenyl)-3-(3-{[4-methyl-5-(4-methyl-1,3-oxazol-5-yl)-4H-1,2,4-triazol-3-yl]thio}propyl)-3-azabicyclo[3.1.0]hexane;
(1S,5R)-1-(4-bromophenyl)-3-(3-{[4-methyl-5-(4-methyl-1,3-oxazol-5-yl)-4H-1,2,4-triazol-3-yl]thio}propyl)-3-azabicyclo[3.1.0]hexane, enantiomer 1;
(1R,5S/1S,5R)-1-(4-tert-butylphenyl)-3-(3-{[4-methyl-5-(4-methyl-1,3-oxazol-5-yl)-4H-1,2,4-triazol-3-yl]thio}propyl)-3-azabicyclo[3.1.0]hexane;
(1R,5S/1S,5R)-1-(3,4-dichlorophenyl)-3-(3-{[4-methyl-5-(4-methyl-1,3-oxazol-5-yl)-4H-1,2,4-triazol-3-yl]thio}propyl)-3-azabicyclo[3.1.0]hexane;
(1S,5R)-1-(3,4-dichlorophenyl)-3-(3-{[4-methyl-5-(4-methyl-1,3-oxazol-5-yl)-4H-1,2,4-triazol-3-yl]thio}propyl)-3-azabicyclo[3.1.0]hexane, enantiomer 2;
(1R,5S/1S,5R)-1-(4-methoxyphenyl)-3-(3-{[4-methyl-5-(4-methyl-1,3-oxazol-5-yl)-4H-1,2,4-triazol-3-yl]thio}propyl)-3-azabicyclo[3.1.0]hexane;
(1R,5R)-1-(4-methoxyphenyl)-3-(3-{[4-methyl-5-(4-methyl-1,3-oxazol-5-yl)-4H-1,2,4-triazol-3-yl]thio}propyl)-3-azabicyclo[3.1.0]hexane, enantiomer 2;
(1R,5S/1S,5R)-1-[4-(5-methyl-3-isoxazolyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;
(1R,5R)-3-(3-{[4-methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane; (1S,5R)-3-(3-{[4-methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane;

(1R,5S/1S,5R)-3-(3-{[4-methyl-5-(4-methyl-1,3-oxazol-5-yl)-4H-1,2,4-triazol-3-yl]thio}propyl)-1-[3-(trifluoromethyl)phenyl]-3-azabicyclo[3.1.0]hexane;
(1R,5S/1S,5R)-1-[4-fluoro-3-(trifluoromethyl)phenyl]-3-(3-[4-methyl-5-(4-methyl-1,3-oxazol-5-yl)-4H-1,2,4-triazol-3-yl]thio}propyl)-3-azabicyclo[3.1.0]hexane;
1-[5-[(1S,5R/1R,5S)-3-(3-{[4-methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]ethanone;
1-[5-[(1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]ethanone, enantiomer 1;
(1S,5R/1R,5S)-1-(4-chlorophenyl)-3-(3-{[4-methyl-5-(4-methyl-1,3-oxazol-5-yl)-4H-1,2,4-triazol-3-yl]thio}propyl)-3-azabicyclo[3.1.0]hexane;
(1S,5R)-1-(4-chlorophenyl)-3-(3-{[4-methyl-5-(4-methyl-1,3-oxazol-5-yl)-4H-1,2,4-triazol-3-yl]thio}propyl)-3-azabicyclo[3.1.0]hexane, enantiomer 1;
(1S,5R/1R,5S)-1-(4-fluorophenyl)-3-(3-{[4-methyl-5-(4-methyl-1,3-oxazol-5-yl)-4H-1,2,4-triazol-3-yl]thio}propyl)-3-azabicyclo[3.1.0]hexane;
(1S,5R)-1-(4-fluorophenyl)-3-(3-{[4-methyl-5-(4-methyl-1,3-oxazol-5-yl)-4H-1,2,4-triazol-3-yl]thio}propyl)-3-azabicyclo[3.1.0]hexane, enantiomer 1;
(1S,5R/1R,5S)-1-(3-chlorophenyl)-5-methyl-3-(3-{[4-methyl-5-(4-methyl-1,3-oxazol-5-yl)-4H-1,2,4-triazol-3-yl]thio}propyl)-3-azabicyclo[3.1.0]hexane;
(1S,5R)-1-(3-chlorophenyl)-5-methyl-3-(3-{[4-methyl-5-(4-methyl-1,3-oxazol-5-yl)-4H-1,2,4-triazol-3-yl]thio}propyl)-3-azabicyclo[3.1.0]hexane, enantiomer 1;
(1S,5R/1R,5S)-1-(3-fluorophenyl)-3-(3-{[4-methyl-5-(4-methyl-1,3-oxazol-5-yl)-4H-1,2,4-triazol-3-yl]thio}propyl)-3-azabicyclo[3.1.0]hexane;
(1S,5R)-1-(3-fluorophenyl)-3-(3-{[4-methyl-5-(4-methyl-1,3-oxazol-5-yl)-4H-1,2,4-triazol-3-yl]thio}propyl)-3-azabicyclo[3.1.0]hexane, enantiomer 1;
(1S,5R/1R,5S)-3-(3-{[4-methyl-5-(4-methyl-1,3-oxazol-5-yl)-4H-1,2,4-triazol-3-yl]thio}propyl)-1,3-(methyloxy)phenyl]-3-azabicyclo[3.1.0]hexane;
(1S,5R)-3-(3-{[4-methyl-5-(4-methyl-1,3-oxazol-5-yl)-4H-1,2,4-triazol-3-yl]thio}propyl)-1-[3-(methyloxy)phenyl]-3-azabicyclo[3.1.0]hexane, enantiomer 1;
(1S,5R)-1-(4-bromophenyl)-3-(3-{[4-methyl-5-(tetrahydro-2H-pyran-4-yl)-4H-1,2,4-triazol-3-yl]thio}propyl)-3-azabicyclo[3.1.0]hexane;
(1S,5R)-1-(4-bromophenyl)-3,3-({4-methyl-5-[4-(trifluoromethyl)phenyl]-4H-1,2,4-triazol-3-yl}thio)propyl]-3-azabicyclo[3.1.0]hexane;
(1S,5R)-1-(4-bromophenyl)-3-(3-{[4-methyl-5-(3-pyridinyl)-4H-1,2,4-triazol-3-yl]thio}propyl)-3-azabicyclo[3.1.0]hexane,
(1S,5R)-1-(4-bromophenyl)-3-(3-{[5-(3,4-difluorophenyl)-4-methyl-4H-1,2,4-triazol-3-yl]thio}propyl)-3-azabicyclo[3.1.0]hexane;
5-[5-({3-[(1S,5R/1R,5S)-1-(4-chlorophenyl)-3-azabicyclo[3.1.0]hex-3-yl]propyl}thio)-4-methyl-4H-1,2,4-triazol-3-yl]-2-methylquinoline;
5-[5-({3-[(1S,5R/1R,5S)-1-(4-chlorophenyl)-3-azabicyclo[3.1.0]hex-3-yl]propyl}thio)-4-methyl-4H-1,2,4-triazol-3-yl]-2-methylquinoline, enantiomer 1;
(1S,5R/1R,5S)-3-(3-{[4-methyl-5-(4-methyl-1,3-oxazol-5-yl)-4H-1,2,4-triazol-3-yl]thio}propyl)-1-{4-[(trifluoromethyl)oxy]phenyl}-3-azabicyclo[3.1.0]hexane;
(1S,5R)-3-(3-{[4-methyl-5-(4-methyl-1,3-oxazol-5-yl)-4H-1,2,4-triazol-3-yl]thio}-propyl)-1-{4-[(trifluoromethyl)oxy]phenyl}-3-azabicyclo[3.1.0]hexane, enantiomer 1;
(1S,5R/1R,5S)-3-(3-{[4-methyl-5-(4-methyl-1,3-oxazol-5-yl)-4H-1,2,4-triazol-3-yl]-thio}propyl)-1-[2-methyl-4-(trifluoromethyl)phenyl]-3-azabicyclo[3.1.0]hexane;
(1S,5R/1R,5S)-3-(3-{[4-methyl-5-(tetrahydro-2H-pyran-4-yl)-4H-1,2,4-triazol-3-yl]thio}propyl)-1-{4-[(trifluoromethyl)oxy]phenyl}-3-azabicyclo[3.1.0]hexane;
(1S,5R)-3-(3-{[4-Methyl-5-(tetrahydro-2H-pyran-4-yl)-4H-1,2,4-triazol-3-yl]thio}propyl)-1-{4-[(trifluoromethyl)oxy]phenyl}-3-azabicyclo[3.1.0]hexane, enantiomer 2;
(1R,5S/1S,5R)-1-(3-bromophenyl)-3-(3-{[4-methyl-5-(4-methyl-1,3-oxazol-5-yl)-4H-1,2,4-triazol-3-yl]thio}propyl)-3-azabicyclo[3.1.0]hexane;
(1S,5R)-3-(1-methyl-3-{[4-methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane;
(1S,5R)-3-(1-methyl-3-{[4-methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane, Diastereoisomer 1;
(1S,5R)-3-(1-methyl-3-{[4-methyl-5-(4-methyl-1,3-oxazol-5-yl)-4H-1,2,4-triazol-3-yl]thio}propyl)-1-[4-(trifluoromethyl)phenyl]-3-azabicyclo[3.1.0]hexane, Diastereoisomer 2;
(1R,5S/1S,5R)-1-[2-fluoro-5-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;
(1S,5R)-1-[2-fluoro-5-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane, enantiomer 2;
1-[4-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]ethanone;
1-[4-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]-1-propanone;
(1R,5S/1S,5R)-3-(3-{[4-Methyl-5-(4-methyl-1,3-oxazol-5-yl)-4H-1,2,4-triazol-3-yl]thio}propyl)-1-[2-(trifluoromethyl)phenyl]-3-azabicyclo[3.1.0]hexane;
(1S,5R)-3-(3-{[4-Methyl-5-(2-methyl-3-pyridinyl)-4H-1,2,4-triazol-3-yl]thio}propyl)-1-[4-(trifluoromethyl)phenyl]-3-azabicyclo[3.1.0]hexane;
(1S,5R)-3-(3-{[5-(1,5-Dimethyl-1H-pyrazol-4-yl)-4-methyl-4H-1,2,4-triazol-3-yl]thio}propyl)-1-[4-(trifluoromethyl)phenyl]-3-azabicyclo[3.1.0]hexane;
(1S,5R)-3-(3-{[4-Methyl-5-(5-pyrimidinyl)-4H-1,2,4-triazol-3-yl]thio}propyl)-1-[4-(trifluoromethyl)phenyl]-3-azabicyclo[3.1.0]hexane;
(1S,5R)-3-(3-{[4-Methyl-5-(3-methyl-2-furanyl)-4H-1,2,4-triazol-3-yl]thio}propyl)-1-[4-(trifluoromethyl)phenyl]-3-azabicyclo[3.1.0]hexane;
(1S,5R)-3-(3-{[4-Methyl-5-(6-methyl-3-pyridinyl)-4H-1,2,4-triazol-3-yl]thio}propyl)-1-[4-(trifluoromethyl)phenyl]-3-azabicyclo[3.1.0]hexane;
(1S,5R)-3-(3-{[5-(2,4-Dimethyl-1,3-thiazol-5-yl)-4-methyl-4H-1,2,4-triazol-3-yl]thio}propyl)-1-[4-(trifluoromethyl)phenyl]-3-azabicyclo[3.1.0]hexane;
(1S,5R)-3-(3-{[4-Methyl-5-(5-methyl-2-pyrazinyl)-4H-1,2,4-triazol-3-yl]thio}propyl)-1-[4-(trifluoromethyl)phenyl]-3-azabicyclo[3.1.0]hexane;

(1S,5R)-3-(3-{[4-Methyl-5-(tetrahydro-2H-pyran-4-yl)-4H-1,2,4-triazol-3-yl]thio}propyl)-1-[4-(trifluoromethyl)phenyl]-3-azabicyclo[3.1.0]hexane; 2-Methyl-6-{4-methyl-5-[(3-{(1S,5R)-1-[4-(trifluoromethyl)phenyl]-3-azabicyclo[3.1.0]hex-3-yl}propyl)thio]-4H-1,2,4-triazol-3-yl}quinoline;

8-Fluoro-2-methyl-5-{4-methyl-5-[(3-{(1S,5R)-1,4-(trifluoromethyl)phenyl]-3-azabicyclo[3.1.0]hex-3-yl}propyl)thio]-4H-1,2,4-triazol-3-yl}quinoline;

2-Methyl-5-{4-methyl-5-[(3-{(1S,5R)-1,4-(trifluoromethyl)phenyl]-3-azabicyclo[3.1.0]hex-3-yl}propyl)thio]-4H-1,2,4-triazol-3-yl}quinoline;

(1S,5R)-1-[2-Fluoro-4-(trifluoromethyl)phenyl]-3-(3-{[4-methyl-5-(2-methyl-3-pyridinyl)-4H-1,2,4-triazol-3-yl]thio}propyl)-3-azabicyclo[3.1.0]hexane;

(1S,5R)-1-[2-Fluoro-4-(trifluoromethyl)phenyl]-3-(3-{[4-methyl-5-(4-pyridazinyl)-4H-1,2,4-triazol-3-yl]thio}propyl)-3-azabicyclo[3.1.0]hexane;

(1S,5R)-1-[2-Fluoro-4-(trifluoromethyl)phenyl]-3-(3-{[4-methyl-5-(5-pyrimidinyl)-4H-1,2,4-triazol-3-yl]thio}propyl)-3-azabicyclo[3.1.0]hexane;

(1S,5R)-3-(3-{[5-(2,4-Dimethyl-1,3-thiazol-5-yl)-4-methyl-4H-1,2,4-triazol-3-yl]thio}propyl)-1-[2-fluoro-4-(trifluoromethyl)phenyl]-3-azabicyclo[3.1.0]hexane;

(1S,5R)-1-[2-Fluoro-4-(trifluoromethyl)phenyl]-3-(3-{[4-methyl-5-(5-methyl-2-pyrazinyl)-4H-1,2,4-triazol-3-yl]thio}propyl)-3-azabicyclo[3.1.0]hexane;

(1S,5R)-1-[2-Fluoro-4-(trifluoromethyl)phenyl]-3-[3-({4-methyl-5-[4-(trifluoro-methyl)phenyl]-4H-1,2,4-triazol-3-yl}thio)propyl]-3-azabicyclo[3.1.0]hexane;

1-{4-[(1R,5S/1S,5R)-3-(3-{[4-Methyl-5-(2-methyl-5-quinolinyl)-4H-1,2,4-triazol-3-yl]thio}propyl)-3-azabicyclo[3.1.0]hex-1-yl]phenyl}-2-pyrrolidinone;

5-{5-[(3-{(1R,5S/1S,5R)-1-[4-(1,1-Dioxido-2-isothiazolidinyl)phenyl]-3-azabicycle-[3.1.0]hex-3-yl}propyl)thio]-4-methyl-4H-1,2,4-triazol-3-yl}-2-methylquinoline;

(1R,5S/1S,5R)-1-[3-Fluoro-4-(trifluoromethyl)phenyl]-5-methyl-3-(3-{[4-methyl-5-(4-methyl-1,3-oxazol-5-yl)-4H-1,2,4-triazol-3-yl]thio}propyl)-3-azabicyclo[3.1.0]hexane;

1-(2-(Methyloxy)-5-{(1R,5S/1S,5R)-3-[3-({4-methyl-5-[4-(trifluoromethyl)phenyl]-4H-1,2,4-triazol-3-yl}thio)propyl]-3-azabicyclo[3.1.0]hex-1-yl}phenyl)ethanone;

1-[5-[(1R,5S/1S,5R)-3-(3-{[5-(3,4-Difluorophenyl)-4-methyl-4H-1,2,4-triazol-3-yl]thio}propyl)-3-azabicyclo[3.1.0]hex-1-yl]-2-(methyloxy)phenyl]ethanone;

1-{2-(Methyloxy)-5-[(1R,5S/1S,5R)-3-(3-{[4-methyl-5-(3-pyridinyl)-4H-1,2,4-triazol-3-yl]thio}propyl)-3-azabicyclo[3.1.0]hex-1-yl]phenyl}ethanone;

1-[5-[(1R,5S/1S,5R)-3-(3-{[4-Methyl-5-(2-methyl-5-quinolinyl)-4H-1,2,4-triazol-3-yl]thio}propyl)-3-azabicyclo[3.1.0]hex-1-yl]-2-(methyloxy)phenyl]ethanone;

1-{2-(Methyloxy)-5-[(1R,5S/1S,5R)-3-(3-{[4-methyl-5-(tetrahydro-2H-pyran-4-yl)-4H-1,2,4-triazol-3-yl]thio}propyl)-3-azabicyclo[3.1.0]hex-1-yl]phenyl}ethanone;

1-(2-Hydroxy-5-{(1R,5S/1S,5R)-3-[3-({4-methyl-5-[4-(trifluoromethyl)phenyl]-4H-1,2,4-triazol-3-yl}thio)propyl]-3-azabicyclo[3.1.0]hex-1-yl}phenyl)ethanone;

1-[5-[(1R,5S/1S,5R)-3-(3-{[5-(3,4-Difluorophenyl)-4-methyl-4H-1,2,4-triazol-3-yl]thio}propyl)-3-azabicyclo[3.1.0]hex-1-yl]-2-hydroxyphenyl]ethanone;

1-{2-Hydroxy-5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]phenyl}ethanone;

1-{2-Hydroxy-5-[(1R,5S/1S,5R)-3-(3-{[4-methyl-5-(2-methyl-5-quinolinyl)-4H-1,2,4-triazol-3-yl]thio}propyl)-3-azabicyclo[3.1.0]hex-1-yl]phenyl}ethanone;

1-[5-[(1R,5S/1S,5R)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]-1-propanone;

1-[5-[(1S,5R)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]-1-propanone enantiomer 1;

2-methyl-5-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole;

2-Methyl-5-[(1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole, enantiomer 1;

2-Methyl-6-[(1R,5S/1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole;

1-Methyl-5-[(1R,5S/1S,5R)-3-(3-{[4-methyl-5-(4-methyl-1,3-oxazol-5-0)-4H-1,2,4-triazol-3-yl]thio}propyl)-3-azabicyclo[3.1.0]hex-1-yl]-1H-indazole;

1-Methyl-5-[(1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1H-indazole, enantiomer 1;

(1R,5S/1S,5R)-3-(3-{[4-Methyl-5-(4-methyl-1,3-oxazol-5-yl)-4H-1,2,4-triazol-3-yl]thio}propyl)-1-[6-(trifluoromethyl)-3-pyridinyl]-3-azabicyclo[3.1.0]hexane;

(1R,5S/1S,5R)-1-(4-Bromophenyl)-3-(3-{[4-methyl-5-(2-methyl-3-pyridinyl)-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(4-pyridazinyl)-4H-1,2,4-triazol-3-yl]thio}propyl)-3-azabicyclo[3.1.0]hexane;

(1R,5S/1S,5R)-1-(4-Bromophenyl)-3-(3-{[5-(5-chloro-1-methyl-1H-pyrazol-4-yl)-4-methyl-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(1-methyl-1H-1,2,3-triazol-4-yl)-4H-1,2,4-triazol-3-yl]thio}propyl)-3-azabicyclo[3.1.0]hexane;

(1R,5S/1S,5R)-1-(4-Bromophenyl)-3-(3-{[5-(1,5-dimethyl-1H-pyrazol-4-yl)-4-methyl-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(5-pyrimidinyl)-4H-1,2,4-triazol-3-yl]thio}propyl)-3-azabicyclo[3.1.0]hexane;

(1R,5S/1S,5R)-1-(4-Bromophenyl)-3-[3-({4-methyl-5-[1-methyl-3-(trifluoromethyl)-1H-pyrazol-4-yl]-4H-1,2,4-triazol-3-yl}thio)propyl]-3-azabicyclo[3.1.0]hexane;

(1R,5S/1S,5R)-1-(4-Bromophenyl)-3-(3-{[4-methyl-5-(3-methyl-2-furanyl)-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(3-methyl-5-isoxazolyl)-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(6-methyl-3-pyridinyl)-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(1-methyl-1H-pyrazol-5-yl)-4H-1,2,4-triazol-3-yl]thio}propyl)-3-azabicyclo[3.1.0]hexane;

(1R,5S/1S,5R)-1-(4-Bromophenyl)-3-(3-{[4-methyl-5-(5-methyl-3-pyridinyl)-4H-1,2,4-triazol-3-yl]thio}propyl)-3-azabicyclo[3.1.0]hexane;

(1R,5S/1S,5R)-1-(4-Bromophenyl)-3-[3-({4-methyl-5-[2-methyl-5-(trifluoromethyl)-1,3-oxazol-4-yl]-4H-1,2,4-triazol-3-yl}thio)propyl]-3-azabicyclo[3.1.0]hexane;

(1R,5S/1S,5R)-1-(4-Bromophenyl)-3-(3-{[4-methyl-5-(3-methyl-2-pyridinyl)-4H-1,2,4-triazol-3-yl]thio}propyl)-3-azabicyclo[3.1.0]hexane;

(1R,5S/1S,5R)-1-(4-Bromophenyl)-3-(3-{[5-(2,4-dimethyl-1,3-thiazol-5-yl)-4-methyl-4H-1,2,4-triazol-3-yl]thio}propyl)-3-azabicyclo[3.1.0]hexane;

(1R,5S/1S,5R)-1-(4-Bromophenyl)-3-(3-{[5-(2,5-dimethyl-3-furanyl)-4-methyl-4H-1,2,4-triazol-3-yl]thio}propyl)-3-azabicyclo[3.1.0]hexane;

(1R,5S/1S,5R)-1-(4-Bromophenyl)-3-(3-{[5-(5-chloro-2-thienyl)-4-methyl-4H-1,2,4-triazol-3-yl]thio}propyl)-3-azabicyclo[3.1.0]hexane;

(1R,5S/1S,5R)-1-(4-Bromophenyl)-3-(3-{[4-ethyl-5-(3-pyridinyl)-4H-1,2,4-triazol-3-yl]thio}propyl)-3-azabicyclo[3.1.0]hexane;

(1R,5S/1S,5R)-1-(4-Bromophenyl)-3-[3-({4-methyl-5-[2-methyl-6-(trifluoromethyl)-3-pyridinyl]-4H-1,2,4-triazol-3-yl}thio)propyl]-3-azabicyclo[3.1.0]hexane;

5-[5-({3-[(1R,5S/1S,5R)-1-(4-Bromophenyl)-3-azabicyclo[3.1.0]hex-3-yl]propyl}thio)-4-methyl-4H-1,2,4-triazol-3-yl]-1-methyl-3-(trifluoromethyl)-1H-thieno[2,3-c]pyrazole;

3-(3-{[4-Methyl-5-(4-methyl-1,3-oxazol-5-yl)-4H-1,2,4-triazol-3-yl]thio}propyl)-(1R,5R/1S,5S)-1-[5-(trifluoromethyl)-2-pyridinyl]-3-azabicyclo[3.1.0]hexane;

3-(3-{[4-Methyl-5-(4-methyl-1,3-oxazol-5-yl)-4H-1,2,4-triazol-3-yl]thio}propyl)-(1R,5R)-1-[5-(trifluoromethyl)-2-pyridinyl]-3-azabicyclo[3.1.0]hexane, enantiomer 2;

3-(3-{[4-methyl-5-(4-methyl-1,3-oxazol-5-yl)-4H-1,2,4-triazol-3-yl]thio}propyl)-(1R,5R/1S,5S)-1-[6-(trifluoromethyl)-2-pyridinyl]-3-azabicyclo[3.1.0]hexane;

(1R,5S/1S,5R)-1-[3-Fluoro-4-(1H-pyrrol-1-ylmethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R/1R,5S)-3-(3-{[4-Methyl-5-(5-methyl-2-pyrazinyl)-4H-1,2,4-triazol-3-yl]thio}propyl)-1-[6-(trifluoromethyl)-3-pyridinyl]-3-azabicyclo[3.1.0]hexane;

(1S,5R/1R,5S)-3-(3-{[4-Methyl-5-(6-methyl-3-pyridinyl)-4H-1,2,4-triazol-3-yl]thio}propyl)-1-[6-(trifluoromethyl)-3-pyridinyl]-3-azabicyclo[3.1.0]hexane;

(1S,5R/1R,5S)-3-(3-{[4-Methyl-5-(2-methyl-3-pyridinyl)-4H-1,2,4-triazol-3-yl]thio}propyl)-1-[6-(trifluoromethyl)-3-pyridinyl]-3-azabicyclo[3.1.0]hexane;

(1S,5R/1R,5S)-3-{3-[(4-Methyl-5-phenyl-4H-1,2,4-triazol-3-yl)thio]propyl}-1-[6-(trifluoromethyl)-3-pyridinyl]-3-azabicyclo[3.1.0]hexane;

(1S,5R/1R,5S)-3-(3-{[5-(2,4-Dimethyl-1,3-thiazol-5-yl)-4-methyl-4H-1,2,4-triazol-3-yl]thio}propyl)-1-[6-(trifluoromethyl)-3-pyridinyl]-3-azabicyclo[3.1.0]hexane;

(1S,5R/1R,5S)-3-[3-({4-Methyl-5-[4-(trifluoromethyl)phenyl]-4H-1,2,4-triazol-3-yl}thio)propyl]-1-[6-(trifluoromethyl)-3-pyridinyl]-3-azabicyclo[3.1.0]hexane;

(1S,5R/1R,5S)-2-Methyl-5-[3-(3-{[4-methyl-5-(5-methyl-2-pyrazinyl)-4H-1,2,4-triazol-3-yl]thio}propyl)-3-azabicyclo[3.1.0]hex-1-yl]-1,3-benzothiazole;

(1S,5R/1R,5S)-2-Methyl-5-[3-(3-{[4-methyl-5-(6-methyl-3-pyridinyl)-4H-1,2,4-triazol-3-yl]thio}propyl)-3-azabicyclo[3.1.0]hex-1-yl]-1,3-benzothiazole;

(1S,5R/1R,5S)-2-Methyl-5-(3-{3-[(4-methyl-5-phenyl-4H-1,2,4-triazol-3-yl)thio]propyl}-3-azabicyclo[3.1.0]hex-1-yl)-1,3-benzothiazole;

(1S,5R/1R,5S)-5-[3-(3-{[5-(2,4-Dimethyl-1,3-thiazol-5-yl)-4-methyl-4H-1,2,4-triazol-3-yl]thio}propyl)-3-azabicyclo[3.1.0]hex-1-yl]-2-methyl-1,3-benzothiazole;

(1S,5R/1R,5S)-2-Methyl-5-{3-[3-({4-methyl-5-[4-(trifluoromethyl)phenyl]-4H-1,2,4-triazol-3-yl}thio)propyl}-3-azabicyclo[3.1.0]hex-1-yl}-1,3-benzothiazole;

(1R,5S/1S,5R)-1-[3-Fluoro-5-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane;

(1S,5R)-1-[3-Fluoro-5-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane, enantiomer 1;

(1R,5S/1S,5R)-1-[2-Fluoro-3-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane;

(1S,5R)-1-[2-Fluoro-3-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane, enantiomer 2;

(1R,5S/1S,5R)-1-[4-(Methyloxy)-5-(trifluoromethyl)phenyl]-3-(3-{[4-methyl-5-(4-methyl-1,3-oxazol-5-yl)-4H-1,2,4-triazol-3-yl]thio}propyl)-azabicyclo[3.1.0]hexane;

(1R,5S/1S,5R)-1-[4-(4-Chloro-2-fluorophenyl)-3-(3-{[4-methyl-5-(4-methyl-1,3-oxazol-5-yl)-4H-1,2,4-triazol-3-yl]thio}propyl)-azabicyclo[3.1.0]hexane;

(1R,5S/1S,5R)-1-[3-(2-{[4-Methyl-5-(4-methyl-1,3-oxazol-5-yl)-4H-1,2,4-triazol-3-yl]thio}propyl)-1-{3-[(trifluoromethyl)oxy]phenyl}-3-azabicyclo[3.1.0]hexane;

(1R,5S/1S,5R)-1-(2-Chloro-4-methylphenyl)-3-(2-{[4-methyl-5-(4-methyl-1,3-oxazol-5-yl)-4H-1,2,4-triazol-3-yl]thio}propyl)-3-azabicyclo[3.1.0]hexane;

(1R,5S/1S,5R)-1-[3-Chloro-4-(methyloxy)phenyl]-3-(2-{[4-methyl-5-(4-methyl-1,3-oxazol-5-yl)-4H-1,2,4-triazol-3-yl]thio}propyl)-3-azabicyclo[3.1.0]hexane;

(1R,5S/1S,5R)-1-[4-(2,4-Dimethyl-1,3-thiazol-5-yl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1R,5S/1S,5R)-3-(3-{[4-methyl-5-(4-methyl-1,3-oxazol-5-yl)-4H-1,2,4-triazol-3-yl]thio}propyl)-1-{4-[6-(trifluoromethyl)-2-pyridinyl]phenyl}-3-azabicyclo[3.1.0]hexane;

(1R,5S/1S,5R)-1-[3-(2,4-dimethyl-1,3-thiazol-5-yl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1R,5S/1S,5R)-3-(3-{[4-methyl-5-(4-methyl-1,3-oxazol-5-yl)-4H-1,2,4-triazol-3-yl]thio}propyl)-1-[3-(5-methyl-2-thienyl)phenyl]-3-azabicyclo[3.1.0]hexane;

(1R,5S/1S,5R)-1-[4-(3,5-dimethyl-4-isoxazolyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane; and (1S,5R)-3-(3-{[5-(2,4-Dimethyl-1,3-oxazol-5-yl)-4-methyl-4H-1,2,4-triazol-3-yl]thio}propyl)-1-[2-fluoro-4-(trifluoromethyl)phenyl]-3-azabicyclo[3.1.0]hexane; or a pharmaceutically acceptable salt thereof.

20. A compound or a pharmaceutically acceptable salt thereof according to claim 1 selected from a group consisting of:

4-[(1S,5R)-3-(3-{[4-Methyl-5-(2-methylquinolin-5-yl)-4H-1,2,4-triazol-3-yl]thio}propyl)-3-azabicyclo[3.1.0]hex-1-yl]benzonitrile;

4-[(1S,5R)-3-(3-{[4-Methyl-5-(2-methylquinolin-5-yl)-4H-1,2,4-triazol-3-yl]thio}propyl)-3-azabicyclo[3.1.0]hex-1-yl]phenol;

(1S,5R)-3-(3-{[4-methyl-5-(4-methyl-1,3-oxazol-5-yl)-4H-1,2,4-triazol-3-yl]thio}propyl)-1-phenyl-3-azabicyclo[3.1.0]hexane;

(1S,5R)-1-(4-tert-Butylphenyl)-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-1-[4-(5-methyl-3-isoxazolyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[4-Methyl-5-(4-methyl-1,3-oxazol-5-yl)-4H-1,2,4-triazol-3-yl]thio}propyl)-1-[3-(trifluoromethyl)phenyl]-3-azabicyclo[3.1.0]hexane;

(1S,5R)-1-[4-Fluoro-3-(trifluoromethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[4-Methyl-5-(4-methyl-1,3-oxazol-5-yl)-4H-1,2,4-triazol-3-yl]-thio}propyl)-1-[2-methyl-4-(trifluoromethyl)phenyl]-3-azabicyclo[3.1.0]hexane;

(1S,5R)-1-(3-Bromophenyl)-3-(3-{[4-methyl-5-(4-methyl-1,3-oxazol-5-yl)-4H-1,2,4-triazol-3-yl]thio}propyl)-3-azabicyclo[3.1.0]hexane;

1-[4-[(1S,5R)-3-(3-{[4-Methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]ethanone;

1-[4-[(1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-2-(methyloxy)phenyl]-1-propanone;

(1S,5R)-3-(3-{[4-Methyl-5-(4-methyl-1,3-oxazol-5-yl)-4H-1,2,4-triazol-3-yl]thio}propyl)-1-[2-(trifluoromethyl)phenyl]-3-azabicyclo[3.1.0]hexane;

1-{4-[(1S,5R)-3-(3-{[4-Methyl-5-(2-methyl-5-quinolinyl)-4H-1,2,4-triazol-3-yl]thio}propyl)-3-azabicyclo[3.1.0]hex-1-yl]phenyl}-2-pyrrolidinone;

5-{5-[(3-[(1S,5R)-1-[4-(1,1-Dioxido-2-isothiazolidinyl)phenyl]-3-azabicyclo-[3.1.0]hex-3-yl]propyl)thio]-4-methyl-4H-1,2,4-triazol-3-yl]-2-methylquinoline;

1-(2-(Methyloxy)-5-{(1S,5R)-3-[3-({4-methyl-5-[4-(trifluoromethyl)phenyl]-4H-1,2,4-triazol-3-yl}thio)propyl]-3-azabicyclo[3.1.0]hex-1-yl}phenyl)ethanone;

1-[5-[(1S,5R)-3-(3-{[5-(3,4-Difluorophenyl)-4-methyl-4H-1,2,4-triazol-3-yl]thio}propyl)-3-azabicyclo[3.1.0]hex-1-yl]-2-(methyloxy)phenyl]ethanone;

1-{2-(Methyloxy)-5[(1S,5R)-3-(3-{[4-methyl-5-(3-pyridinyl)-4H-1,2,4-triazol-3-yl]thio}propyl)-3-azabicyclo[3.1.0]hex-1-yl]phenyl}ethanone;

1-[5-[(1S,5R)-3-(3-{[4-Methyl-5-(2-methyl-5-quinolinyl)-4H-1,2,4-triazol-3-yl]thio}propyl)-3-azabicyclo[3.1.0]hex-1-yl]-2-(methyloxy)phenyl]ethanone;

1-{2-(Methyloxy)-5-[(1S,5R)-3-(3-{[4-methyl-5-(tetrahydro-2H-pyran-4-yl)-4H-1,2,4-triazol-3-yl]thio}propyl)-3-azabicyclo[3.1.0]hex-1-yl]phenyl}ethanone;

1-(2-Hydroxy-5-{(1S,5R)-3-[3-({4-methyl-5-[4-(trifluoromethyl)phenyl]-4H-1,2,4-triazol-3-yl}thio)propyl]-3-azabicyclo[3.1.0]hex-1-yl}phenyl)ethanone;

1-{5-[(1S,5R)-3-(3-{[5-(3,4-Difluorophenyl)-4-methyl-4H-1,2,4-triazol-3-yl]thio}propyl)-3-azabicyclo[3.1.0]hex-1-yl]-2-hydroxyphenyl}ethanone;

1-{2-Hydroxy-5-[(1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]phenyl}ethanone;

1-{2-Hydroxy-5-[(1S,5R)-3-(3-{[4-methyl-5-(2-methyl-5-quinolinyl)-4H-1,2,4-triazol-3-yl]thio}propyl)-3-azabicyclo[3.1.0]hex-1-yl]phenyl}ethanone;

2-Methyl-6-[(1S,5R)-3-(3-{[4-methyl-5-(4-methyl-1,3-oxazol-5-yl)-4H-1,2,4-triazol-3-yl]thio}propyl)-3-azabicyclo[3.1.0]hex-1-yl]-1,3-benzothiazole;

(1S,5R)-3-(3-{[4-Methyl-5-(4-methyl-1,3-oxazol-5-yl)-4H-1,2,4-triazol-3-yl]thio}propyl)-1-[6-(trifluoromethyl)-3-pyridinyl]-3-azabicyclo[3.1.0]hexane; 5R)-1-(4-Bromophenyl)-3-(3-{[4-methyl-5-(2-methyl-3-pyridinyl)-4H-1,2,4-triazol-3-yl]thio}propyl)-3-azabicyclo[3.1.0]hexane;

(1S,5R)-1-(4-Bromophenyl)-3-(3-{[4-methyl-5-(4-pyridazinyl)-4H-1,2,4-triazol-3-yl]thio}propyl)-3-azabicyclo[3.1.0]hexane;

(1S,5R)-1-(4-Bromophenyl)-3-(3-{[5-(5-chloro-1-methyl-1H-pyrazol-4-yl)-4-methyl-4H-1,2,4-triazol-3-yl]thio}propyl)-3-azabicyclo[3.1.0]hexane;

(1S,5R)-1-(4-Bromophenyl)-3-(3-{[4-methyl-5-(1-methyl-1H-1,2,3-triazol-4-yl)-4H-1,2,4-triazol-3-yl]thio}propyl)-3-azabicyclo[3.1.0]hexane;

(1S,5R)-1-(4-Bromophenyl)-3-(3-{[5-(1,5-dimethyl-1H-pyrazol-4-yl)-4-methyl-4H-1,2,4-triazol-3-yl]thio}propyl)-3-azabicyclo[3.1.0]hexane;

(1S,5R)-1-(4-Bromophenyl)-3-(3-{[4-methyl-5-(5-pyrimidinyl)-4H-1,2,4-triazol-3-yl]thio}propyl)-3-azabicyclo[3.1.0]hexane;

(1S,5R)-1-(4-Bromophenyl)-3-[3-({4-methyl-5-[1-methyl-3-(trifluoromethyl)-1H-pyrazol-4-yl]-4H-1,2,4-triazol-3-yl}thio)propyl]-3-azabicyclo[3.1.0]hexane;

(1S,5R)-1-(4-Bromophenyl)-3-(3-{[4-methyl-5-(3-methyl-2-furanyl)-4H-1,2,4-triazol-3-yl]thio}propyl)-3-azabicyclo[3.1.0]hexane;

(1S,5R)-1-(4-Bromophenyl)-3-(3-{([4-methyl-5-(3-methyl-5-isoxazolyl)-4H-1,2,4-triazol-3-yl]thio}propyl)-3-azabicyclo[3.1.0]hexane;

(1S,5R)-1-(4-Bromophenyl)-3-(3-{([4-methyl-5-(6-methyl-3-pyridinyl)-4H-1,2,4-triazol-3-yl]thio}propyl)-3-azabicyclo[3.1.0]hexane;

(1S,5R)-1-(4-Bromophenyl)-3-(3-{[4-methyl-5-(1-methyl-1H-pyrazol-5-yl)-4H-1,2,4-triazol-3-yl]thio}propyl)-3-azabicyclo[3.1.0]hexane;

(1S,5R)-1-(4-Bromophenyl)-3-(3-{([4-methyl-5-(5-methyl-3-pyridinyl)-4H-1,2,4-triazol-3-yl]thio}propyl)-3-azabicyclo[3.1.0]hexane;

(1S,5R)-1-(4-Bromophenyl)-3-[3-({4-methyl-5-[2-methyl-5-(trifluoromethyl)-1,3-oxazol-4-yl]-4H-1,2,4-triazol-3-yl}thio)propyl]-3-azabicyclo[3.1.0]hexane;

(1S,5R)-1-(4-Bromophenyl)-3-(3-{([4-methyl-5-(3-methyl-2-pyridinyl)-4H-1,2,4-triazol-3-yl]thio}propyl)-3-azabicyclo[3.1.0]hexane;

(1S,5R)-1-(4-Bromophenyl)-3-(3-{([5-(2,4-dimethyl-1,3-thiazol-5-yl)-4-methyl-4H-1,2,4-triazol-3-yl]thio}propyl)-3-azabicyclo[3.1.0]hexane;

(1S,5R)-1-(4-Bromophenyl)-3-(3-{([5-(2,5-dimethyl-3-furanyl)-4-methyl-4H-1,2,4-triazol-3-yl]thio}propyl)-3-azabicyclo[3.1.0]hexane;

(1S,5R)-1-(4-Bromophenyl)-3-(3-{([5-(5-chloro-2-thienyl)-4-methyl-4H-1,2,4-triazol-3-yl]thio}propyl)-3-azabicyclo[3.1.0]hexane;

(1S,5R)-1-(4-Bromophenyl)-3-(3-{[4-ethyl-5-(3-pyridinyl)-4H-1,2,4-triazol-3-yl]thio}propyl)-3-azabicyclo[3.1.0]hexane;

(1S,5R)-1-(4-Bromophenyl)-3-[3-({4-methyl-5-[2-methyl-6-(trifluoromethyl)-3-pyridinyl]-4H-1,2,4-triazol-3-yl}thio)propyl]-3-azabicyclo[3.1.0]hexane;

5-[5-({3-[(1S,5R)-1-(4-Bromophenyl)-3-azabicyclo[3.1.0]hex-3-yl]propyl}thio)-4-methyl-4H-1,2,4-triazol-3-yl]-1-methyl-3-(trifluoromethyl)-1H-thieno[2,3-c]pyrazole;

3-(3-{([4-methyl-5-(4-methyl-1,3-oxazol-5-yl)-4H-1,2,4-triazol-3-yl]thio}propyl)-(1R,5R)-1-[6-(trifluoromethyl)-2-pyridinyl]-3-azabicyclo[3.1.0]hexane;

(1S,5R)-1-[3-Fluoro-4-(1H-pyrrol-1-ylmethyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{([4-Methyl-5-(5-methyl-2-pyrazinyl)-4H-1,2,4-triazol-3-yl]thio}propyl)-1-[6-(trifluoromethyl)-3-pyridinyl]-3-azabicyclo[3.1.0]hexane;

(1S,5R)-3-(3-{([4-Methyl-5-(6-methyl-3-pyridinyl)-4H-1,2,4-triazol-3-yl]thio}propyl)-1-[6-(trifluoromethyl)-3-pyridinyl]-3-azabicyclo[3.1.0]hexane;

(1S,5R)-3-(3-{([4-Methyl-5-(2-methyl-3-pyridinyl)-4H-1,2,4-triazol-3-yl]thio}propyl)-1-[6-(trifluoromethyl)-3-pyridinyl]-3-azabicyclo[3.1.0]hexane;

(1S,5R)-3-{3-[(4-Methyl-5-phenyl-4H-1,2,4-triazol-3-yl)thio]propyl}-1-[6-(trifluoromethyl)-3-pyridinyl]-3-azabicyclo[3.1.0]hexane;

(1S,5R)-3-(3-{[5-(2,4-Dimethyl-1,3-thiazol-5-yl)-4-methyl-4H-1,2,4-triazol-3-yl]thio}propyl)-1-[6-(trifluoromethyl)-3-pyridinyl]-3-azabicyclo[3.1.0]hexane;

(1S,5R)-3-[3-({4-Methyl-5-[4-(trifluoromethyl)phenyl]-4-1-1,2,4-triazol-3-yl}thio)propyl]-1-[6-(trifluoromethyl)-3-pyridinyl]-3-azabicyclo[3.1.0]hexane;

(1S,5R)-2-Methyl-5-[3-(3-{[4-methyl-5-(5-methyl-2-pyrazinyl)-4H-1,2,4-triazol-3-yl]thio}propyl)-3-azabicyclo[3.1.0]hex-1-yl]-1,3-benzothiazole;

(1S,5R)-2-Methyl-5-[3-(3-{[4-methyl-5-(6-methyl-3-pyridinyl)-4H-1,2,4-triazol-3-yl]thio}propyl)-3-azabicyclo[3.1.0]hex-1-yl]-1,3-benzothiazole;

(1S,5R)-2-Methyl-5-(3-{3-[(4-methyl-5-phenyl-4H-1,2,4-triazol-3-yl)thio]propyl}-3-azabicyclo[3.1.0]hex-1-yl)-1,3-benzothiazole;

(1S,5R)-5-[3-(3-{[5-(2,4-Dimethyl-1,3-thiazol-5-yl)-4-methyl-4H-1,2,4-triazol-3-yl]thio}propyl)-3-azabicyclo[3.1.0]hex-1-yl]-2-methyl-1,3-benzothiazole;

(1S,5R/1R,5S)-2-Methyl-5-{3-[3-([4-methyl-5-[4-(trifluoromethyl)phenyl]-4H-1,2,4-triazol-3-yl}thio)propyl]-3-azabicyclo[3.1.0]hex-1-yl}-1,3-benzothiazole;

(1S,5R)-1-[4-(4-Chloro-2-fluorophenyl)-3-(3-{[4-methyl-5-(4-methyl-1,3-oxazol-5-yl)-4H-1,2,4-triazol-3-yl]thio}propyl)-azabicyclo[3.1.0]hexane;

(1S,5R)-1-[3-(2-{[4-Methyl-5-(4-methyl-1,3-oxazol-5-yl)-4H-1,2,4-triazol-3-yl]thio}propyl)-1-{3-[(trifluoromethyl)oxy]phenyl}-3-azabicyclo[3.1.0]hexane;

(1S,5R)-1-(2-Chloro-4-methylphenyl)-3-(2-{([4-methyl-5-(4-methyl-1,3-oxazol-5-yl)-4H-1,2,4-triazol-3-yl]thio}propyl)-3-azabicyclo[3.1.0]hexane;

(1S,5R)-1-[3-Chloro-4-(methyloxy)phenyl]-3-(2-{[4-methyl-5-(4-methyl-1,3-oxazol-5-yl)-4H-1,2,4-triazol-3-yl]thio}propyl)-3-azabicyclo[3.1.0]hexane;

(1S,5R)-1-[4-(2,4-Dimethyl-1,3-thiazol-5-yl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[4-methyl-5-(4-methyl-1,3-oxazol-5-yl)-4H-1,2,4-triazol-3-yl]thio}propyl)-1-{4-[6-(trifluoromethyl)-2-pyridinyl]phenyl}-3-azabicyclo[3.1.0]hexane;

(1S,5R)-1-[3-(2,4-dimethyl-1,3-thiazol-5-yl)phenyl]-3-(3-{[4-methyl-5-(4-methyl-1,3-oxazol-5-yl)-4H-1,2,4-triazol-3-yl]thio}propyl)-3-azabicyclo[3.1.0]hexane;

(1S,5R)-3-(3-{[4-methyl-5-(4-methyl-1,3-oxazol-5-yl)-4H-1,2,4-triazol-3-yl]thio}propyl)-1-[3-(5-methyl-2-thienyl)phenyl]-3-azabicyclo[3.1.0]hexane;

(1S,5R)-1-[4-(3,5-dimethyl-4-isoxazolyl)phenyl]-3-(3-{[4-methyl-5-(4-methyl-1,3-oxazol-5-yl)-4H-1,2,4-triazol-3-yl]thio}propyl)-3-azabicyclo[3.1.0]hexane; and (1S,5R)-3-(3-{[5-(2,4-Dimethyl-1,3-oxazol-5-yl)-4-methyl-4H-1,2,4-triazol-3-yl]thio}propyl)-1-[2-fluoro-4-(trifluoromethyl)phenyl]-3-azabicyclo[3.1.0].

21. A method for treating substance abuse comprising administering to a patient in need thereof a therapeutically effective amount of a compound of formula (I) according to claim 1, either neat or admixed with a pharmaceutically acceptable carrier.

22. A pharmaceutical composition comprising a compound of formula (I) according to claim 1 or a pharmaceutically acceptable salt thereof and a pharmaceutically acceptable carrier.

* * * * *